United States Patent
Rothberg et al.

(10) Patent No.: US 10,712,273 B2
(45) Date of Patent: Jul. 14, 2020

(54) ACTIVE-SOURCE-PIXEL, INTEGRATED DEVICE FOR RAPID ANALYSIS OF BIOLOGICAL AND CHEMICAL SPECIMENS

(71) Applicant: Quantum-Si Incorporated, Guilford, CT (US)

(72) Inventors: Jonathan M. Rothberg, Guilford, CT (US); Ali Kabiri, Madison, CT (US); Jason W. Sickler, Madison, CT (US); Brett J. Gyarfas, Guilford, CT (US); Jeremy Lackey, Guilford, CT (US); Gerard Schmid, Guilford, CT (US)

(73) Assignee: Quantum-Si Incorporated, Guilford, CT (US)

( * ) Notice: Subject to any disclaimer, the term of this patent is extended or adjusted under 35 U.S.C. 154(b) by 112 days.

(21) Appl. No.: 15/960,751

(22) Filed: Apr. 24, 2018

(65) Prior Publication Data

US 2018/0348132 A1    Dec. 6, 2018

Related U.S. Application Data

(62) Division of application No. 14/543,888, filed on Nov. 17, 2014, now Pat. No. 9,983,135.

(Continued)

(51) Int. Cl.
*G01N 21/00* (2006.01)
*G01N 21/64* (2006.01)
(Continued)

(52) U.S. Cl.
CPC ........ *G01N 21/6486* (2013.01); *B01L 3/5085* (2013.01); *C12Q 1/6869* (2013.01);
(Continued)

(58) Field of Classification Search
None
See application file for complete search history.

(56) References Cited

U.S. PATENT DOCUMENTS

| | | |
|---|---|---|
| 5,198,543 A | 3/1993 | Blanco et al. |
| 5,302,509 A | 4/1994 | Cheeseman |

(Continued)

FOREIGN PATENT DOCUMENTS

| | | |
|---|---|---|
| CN | 102713572 A | 10/2012 |
| EP | 1681356 A1 | 7/2006 |

(Continued)

OTHER PUBLICATIONS

Invitation to Pay Additional Fees for International Application No. PCT/US2014/066014 dated Jan. 28, 2015.

(Continued)

*Primary Examiner* — Aaron A Priest
(74) *Attorney, Agent, or Firm* — Wolf, Greenfield & Sacks, P.C.

(57) ABSTRACT

An active-source-pixel, integrated device capable of performing biomolecule detection and/or analysis, such as single-molecule nucleic acid sequencing, is described. An active pixel of the integrated device includes a sample well into which a sample to be analyzed may diffuse, an excitation source for providing excitation energy to the sample well, and a sensor configured to detect emission from the sample. The sensor may comprise two or more segments that produce a set of signals that are analyzed to differentiate between and identify tags that are attached to, or associated with, the sample. Tag differentiation may be spectral and/or temporal based. Identification of the tags may be used to detect, analyze, and/or sequence the biomolecule.

49 Claims, 68 Drawing Sheets

Related U.S. Application Data

(60) Provisional application No. 61/941,916, filed on Feb. 19, 2014, provisional application No. 61/917,926, filed on Dec. 18, 2013, provisional application No. 61/905,282, filed on Nov. 17, 2013.

(51) Int. Cl.
*C12Q 1/6874* (2018.01)
*G01N 21/77* (2006.01)
*B01L 3/00* (2006.01)
*C12Q 1/6869* (2018.01)

(52) U.S. Cl.
CPC ........... *C12Q 1/6874* (2013.01); *G01N 21/64* (2013.01); *G01N 21/645* (2013.01); *G01N 21/648* (2013.01); *G01N 21/6452* (2013.01); *G01N 21/7743* (2013.01); *G01N 21/7746* (2013.01); *B01L 2200/12* (2013.01); *B01L 2300/0829* (2013.01); *B01L 2300/0887* (2013.01); *B01L 2300/0893* (2013.01); *B01L 2300/168* (2013.01); *C12Q 2521/101* (2013.01); *C12Q 2525/101* (2013.01); *C12Q 2537/157* (2013.01); *C12Q 2563/107* (2013.01); *C12Q 2565/607* (2013.01); *G01N 2021/6419* (2013.01); *G01N 2021/6441* (2013.01); *G01N 2021/6478* (2013.01); *G01N 2201/02* (2013.01); *G01N 2201/062* (2013.01); *G01N 2201/068* (2013.01); *G01N 2201/0612* (2013.01); *G01N 2201/06113* (2013.01); *G01N 2201/125* (2013.01); *Y10T 29/49016* (2015.01)

(56) References Cited

U.S. PATENT DOCUMENTS

| | | | |
|---|---|---|---|
| 5,343,038 | A * | 8/1994 | Nishiwaki ........... G02B 21/002 |
| | | | 250/234 |
| 5,471,515 | A | 11/1995 | Fossum et al. |
| 5,674,743 | A | 10/1997 | Ulmer |
| 5,822,472 | A | 10/1998 | Danielzik et al. |
| 5,912,155 | A | 6/1999 | Chatterjee et al. |
| 6,134,002 | A | 10/2000 | Stimson et al. |
| 6,137,117 | A | 10/2000 | Feldstein et al. |
| 6,198,869 | B1 | 3/2001 | Kraus et al. |
| 6,210,896 | B1 | 4/2001 | Chan |
| 6,232,103 | B1 | 5/2001 | Short |
| 6,255,083 | B1 | 7/2001 | Williams |
| 6,261,797 | B1 | 7/2001 | Sorge et al. |
| 6,265,193 | B1 | 7/2001 | Brandis et al. |
| 6,280,939 | B1 | 8/2001 | Allen |
| 6,327,410 | B1 | 12/2001 | Walt et al. |
| 6,355,420 | B1 | 3/2002 | Chan |
| 6,399,320 | B1 | 6/2002 | Markau et al. |
| 6,399,335 | B1 | 6/2002 | Kao et al. |
| 6,437,345 | B1 | 8/2002 | Bruno-Raimondi et al. |
| 6,607,883 | B1 | 8/2003 | Frey et al. |
| 6,716,394 | B2 | 4/2004 | Jensen et al. |
| 6,825,921 | B1 | 11/2004 | Modlin et al. |
| 6,936,702 | B2 | 8/2005 | Williams et al. |
| 7,033,762 | B2 | 4/2006 | Nelson et al. |
| 7,052,847 | B2 | 5/2006 | Korlach et al. |
| 7,057,026 | B2 | 6/2006 | Barnes et al. |
| 7,153,672 | B1 | 12/2006 | Eickbush et al. |
| 7,158,224 | B2 | 1/2007 | Montagu |
| 7,170,050 | B2 | 1/2007 | Turner et al. |
| 7,179,654 | B2 | 2/2007 | Verdonk et al. |
| 7,270,951 | B1 | 9/2007 | Stemple et al. |
| 7,277,166 | B2 | 10/2007 | Padmanabhan et al. |
| 7,345,764 | B2 | 3/2008 | Bulovic et al. |
| 7,393,640 | B2 | 7/2008 | Kumar et al. |
| 7,405,281 | B2 | 7/2008 | Xu et al. |
| 7,462,452 | B2 | 12/2008 | Williams et al. |
| 7,595,883 | B1 | 9/2009 | El Gamal et al. |
| 7,630,073 | B2 | 12/2009 | Lundquist et al. |
| 7,738,086 | B2 | 6/2010 | Shepard et al. |
| 7,745,116 | B2 | 6/2010 | Williams |
| 7,820,983 | B2 | 10/2010 | Lundquist et al. |
| 7,871,777 | B2 | 1/2011 | Schneider et al. |
| 7,873,085 | B2 | 1/2011 | Babushkin et al. |
| 7,875,440 | B2 | 1/2011 | Williams et al. |
| 7,968,702 | B2 | 6/2011 | Wegener et al. |
| 7,973,146 | B2 | 7/2011 | Shen et al. |
| 7,981,604 | B2 | 7/2011 | Quake |
| 8,058,030 | B2 | 11/2011 | Smith et al. |
| 8,133,672 | B2 | 3/2012 | Bjornson et al. |
| 8,153,375 | B2 | 4/2012 | Travers et al. |
| 8,174,696 | B2 | 5/2012 | Ebbesen et al. |
| 8,274,034 | B2 | 9/2012 | Vogel et al. |
| 8,274,040 | B2 | 9/2012 | Zhong et al. |
| 8,278,728 | B2 | 10/2012 | Murshid |
| 8,323,939 | B2 | 12/2012 | Hanzel et al. |
| 8,343,746 | B2 | 1/2013 | Rank et al. |
| 8,465,699 | B2 | 6/2013 | Fehr et al. |
| 8,471,230 | B2 | 6/2013 | Zhong et al. |
| 8,481,264 | B2 | 7/2013 | Bjornson et al. |
| 8,501,406 | B1 | 8/2013 | Gray et al. |
| 8,501,922 | B2 | 8/2013 | Otto et al. |
| 8,502,169 | B2 | 8/2013 | Rigneault et al. |
| 8,580,539 | B2 | 11/2013 | Korlach |
| 8,654,427 | B1 | 2/2014 | DeAngelo |
| 8,865,077 | B2 | 10/2014 | Chiou et al. |
| 8,921,086 | B2 | 12/2014 | Hanzel et al. |
| 9,062,091 | B2 | 6/2015 | Bjornson et al. |
| 9,127,259 | B2 | 9/2015 | Bjornson et al. |
| 9,983,135 | B2 | 5/2018 | Rothberg et al. |
| 2002/0031836 | A1 | 3/2002 | Feldstein |
| 2002/0182631 | A1 * | 12/2002 | Schurmann-Mader ...................... B01L 3/5025 |
| | | | 435/6.19 |
| 2003/0223059 | A1 * | 12/2003 | Li ...................... G01N 21/6452 |
| | | | 356/317 |
| 2004/0169842 | A1 | 9/2004 | Dosluoglu et al. |
| 2006/0238767 | A1 * | 10/2006 | Chen .................. G01N 21/7703 |
| | | | 356/445 |
| 2007/0281288 | A1 | 12/2007 | Belkin et al. |
| 2008/0050747 | A1 | 2/2008 | Korlach et al. |
| 2009/0140128 | A1 * | 6/2009 | Oldham ............... G01N 21/648 |
| | | | 250/216 |
| 2010/0009872 | A1 | 1/2010 | Eid et al. |
| 2010/0065726 | A1 | 3/2010 | Zhong et al. |
| 2010/0173394 | A1 | 7/2010 | Colston et al. |
| 2010/0255461 | A1 * | 10/2010 | Callenbach ............ B29C 33/38 |
| | | | 435/5 |
| 2010/0255487 | A1 | 10/2010 | Beechem et al. |
| 2010/0256016 | A1 * | 10/2010 | Blair ...................... B82Y 15/00 |
| | | | 506/13 |
| 2010/0323406 | A1 | 12/2010 | Vatta et al. |
| 2011/0136201 | A1 | 6/2011 | Mao et al. |
| 2011/0165652 | A1 | 7/2011 | Hardin et al. |
| 2011/0236983 | A1 | 9/2011 | Beechem et al. |
| 2012/0094332 | A1 | 4/2012 | Lee et al. |
| 2012/0322692 | A1 | 12/2012 | Pham et al. |
| 2013/0023039 | A1 | 1/2013 | Zaccarin et al. |
| 2013/0071849 | A1 | 3/2013 | Kong et al. |
| 2013/0177903 | A1 | 7/2013 | Thomas et al. |
| 2013/0217007 | A1 | 8/2013 | Kamtekar et al. |
| 2014/0206562 | A1 | 7/2014 | Mccormack et al. |
| 2014/0335527 | A1 | 11/2014 | Goel |
| 2015/0141267 | A1 | 5/2015 | Rothberg et al. |
| 2015/0141268 | A1 | 5/2015 | Rothberg et al. |
| 2016/0041095 | A1 | 2/2016 | Rothberg et al. |
| 2016/0084761 | A1 | 3/2016 | Rothberg et al. |
| 2016/0133668 | A1 | 5/2016 | Rothberg et al. |
| 2016/0334618 | A1 | 11/2016 | Hargis et al. |
| 2016/0341664 | A1 | 11/2016 | Rothberg et al. |
| 2016/0355869 | A1 * | 12/2016 | Blair ............... G01N 33/54373 |
| 2016/0369332 | A1 | 12/2016 | Rothberg et al. |
| 2017/0219492 | A1 | 8/2017 | Lundquist et al. |
| 2017/0322156 | A1 | 11/2017 | Saxena et al. |

(56) References Cited

U.S. PATENT DOCUMENTS

| | | | |
|---|---|---|---|
| 2018/0348133 | A1 | 12/2018 | Rothberg et al. |
| 2019/0025214 | A1 | 1/2019 | Rothberg et al. |

FOREIGN PATENT DOCUMENTS

| | | | | |
|---|---|---|---|---|
| EP | | 2182523 | A1 | 5/2010 |
| EP | | 2339632 | A1 | 6/2011 |
| EP | | 2391639 | | 12/2011 |
| EP | | 2134871 | B1 | 3/2012 |
| JP | | 2009-045057 | A | 3/2009 |
| JP | | 2010-000048 | A | 1/2010 |
| JP | | 2010-243223 | A | 10/2010 |
| JP | | 2011-038932 | A | 2/2011 |
| JP | | 2011-530832 | A | 12/2011 |
| JP | | 2013-522605 | | 6/2013 |
| WO | WO | 91/06678 | A1 | 5/1991 |
| WO | WO | 2005/073407 | A1 | 8/2005 |
| WO | WO | 2007/015168 | A2 | 2/2007 |
| WO | WO | 2011/153962 | A1 | 12/2011 |
| WO | WO | 2013/060989 | A1 | 5/2013 |
| WO | WO | 2013/154770 | A1 | 10/2013 |
| WO | WO | 2013/171197 | A1 | 11/2013 |
| WO | WO- | 2013171197 | A1 * | 11/2013 .......... G01N 21/648 |

OTHER PUBLICATIONS

International Search Report and Written Opinion for International Application No. PCT/US2014/066014 dated Apr. 7, 2015.
International Preliminary Report on Patentability for International Application No. PCT/US2014/066014 dated May 26, 2016.
Invitation to Pay Additional Fees for International Application No. PCT/US2015/044360 dated Nov. 20, 2015.
International Search Report and Written Opinion for International Application No. PCT/US2015/044360 dated Feb. 3, 2016.
Invitation to Pay Additional Fees for International Application No. PCT/US2015/044378 dated Oct. 30, 2015.
International Search Report and Written Opinion for International Application No. PCT/US2015/044378 dated Jan. 15, 2016.
Invitation to Pay Additional Fees for International Application No. PCT/US2015/044379 dated Nov. 2, 2015.
International Search Report and Written Opinion for International Application No. PCT/US2015/044379 dated Jan. 15, 2016.
Invitation to Pay Additional Fees for International Application No. PCT/US2014/066013 dated Jan. 28, 2015.
International Search Report and Written Opinion for International Application No. PCT/US2014/066013 dated Apr. 7, 2015.
International Preliminary Report on Patentability for International Application No. PCT/US2014/066013 dated May 26, 2016.
Invitation to Pay Additional Fees for International Application No. PCT/US2014/066010 dated Jan. 28, 2015.
International Search Report and Written Opinion for International Application No. PCT/US2014/066010 dated Apr. 7, 2015.
International Preliminary Report on Patentability for International Application No. PCT/US2014/066010 dated May 26, 2016.
[No Author Listed] 5.2 Megapixels, 1-inch, 250fps, global-shutter CMOS image sensor, Anafocus, Oct. 2012, 4 pages, Sevilla, Spain.
[No Author Listed] Description of our technology, CrackerBio, 4 pages, Taiwan.
[No Author Listed] Detect Cancer with our 4 Picos ICCD camera, Stanford Computer Optics, 2013, 2 pages, http://www.stanfordcomputeroptics.com/applications/life-science/time-resolved-flim.html [last accessed May 9, 2014].
[No Author Listed] ICCD camera applications in the field of Life Science, Stanford Computer Optics, 2013, 2 pages, http://www.stanfordcomputeroptics.com/applications/life-science.html [last accessed May 9, 2014].
[No Author Listed] OLED-on-CMOS for Sensors and Microdisplays, IPMS Fraunhofer Institut Photonische Mikrosysteme, 2 pages, Dresden, Germany.

Achermann, Exciton—Plasmon Interactions in Metal—Semiconductor Nanostructures, The Journal Physical Chemistry Letters, Sep. 13, 2010, 1(19):2837-43.
Akselrod et al, Twenty-fold enhancement of molecular fluorescence by coupling to a J-aggregate critically coupled resonator. ACS Nano. Jan. 24, 2012;6(1):467-71. doi: 10.1021/nn203789t. Epub Dec. 1, 2011.
Algar et al., Interfacial Chemistry and the Design of Solid-Phase Nucleic Acid Hybridization Assays Using Immobilized Quantum Dots as Donors in Fluorescence Resonance Energy Transfer, Sensors, Jun. 2011, 11(6):6214-36.
Aouani et al., Bright unidirectional fluorescence emission of molecules in a nanoaperture with plasmonic corrugations. Nano Lett. Feb. 9, 2011;11(2):637-44. doi: 10.1021/nl103738d. Epub Jan. 19, 2011.
Aouani et al., Plasmonic Antennas for Directional Sorting of Fluorescence Emission, Nano Letters, May 18, 2011, 11(6):2400-6.
Aouani et al., Saturated excitation of fluorescence to quantify excitation enhancement in aperture antennas, Optics Express, Jul. 30, 2012, 20(16):18085-90.
Aouani et al., Supporting Information for Bright unidirectional fluorescence emission of molecules in a nanoaperture with plasmonic corrugations. Nano Lett. Feb. 9, 2011;11(2):19 pages.
Aouani et al., Supporting Information for Plasmonic Antennas for Directional Sorting of Fluorescence Emission, Nano Letters, May 18, 2011, 11(6):9 pages.
Bergman et al., Surface Plasmon Amplification by Stimulated Emission of Radiation: Quantum Generation of Coherent Surface Plasmons in Nanosystems, Physical Review Letters, Jan. 17, 2013, 90(2):027402-1-4.
Bogaerts et al., High speed 36 Gbps 12Mpixel global pipelined shutter CMOS image sensor with CDS, 2011 International Image Sensor Workshop, Jun. 8-11, 2011, 4 pages, Hokkaido, Japan.
Carretero-Palacious et al., Mechanisms for extraordinary optical transmission through bull's eye structures, Optics Express, May 23, 2011, 19(11):10429-42.
Chanyawadee et al., Nonradiative exciton energy transfer in hybrid organic-inorganic heterostructures, Phys. Rev. B., May 14, 2008, 77(19): 193402-1-4.
Daldosso et al., Fabrication and optical characterization of thin two-dimensional Si3N4 waveguides, Materials Science in Semiconductor Processing, Oct. 18, 2004, 7(4-6): 453-8.
Davies et al., Plasmonic Nanogap Tilings: Light-Concentrating Surfaces for Low-Loss Photonic Integration, ACS Nano, Jul. 4, 2013, 7(8):7093-100, arXiv:1305.2839v2, http://arxiv.org/abs/1305.2839v2.
Deshpande et al., Electrically driven polarized single-photon emission from an InGaN quantum dot in a GaN nanowire, Nature Communcations, Apr. 9, 2013, 8 pages.
Deutsch et al., Luminescence upconversion in colloidal double quantum dots, Nature Nanotechnology Letter, Sep. 2013, 8(9):649-53.
Edel et al., Accurate Single Molecule FRET Efficiency Determination for Surface Immobilized DNA Using Maximum Likelihood Calculated Lifetimes, J. Phys. Chem, Mar. 22, 2007, 111(11):2986-90.
Eid et al., Real-time DNA sequencing from single polymerase molecules. Science. Jan. 2, 2009;323(5910):133-8. doi:10.1126/science.1162986. Epub Nov. 20, 2008.
Eid et al., Supporting Online Material for Real-time DNA sequencing from single polymerase molecules. Science. Jan. 2, 2009;323(5910):21 pages.
Feldman et al., Wafer-Level Camera Technologies Shrink Camera Phone Handsets, Photonics.com, Aug. 1, 2007, 3 pages, http://www.photonics.com/Article.aspx?AID=30459 . [last accessed Dec. 17, 2013].
Fu et al., A microfabricated fluorescence-activated cell sorter. Nature Biotechnology. Nov. 1999; 17(11): 1109-1111.
Gorin et al., Fabrication of silicon nitride waveguides for visible-light using PECVD: a study of the effect of plasma frequency on optical properties, Optics Express, Sep. 1, 2008, 16(18):13509-16.

(56) References Cited

OTHER PUBLICATIONS

Gryczynski et al., Two-photon excitation by the evanescent wave from total internal reflection. Anal Biochem., Apr. 5, 1997;247(1):69-76.

Haase et al., Upconverting Nanoparticles, Angewandte Chemie International Edition, Jun. 20, 2011, 50(26):5808-29.

Hallman et al., 3 nJ, 100 ps laser pulses generated with an asymmetric waveguide laser diode for a single-photon avalanche diode time-of-flight (SPAD TOF) rangefinder application, Measurement Science and Technology, Jan. 5, 2012, 23(2): 8 pages.

Hansard et al., Time-of-Flight Cameras: Principles, Methods and Applications, Nov. 2012, 102 pages, Springer-Verlag, London, UK.

He et al., DNA Sequencing by Capillary Electrophoresis with Four-Decay Fluorescence Detection, Anal. Chem., Dec. 15, 2000, 72(24):5865-73.

Herold et al., OLED-on-CMOS Integration for Augmented-Reality Systems, IEEE 2008 International Students and Young Scientists Workshop Photonics and Microsystems, Jun. 20-22, 2008, 19-22, Wroclaw—Szlarska Poreba, Poland.

Heucke et al., Placing Individual Molecules in the Center of Nanoapertures, Nano Letters, Feb. 12, 2014, 14(2):391-5.

Inoue et al., CMOS active pixel image sensor with in-pixel CDS for high-speed cameras, Proc. SPIE, Sensors and Camera Systems for Scientific, Industrial, and Digital Photography Applications V, 250, Jun. 7, 2004, 5301(4):8 pages.

Ishii et al., Self-matched high-voltage rectangular wave pulse generator, Rev. Sci. Instrum, Nov. 1985, 56(11):2116-8.

Jun et al., Plasmonic beaming and active control over fluorescent emission, Nature Communications, Apr. 19, 2011, 6 pages.

Juodawlkis et al., High-Power, Low-Noise Slab-Coupled Optical Waveguide (SCOW) Amplifiers and Lasers, IEEE Optical Society of America Optical Fiber Communication Conference and Exposition and the National FiberOptic Engineers Conference, Mar. 6-10, 2011, 3 pages, Los Angeles, CA.

Juodawlkis et al., High-Power, Ultralow-Noise Semiconductor External Cavity Lasers Based on Low-Confinement Optical Waveguide Gain Media, Proc. of SPIE Novel In-Plane Semiconductor Lasers IX, Feb. 12, 2010, vol. 7616:76160X-1-9.

Kano et al., Two-photon-excited fluorescence enhanced by a surface plasmon. Opt Lett. Nov. 15, 1996;21(22):1848-50.

Karow, PacBio Aims to Boost Throughput of SMRT Technology with Microchip Co-development Deal, in Sequence and Clinical Sequencing News, Jul. 24, 2012, 3 pages, GenomeWeb.

Klein et al., Controlling plasmonic hot spots by interfering Airy beams, Optics Letters, Aug. 15, 2012, 37(16): 3402-4.

Korlach et al., Real-time DNA sequencing from single polymerase molecules. Methods Enzymol. May 2010;472:431-55. doi:10.1016/S0076-6879(10)72001-2.

Kreye et al, P-200: Evaluation of different OLED-Stacks for Active-Matrix OLED Microdisplays on CMOS-Substrates, SID 06 Digest, Jun. 2006, 37(1); 979-81.

Kumar et al., Terminal phosphate labeled nucleotides: synthesis, applications, and linker effect on incorporation by DNA polymerases. Nucleosides Nucleotides Nucleic Acids. Nov. 2005;24(5-7):401-8.

Lenne et al., Fluorescence fluctuations analysis in nanoapertures: physical concepts and biological applications, Histochem Cell Biol, Sep. 2008, 130:795-805.

Leslie et al., Convex Lens-Induced Confinement for Imaging Single Molecules, Anal. Chem., Jul. 15, 2010, 82(14):6224-9.

Levy et al., An 852x600 Pixel OLED-on-Silicon Color Microdisplay Using CMOS Subthreshold-Voltage-Scaling Current Drivers, IEEE Journal of Solid-State Circuits, Dec. 2002, 37(12): 1879-89.

Lezec et al., Beaming Light from a Subwavelength Aperture, Science, Aug. 2, 2002, 297(5582):820-2.

Li et al., Employing~100% Excitons in OLEDs by Utilizing a Fluorescent Molecule with Hybridized Local and Charge-Transfer Excited State, Advanced Functional Materials, Mar. 19, 2014, 24(11):1609-14.

Lin et al., Cosine-Gauss Plasmon Beam: A Localized Long-Range Nondiffracting Surface Wave, Physical Review Letters, Aug. 31, 2012, 109(9):093904-1-5.

McGinty et al., Wide-field fluorescence lifetime imaging of cancer, Biomedical Optics Express, Sep. 1, 2010, 1(2): 627-40.

Misra et al., White organic LEDs and their recent advancements, Semiconductor Science and Technology, Apr. 25, 2006, 21(7):R35-47.

Mitchell et al., Nanosecond Fluorescence Lifetime Imaging with gated CCD detection and pulsed laser excitation, Photonic Research Systems Ltd., May 1, 2013, 13 pages, Newhaven East Sussex UK.

Murshid et al., Array of concentric CMOS photodiodes for detection and de-multiplexing of spatially modulated optical channels, Optics & Laser Technology, Sep. 2009, 41(6):764-9.

Murshid et al., CMOS Detectors: Concentric photodiode array enables spatial-domain multiplexing, Laser Focus World, Apr. 1, 2009, 10 pages, http://www.laserfocusworld.com/articles/print/volume-45/issue-4/features/cmos-detectors-concentric-photodiode-array-enables-spatial-domain-multiplexing.html , [last accessed Dec. 12, 2013].

Murshid et al., Concentric octagonal CMOS photodiodes for direct detection of spatially multiplexed optical fiber channels, Optical Society of America, Oct. 2008, 1 page.

Nozik, Multiple exciton generation in semiconductor quantum dots, Chemical Physics Letters, May 20, 2008, 457(1-3):3-11.

Park et al., A dual-modality optical coherence tomography and fluorescence lifetime imaging microscopy system for simultaneous morphological and biochemical tissue characterization, Biochemical Optics Express, Aug. 2, 2010, 1(1):186-200.

Pfeifer et al., Improved optical outcoupling of OLED microdisplays by nanostructured substrates, IEEE Semiconductor Conference Dresden, 27-18 Sep. 2011, 4 pages, Dresden, Germany.

Poddubny et al., Photonic quasicrystalline and aperiodic structures, Physica E: Low-dimensional Systems and Nanostructures, May 2010, 42(7): 1871-95.

Pons et al., Solution-phase single quantum dot fluorescence resonance energy transfer. J Am Chem Soc., Nov. 29, 2006;128(47):15324-31.

Pudavar, Fluorescence Lifetime Imaging (FILM), Leica Microsystems Inc., Oct. 25, 2009, 60 pages, Exton, PA.

Punj et al., Plasmonic antennas and zero-mode waveguides to enhance single molecule fluorescence detection and fluorescence correlation spectroscopy toward physiological concentrations. Wiley Interdiscip Rev Nanomed Nanobiotechnol. May-Jun. 2014;6(3):268-82. doi: 10.1002/wnan.1261. Epub Feb. 24, 2014.

Ramuz et al., Coupling light from an organic light emitting diode (OLED) into a single-mode waveguide: Toward monolithically integrated optical sensors, Journal of Applied Physics, Apr. 2009, 105(8):084508-1-7.

Ran et al., Design of a 16 gray scales 320 × 240 pixels OLED-on-silicon driving circuit, Journal of Semiconductors, Jan. 2009, 30(1):015010-1-4.

Reckziegel et al., Optical sensors based on monlithic integrated organic light-emitting diodes (OLEDs), Proceedings of SPIE Optical Sensors, Apr. 28, 2008, vol. 7003: 8 pages.

Richter et al., Bidirectional OLED microdisplay: Combining display and image sensor functionality into a monolithic CMOS chip, 2011 IEEE International Solid-State Circuits Conference Digest of Technical Papers (ISSCC), Feb. 20-24, 2011, 3 pages, San Francisco, CA.

Richter et al., OLED-on-CMOS based bidirectional microdisplay for near-to-eye and sensor applications, IEEE Semiconductor Conference Dresden, Sep. 27-28, 2011, 3 pages, Dresden, Germany.

Rigneault et al., Enhancement of Single-Molecule Fluorescence Detection in Subwavelength Apertures, Physical Review Letters, Sep. 9, 2005, 95(11): 117401-1-4.

Romero-Garcia et al., Silicon nitride back-end optics for biosensor applications, Proc. of SPIE Integrated Optics: Physics and Simulations, May 7, 2013, vol. 8781: 87810W-1-11.

Romero-Garcia et al., Visible wavelength silicon nitride focusing grating coupler with AlCu/TiN reflector. Optics Letters. Jul. 15, 2013, 38(14):2521-3.

(56) References Cited

OTHER PUBLICATIONS

Rui et al., Demonstration of beam steering via dipole-coupled plasmonic spiral antenna, Scientific Reports, Jul. 19, 2013, 7 pages.
Sakadzic et al., Multi-photon microscopy with a low-cost and highly efficient Cr:LiCAF laser, Optics Express, Dec. 8, 2008, 16(25):20848-63.
Salthouse et al., Development of a Time Domain Fluorimeter for Fluorescent Lifetime Multiplexing Analysis, IEEE Biomed Circuits Syst., Sep. 1, 2008, 2(3): 204-11.
Schalberger et al., 60.4: Distinguished Paper: A Fully Integrated 1" AMOLED Display Using Current Feedback Based on a Five Mask LTPS CMOS Process, SID 10 Digest, May 2010, 41(1): 905-8.
Schmidt, Direct Encapsulation of OLED on CMOS, Bio and Nano Packaging Techniques for Electron Devices, Jul. 17, 2012, Chapter 29, 581-99, Springer-Verlag Berling Heidelberg.
Siegfried et al., Gap Plasmons and Near-Field Enhancement in Closely Packed Sub-10 nm Gap Resonators, Nano Lett., Oct. 10, 2013, 13(11):5449-53.
Sorokina et al., Fluorescent Lifetime Trajectories of a Single Fluorophore Reveal Reaction Intermediates During Transcription Initiation, J. Am. Chem. Soc., Jul. 22, 2009, 131(28):9630-31.
Sorokina et al., Supporting Information for Fluorescent Lifetime Trajectories of a Single Fluorophore Reveal Reaction Intermediates During Transcription Initiation, J. Am. Chem. Soc., Jul. 22, 2009, 131(28):4 pages.
Sun et al., Fluorescence lifetime imaging microscopy (FLIM) for image guided surgery, Stanford Computer Optics, 2013, 2 pages, http://www.stanfordcomputeroptics.com/applications/life-science/flim-guided-surgery.html , [last accessed May 9, 2014].
Taitt et al., Evanescent wave fluorescence biosensors. Biosens Bioelectron. Jun. 2005;20(12):2470-87. Epub Dec. 8, 2004.
Takkellapati et al., Synthesis of aminomethyl- and bis-aminomethyl-fluorescein energy transfer terminators. Nucleosides Nucleotides Nucleic Acids. Dec. 2007;26(10-12):1467-70.
Toerker et al., Integration of Top-Emitting Organic Light Emitting Diodes on CMOS Substrates, Proc. of SPIE Organic Optoelectronics and Photonics III, Apr. 16, 2008, vol. 6999, 4 pages.
Toma et al., Compact surface plasmon-enhanced fluorescence biochip, Opt. Express Apr. 22, 2013, 21(8): 10121-10132.
Toma et al., Surface plasmon-coupled emission on plasmonic Bragg gratings, Optics Express, Jun. 18, 2012, 20(13):14042-53.
Uhring et al., 200 ps FWHM and 100 MHz Repetition Rate Ultrafast Gated Camera for Optical Medical Functional Imaging, Proc. of SPIE Optical Sensing and Detection II, May 9, 2012, vol. 8439, 10 pages.
Unfricht et al., Grating-coupled surface plasmon resonance: a cell and protein microarray platform. Proteomics. Nov. 2005;5(17):4432-42.
Vogel et al., OLED-on-CMOS Integration for Optoelectronic Sensor Applications, Proc. of SPIE Silicon Photonics II, Mar. 1, 2007, vol. 6477:8 pages.
Vogel et al., Optoelectronic Sensors based on OLED-on-CMOS, 2008 2nd European Conference & Exhibition on Integration Issues of Minaturized Systems—MOMS, MOEMS, ICS, and Electronic Components (SSI), Apr. 9-10, 2008, 3 pages, Barcelona, Spain.
Von Ketteler et al., Fluorescence Lifetime-Based Glucose Sensing using NADH, Proc. of SPIE Optical Diagnostics and Sensing XII: Toward Point-of-Care Diagnostics; and Design and Performance Validation of Phantoms Used in Conjunction with Optical Measurement of Tissue IV, Feb. 1, 2012, vol. 8229, 8 pages.
Walpole, Slab-coupled optical waveguide lasers: a review, Proc. SPIE Novel In-Plane Semiconductor Lasers III, May 11, 2004, vol. 5365, 124-32.
Wenger et al., Emission and excitation contributions to enhanced single molecule fluorescence by gold nanometric apertures, Optics Express, Mar. 3, 2008, 16(5):3008-20.
Wenger et al., Enhanced fluorescence from metal nanoapertures: physical characterizations and biophotonic applications, Proc. SPIE Plasmonics in Biology and Medicine VII, Feb. 16, 2010, 8 pages.
Wenger, Aperture optical antennas, Optical Antennas, Feb. 2013, 25pages, Cambridge University Press, Cambridge, UK.
Willoughby, Elastically Averaged Precision Alignment, Massachusetts Institute of Technology, Jun. 2005, 158 pages, Cambridge, MA.
Xiong et al., Aluminum nitrade as a new material for chip-scale optomechanics and nonlinear optics, New Journal of Physics, Sep. 17, 2012, 14: 21 pages.
Yan-Yan et al., OLED-on-silicon chip with new pixel circuit, J. Cent. South Univ., May 2012 19(5):1276-82.
Yu et al., Light Propagation with Phase Discontinuities: Generalized Laws of Reflection and Refraction, Science, Oct. 21, 2011, 334 (6054):333-7.
Yuk et al. Analysis of immunoarrays using a gold grating-based dual mode surface plasmon-coupled emission (SPCE) sensor chip. Analyst. Jun. 7, 2012;137(11):2574-81. doi: 10.1039/c2an35143a. Epub Apr. 13, 2013.
Zhang et al., Continuous metal plasmonic frequency selective surfaces, Optics Express, Nov. 7, 2011, 19(23):23279-85.
Zhao et al., Plasmonic demultiplexer and guiding. ACS Nano. Nov. 23, 2010;4(11):6433-8. doi: 10.1021/nn101334a. Epub Oct. 6, 2010.
Zhu et al., Zero-Mode Waveguides for Single-Molecule Analysis, Annu. Rev. Biophys., Jun. 2012, 41:269-93.
Zong et al., Equivalent Circuit Model of Top-emitting OLED for the Designing of OLED-on-Silicon Microdisplay, Advanced Materials Research, Nov. 2011, 383-90:7037-42.
European Communication for European Application No. 14809194.5 dated Nov. 22, 2018.
International Search Report and Written Opinion for International Application No. PCT/US18/43390 dated Oct. 23, 2018.

* cited by examiner

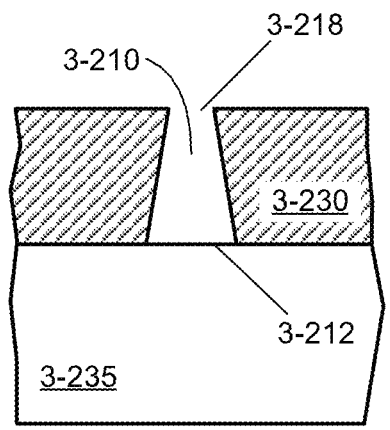
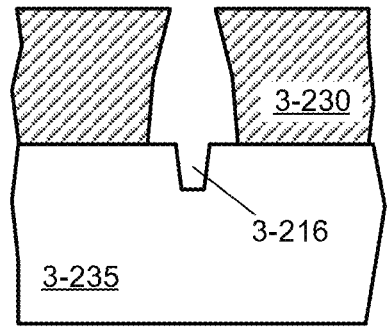
*FIG. 3-7A*  *FIG. 3-7B*
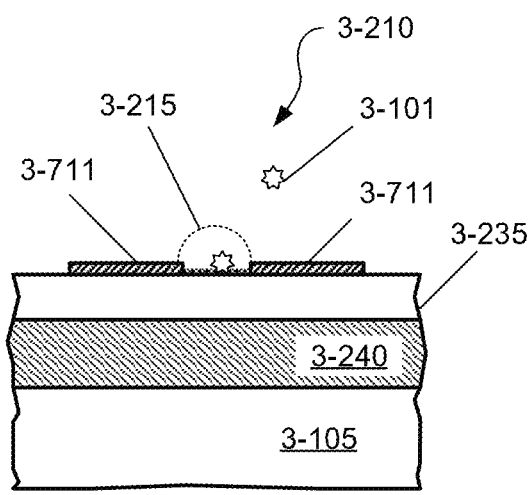
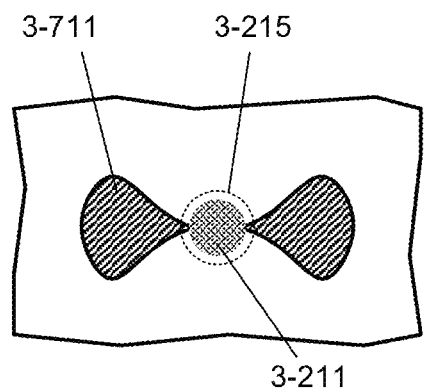
*FIG. 3-7C*  *FIG. 3-7D*
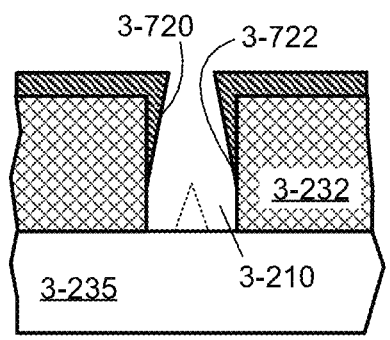
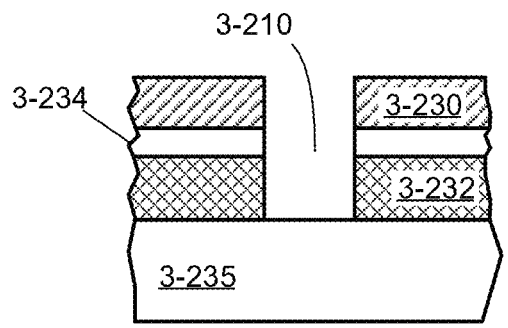
*FIG. 3-7E*  *FIG. 3-7F*

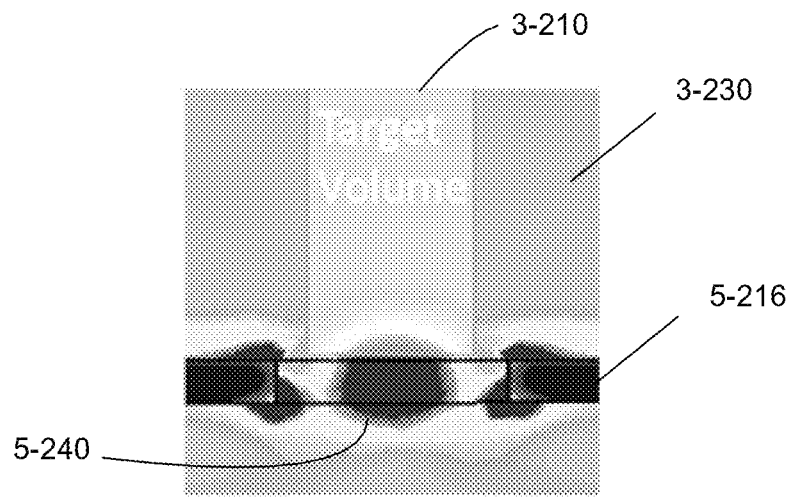
FIG. 5-2D
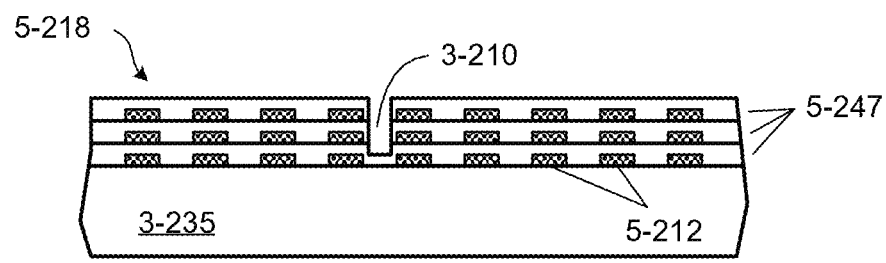
FIG. 5-2E
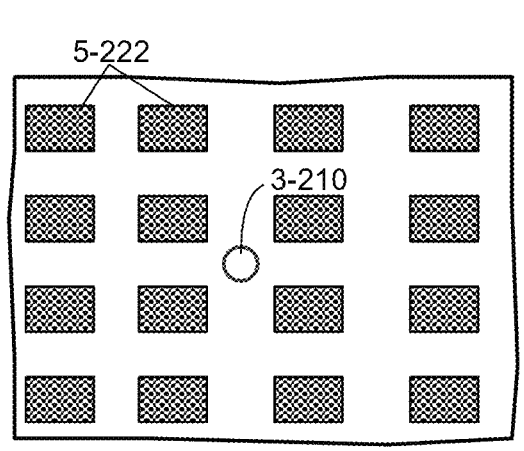  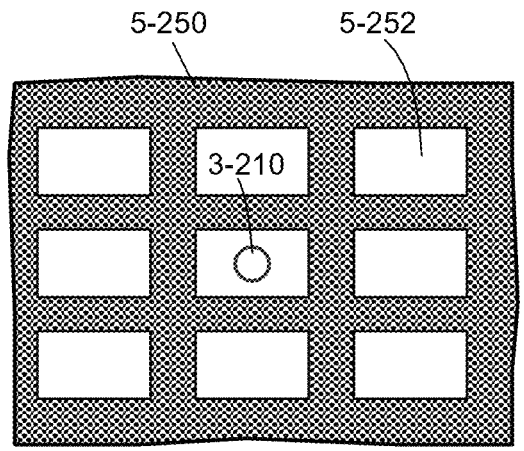
FIG. 5-2F  FIG. 5-2G

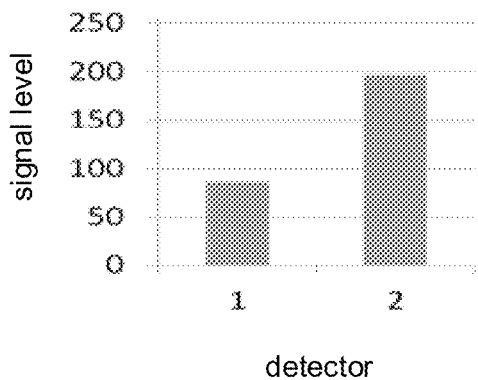 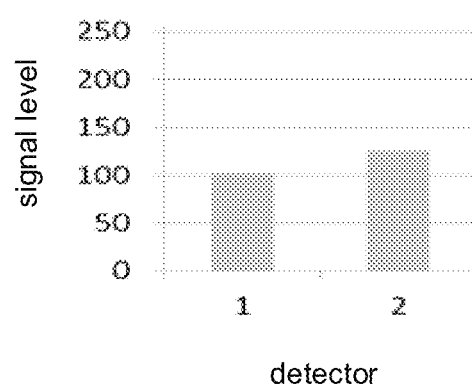
FIG. 7-2E  FIG. 7-2F
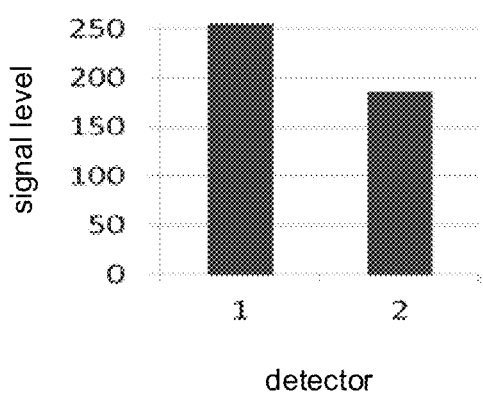 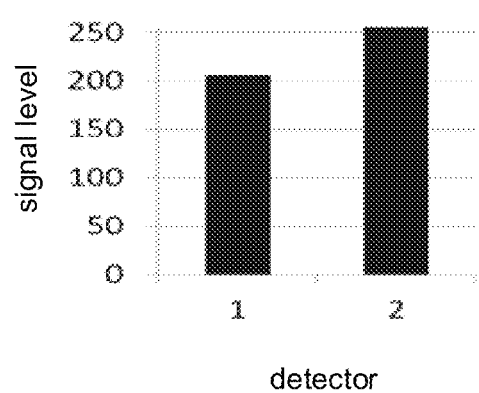
FIG. 7-2G  FIG. 7-2H
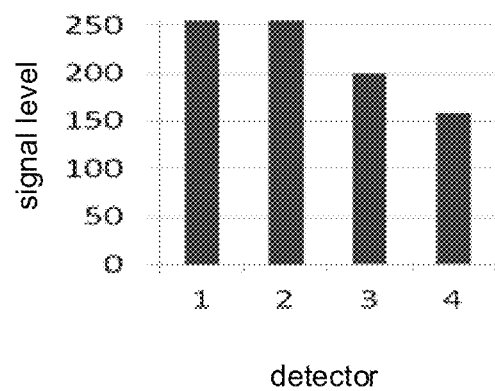 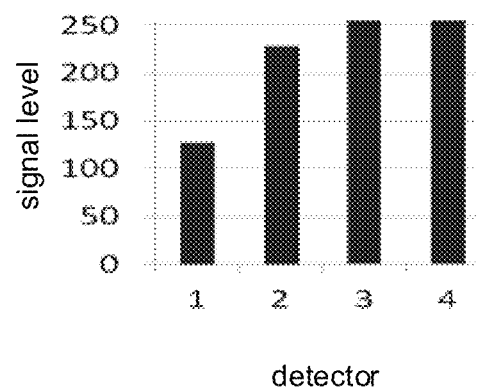
FIG. 7-2I  FIG. 7-2J

ACTIVE-SOURCE-PIXEL, INTEGRATED DEVICE FOR RAPID ANALYSIS OF BIOLOGICAL AND CHEMICAL SPECIMENS

RELATED APPLICATIONS

This application is a divisional of U.S. application Ser. No. 14/543,888, filed Nov. 17, 2014, entitled "ACTIVE-SOURCE-PIXEL, INTEGRATED DEVICE FOR RAPID ANALYSIS OF BIOLOGICAL AND CHEMICAL SPECIMENS," which claims priority to U.S. provisional application No. 61/905,282, filed Nov. 17, 2013, entitled "INTEGRATED DEVICE FOR PROBING, DETECTING AND ANALYZING MOLECULES" and to U.S. provisional application No. 61/917,926, filed Dec. 18, 2013, entitled "INTEGRATED DEVICE FOR PROBING, DETECTING AND ANALYZING MOLECULES" and to U.S. provisional application No. 61/941,916, filed Feb. 19, 2014, entitled "INTEGRATED DEVICE FOR PROBING, DETECTING AND ANALYZING MOLECULES." The entire disclosures of the foregoing applications are incorporated herein by reference.

FIELD

The present application is directed to devices and methods for analyses of biological and chemical specimens and reactions involving biological and chemical samples.

BACKGROUND

Analyses of biological and chemical specimens may be performed conventionally using large, expensive laboratory equipment requiring skilled scientists trained to operate the equipment and interpret the results. Specimens may analyzed to determine the presence of one or more analytes within the specimen, e.g., a pathogen or virus, a particular chemical, and antigen or antibody, etc, for medical purposes. In some cases, bioassays are performed by tagging a sample with a fluorescent tag that emit light of a particular wavelength. The tag may be illuminated with an excitation light source to cause fluorescence. The fluorescence is detected with a photodetector, and the signal analyzed to determine a property about the sample. Bioassays using fluorescent tags conventionally involve expensive laser light sources and optics arranged to illuminate samples. The assays may further involve bulky, expensive collection optics arranged to collect the fluorescence from the samples as well as expensive electronic instrumentation to process the signals.

Because conventional analytical equipment is typically expensive and requires a skilled operator, specimens to be analyzed may need to be sent to an on-site or off-site facility for processing. This can introduce appreciable delay and cost associated with even routine analysis of a specimen. For example, a patient may have to wait several days and schedule a return visit to a doctor's office to learn about the results of a laboratory test on a specimen provided by the patient.

SUMMARY

The technology described herein relates to apparatus and methods for analyzing specimens rapidly using an active-source-pixel, integrated device that can be interfaced with a mobile computing instrument. The integrated device may be in the form of a disposable or recyclable lab-on-chip or a packaged module that is configured to receive a small amount of a specimen and execute, in parallel, a large number of analyses of samples within the specimen. The integrated device may be used to detect the presence of particular chemical or biological analytes in some embodiments, to evaluate a chemical or biological reactions in some embodiments, and to determine genetic sequences in some embodiments. According to some implementations, the integrated device may be used for single-molecule gene sequencing.

According to some implementations, a user deposits a specimen in a chamber on the integrated device, and inserts the integrated device into a receiving instrument. The receiving instrument, alone or in communication with a computer, automatically interfaces with the integrated device, receives data from the integrated device, processes the received data, and provides results of the analysis to the user. As may be appreciated, integration and computing intelligence on the chip, receiving instrument, and or computer reduce the skill level required from the user.

Embodiments include methods for sequencing nucleic acid molecules. According to some embodiments, a first method of sequencing a nucleic acid molecule may comprise providing excitation energy to a sample well formed at a first pixel on a substrate, and receiving, at a sensor formed at the first pixel, a first emission from the sample well, wherein the first emission is associated with a type of nucleic acid subunit from among different types of nucleic acid subunits. The method may further include producing, by the sensor, a first signal and a second signal representative of the received first emission, analyzing the first signal and the second signal, and identifying the type of the nucleic acid subunit based upon the analysis of the first signal and the second signal.

According to some embodiments, a second method for sequencing a target nucleic acid molecule may comprise providing a integrated device that includes (i) a sample well containing said target nucleic acid molecule, a polymerizing enzyme and a plurality of types of nucleotides or nucleotide analogs, and (ii) at least one excitation source that directs excitation energy to said sample well, and performing an extension reaction at a priming location of said target nucleic acid molecule in the presence of said polymerizing enzyme to sequentially incorporate said nucleotides or nucleotide analogs into a growing strand that is complementary to said target nucleic acid molecule, wherein upon incorporation and excitation by excitation energy from said excitation source, said nucleotides or nucleotide analogs produce emissions from said sample well. The second method may further include detecting said emissions at a sensor that is configured to receive said emissions from said sample well, receiving signal sets from the sensor for each detected emission, wherein the signal sets are representative of spatial and/or temporal distributions of said detected emissions and distinguish types of nucleotides or nucleotide analogs, and identifying the types of nucleotides or nucleotide analogs based on said received signal sets, thereby sequencing said target nucleic acid molecule.

Various embodiments of integrated devices are contemplated. According to some embodiments, an integrated device for analyzing a plurality of samples in parallel may comprise a plurality of pixels arranged on a substrate, wherein an individual pixel of the plurality of pixels comprises (i) a sample well having an excitation region configured to retain a biological sample, (ii) a first structure located adjacent to or within the sample well and configured to affect coupling of at least excitation energy into the excitation region, and (iii) a sensing system including a sensor that is configured to discriminate between at least two different emissions from the sample well, wherein the two different emissions comprise spectral and/or temporal differences. The first structure may additionally affect coupling of emission from the sample well to the sensor. The integrated device may further include at least one excitation source on the substrate that is arranged to provide the excitation energy to the sample well, and circuitry arranged on the substrate to receive at least one signal from the sensor.

In some embodiments, an integrated device may comprise a plurality of sample wells, excitation sources, and sensors having any suitable combination of the foregoing features and functionalities. Further, the plurality of sample wells, excitation sources, and sensors on an integrated device may be substantially identical for some embodiments of an integrated device, whereas in other embodiments, the sample wells, excitation sources, and sensors may differ across an integrated device. For example, there may be groups of sample wells, excitation sources, and sensors on an integrated device, each group having a distinguishable subset of the foregoing features and functionalities associated with a sample well, excitation source, and/or sensor.

Instruments are also contemplated that may be configured to receive and communicated with an integrated device. According to some embodiments, a portable instrument configured to receive and communicate with an integrated device may comprise at least one processor, a dock configured to receive an integrated device as described in any of the above embodiments, a cover configured to exclude a majority external light from entering the dock, and a first plurality of electrical contacts configured to connect to a second plurality of electrical contacts on the integrated device, wherein power may be provide to the integrated device through at least some of the first plurality of electrical contacts and the at least one signal from each sensor may be received through at least some of the first plurality of electrical contacts. In some implementations, the first plurality of electrical contacts is formed on a user-removable interposer. In some implementations, the first plurality of electrical contacts is configured to contact a third plurality of contacts on a user-replaceable interposer. According to some embodiments, a the portable instrument further comprises a communication interface, wherein the communication interface comprises a USB interface, a Thunderbolt interface, or a high-speed digital interface.

According to some embodiments, a third method of analyzing a plurality of samples in parallel may comprise receiving, at a surface of a substrate, a specimen containing samples, retaining, in a plurality of sample wells located in a plurality of pixels on the substrate, samples from the fluid suspension, and providing excitation energy to one or more of the sample wells from at least one excitation source. The third method may further include, at least for one of the plurality of pixels, detecting an emission from a sample well at a sensor that is arranged to receive emission from the sample well, receiving a signal set from the sensor representative of the detected emission, and identifying a property of a sample retained in the sample well based on an analysis of the signal set.

Methods associated with fabrication of an integrated device are also contemplated. According to some embodiments, a first method for fabricating a sample well and optical structure aligned to the sample well may comprise acts of forming, in a same patterning step, a pattern for the sample well and for the optical structure in a first resist layer disposed on a substrate, covering at least the pattern of the sample well with a second resist layer, etching a pattern of the optical structure into the substrate, removing portions of the first resist layer not covered by the second resist layer, removing the second resist layer, depositing a material over the substrate, and removing the remaining portion of the first resist layer.

According to some embodiments, a second method for fabricating a sample well may comprise forming, in a same patterning step, a pattern for the sample well and for the optical structure in a first layer disposed on a substrate, etching the pattern of the sample well and the optical structure into the substrate, covering at least the pattern of the sample well with a resist layer, depositing a material over the substrate, wherein the material fills voids etched into the substrate from the etching of the pattern of the optical structure, and removing the resist layer. In some implementations, the first layer comprises a conductive material. In some aspects, the optical structure comprises a circular grating. In some implementations, the substrate is optically transparent. According to some implementations, removing the resist layer leaves a sample well having a transverse dimension less than 500 nm and including a divot at a bottom of the sample well etched into the substrate.

Methods for fabricating excitation sources are also contemplated. According to some embodiments, a method of forming a nano-scale excitation source aligned to a sample well may comprise etching a via into an insulating layer of a substrate, the substrate comprising a semiconductor layer, an insulating layer adjacent the semiconductor layer, and a first conductive layer adjacent the insulating layer, forming a sacrificial coating on walls of the via, etching the via to the semiconductor layer, and epitaxially growing a semiconductor pillar having a first conductivity type within the via from the semiconductor layer. In some implementations, the method may further comprise removing the sacrificial coating to expose walls of the pillar at a portion of the pillar, epitaxially growing a semiconductor layer having a second conductivity type over the portion of the pillar, and conformally depositing a second conductive layer over the semiconductor layer, wherein the second conductive layer electrically connects to the first conductive layer. In some aspects, the semiconductor pillar and semiconductor layer comprise a light-emitting diode or laser diode. In some aspects, the semiconductor pillar and semiconductor layer comprise a semiconductor diode. In some implementations, an end of the epitaxially-grown semiconductor pillar nearest the first conductive layer lies a distance from a nearest surface of the first conductive layer. In some implementations, an unfilled region of the via forms a sample well. According to some implementations, a transverse dimension of the semiconductor pillar is less than 200 nm. In some aspects, the insulating layer is optically transparent.

The foregoing features and acts associated with aspects and implementations of the method for forming an excitation source may be included in any suitable combination in one or more embodiments of a method for forming an excitation source.

Although the foregoing methods and devices may be described in reference to a single element (e.g., a sample well, an excitation source, a sensor, an excitation-coupling structure, an emission-coupling structure), the methods may be implemented in parallel to fabricate a large number of devices in parallel (e.g., using micro- and nano-fabrication processes). Further, the devices may be arranged in a large number on an integrated device.

The term "pixel" may be used in the present disclosure to refer to a unit cell of an integrated device. The unit cell may include a sample well and a sensor. The unit cell may further include an excitation source. The unit cell may further include at least one excitation-coupling optical structure (which may be referred to as a "first structure") that is configured to enhance coupling of excitation energy from the excitation source to the sample well. The unit cell may further include at least one emission-coupling structure that is configured to enhance coupling of emission from the sample well to the sensor. The unit cell may further include integrated electronic devices (e.g., CMOS devices). There may be a plurality of pixels arranged in an array on an integrated device.

The term "optical" may be used in the present disclosure to refer to visible, near infrared, and short-wavelength infrared spectral bands.

The term "tag" may be used in the present disclosure to refer to a tag, probe, marker, or reporter attached to a sample to be analyzed or attached to a reactant that may be reacted with a sample.

The phrase "excitation energy" may be used in the present disclosure to refer to any form of energy (e.g., radiative or non-radiative) delivered to a sample and/or tag within the sample well. Radiative excitation energy may comprise optical radiation at one or more characteristic wavelengths.

The phrase "characteristic wavelength" may be used in the present disclosure to refer to a central or predominant wavelength within a limited bandwidth of radiation. In some cases, it may refer to a peak wavelength of a bandwidth of radiation. Examples of characteristic wavelengths of fluorophores are 563 nm, 595 nm, 662 nm, and 687 nm.

The phrase "characteristic energy" may be used in the present disclosure to refer to an energy associated with a characteristic wavelength.

The term "emission" may be used in the present disclosure to refer to emission from a tag and/or sample. This may include radiative emission (e.g., optical emission) or non-radiative energy transfer (e.g., Dexter energy transfer or Förster resonant energy transfer). Emission results from excitation of a sample and/or tag within the sample well.

The phrase "emission from a sample well" or "emission from a sample" may be used in the present disclosure to refer to emission from a tag and/or sample within a sample well. The phrase "emission from a sample well" may also be used in the present disclosure to refer to emission from a calibration particle (e.g., a fluorescent polystyrene bead, a quantum dot, etc.) within a sample well.

The term "self-aligned" may be used in the present disclosure to refer to a microfabrication process in which at least two distinct elements (e.g., a sample well and an emission-coupling structure, a sample well and an excitation-source) may be fabricated and aligned to each other without using two separate lithographic patterning steps in which a first lithographic patterning step (e.g., photolithography, ion-beam lithography, EUV lithography) prints a pattern of a first element and a second lithographic patterning step is aligned to the first lithographic patterning step and prints a pattern of the second element. A self-aligned process may comprise including the pattern of both the first and second element in a single lithographic patterning step, or may comprise forming the second element using features of a fabricated structure of the first element.

The term "sensor" may be used in the present disclosure to refer to one or more integrated circuit devices configured to sense emission from the sample well and produce at least one electrical signal representative of the sensed emission.

The term "nano-scale" may be used in the present disclosure to refer to a structure having at least one dimension or minimum feature size on the order of 150 nanometers (nm) or less, but not greater than approximately 500 nm.

The term "micro-scale" may be used in the present disclosure to refer to a structure having at least one dimension or minimum feature size between approximately 500 nm and approximately 100 microns.

The term "nanoaperture" may be used in the present disclosure to refer to a nano-scale opening or aperture in at least one layer of material. For example, a diameter or width of the opening is less than approximately 500 nm.

The term "nanohole" may be used in the present disclosure to refer to a nano-scale hole formed in at least one layer of material. A nanohole may have a length or longitudinal dimension that is greater than a nanoaperture.

The term "sub-cutoff nanoaperture" may be used in the present disclosure to refer to a waveguide structure that does not support a propagating mode for a selected wavelength of radiation that may be incident on the waveguide structure. For example, the selected wavelength may be longer than a cut-off wavelength for the waveguide structure, and power decays exponentially into the waveguide.

The phrase "enhance excitation energy" may be used in the present disclosure to refer to increasing an intensity of excitation energy at an excitation region of a sample well. The intensity may be increased by concentrating and/or resonating excitation energy incident on the sample well, for example. In some cases, the intensity may be increased by anti-reflective coatings or lossy layers that allow the excitation energy to penetrate further into the excitation region of a sample well. An enhancement of excitation energy may be a comparative reference to an embodiment that does not include structures to enhance the excitation energy at an excitation region of a sample well.

The terms "about," "approximately," and "substantially" may be used in the present disclosure to refer to a value, and are intended to encompass the referenced value plus and minus acceptable variations. The amount of variation could be less than 5% in some embodiments, less than 10% in some embodiments, and yet less than 20% in some embodiments. In embodiments where an apparatus may function properly over a large range of values, e.g., a range including one or more orders of magnitude, the amount of variation could be a factor of two. For example, if an apparatus functions properly for a value ranging from 20 to 350, "approximately 80" may encompass values between 40 and 160.

The term "adjacent" may be used in the present disclosure to refer to two elements arranged within close proximity to one another (e.g., within a distance that is less than about one-fifth of a transverse or vertical dimension of a pixel). In some cases there may be intervening structures or layers between adjacent elements. In some cases adjacent elements may be immediately adjacent to one another with no intervening structures or elements.

The term "detect" may be used in the present disclosure to refer to receiving an emission at a sensor from a sample well and producing at least one electrical signal representative of or associated with the emission. The term "detect" may also be used in the present disclosure to refer to determining the presence of, or identifying a property of, a particular sample or tag in the sample well based upon emission from the sample well.

The foregoing and other aspects, implementations, acts, functionalities, features and, embodiments of the present teachings can be more fully understood from the following description in conjunction with the accompanying drawings.

BRIEF DESCRIPTION OF THE DRAWINGS

The skilled artisan will understand that the figures, described herein, are for illustration purposes only. It is to be understood that in some instances various aspects of the invention may be shown exaggerated or enlarged to facilitate an understanding of the invention. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

FIG. 1-2A depicts absorption wavelength spectra, according to some embodiments.

FIG. 1-2B depicts emission wavelength spectra, according to some embodiments.

FIG. 2-1 is a block diagram representation of a compact apparatus that may be used for rapid, mobile analysis of biological and chemical specimens, according to some embodiments.

FIG. 2-2 depicts and integrated device, according to some embodiments.

FIG. 2-3 depicts a computing system, according to some embodiments.

FIG. 3-1 depicts a sample well formed in a pixel region of an integrated device, according to one embodiment.

FIG. 3-2 depicts excitation energy incident on a sample well, according to some embodiments.

FIG. 3-3 illustrates attenuation of excitation energy along a sample well that is formed as a zero-mode waveguide, according to some embodiments.

FIG. 3-4 depicts a sample well that includes a divot, which increases excitation energy at an excitation region associated with the sample well in some embodiments.

FIG. 3-5 compares excitation intensities for sample wells with and without a divot, according to one embodiment.

FIG. 3-6 depicts a sample well and divot formed at a protrusion, according to some embodiments.

FIG. 3-7A depicts a sample well having tapered sidewalls, according to some embodiments.

FIG. 3-7B depicts a sample well having curved sidewalls and a divot with a smaller transverse dimension, according to some embodiments.

FIG. 3-7C and FIG. 3-7D depict a sample well formed from surface plasmonic structures.

FIG. 3-7E depicts a sample well that includes an excitation-energy-enhancing structure formed along sidewalls of the sample well, according to some embodiments.

FIG. 3-7F depicts a sample well formed in a multi-layer stack, according to some embodiments.

FIG. 3-8 illustrates surface coating formed on surfaces of a sample well, according to some embodiments.

FIG. 3-9A through FIG. 3-9E depict structures associated with a lift-off process of forming a sample well, according to some embodiments.

FIG. 3-9F depicts a structure associated with an alternative lift-off process of forming a sample well, according to some embodiments.

FIG. 3-10A through FIG. 3-10D depict structures associated with a direct etching process of forming a sample well, according to some embodiments.

FIG. 3-11 depicts a sample well that may be formed in multiple layers using a lift-off process or a direct etching process, according to some embodiments.

FIG. 3-12 depicts a structure associated with an etching process that may be used to form a divot, according to some embodiments.

FIG. 3-13A through FIG. 3-13C depict structures associated with an alternative process of forming a divot, according to some embodiments.

FIG. 3-14A through FIG. 3-14D depict structures associated with a process for depositing an adherent and passivating layers, according to some embodiments.

FIG. 3-15 depicts a structure associated with a process for depositing an adherent centrally within a sample well, according to some embodiments.

FIG. 4-1A and FIG. 4-1B depict spectral excitation bands of excitation sources, according to some embodiments.

FIG. 4-2A through FIG. 4-2D depict, in plan view, various arrangements of excitation sources that may be included on an integrated device, according to some implementations.

FIG. 4-2E depicts, in elevation view, an arrangement of an excitation source located adjacent to a pixel region, according to some embodiments.

FIG. 4-3A depicts an organic light emitting diode (OLED) integrated within a pixel, according to some embodiments.

FIG. 4-3B depicts further details of a light emitting diode structure integrated within a pixel, according to some embodiments.

FIG. 4-3C depicts a vertical cavity surface emitting laser (VCSEL) integrated within a pixel, according to some embodiments.

FIG. 4-3D depicts a self-aligned nano-LED integrated within a pixel, according to some embodiments.

FIG. 4-3E depicts a self-aligned nano-VCSEL integrated within a pixel, according to some embodiments.

FIG. 4-4A through FIG. 4-4F depict structures associated with process steps for fabricating a nano-LED or nano-VCSEL, according to some embodiments.

FIG. 4-4G through FIG. 4-4I depict structures associated with alternative process steps for fabricating a nano-LED, according to some embodiments.

FIG. 4-5A depicts a non-radiative excitation source that may be integrated in a pixel, according to some embodiments.

FIG. 4-5B depicts, in elevation view, a non-radiative excitation source that may be integrated in a pixel, according to some embodiments.

FIG. 4-5C depicts, in plan view, interconnects for a non-radiative excitation source, according to some embodiments.

FIG. 4-5D depicts a nano-diode, non-radiative excitation source that may be integrated in a pixel, according to some embodiments.

FIG. 4-6A through FIG. 4-6U depict structures associated with process steps for fabricating a self-aligned, non-radiative excitation sources, according to some embodiments.

FIG. 5-1A and FIG. 5-1B depict a surface-plasmon structure, according to just one embodiment.

FIG. 5-1C depicts a surface-plasmon structure formed adjacent a sample well, according to some embodiments.

FIG. 5-1D and FIG. 5-1E depict surface-plasmon structures formed in a sample well, according to some embodiments.

FIG. 5-2A through FIG. 5-2C depict examples of periodic surface-plasmon structures, according to some embodiments.

FIG. 5-2D depicts a numerical simulation of excitation radiation at a sample well formed adjacent a periodic surface-plasmon structure, according to some embodiments.

FIG. 5-2E through FIG. 5-2G depict periodic surface-plasmon structures, according to some embodiments.

FIG. 5-2H and FIG. 5-2I depict a nano-antenna comprising surface-plasmon structures, according to some embodiments.

FIG. 5-3A through FIG. 5-3E depict structures associated with process steps for forming a surface-plasmon structure, according to some embodiments.

FIG. 5-4A through FIG. 5-4G depict structures associated with process steps for forming a surface-plasmon structure and self-aligned sample well, according to some embodiments.

FIG. 5-5A through FIG. 5-5E depict structures associated with process steps for forming a surface-plasmon structure and self-aligned sample well, according to some embodiments.

FIG. 5-6A depicts a thin lossy film formed adjacent a sample well, according to some embodiments.

FIG. 5-6B and FIG. 5-6C depict results from numerical simulations of excitation radiation in the vicinity of a sample well and thin lossy film, according to some embodiments.

FIG. 5-6D depicts a thin lossy film spaced from a sample well, according to some embodiments.

FIG. 5-6E depicts a thin lossy film stack formed adjacent a sample well, according to some embodiments.

FIG. 5-7A illustrates a reflective stack that may be used to form a resonant cavity adjacent a sample well, according to some embodiments.

FIG. 5-7B depicts a dielectric structure that may be used to concentrate excitation radiation at a sample well, according to some embodiments.

FIG. 5-7C and FIG. 5-7D depict a photonic bandgap structure that may be patterned adjacent a sample well, according to some embodiments.

FIG. 5-8A through FIG. 5-8G depict structures associated with process steps for forming dielectric structures and a self-aligned sample well, according to some embodiments.

FIG. 5-9A and FIG. 5-9B depict structures for coupling excitation energy to a sample via a non-radiative process, according to some embodiments.

FIG. 5-9C and FIG. 5-9D depicts a structure for coupling excitation energy to a sample by multiple non-radiative processes, according to some embodiments.

FIG. 5-9E depicts a structure that incorporates one or more energy-converting particles to couple excitation energy to a sample via a radiative or non-radiative process, according to some embodiments.

FIG. 5-9F depicts spectra associated with down conversion of excitation energy to a sample, according to some embodiments.

FIG. 5-9G depicts spectra associated with up conversion of excitation energy to a sample, according to some embodiments.

FIG. 6-1A depicts a concentric, plasmonic circular grating, according to some embodiments.

FIG. 6-1B depicts a spiral plasmonic grating, according to some embodiments.

FIG. 6-2A through FIG. 6-2D depict emission spatial distribution patterns from a concentric, plasmonic circular grating for various emission wavelengths, according to some embodiments.

FIG. 6-3A through FIG. 6-3D depict plasmonic nano-antennas, according to some embodiments.

FIG. 6-4A depicts a pattern for a spiral, plasmonic nano-antenna, according to some embodiments.

FIG. 6-4B depicts results from a numerical simulation of electromagnetic field in the vicinity of the spiral, plasmonic nano-antenna of FIG. 6-4A, according to some embodiments.

FIG. 6-4C through FIG. 6-4E illustrate various configurations of spiral, plasmonic nano-antennas, according to some embodiments.

FIG. 6-5A through FIG. 6-5D depicts results from numerical simulations of spatial distribution patterns associated with different wavelengths that emit from a sample well surrounded by a plasmonic nano-antenna, according to some embodiments.

FIG. 6-6A and FIG. 6-6B depicts far-field spectral sorting optics, according to some embodiments.

FIG. 6-7A and FIG. 6-7B depicts far-field spectral filtering optics, according to some embodiments.

FIG. 7-1A depicts, in elevation view, a sensor 3-260 within a pixel, according to some embodiments.

FIG. 7-1B depicts a bulls-eye sensor having two separate and concentric active areas, according to some embodiments.

FIG. 7-1C depicts a stripe sensor having four separate active areas, according to some embodiments.

FIG. 7-1D depicts a quad sensor having four separate active areas, according to some embodiments.

FIG. 7-1E depicts an arc-segment sensor having four separate active areas, according to some embodiments.

FIG. 7-1F depicts a stacked-segment sensor, according to some embodiments.

FIG. 7-2A depicts an emission distribution from a sample well for radiation emitted at a first wavelength, according to some embodiments.

FIG. 7-2B depicts a radiation pattern received by a bulls-eye sensor corresponding to the emission distribution depicted in FIG. 7-2A, according to some embodiments.

FIG. 7-2C depicts an emission distribution from a sample well for radiation emitted at a second wavelength, according to some embodiments.

FIG. 7-2D depicts a radiation pattern received by a bulls-eye sensor corresponding to the emission distribution depicted in FIG. 7-2C, according to some embodiments.

FIG. 7-2E represents results from a numerical simulation of signal detection for a bulls-eye sensor having two active areas for a first emission wavelength from a sample, according to some embodiments.

FIG. 7-2F represents results from a numerical simulation of signal detection for the bulls-eye sensor associated with FIG. 7-2E for a second emission wavelength from a sample, according to some embodiments.

FIG. 7-2G represents results from a numerical simulation of signal detection for the bulls-eye sensor associated with FIG. 7-2E for a third emission wavelength from a sample, according to some embodiments.

FIG. 7-2H represents results from a numerical simulation of signal detection for the bulls-eye sensor associated with FIG. 7-2E for a fourth emission wavelength from a sample, according to some embodiments.

FIG. 7-2I represents results from a numerical simulation of signal detection for a bulls-eye sensor having four active areas for a first emission wavelength from a sample, according to some embodiments.

FIG. 7-2J represents results from a numerical simulation of signal detection for the bulls-eye sensor associated with FIG. 7-2I for a second emission wavelength from a sample, according to some embodiments.

FIG. 7-3A depicts circuitry on an integrated device that may be used to read signals from a sensor comprising two active areas, according to some embodiments.

FIG. 7-3B depicts a three-transistor circuit that may be included at a sensor segment for signal accumulation and read-out, according to some embodiments.

FIG. 7-3C depicts circuitry on an integrated device that may be used to read signals from a sensor comprising four active areas, according to some embodiments.

FIG. 7-4A depicts temporal emission characteristics for two different emitters that may be used for sample analysis, according to some embodiments.

FIG. 7-4B depicts temporal evolution of an excitation source and luminescence from a sample, according to some embodiments.

FIG. 7-4C illustrates time-delay sampling, according to some embodiments.

FIG. 7-4D depicts temporal emission characteristics for two different emitters, according to some embodiments.

FIG. 7-4E depicts voltage dynamics at a charge-accumulation node of a sensor, according to some embodiments.

FIG. 7-4F depicts a double read of a sensor segment without reset, according to some embodiments.

FIG. 7-4G and FIG. 7-4H illustrate first and second read signal levels associated with two emitters having temporally-distinct emission characteristics, according to some embodiments.

FIG. 8-1 depicts a method of operation of a compact apparatus that may be used for rapid, mobile analysis of biological and chemical specimens, according to some embodiments.

FIG. 8-2 depicts a calibration procedure, according to some embodiments.

FIG. 8-3 depicts a data-analysis procedure, according to some embodiments.

Figure 1:
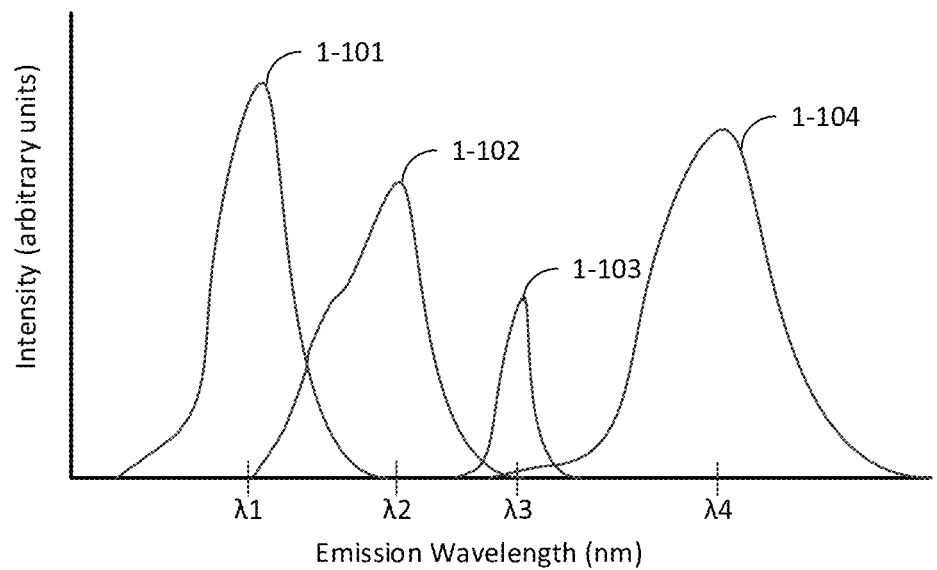
FIG. 1-1 depicts emission wavelength spectra, according to some embodiments.

The features and advantages of the present invention will become more apparent from the detailed description set forth below when taken in conjunction with the drawings.

When describing embodiments in reference to the drawings, direction references ("above," "below," "top," "bottom," "left," "right," "horizontal," "vertical," etc.) may be used. Such references are intended merely as an aid to the reader viewing the drawings in a normal orientation. These directional references are not intended to describe a preferred or only orientation of an embodied device. A device may be embodied in other orientations.

DETAILED DESCRIPTION

I. Introduction

The inventors have recognized and appreciated that conventional apparatuses for performing bioassays are large, expensive, and require advanced laboratory techniques to perform. The inventors have recognized and appreciated that there is a need for a compact device that can simply and inexpensively analyze biological and/or chemical specimens for medical, forensic, research, and various diagnostic purposes. An application of such device may be for sequencing a biomolecule, such as a nucleic acid molecule or a polypeptide (e.g., protein) having a plurality of amino acids. A compact, high-speed apparatus for performing detection and quantitation of single molecules or particles could reduce the cost of performing complex quantitative measurements of biological and/or chemical samples and rapidly advance the speed of research and development in various fields of biochemistry. Moreover, a cost-effective device that is readily transportable could transform not only the way bioassays are performed in the developed world, but provide people in developing regions, for the first time, ready access to essential diagnostic tests that could dramatically improve their health and well-being. For example, in some embodiments, an apparatus for performing bioassays is used to perform diagnostic tests of biological samples, such as blood, urine and/or saliva that may be used by individuals in their home, by a doctor in the field, or at a remote clinic in developing countries or any other location, such as rural doctors' offices. Such diagnostic tests can include the detection of biomolecules in a biological sample of a subject, such as a nucleic acid molecule or protein. In some examples, diagnostic tests include sequencing a nucleic acid molecule in a biological sample of a subject, such as sequencing of cell free deoxyribonucleic acid molecules or expression products in a biological sample of the subject.

Although a compact instrument may be used for detecting the presence of biochemical species (e.g., nucleic acids, proteins, antigens, antibodies, viruses, small molecules, etc.) in specimens or biological samples, the instrument may be used for more complicated tasks, such as analyzing dynamic biochemical processes. One field of interest in which the instrument may be used is single-molecule genetic sequencing. According to some embodiments, real-time, single-molecule nucleic acid sequencing may be performed with the instrument to decode genes or gene segments. This may allow clinicians, for example, to track mutations of harmful viruses in real time.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. In some examples, a nucleic acid is deoxyribonucleic acid (DNA) or ribonucleic acid (RNA), or derivatives thereof. A nucleic acid may be single-stranded or double stranded. A nucleic acid may be circular.

The term "nucleotide," as used herein, generally refers to a nucleic acid subunit, which can include A, C, G, T or U, or variants or analogs thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant or analogs thereof) or a pyrimidine (i.e., C, T or U, or variant or analogs thereof). A subunit can enable individual nucleic acid bases or groups of bases (e.g., AA, TA, AT, GC, CG, CT, TC, GT, TG, AC, CA, or uracil-counterparts thereof) to be resolved.

A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides are nucleotides in which the sugar is ribose. Deoxyribonucleotides are nucleotides in which the sugar is deoxyribose. A nucleotide can be a nucleoside monophosphate or a nucleoside polyphosphate. A nucleotide can be a deoxyribonucleoside polyphosphate, such as, e.g., a deoxyribonucleoside triphosphate, which can be selected from deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include detectable tags, such as luminescent tags or markers (e.g., fluorophores).

A nucleoside polyphosphate can have 'n' phosphate groups, where 'n' is a number that is greater than or equal to 2, 3, 4, 5, 6, 7, 8, 9, or 10. Examples of nucleoside polyphosphates include nucleoside diphosphate and nucleoside triphosphate. A nucleotide can be a terminal phosphate labeled nucleoside, such as a terminal phosphate labeled nucleoside polyphosphate. Such label can be a luminescent (e.g., fluorescent or chemiluminescent) label, a fluorogenic label, a colored label, a chromogenic label, a mass tag, an electrostatic label, or an electrochemical label. A label (or marker) can be coupled to a terminal phosphate through a linker. The linker can include, for example, at least one or a plurality of hydroxyl groups, sulfhydryl groups, amino groups or haloalkyl groups, which may be suitable for forming, for example, a phosphate ester, a thioester, a phosphoramidate or an alkyl phosphonate linkage at the terminal phosphate of a natural or modified nucleotide. A linker can be cleavable so as to separate a label from the terminal phosphate, such as with the aid of a polymerization enzyme. Examples of nucleotides and linkers are provided in U.S. Pat. No. 7,041,812, which is entirely incorporated herein by reference.

The term "polymerase," as used herein, generally refers to any enzyme (or polymerizing enzyme) capable of catalyzing a polymerization reaction. Examples of polymerases include, without limitation, a nucleic acid polymerase, a transcriptase or a ligase. A polymerase can be a polymerization enzyme.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes the human genome.

The present disclosure provides devices, systems and methods for detecting biomolecules or subunits thereof, such as nucleic acid molecules. Such detection can include sequencing. A biomolecule may be extracted from a biological sample obtained from a subject. The biological sample may be extracted from a bodily fluid or tissue of the subject, such as breath, saliva, urine or blood (e.g., whole blood or plasma). The subject may be suspected of having a health condition, such as a disease (e.g., cancer). In some examples, one or more nucleic acid molecules are extracted from the bodily fluid or tissue of the subject. The one or more nucleic acids may be extracted from one or more cells obtained from the subject, such as part of a tissue of the subject, or obtained from a cell-free bodily fluid of the subject, such as whole blood.

A biological sample may be processed in preparation for detection (e.g., sequencing). Such processing can include isolation and/or purification of the biomolecule (e.g., nucleic acid molecule) from the biological sample, and generation of more copies of the biomolecule. In some examples, one or more nucleic acid molecules are isolated and purified form a bodily fluid or tissue of the subject, and amplified through nucleic acid amplification, such as polymerase chain reaction (PCR). Then, the one or more nucleic acids molecules or subunits thereof can be identified, such as through sequencing.

Sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (i.e., sequencing by synthesis). As an alternative, sequencing can include the direct identification of individual subunits of the biomolecule.

During sequencing, signals indicative of individual subunits of a biomolecule may be collected in memory and processed in real time or at a later point in time to determine a sequence of the biomolecule. Such processing can include a comparison of the signals to reference signals that enable the identification of the individual subunits, which in some cases yields reads. Reads may be sequences of sufficient length (e.g., at least about 30 base pairs (bp)) that can be used to identify a larger sequence or region, e.g., that can be aligned to a location on a chromosome or genomic region or gene.

Sequence reads can be used to reconstruct a longer region of a genome of a subject (alignment). Reads can be used to reconstruct chromosomal regions, whole chromosomes, or the whole genome. Sequence reads or a larger sequence generated from such reads can be used to analyze a genome of a subject, such as identify variants or polymorphisms. Examples of variants include, but are not limited to, single nucleotide polymorphisms (SNPs) including tandem SNPs, small-scale multi-base deletions or insertions, also referred to as indels or deletion insertion polymorphisms or DIPs), Multi-Nucleotide Polymorphisms (MNPs), Short Tandem Repeats (STRs), deletions, including microdeletions, insertions, including microinsertions, structural variations, including duplications, inversions, translocations, multiplications, complex multi-site variants, copy number variations (CNV). Genomic sequences can comprise combinations of variants. For example, genomic sequences can encompass the combination of one or more SNPs and one or more CNVs.

Individual subunits of biomolecules may be identified using markers. In some examples, luminescent markers are used to identify individual subunits of biomolecules, as described elsewhere herein.

Nucleic acid (e.g., DNA) sequencing allows for the determination of the order and position of nucleotides in a target nucleic acid molecule. Nucleic acid sequencing technologies may vary in the methods used to determine the nucleic acid sequence as well as in the rate, read length, and incidence of errors in the sequencing process. For example, some nucleic acid sequencing methods are based on sequencing by synthesis, in which the identity of a nucleotide is determined as the nucleotide is incorporated into a newly synthesized strand of nucleic acid that is complementary to the target nucleic acid molecule.

During sequencing, a polymerizing enzyme may couple (e.g., attach) to a priming location of a target nucleic acid molecule. The priming location can be a primer that is complementary to the target nucleic acid molecule. As an alternative the priming location is a gap or nick that is provided within a double stranded segment of the target nucleic acid molecule. A gap or nick can be from 0 to at least 1, 2, 3, 4, 5, 6, 7, 8, 9, 10, 20, 30, or 40 nucleotides in length. A nick can provide a break in one strand of a double stranded sequence, which can provide a priming location for a polymerizing enzyme, such as, for example, a strand displacing polymerase enzyme.

In some cases, a sequencing primer can be annealed to a target nucleic acid molecule that may or may not be immobilized to a solid support, such as a sample well. In some embodiments, a sequencing primer may be immobilized to a solid support and hybridization of the target nucleic acid molecule also immobilizes the target nucleic acid molecule to the solid support. Via the action of an enzyme (e.g., a polymerase) capable of adding or incorporating a nucleotide to the primer, nucleotides can be added to the primer in 5' to 3', template bound fashion. Such incorporation of nucleotides to a primer (e.g., via the action of a polymerase) can generally be referred to as a primer extension reaction. Each nucleotide can be associated with a detectable tag that can be detected and used to determine each nucleotide incorporated into the primer and, thus, a sequence of the newly synthesized nucleic acid molecule. Via sequence complementarity of the newly synthesized nucleic acid molecule, the sequence of the target nucleic acid molecule can also be determined. In some cases, annealing of a sequencing primer to a target nucleic acid molecule and incorporation of nucleotides to the sequencing primer can occur at similar reaction conditions (e.g., the same or similar reaction temperature) or at differing reaction conditions (e.g., different reaction temperatures). Moreover, some sequencing by synthesis methods can include the presence of a population of target nucleic acid molecules (e.g, copies of a target nucleic acid) and/or a step of amplification of the target nucleic acid to achieve a population of target nucleic acids.

Devices and systems of the present disclosure are capable of sequencing single nucleic acid molecules with high accuracy and long read lengths, such as an accuracy of at least about 50%, 60%, 70%, 75%, 80%, 85%, 90%, 95%, 96%, 97%, 98%, 99%, 99.9%, 99.99%, 99.999%, or 99.9999%, and/or read lengths greater than or equal to about 10 base pairs (bp), 50 bp, 100 bp, 200 bp, 300 bp, 400 bp, 500 bp, 1000 bp, 10,000 bp, 20,000 bp, 30,000 bp, 40,000 bp, 50,000 bp, or 100,000 bp. In some embodiments, the target nucleic acid molecule used in single molecule sequencing is a single-stranded target nucleic acid (e.g., deoxyribonucleic acid (DNA), DNA derivatives, ribonucleic acid (RNA), RNA derivatives) template that is added or immobilized to a sample well containing at least one additional component of a sequencing reaction (e.g., a polymerase such as, a DNA polymerase, a sequencing primer) immobilized or attached to a solid support such as the bottom of the sample well. The target nucleic acid molecule or the polymerase can be attached to a sample wall, such as at the bottom of the sample well directly or through a linker. The sample well can also contain any other reagents needed for nucleic acid synthesis via a primer extension reaction, such as, for example suitable buffers, co-factors, enzymes (e.g., a polymerase) and deoxyribonucleoside polyphosphates, such as, e.g., deoxyribonucleoside triphosphates, including deoxyadenosine triphosphate (dATP), deoxycytidine triphosphate (dCTP), deoxyguanosine triphosphate (dGTP), deoxyuridine triphosphate (dUTP) and deoxythymidine triphosphate (dTTP) dNTPs, that include luminescent tags, such as fluorophores. Each class of dNTPs (e.g. adenine-containing dNTPs (e.g., dATP), cytosine-containing dNTPs (e.g., dCTP), guanine-containing dNTPs (e.g., dGTP), uracil-containing dNTPs (e.g., dUTPs) and thymine-containing dNTPs (e.g., dTTP)) is conjugated to a distinct luminescent tag such that detection of light emitted from the tag indicates the identity of the dNTP that was incorporated into the newly synthesized nucleic acid. Emitted light from the luminescent tag can be detected and attributed to its appropriate luminescent tag (and, thus, associated dNTP) via any suitable device and/or method, including such devices and methods for detection described elsewhere herein. The luminescent tag may be conjugated to the dNTP at any position such that the presence of the luminescent tag does not inhibit the incorporation of the dNTP into the newly synthesized nucleic acid strand or the activity of the polymerase. In some embodiments, the luminescent tag is conjugated to the terminal phosphate (the gamma phosphate) of the dNTP.

The single-stranded target nucleic acid template can be contacted with a sequencing primer, dNTPs, polymerase and other reagents necessary for nucleic acid synthesis. In some embodiments, all appropriate dNTPs can be contacted with the single-stranded target nucleic acid template simultaneously (e.g., all dNTPs are simultaneously present) such that incorporation of dNTPs can occur continuously. In other embodiments, the dNTPs can be contacted with the single-stranded target nucleic acid template sequentially, where the single-stranded target nucleic acid template is contacted with each appropriate dNTP separately, with washing steps in between contact of the single-stranded target nucleic acid template with differing dNTPs. Such a cycle of contacting the single-stranded target nucleic acid template with each dNTP separately followed by washing can be repeated for each successive base position of the single-stranded target nucleic acid template to be identified.

The sequencing primer anneals to the single-stranded target nucleic acid template and the polymerase consecutively incorporates the dNTPs (or other deoxyribonucleoside polyphosphate) to the primer via the single-stranded target nucleic acid template. The unique luminescent tag associated with each incorporated dNTP can be excited with the appropriate excitation light during or after incorporation of the dNTP to the primer and its emission can be subsequently detected, using, any suitable device(s) and/or method(s), including devices and methods for detection described elsewhere herein. Detection of a particular emission of light can be attributed to a particular dNTP incorporated. The sequence obtained from the collection of detected luminescent tags can then be used to determine the sequence of the single-stranded target nucleic acid template via sequence complementarity.

While the present disclosure makes reference to dNTPs, devices, systems and methods provided herein may be used with various types of nucleotides, such as ribonucleotides and deoxyribonucleotides (e.g., deoxyribonucleoside polyphophates with at least 4, 5, 6, 7, 8, 9, or 10 phosphate groups). Such ribonucleotides and deoxyribonucleotides can include various types of tags (or markers) and linkers.

Signals emitted upon the incorporation of nucleosides can be stored in memory and processed at a later point in time to determine the sequence of the target nucleic acid template. This may include comparing the signals to a reference signals to determine the identities of the incorporated nucleosides as a function of time. Alternative or in addition to, signal emitted upon the incorporation of nucleoside can be collected and processed in real time (i.e., upon nucleoside incorporation) to determine the sequence of the target nucleic acid template in real time.

Nucleic acid sequencing of a plurality of single-stranded target nucleic acid templates may be completed where multiple sample wells are available, as is the case in devices described elsewhere herein. Each sample well can be provided with a single-stranded target nucleic acid template and a sequencing reaction can be completed in each sample well. Each of the sample wells may be contacted with the appropriate reagents (e.g., dNTPs, sequencing primers, polymerase, co-factors, appropriate buffers, etc.) necessary for nucleic acid synthesis during a primer extension reaction and the sequencing reaction can proceed in each sample well. In some embodiments, the multiple sample wells are contacted with all appropriate dNTPs simultaneously. In other embodiments, the multiple sample wells are contacted with each appropriate dNTP separately and each washed in between contact with different dNTPs. Incorporated dNTPs can be detected in each sample well and a sequence determined for the single-stranded target nucleic acid in each sample well as is described above.

Embodiments directed towards single molecule nucleic acid sequencing may use any polymerase that is capable of synthesizing a nucleic acid complementary to a target nucleic acid molecule. Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase φ29 (psi29) DNA polymerase, Taq polymerase, Tth polymerase, Tli polymerase, Pfu polymerase, Pwo polymerase, VENT polymerase, DEEPVENT polymerase, EX-Taq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Tth polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. In some embodiments, the polymerase is a single subunit polymerase. In some embodiments, the polymerase is a polymerase with high processivity. Polymerase processivity generally refers to the capability of a polymerase to consecutively incorporate dNTPs into a nucleic acid template without releasing the nucleic acid template. Upon base pairing between a nucleobase of a target nucleic acid and the complementary dNTP, the polymerase incorporates the dNTP into the newly synthesized nucleic acid strand by forming a phosphodiester bond between the 3' hydroxyl end of the newly synthesized strand and the alpha phosphate of the dNTP. In examples in which the luminescent tag conjugated to the dNTP is a fluorophore, its presence is signaled by excitation and a pulse of emission is detected during or after the step of incorporation. For detection labels that are conjugated to the terminal (gamma) phosphate of the dNTP, incorporation of the dNTP into the newly synthesized strand results in release of the beta and gamma phosphates and the detection label, which is free to diffuse in the sample well, resulting in a decrease in emission detected from the fluorophore.

Embodiments directed toward single molecule RNA sequencing may use any reverse transcriptase that is capable of synthesizing complementary DNA (cDNA) from an RNA template. In such embodiments, a reverse transcriptase can function in a manner similar to polymerase in that cDNA can be synthesized from an RNA template via the incorporation of dNTPs to a reverse transcription primer annealed to an RNA template. The cDNA can then participate in a sequencing reaction and its sequence determined as described above. The determined sequence of the cDNA can then be used, via sequence complementarity, to determine the sequence of the original RNA template. Examples of reverse transcriptases include Moloney Murine Leukemia Virus reverse transcriptase (M-MLV), avian myeloblastosis virus (AMV) reverse transcriptase, human immunodeficiency virus reverse transcriptase (HIV-1) and telomerase reverse transcriptase.

Having recognized the need for simple, less complex apparatuses for performing single molecule detection and/or nucleic acid sequencing, the present disclosure provides techniques for detecting single molecules using sets of tags, such as optical (e.g., luminescent) tags, to label different molecules. Such single molecules may be nucleotides or amino acids having tags. Tags may be detected while bound to single molecules, upon release from the single molecules, or while bound to and upon release from the single molecules. In some examples, tags are luminescent tags. Each luminescent tag in a selected set is associated with a respective molecule. For example, a set of four tags may be used to "label" the nucleobases present in DNA—each tag of the set being associated with a different nucleobase, e.g., a first tag being associated with adenine (A), a second tag being associated with cytosine (C), a third tag being associated with guanine (G), and a fourth tag being associated with thymine (T). Moreover, each of the luminescent tags in the set of tags has different properties that may be used to distinguish a first tag of the set from the other tags in the set. In this way, each tag is uniquely identifiable using one or more of these distinguishing characteristics. By way of example and not limitation, the characteristics of the tags that may be used to distinguish one tag from another may include the emission energy and/or wavelength of the light that is emitted by the tag in response to excitation and/or the energy and/or wavelength of the excitation light that excites a particular tag.

Embodiments may use any suitable combination of tag characteristics to distinguish a first tag in a set of tags from the other tags in the same set. For example, some embodiments may use only the wavelength of the emission light from the tags to identify the tags. In such embodiments, each tag in a selected set of tags has a different peak emission wavelength from the other tags in the set and the luminescent tags are all excited by light from a single excitation source. FIG. 1-1 illustrates the emission spectra from four luminescent tags according to an embodiment where the four tags exhibit their respective intensity peak at different emission wavelengths, referred to herein as the tag's "peak emission wavelength." A first emission spectrum 1-101 from a first luminescent tag has a peak emission wavelength at $\lambda 1$, a second emission spectrum 1-102 from a second luminescent tag has a peak emission wavelength at $\lambda 2$, a third emission spectrum 1-103 from a third luminescent tag has a peak emission wavelength at $\lambda 3$, and a fourth emission spectrum 1-104 from a fourth luminescent tag has a peak emission wavelength at $\lambda 4$. In this embodiment, the emission peaks of the four luminescent tags may have any suitable values that satisfy the relation $\lambda 1 < \lambda 2 < \lambda 3 < \lambda 4$. The four emission spectra may or may not overlap. However, if the emission spectra of two or more tags overlap, it is desirable to select a luminescent tag set such that one tag emits substantially more light than any other tag at each respective peak wavelength. In this embodiment, the excitation wavelength at which each of the four tags maximally absorbs light from the excitation source is substantially the same, but that need not be the case. Using the above tag set, four different molecules may be labeled with a respective tag from the tag set, the tags may be excited using a single excitation source, and the tags can be distinguished from one another by detecting the emission wavelength of the tags using an optical system and sensors. While FIG. 1-1 illustrates four different tags, it should be appreciated that any suitable number of tags may be used.

Figures 1, 2, 2A:
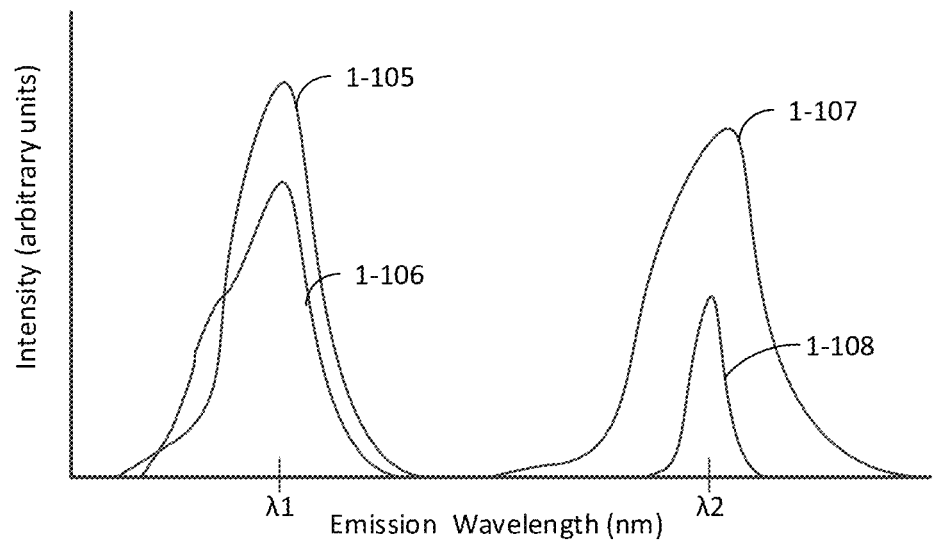
Figures 1, 2, 2B:
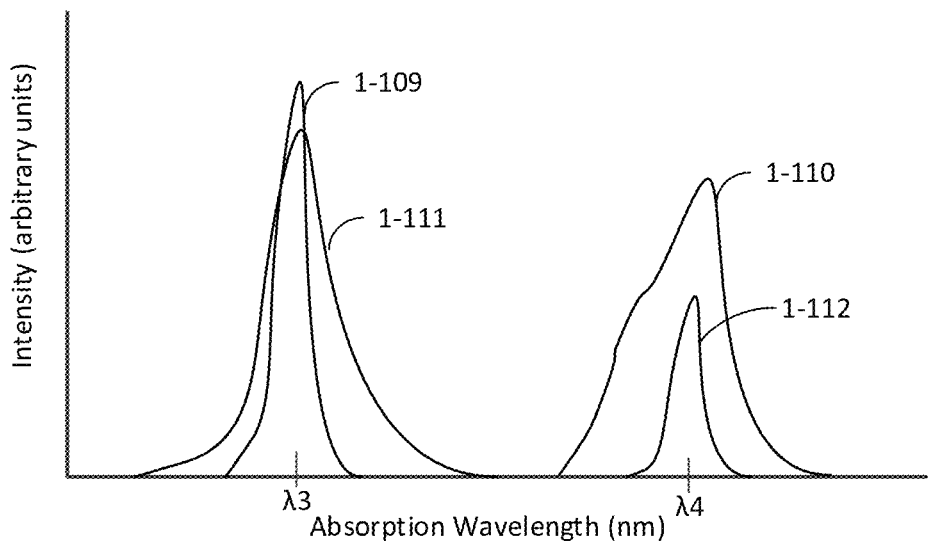

Other embodiments may use both the wavelength of the emission light from the tags and the wavelength at which the tags absorb excitation light to identify the tags. In such embodiments, each tag in a selected set of tags has a different combination of emission wavelength and excitation wavelength from the other tags in the set. Thus, some tags within a selected tag set may have the same emission wavelength, but be excited by light of different wavelengths. Conversely, some tags within a selected tag set may have the same excitation wavelength, but emit light at different wavelengths. FIG. 1-2A illustrates the emission spectra from four luminescent tags according to an embodiment where two of the tags have a first peak emission wavelength and the other two tags have a second peak emission wavelength. A first emission spectrum 1-105 from a first luminescent tag has a peak emission wavelength at $\lambda 1 < \lambda 2$, a second emission spectrum 1-106 from a second luminescent tag also has a peak emission wavelength at $\lambda 1$, a third emission spectrum 1-107 from a third luminescent tag has a peak emission wavelength at $\lambda 2$, and a fourth emission spectrum 1-108 from a fourth luminescent tag also has a peak emission wavelength at $\lambda 2$. In this embodiment, the emission peaks of the four luminescent tags may have any suitable values that satisfy the relation $\lambda 1 < \lambda 2$. FIG. 1-2B illustrates the absorption spectra from the four luminescent tags, where two of the tags have a first peak absorption wavelength and the other two tags have a second peak absorption wavelength. A first absorption spectrum 1-109 for the first luminescent tag has a peak absorption wavelength at $\lambda 3$, a second absorption spectrum 1-110 for the second luminescent tag has a peak absorption wavelength at $\lambda 4$, a third absorption spectrum 1-111 for the third luminescent tag has a peak absorption wavelength at $\lambda 3$, and a fourth absorption spectrum 1-112 for the fourth luminescent tag has a peak absorption wavelength at $\lambda 4$. Note that the tags that share an emission peak wavelength in FIG. 1-2A do not share an absorption peak wavelength in FIG. 1-2B. Using such a tag set allows distinguishing between four tags even when there are only two emission wavelengths for the four dyes. This is possible using two excitation sources that emit at different wavelengths or a single excitation source capable of emitting at multiple wavelengths. If the wavelength of the excitation light is known for each detected emission event, then it can be determined which tag was present. The excitation source(s) may alternate between a first excitation wavelength and a second excitation wavelength, which is referred to as interleaving. Alternatively, two or more pulses of the first excitation wavelength may be used followed by two or more pulses of the second excitation wavelength.

While not illustrated in the figures, other embodiments may determine the identity of a luminescent tag based on the absorption frequency alone. Such embodiments are possible if the excitation light can be tuned to specific wavelengths that match the absorption spectrum of the tags in a tag set. In such embodiments, the optical system and sensor used to direct and detect the light emitted from each tag does not need to be capable of detecting the wavelength of the emitted light. This may be advantageous in some embodiments because it reduces the complexity of the optical system and sensors because detecting the emission wavelength is not required in such embodiments.

As discussed above, the inventors have recognized and appreciated the need for being able to distinguish different luminescent tags from one another using various characteristics of the tags. The type of characteristics used to determine the identity of a tag impact the physical device used to perform this analysis. The present application discloses several embodiments of an apparatus, device, instrument and methods for performing these different experiments.

Briefly, the inventors have recognized and appreciated that a pixelated device with a large number of pixels (e.g., hundreds, thousands, millions or more) allows for the detection of a plurality of individual molecules or particles in parallel. The molecules may be, by way of example and not limitation, proteins and/or DNA. Moreover, a high-speed device that can acquire data at more than one hundred frames per second allows for the detection and analysis of dynamic processes or changes that occur over time within the sample being analyzed.

The compact apparatus described herein may be used to bring automated bioanalytics to regions of the world that previously could not perform quantitative analysis of biological samples. For example, blood tests for infants may be performed by placing a blood sample on a disposable or recyclable integrated assay chip (also referred to herein as an "integrated device"), placing the integrated device into the small, portable instrument for analysis, and processing the results by a computer that connects to the instrument for immediate review by a user. The data may also be transmitted over a data network to a remote location to be analyzed, and/or archived for subsequent clinical analyses. Alternatively, the instrument may include one or more processors capable of analyzing data obtained from the integrated device, and provide results for review without the need of an external computer.

II. Overview of Apparatus

A schematic overview of apparatus 2-100 for analyzing specimens is illustrated in FIG. 2-1. According to some embodiments, the apparatus 2-100 comprises an integrated assay chip (also referred to herein as an "integrated device") 2-110 and a base instrument 2-120, into which the integrated device may be inserted. The base instrument 2-120 may comprise a computer interface 2-124, at least one electronic processor 2-123, and a user interface 2-125. The integrated device may comprise an instrument interface 2-130, at least one sample well 2-111, at least one excitation source 2-121, and at least one sensor 2-122, though in preferred embodiments, there will be a plurality of sample wells, excitation sources, and sensors disposed on an integrated device 2-110. According to some embodiments, the instrument 2-120 includes any suitable socket for interfacing with the integrated device 2-110. For example, the instrument 2-120 may include a socket (not illustrated) comprising mechanical registration and multi-pin electrical connection for receiving the integrated device 2-110.

In some embodiments, a computer interface 2-124 is used to connect with a computing device 2-130. Any suitable computer interface 2-124 and computing device 2-130 may be used. For example, the computer interface 2-124 may be a USB interface or a Firewire interface. The computing device 2-130 may be any general purpose computer, such as a laptop or desktop computer. The computer interface 2-124 facilitates communication of information between the instrument 2-120 and the computing device 2-130. Input information for controlling and/or configuring the instrument 2-120 may be provided through the computing device 2-130 connected to the computer interface 2-124 of the instrument. Additionally, output information from the instrument may be received by the computing device 2-130 through the computer interface 2-124. Such output information may include feedback about performance of the instrument 2-120 and information relating to signals from the sensors 2-122, which may comprise raw and/or processed data in some embodiments.

The instrument 2-120 may also include at least one processing device 2-123 for analyzing data received from the sensors 2-122. In some embodiments, the processing device 2-123 may comprise a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) Memory (not) shown may store machine-readable instructions that specially adapt the processor 2-123 to execute instrument management functions, signal collection and processing functions, as well as issue control signals to the integrated device for various purposes such as operation of the excitation sources. In some embodiments, the processing of data from the sensors 2-122 may be performed by both the processing device 2-123 and the external computing device 2-130. In other embodiments, the computing device 2-130 may be omitted and processing of data from the sensor 2-122 may be performed solely by processing device 2-123.

In some embodiments, the instrument 2-120 includes a user interface 2-125 for interactive operation of the instrument. The user interface 2-125 may be configured to allow a user to input information into the instrument, such as commands and/or settings used to control the functioning of the instrument. In some embodiments, the user interface 2-125 may include any one of or a combination of buttons, switches, dials, touch screen, touch pad, display, and microphone for receiving voice commands Additionally, the user interface 2-125 may allow a user to receive feedback on the performance of the instrument and/or integrated device, such as proper alignment and/or information obtained by readout signals from the sensors on the integrated device. In some embodiments, the user interface 2-125 may provide feedback using a speaker to provide audible feedback, and/or indicator lights and/or a display screen for providing visual feedback.

In some embodiments, the integrated device 2-110 comprises a plurality of pixels, each pixel associated with its own individual sample well 2-111 and its own associated sensor 2-122. The plurality of pixels may be arranged in an array, and there may be any suitable number of pixels. For example, the integrated device may include between 100 and 1,000 pixels according to some embodiments, between 1,000 and 10,000 pixels according to some embodiments, between 10,000 and 100,000 pixels according to some embodiments, between 100,000 and 1,000,000 pixels according to some embodiments, and yet between 1,000,000 and 10,000,000 pixels according to some embodiments. In some implementations, there may be fewer or more pixels on an integrated device. The integrated device 2-110 and instrument 2-120 may include multi-channel, high-speed communication links for handling data associated with large pixel arrays (e.g., more than 1000 pixels).

An integrated device may appear as depicted in FIG. 2-2. Electronic, optical, and related structures may all be incorporated onto a single substrate 2-200. The integrated device may include an array of active-source pixels 2-205 and integrated electronic circuitry. The integrated electronic circuitry may include drive and read-out circuitry 2-215 coupled to the sensors of the pixel array, and signal processing circuitry. The signal processing circuitry may include analog-to-digital converters 2-217 and one or more field-programmable gate arrays and/or digital signal processors 2-219. Some embodiments may have more circuit components, and some embodiments may have fewer circuit components integrated on the substrate. Although the components of the integrated device 2-110 are depicted on a single level in FIG. 2-2, the components may be fabricated on multiple levels on the substrate 2-200.

According to some embodiments, there may be a walled chamber formed around a plurality of pixels 2-205 on the integrated device. The walled chamber may be configured to hold a fluid specimen over the plurality of pixels. In some implementations, there may be a cover that can close over the walled chamber to exclude light external to the walled chamber from illuminating the plurality of pixels. According to some implementations, there may be a ridge running around the plurality of pixels 2-205, or the plurality of pixels may be formed in a depression. The walled chamber, ridge, or depression may be configured to retain a fluid specimen over the plurality of pixels. The integrated device may be inserted into a receiving dock of an instrument 2-120, and a cover closed over the receiving dock to exclude light external to the receiving dock from illuminating the plurality of pixels. In some embodiments, the integrated device 2-110 and chamber are packaged in a single module. The module may have exterior electrical contacts that are arranged to electrically contact pins of a receiving dock of an instrument 2-120.

In some embodiments, there may be optical elements (not shown) located on the integrated device 2-110 that are arranged for guiding and coupling excitation energy from one or more excitation sources 2-121 to the sample wells 2-111. Such source-to-well elements may include plasmonic structures and other microfabricated structures located adjacent the sample wells. Additionally, in some embodiments, there may be optical elements located on the integrated device that are configured for guiding emission energy from the sample wells 2-111 to corresponding sensors 2-122. Such well-to-sample elements may include may include plasmonic structures and other microfabricated structures located adjacent the sample wells. In some embodiments, a single component may play a role in both in coupling excitation energy to a sample well and delivering emission energy from the sample well to a corresponding sensor.

In some implementations, an integrated device 2-110 may include more than one type of excitation source that is used to excite samples at a sample well. For example, there may be multiple excitation sources configured to produce multiple excitation energies or wavelengths for exciting a sample. In some embodiments, a single excitation source may be configured to emit multiple wavelengths that are used to excite samples in the sample wells. In some embodiments, each sensor at a pixel of the integrated device 2-110 may include multiple sub-sensors configured to detect different emission energy characteristics from the sample.

In operation, parallel analyses of samples within the sample wells 2-111 are carried out by exciting the samples within the wells using the excitation source 2-121 and detecting signals from sample emission with the sensors 2-122. Emission energy from a sample may be detected by a corresponding sensor 2-122 and converted to at least one electrical signal. The resulting signal, or signals, may be processed on the integrated device 2-110 in some embodiments, or transmitted to the instrument 2-120 for processing by the processing device 2-123 and/or computing device 2-130. Signals from a sample well may be received and processed independently from signals associated with the other pixels.

When an excitation source 2-121 delivers excitation energy to a sample well, at least one sample within the well may luminesce, and the resulting emission may be detected by a sensor. As used herein, the phrases "a sample may luminesce" or "a sample may emit radiation" or "emission from a sample" mean that a luminescent tag, marker, or reporter, the sample itself, or a reaction product associated with the sample may produce the emitted radiation.

In some embodiments, samples may be labeled with one or more tags, and emission associated with the tags is discernable by the instrument. For example, components of the integrated device may affect the emission from a sample well to produce a spatial emission distribution pattern that is dependent on the emission wavelength. A corresponding sensor for the sample well may be configured to detect the spatial distribution patterns from a sample well and produce signals that differentiate between the different emission wavelengths, as described in further detail below.

Various tags, markers, or reporters may be used with the integrated device and instrument. Luminescent markers (also referred to herein as "markers") may be exogenous or endogenous markers. Exogenous markers may be external luminescent markers used as a reporter and/or tag for luminescent labeling. Examples of exogenous markers may include but are not limited to fluorescent molecules, fluorophores, fluorescent dyes, fluorescent stains, organic dyes, fluorescent proteins, species that participate in fluorescence resonance energy transfer (FRET), enzymes, and/or quantum dots. Other exogenous markers are known in the art. Such exogenous markers may be conjugated to a probe or functional group (e.g., molecule, ion, and/or ligand) that specifically binds to a particular target or component. Attaching an exogenous tag or reporter to a probe allows identification of the target through detection of the presence of the exogenous tag or reporter. Examples of probes may include proteins, nucleic acid (e.g., DNA, RNA) molecules, lipids and antibody probes. The combination of an exogenous marker and a functional group may form any suitable probes, tags, and/or labels used for detection, including molecular probes, labeled probes, hybridization probes, antibody probes, protein probes (e.g., biotin-binding probes), enzyme labels, fluorescent probes, fluorescent tags, and/or enzyme reporters.

Although the present disclosure makes reference to luminescent markers, other types of markers may be used with devices, systems and methods provided herein. Such markers may be mass tags, electrostatic tags, or electrochemical labels.

While exogenous markers may be added to a sample, endogenous markers may be already part of the sample. Endogenous markers may include any luminescent marker present that may luminesce or "autofluoresce" in the presence of excitation energy. Autofluorescence of endogenous fluorophores may provide for label-free and noninvasive labeling without requiring the introduction of exogenous fluorophores. Examples of such endogenous fluorophores may include hemoglobin, oxyhemoglobin, lipids, collagen and elastin crosslinks, reduced nicotinamide adenine dinucleotide (NADH), oxidized flavins (FAD and FMN), lipofuscin, keratin, and/or prophyrins, by way of example and not limitation.

Figures 1, 2:
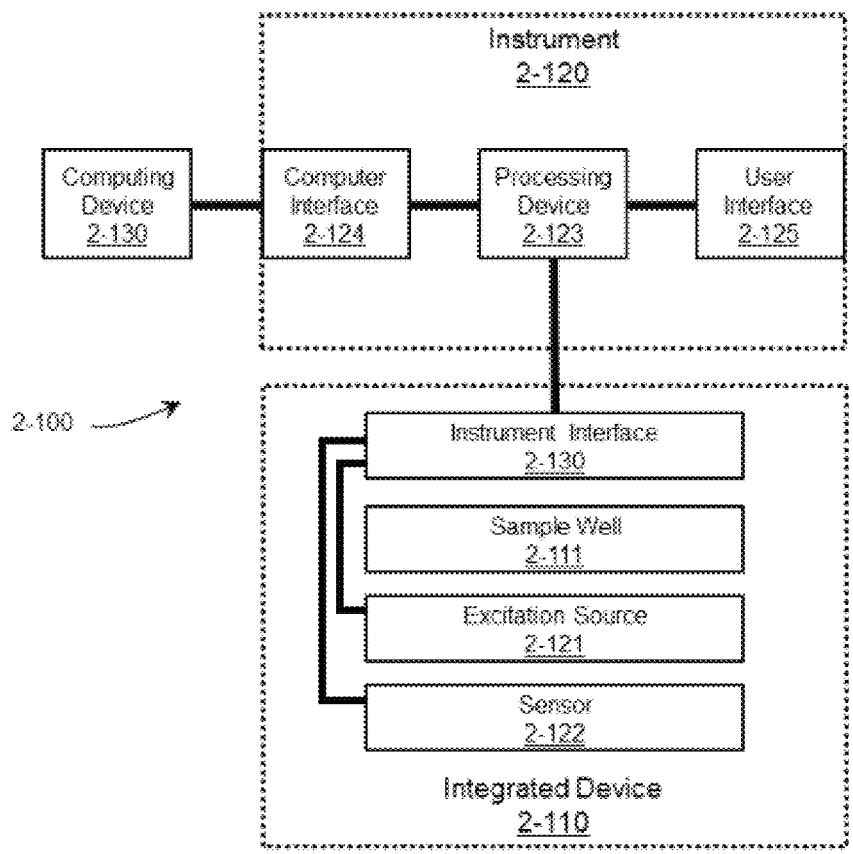
Figure 2:
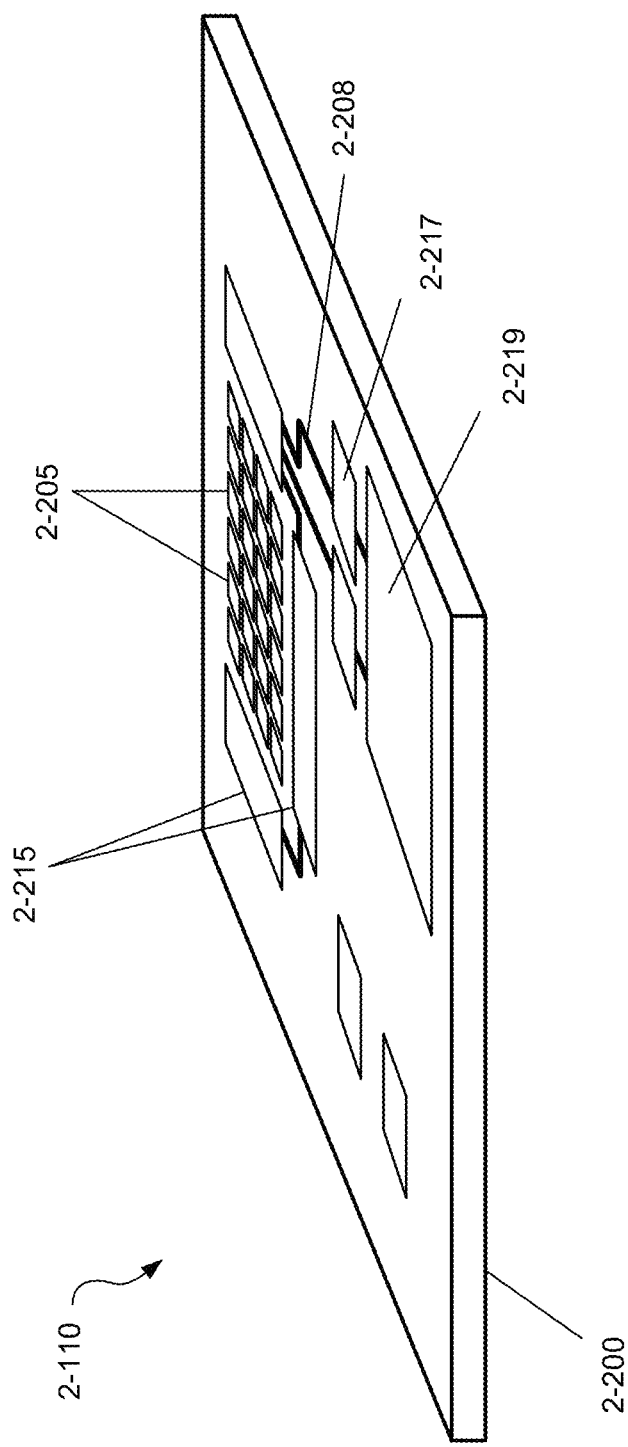
Figures 2, 3:
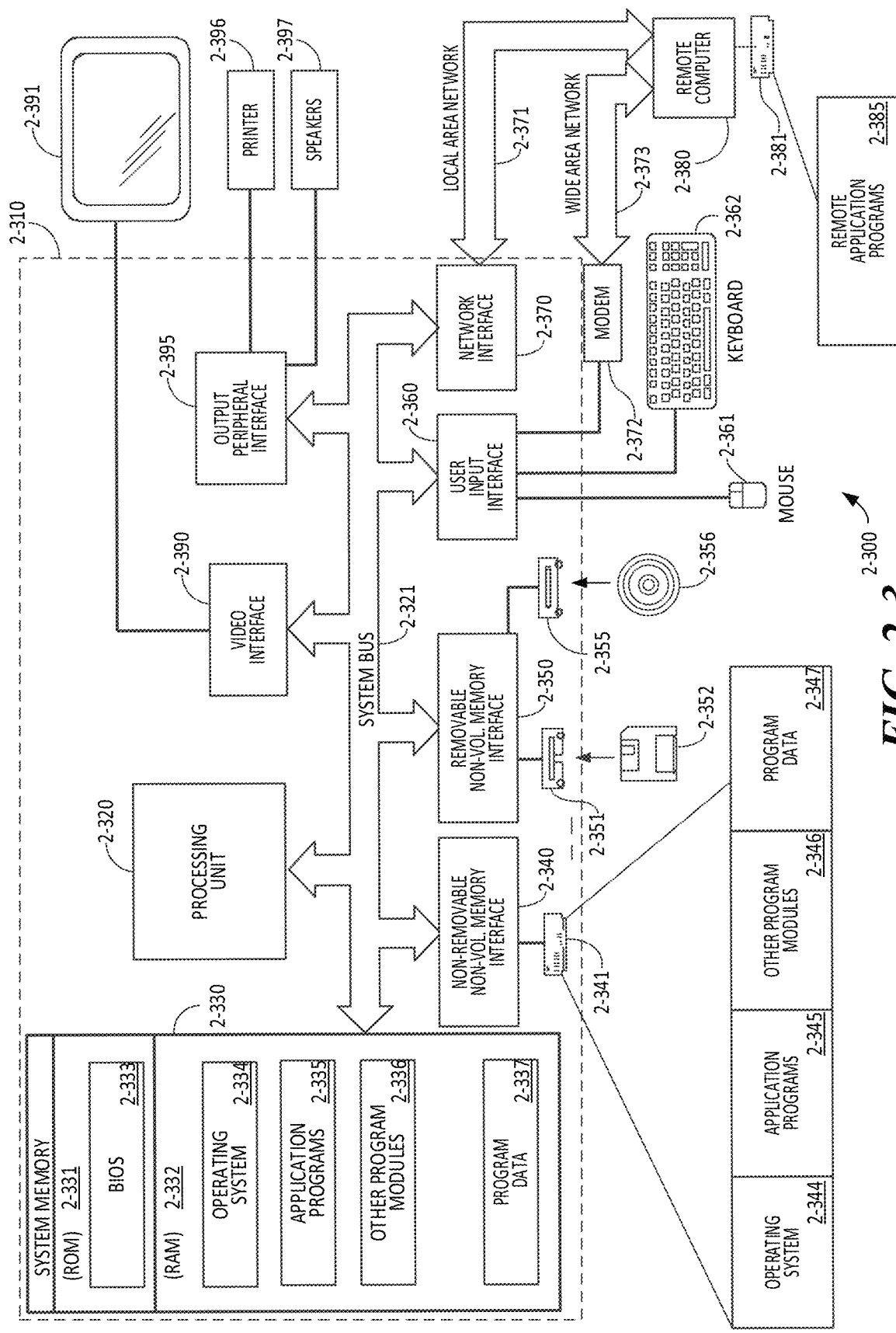

FIG. 2-3 depicts components of a computing device 2-310. Some or all of the components shown may be present in embodiments of an apparatus 2-100 for analyzing specimens. In a distributed computing environment, some components may be located on a server and some components may be located on a client device. In some implementations, a computing device 2-130 in communication with a base instrument 2-120 may comprise some or all components of a computing system 2-300 that is depicted in FIG. 2-3. In some embodiments, a base instrument 2-120 may include some or all of the components of a computing device 2-310.

Components of computing device 2-310 may include, but are not limited to, a processing unit 2-320, a memory 2-330, and a bus 2-321 that couples various components including the memory to the processing unit 2-320. The bus 2-321 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 2-310 may include one or more types of machine-readable media. Machine-readable media can be any available media that can be accessed by computer 2-310 and includes both volatile and nonvolatile, manufactured storage media, removable and non-removable manufactured storage media. By way of example, and not limitation, machine-readable media may comprise information such as computer-readable instructions, data structures, program modules or other data. Machine-readable media includes, but is not limited to, RAM, ROM, EEPROM, flash memory or other memory-device technology, CD-ROM, digital versatile disks (DVD) or other optical disk storage, magnetic cassettes, magnetic tape, magnetic disk storage or other magnetic storage devices, or any other manufactured data-storage device which can be used to store the desired information and which can accessed by computer 2-310.

The memory 2-330 may include computer storage media in the form of volatile and/or nonvolatile memory such as read only memory (ROM) 2-331 and random access memory (RAM) 2-332. A basic input/output system 2-333 (BIOS), containing the basic routines that help to transfer information between elements within computer 2-310, such as during start-up, may be stored in ROM 2-331. RAM 2-332 may contain data and/or program modules that are immediately accessible to and/or presently being operated on by processing unit 2-320. By way of example, and not limitation, FIG. 2-3 illustrates an operating system 2-334, application programs 2-335, other program modules 2-336, and program data 2-337.

The computer 2-310 may also include other removable/non-removable, volatile/nonvolatile machine-readable media. By way of example only, FIG. 2-3 illustrates a hard disk drive 2-341 that reads from or writes to non-removable, nonvolatile magnetic media, a magnetic disk drive 2-351 that reads from or writes to a removable, nonvolatile magnetic disk 2-352, and an optical disk drive 2-355 that reads from or writes to a removable, nonvolatile optical disk 2-356 such as a CD ROM or other optical media. Other removable/non-removable, volatile/nonvolatile machine-readable media that can be used in the exemplary operating environment include, but are not limited to, magnetic tape cassettes, flash memory cards, digital versatile disks, digital video tape, solid state RAM, solid state ROM, and the like. The hard disk drive 2-341 may be connected to the system bus 2-321 through a non-removable memory interface such as interface 2-340, and magnetic disk drive 2-351 and optical disk drive 2-355 may be connected to the system bus 2-321 by a removable memory interface, such as interface 2-350.

The drives and their associated machine-readable media discussed above and illustrated in FIG. 2-3, provide storage of machine-readable instructions, data structures, program modules and other data for the computer 2-310. In FIG. 2-3, for example, hard disk drive 2-341 is illustrated as storing operating system 2-344, application programs 2-345, other program modules 2-346, and program data 2-347. These components may either be the same as, or different from, operating system 2-334, application programs 2-335, other program modules 2-336, and program data 2-337. Operating system 2-344, application programs 2-345, other program modules 2-346, and program data 2-347 are given different numbers here to illustrate that, at a minimum, they are different copies.

A user may enter commands and information into the computer 2-310 through input devices such as a keyboard 2-362 and pointing device 2-361, commonly referred to as a mouse, trackball or touch pad. Other input devices (not shown) may include a microphone, joystick, game pad, satellite dish, scanner, or the like. These and other input devices may be connected to the processing unit 2-320 through a user input interface 2-360 that is coupled to the system bus, but may be connected by other interface and bus structures, such as a parallel port, game port or a universal serial bus (USB). A monitor 2-391 or other type of display device may also be connected to the system bus 2-321 via an interface, such as a video interface 2-390. In addition to the monitor, a computing device 2-310 may also include other peripheral output devices such as speakers 2-397 and printer 2-396, which may be connected through a output peripheral interface 2-395.

The computer 2-310 may operate in a networked environment using logical connections to one or more remote devices, such as a remote computer 2-380. The remote computer 2-380 may be a personal computer, a server, a router, a network PC, a peer device or other common network node, and may include many or all of the elements described above relative to the computer 2-310, although only a memory storage device 2-381 has been illustrated in FIG. 2-3. The logical connections depicted in FIG. 2-3 include a local area network (LAN) 2-371 and a wide area network (WAN) 2-373, but may also include other networks. Such networking environments may be commonplace in offices, enterprise-wide computer networks, intranets and the Internet. Network connections may be wired, optical fiber based, or wireless.

When used in a LAN networking environment, the computer 2-310 may be connected to the LAN 2-371 through a network interface or adapter 2-370. When used in a WAN networking environment, the computer 2-310 may include a modem 2-372 or other means for establishing communications over the WAN 2-373, such as the Internet. The modem 2-372, which may be internal or external, may be connected to the system bus 2-321 via the user input interface 2-360, or other appropriate mechanism. In a networked environment, program modules depicted relative to the computer 2-310, or portions thereof, may be stored in a remote memory storage device. By way of example, and not limitation, FIG. 2-3 illustrates remote application programs 2-385 as residing on memory device 2-381. It will be appreciated that the network connections shown are exemplary and other means of establishing a communications link between the computers may be used.

III. Active Source Pixel and Sample Well

III. A. Active Source Pixel

Referring now to FIG. 3-1, in various embodiments, an integrated device may include a plurality of active source pixels 3-100. An active source pixel (also referred to as "pixel" herein) may comprise an excitation source located at the pixel. The plurality of pixels may be arranged on a substrate 3-105 in a regular array (e.g., a one-dimensional or two-dimensional array). The pixels 3-100 may be arranged to have at least one periodic spacing between pixels, according to one embodiment. For example, pixels along a first direction (a row direction) may have a first periodic spacing, and pixels along a second direction (a column direction) may have a second periodic spacing. However, some implementations may not have regular periodic spacings between pixels, or may have other arrangements of the pixels that may include more than two periodic spacings. There may be between 100 pixels and 1 million pixels on an integrated device 2-110, though in some embodiments, there may be more pixels on an integrated device.

As depicted in FIG. 3-1 and according to one embodiment of an integrated device 2-110, an active pixel may include a sample well 3-210 in which at least one sample 3-101 from a specimen may be retained for observation. A pixel may further include at least one excitation source 3-240 that provides energy to excite a sample in the sample well and a sensor 3-260 that detects emission from the sample. According to some embodiments, a pixel 3-100 may include additional structures. For example, a pixel 3-100 may include an excitation-coupling structure 3-220 that affects coupling of excitation energy to a sample within the sample well. A pixel may also include an emission-coupling structure 3-250 that affects coupling of emission energy from a sample within the well to the sensor 3-260.

In some embodiments, a pixel 3-100 may include at least one integrated complementary metal-oxide-semiconductor (CMOS) device (e.g., at least one integrated amplifier, at least one gating transistor, etc, not shown in the drawing) that is used for processing signals from the sensor 3-260. Integrated CMOS circuitry may be located on one or more levels near the sensor 3-260. Ground planes and/or interconnects may also be located within a pixel of an integrated device.

The arrangement of components in a pixel is not limited to those shown in FIG. 3-1. In some embodiments, the first structure 3-220, excitation source 3-240, second structure 3-250, and sensor 3-260 may be arranged in an order, from top to bottom, different than shown in the drawing.

III. B Sample Well Embodiments

According to some embodiments, a sample well 3-210 may be formed at one or more pixels of an integrated device. A sample well may comprise a small volume or region formed at a surface of a substrate 3-105 and arranged such that samples 3-101 may diffuse into and out of the sample well from a specimen deposited on the surface of the substrate, as depicted in FIG. 3-1 and FIG. 3-2. The sample well 3-210 may have a length or depth extending in a direction normal to the substrate surface, sometimes referred to as a longitudinal direction of the sample well. In various embodiments, a sample well 3-210 may be arranged to receive excitation energy from an excitation source 3-240. Samples 3-101 that diffuse into the sample well may be retained, temporarily or permanently, within an excitation region 3-215 of the sample well by an adherent 3-211. In the excitation region, a sample may be excited by excitation energy (e.g., excitation radiation 3-247), and subsequently emit radiation that may be observed and evaluated to characterize the sample.

In further detail of operation, at least one sample 3-101 to be analyzed may be introduced into a sample well 3-210, e.g., from a specimen (not shown) containing a fluid suspension of samples. Energy from an excitation source 3-240 on the substrate may excite the sample or at least one tag (also referred to as a biological marker, reporter, or probe) attached to the sample or otherwise associated with the sample while it is within an excitation region 3-215 within the sample well. According to some embodiments, a tag may be a luminescent molecule (e.g., a luminescent tag or probe) or quantum dot. In some implementations, there may be more than one tag that is used to analyze a sample (e.g., distinct tags that are used for single-molecule genetic sequencing as described in "Real-Time DNA Sequencing from Single Polymerase Molecules," by J. Eid, et al., Science 323, p. 133 (2009), which is incorporated by reference). During and/or after excitation, the sample or tag may emit emission energy. When multiple tags are used, they may emit at different characteristic energies and/or emit with different temporal characteristics. The emissions from the sample well may radiate or otherwise travel to a sensor 3-260 where they are detected and converted into electrical signals that can be used to characterize the sample.

According to some embodiments, a sample well 3-210 may be a partially enclosed structure, as depicted in FIG. 3-2. In some implementations, a sample well 3-210 comprises a sub-micron-sized hole or opening (characterized by at least one transverse dimension $D_{sw}$) formed in at least one layer of material 3-230. In some cases, the hole may be referred to as a "nanohole." The transverse dimension of the sample well may be between approximately 20 nanometers and approximately 1 micron, according to some embodiments, though larger and smaller sizes may be used in some implementations. A volume of the sample well 3-210 may be between about $10^{-21}$ liters and about $10^{-15}$ liters, in some implementations. A sample well may be formed as a waveguide that may, or may not, support a propagating mode. In some embodiments, a sample well may be formed as a zero-mode waveguide (ZMW) having a cylindrical shape (or similar shape) with a diameter (or largest transverse dimension) $D_{sw}$. A ZMW may be formed in a single metal layer as a nanoscale hole that does not support a propagating optical mode through the hole.

Because the sample well 3-210 has a small volume, detection of single-sample events (e.g., single-molecule events) at each pixel may be possible even though samples may be concentrated in an examined specimen at concentrations that are similar to those found in natural environments. For example, micromolar concentrations of the sample may be present in a specimen that is placed in contact with the integrated device, but at the pixel level only about one sample (or single molecule event) may be within a sample well at any given time. Statistically, some sample wells may contain no samples and some may contain more than one sample. However, an appreciable number of sample wells may contain a single sample (e.g. at least 30% in some embodiments), so that single-molecule analysis can be carried out in parallel for a large number of pixels. Because single-molecule or single-sample events may be analyzed at each pixel, the integrated device makes it possible to detect rare events that may otherwise go unnoticed in ensemble averages.

A transverse dimension $D_{sw}$ of a sample well may be between about 500 nanometers (nm) and about one micron in some embodiments, between about 250 nm and about 500 nm in some embodiments, between about 100 nm and about 250 nm in some embodiments, and yet between about 20 nm and about 100 nm in some embodiments. According to some implementations, a transverse dimension of a sample well is between approximately 80 nm and approximately 180 nm, or between approximately one-quarter and one-eighth of the excitation wavelength or emission wavelength. In some embodiments, the depth or height of the sample well 3-210 may be between about 50 nm and about 500 nm. In some implementations, the depth or height of the sample well 3-210 may be between about 80 nm and about 250 nm.

A sample well 3-210 having a sub-wavelength, transverse dimension can improve operation of a pixel 3-100 of an integrated device 2-110 in at least two ways. For example, excitation energy incident on the sample well from a side opposite the specimen may couple into the excitation region 3-215 with an exponential decay in power, and not propagate as a propagating mode through the sample well to the specimen. As a result, excitation energy is increased in the excitation region where it excites a sample of interest, and is reduced in the specimen where it may excite other samples that may contribute to background noise. Also, emission from a sample retained at a base of the well (e.g., nearer to the sensor 3-260) is preferably directed toward the sensor, since emission propagating up through the sample well is highly suppressed. Both of these effects can improve signal-to-noise ratio at the pixel. The inventors have recognized several aspects of the sample well that can be improved to further boost signal-to-noise levels at the pixel. These aspects relate to well shape and structure, and also to adjacent optical and plasmonic structures (described below) that aid in coupling excitation energy to the sample well and emitted radiation from the sample well.

According to some embodiments, a sample well 3-210 may be formed as a sub-cutoff nanoaperture (SCN). For example, the sample well 3-210 may comprise a cylindrically-shaped hole or bore in a conductive layer. The cross-section of a sample well need not be round, and may be elliptical, square, rectangular, or polygonal in some embodiments. Excitation energy 3-247 (e.g., optical radiation) may enter the sample well through an entrance aperture 3-212 that may be defined by walls 3-214 of the sample well at a first end of the well, as depicted in FIG. 3-2. When formed as an SCN, the excitation energy may decay exponentially along a length of the SCN (e.g., in the direction of the specimen). In some implementations, the waveguide may comprise an SCN for emitted radiation from the sample, but may not be an SCN for excitation energy. For example, the aperture and waveguide formed by the sample well may be large enough to support a propagating mode for the excitation energy, since it may have a shorter wavelength than the emitted radiation. The emission, at a longer wavelength, may be beyond a cut-off wavelength for a propagating mode in the waveguide. According to some embodiments, the sample well 3-210 may comprise an SCN for the excitation energy, such that the greatest intensity of excitation energy is localized to an excitation region 3-215 of the sample well at an entrance to the sample well 3-210 (e.g., localized near the interface between layer 3-235 and layer 3-230 as depicted in the drawing). Such localization of the excitation energy can improve localization of emission energy from the sample, and limit the observed emission to that emitted from a single sample (e.g., a single molecule).

An example of excitation localization near an entrance of a sample well that comprises an SCN is depicted in FIG. 3-3. A numerical simulation was carried out to determine intensity of excitation radiation within and near a sample well 3-210 formed as an SCN. The results show that the intensity of the excitation radiation is about 70% of the incident energy at an entrance aperture of the sample well and drops to about 20% of the incident intensity within about 100 nm in the sample well. For this simulation, the characteristic wavelength of the excitation energy was 633 nm and the diameter of the sample well 3-210 was 140 nm. The sample well 3-210 was formed in a layer of gold metal. Each horizontal division in the graph is 50 nm. As shown by the graph, more than one-half of the excitation energy received in the sample well is localized to about 50 nm within the entrance aperture 3-212 of the sample well.

Figures 1, 3:
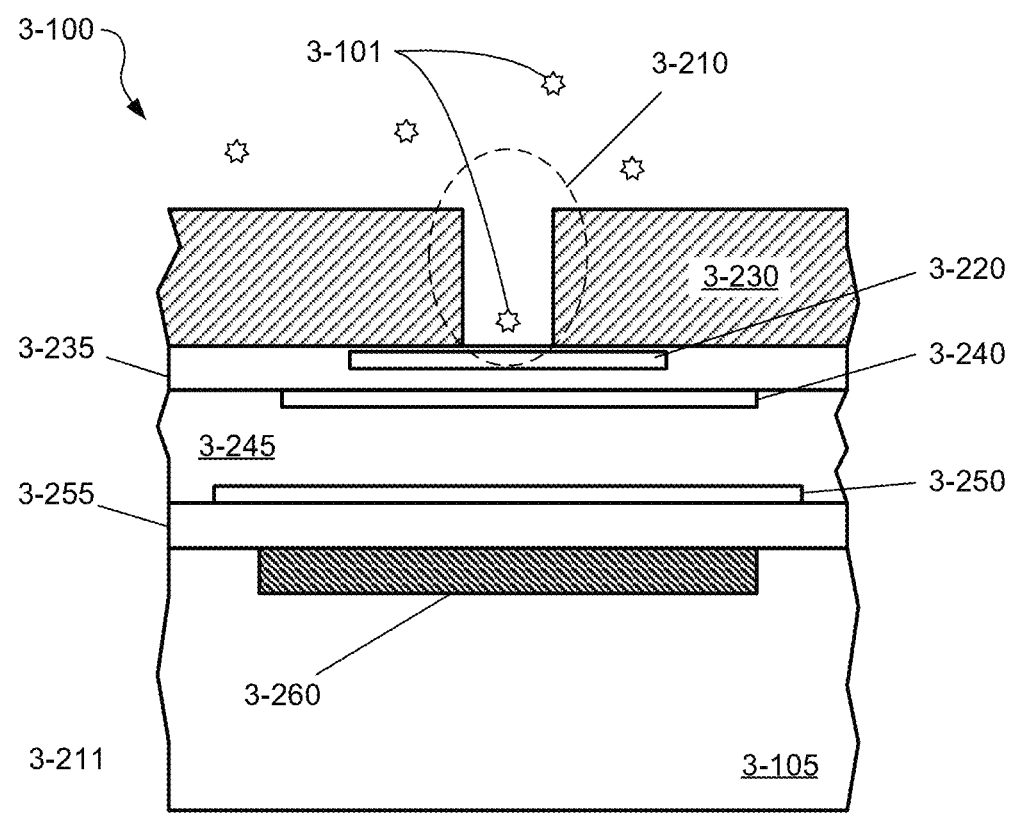
Figures 2, 3:
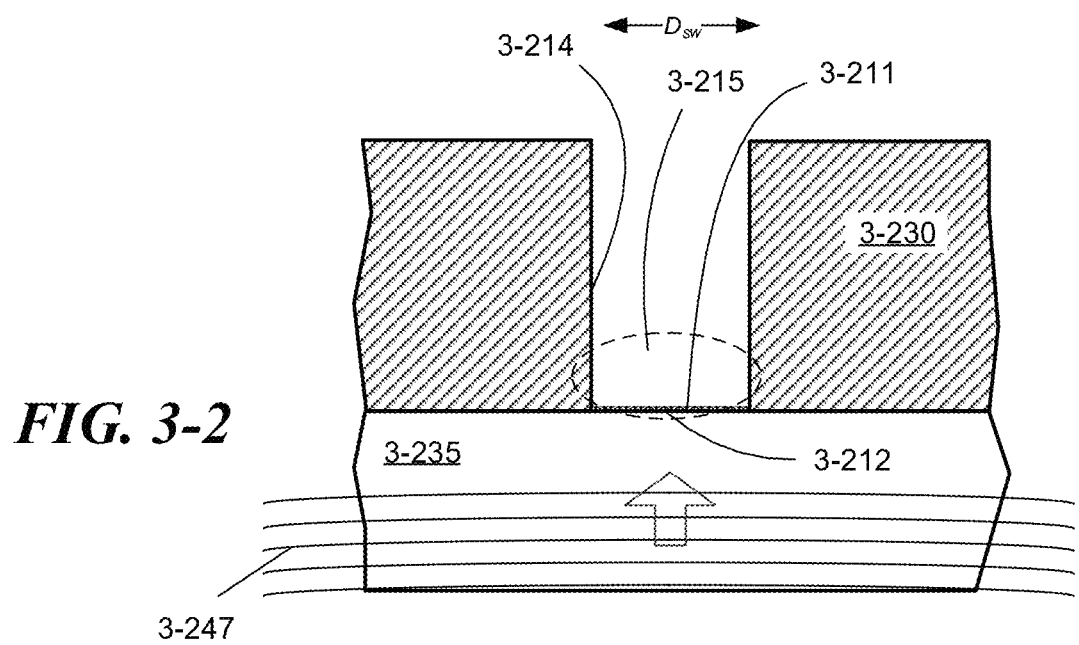
Figure 3:
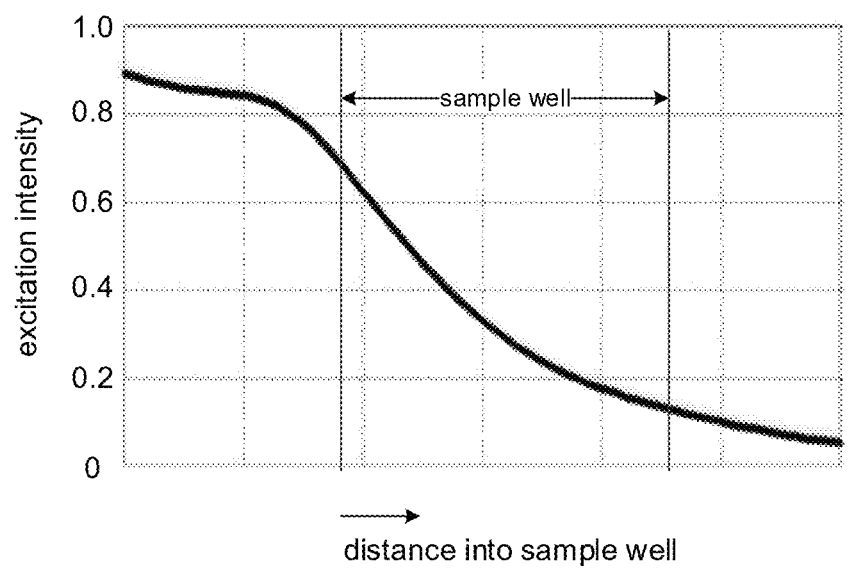
Figures 3, 4:
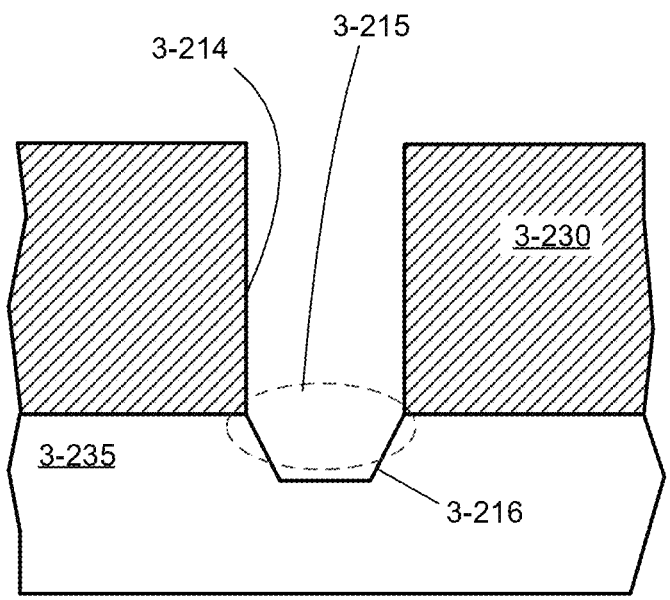

To improve the intensity of excitation energy that is localized at the sample well, other sample well structures were developed and studied by the inventors. FIG. 3-4 depicts an embodiment of a sample well that includes a cavity or divot 3-216 at an excitation end of the sample well 3-210. As can be seen in the simulation results of FIG. 3-3, a region of higher excitation intensity exists just before the entrance aperture 3-212 of the sample well. Adding a divot 3-216 to extend the sample well, as depicted in FIG. 3-4 for example, allows a sample to move into a region of higher excitation intensity, according to some embodiments. In some implementations, the shape and structure of the divot alters the local excitation field (e.g., because of a difference in refractive index between the layer 3-235 and fluid in the sample well), and can further increase the intensity of the excitation energy in the divot.

The divot may have any suitable shape. The divot may have a transverse shape that is substantially equivalent to a transverse shape of the sample well, e.g., round, elliptical, square, rectangular, polygonal, etc. In some embodiments, the sidewalls of the divot may be substantially straight and vertical, like the walls of the sample well. In some implementations, the sidewalls of the divot may be sloped and/or curved, as depicted in the drawing. The transverse dimension of the divot may be approximately the same size as the transverse dimension of the sample well in some embodiments, may be smaller than the transverse dimension of the sample well in some embodiments, or may be larger than the transverse dimension of the sample well in some embodiments. The divot 3-216 may extend between approximately 10 nm and approximately 200 nm beyond the sample well. In some implementations, the divot may extend between approximately 50 nm and approximately 150 nm beyond the sample well. By forming the divot, the excitation region 3-215 may extend outside the region of the sample well that is surrounded by the layer 3-230, as depicted in FIG. 3-4.

Figures 3, 4, 5:
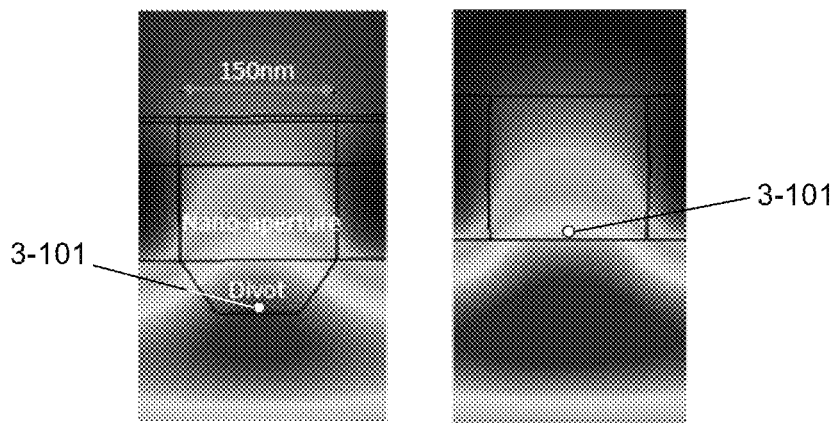

FIG. 3-5 depicts improvement of excitation energy at the excitation region for a sample well containing a divot (shown in the left simulation image). For comparison, the excitation field is also simulated for a sample well without a divot, shown on the right. The field magnitude has been converted from a color rendering in these plots, and the dark region at the base of the divot represents higher intensity than the light region within the sample well. The dark regions above the sample well represents the lowest intensity. As can be seen, the divot allows a sample 3-101 to move to a region of higher excitation intensity, and the divot also increases the localization of region of highest intensity at an excitation end of the sample well. Note that the region of high intensity is more distributed for the sample well without the divot. In some embodiments, the divot 3-216 provides an increase in excitation energy at the excitation region by a factor of two or more. In some implementations, an increase of more than a factor of two can be obtained depending on the shape and length of the divot. In these simulations, the sample well comprises a layer 3-230 of Al that is 100 nm thick, with a divot 3-216 that is 50 nm deep, with excitation energy at 635 nm wavelength.

FIG. 3-6 depicts another embodiment of a sample well 3-210 in which the sample well and divot are formed using a protrusion 3-615 at a surface of a substrate. A resulting structure for the sample well may increase the excitation energy at the sample by more than a factor of two compared to a sample well shown in FIG. 3-1, and may condense emission from the sample well to a sensor 3-260. According to some embodiments, a protrusion 3-615 is patterned in a first layer 3-610 of material. The protrusion may be formed as a circular pedestal in some implementations, and a second layer 3-620 of material may be deposited over the first layer and the protrusion. At the protrusion, the second layer may form a shape above the protrusion that approximates a spherical portion 3-625, as depicted. In some embodiments, a conductive layer 3-230 (e.g., a reflective metal) may be deposited over the second layer 3-620 and patterned to form a sample well 3-210 in the conductive layer above the protrusion. A divot 3-216 may then be etched into the second layer. The divot may extend between about 50 nm and about 150 nm below the conductive layer 3-230. According to some embodiments, the first layer 3-610 and second layer 3-620 may be optically transparent, and may or may not be formed of a same material. In some implementations, the first layer 3-610 may be formed from an oxide (e.g., $SiO_2$) or a nitride (e.g., $Si_3N_4$), and the second layer 3-620 may be formed from an oxide or a nitride.

According to some embodiments, the conductive layer 3-230 above the protrusion 3-625 is shaped approximately as a spherical reflector 3-630. The shape of the spherical portion may be controlled by selection of the protrusion height h, diameter or transverse dimension w of the protrusion, and a thickness t of the second layer 3-620. The location of the excitation region and position of the sample can be adjusted with respect to an optical focal point of the spherical reflector by selection of the divot depth d. It may be appreciated that the spherical reflector 3-630 can concentrate excitation energy at the excitation region 3-215, and can also collect radiation emitted from a sample and reflect and concentrate the radiation toward the sensor 3-260.

As noted above, a sample well may be formed in any suitable shape, and is not limited to only cylindrical shapes. In some implementations, a sample well may be conic, tetrahedron, pentahedron, etc. FIG. 3-7A-FIG. 3-7F illustrates some example sample well shapes and structures that may be used in some embodiments. A sample well 3-210 may be formed to have an entrance aperture 3-212 that is larger than an exit aperture 3-218 for the excitation energy, according to some embodiments. The sidewalls of the sample well may be tapered or curved. Forming a sample well in this manner can admit more excitation energy to the excitation region, yet still appreciably attenuate excitation energy that travels toward the specimen. Additionally, emission radiated by a sample may preferentially radiate toward the end of the sample well with the larger aperture, because of favorable energy transfer in that direction.

In some embodiments, a divot 3-216 may have a smaller transverse dimension than the base of the sample well, as depicted in FIG. 3-7B. A smaller divot may be formed by coating sidewalls of the sample well with a sacrificial layer before etching the divot, and subsequently removing the sacrificial layer. A smaller divot may be formed to retain a sample in a region that is more equidistant from the conductive walls of the sample well. Retaining a sample equidistant from the walls of the sample well may reduce undesirable effects of the sample well walls on the radiating sample, e.g., quenching of emission, and/or altering of radiation lifetimes.

FIGS. 3-7C and 3-7D depict another embodiment of a sample well. According to this embodiment, a sample well 3-210 may comprise excitation-energy-enhancing structures 3-711 and an adherent 3-211 formed adjacent the excitation-energy-enhancing structures. The energy-enhancing structures 3-711 may comprise surface plasmon or nano-antenna structures formed in conductive materials on an optically transparent layer 3-235, according to some embodiments. FIG. 3-7C depicts an elevation view of the sample well 3-210 and FIG. 3-7D depicts a plan view. The excitation-energy-enhancing structures 3-711 may be shaped and arranged to enhance excitation energy in a small localized region. For example, the structures may include pointed conductors having acute angles at the sample well that increase the intensity of the excitation energy within an excitation region 3-215. In the depicted example, the excitation-energy-enhancing structures 3-711 are in the form of a bow-tie. Samples 3-101 diffusing into the region may be retained, temporarily or permanently, by the adherent 3-211 and excited by excitation energy that may be delivered from an excitation source 3-240 located adjacent the sample well 3-210. According to some embodiments, the excitation energy may drive surface-plasmon waves in the energy-enhancing structures 3-711. The resulting surface-plasmon waves may produce high electric fields at the sharp points of the structures 3-711, and these high fields may excite a sample retained in the excitation region 3-215. In some embodiments, a sample well 3-210 depicted in FIG. 3-7C may include a divot 3-216.

Another embodiment of a sample well is depicted in FIG. 3-7E, and shows an excitation-energy-enhancing structure 3-720 formed along interior walls of the sample well 3-210. The excitation-energy-enhancing structure 3-720 may comprise a metal or conductor, and may be formed using an angled (or shadow), directional deposition where the substrate on which the sample well is formed is rotated during the deposition. During the deposition, the base of the sample well 3-210 is obscured by the upper walls of the well, so that the deposited material does not accumulate at the base. The resulting structure 3-720 may form an acute angle 3-722 at the bottom of the structure, and this acute angle of the conductor can enhance excitation energy within the sample well.

In an embodiment as depicted in FIG. 3-7E, the material 3-232 in which the sample well is formed need not be a conductor, and may be any suitable dielectric. According to some implementations, the sample well 3-210 and excitation-energy-enhancing structure 3-720 may be formed at a blind hole etched into a dielectric layer 3-235, and a separate layer 3-232 need not be deposited.

In some implementations, a shadow evaporation may be subsequently performed on the structure shown in FIG. 3-7E to deposit a metallic or conductive energy-enhancing structure, e.g., a trapezoidal structure or pointed cone at the base of the sample well, as depicted by the dashed line. The energy-enhancing structure may enhance the excitation energy within the well via surface plasmons. After the shadow evaporation, a planarizing process (e.g., a chemical-mechanical polishing step or a plasma etching process) may be performed to remove or etch back the deposited material at the top of the sample well, while leaving the energy-enhancing structure within the well.

In some embodiments, a sample well 3-210 may be formed from more than a single metal layer. FIG. 3-7F illustrates a sample well formed in a multi-layer structure, where different materials may be used for the different layers. According to some embodiments, a sample well 3-210 may be formed in a first layer 3-232 (which may be a semiconducting or conducting material), a second layer 3-234 (which may be an insulator or dielectric), and a third layer 3-230 (which may be a conductor or semiconductor). In some embodiments, a degeneratively-doped semiconductor or graphene may be used for a layer of the sample well.

In some implementations, a sample well may be formed in two layers, and in other implementations a sample well may be formed in four or more layers. In some embodiments, multi-layer materials used for forming a sample well may be selected to increase surface-plasmon generation at a base of the sample well or suppress surface-plasmon radiation at a top of the well. In some embodiments, multi-layer materials used for forming a sample well may be selected to suppress excitation radiation from propagating beyond the sample well and multi-layer structure into the bulk specimen.

In some embodiments, multi-layer materials used for forming a sample well may be selected to increase or suppress interfacial excitons which may be generated by excitation radiation incident on the sample well. For example, multi-excitons, such as biexcitons and triexitons, may be generated at an interface between two different semiconductor layers adjacent a sample well. The sample well may be formed in both the metal layer and the first semiconductor layer such that the interface between the first semiconductor layer and a second semiconductor layer is at an excitation region 3-215 of the sample well. Interfacial excitons may have longer lifetimes than excitons within the volume of a single semiconductor layer, increasing the likelihood that the excitons will excite a sample or tag via FRET or DET. In some embodiments, at least one quantum dot at which multi-excitons may be excited may be attached to a bottom of the sample well (e.g., by a linking molecule). Excitons excited at a quantum dot may also have longer lifetimes than excitons within the volume of a single semiconductor layer. Interfacial excitons or excitons generated at a quantum dot may increase the rate of FRET or DET, according to some embodiments.

Various materials may be used to form sample wells described in the foregoing embodiments. According to some embodiments, a sample well 3-210 may be formed from at least one layer of material 3-230, which may comprise any one of or a combination of a conductive material, a semiconductor, and an insulator. In some embodiments, the sample well 3-210 comprises a highly conductive metallic layer, e.g., gold, silver, aluminum, copper. In some embodiments, the layer 3-230 may comprise a multi-layer stack that includes any one of or a combination of gold, silver, aluminum, copper, titanium, titanium nitride, palladium, platinum, and chromium. In some implementations, other metals may be used additionally or alternatively. According to some embodiments, a sample well may comprise an alloy such as AlCu or AlSi.

In some embodiments, the multiple layers of different metals or alloys may be used to form a sample well. In some implementations, the material in which the sample well 3-210 is formed may comprise alternating layers of metals and non-metals, e.g., alternating layers of metal and one or more oxides. In some embodiments, the non-metal may include a polymer, such as polyvinyl phosphonic acid or a polyethylene glycol (PEG)-thiol.

A layer 3-230 in which a sample well is formed may be deposited on or adjacent to at least one optically transparent layer 3-235, according to some embodiments, so that excitation energy (in the form of optical) and emission energy (in the form of optical) may travel to and from the sample well 3-210 without significant attenuation. For example, excitation energy from an excitation source 3-240 may pass through the at least one optically transparent layer 3-235 to the excitation region 3-215, and emission from the sample may pass through the same layer or layers to the sensor 3-260.

In some embodiments, at least one surface of the sample well 3-210 may be coated with one or more layers 3-211, 3-280 of material that affect the action of a sample within the sample well, as depicted in FIG. 3-8. For example, a thin dielectric layer 3-280 (e.g., alumina, titanium nitride, or silica) may be deposited as a passivating coating on sidewalls of the sample well. Such a coating may be implemented to reduce sample adhesion of a sample outside the excitation region 3-215, or to reduce interaction between a sample and the material 3-230 in which the sample well 3-210 is formed. The thickness of a passivating coating within the sample well may be between about 5 nm and about 50 nm, according to some embodiments.

In some implementations, a material for a coating layer 3-280 may be selected based upon an affinity of a chemical agent for the material, so that the layer 3-280 may be treated with a chemical or biological substance to further inhibit adhesion of a sample species to the layer. For example, a coating layer 3-280 may comprise alumina, which may be passivated with a polyphosphonate passivation layer, according to some embodiments. Additional or alternative coatings and passivating agents may be used in some embodiments.

According to some embodiments, at least a bottom surface of the sample well 3-210 and/or divot 3-216 may be treated with a chemical or biological adherent 3-211 (e.g., biotin) to promote retention of a sample. The sample may be retained permanently or temporarily, e.g., for at least a period of time between about 0.5 milliseconds and about 50 milliseconds. In another embodiment, the adherent may promote temporary retention of a sample 3-101 for longer periods. Any suitable adherent may be used in various embodiments, and is not limited to biotin.

According to some embodiments, the layer of material 3-235 adjacent the sample well may be selected based upon an affinity of an adherent for the material of that layer. In some embodiments, passivation of the sample well's side walls may inhibit coating of an adherent on the sidewalls, so that the adherent 3-211 preferentially deposits at the base of the sample well. In some embodiments, an adherent coating may extend up a portion of the sample well's sidewalls. In some implementations, an adherent may be deposited by an anisotropic physical deposition process (e.g., evaporation, sputtering), such that the adherent accumulates at the base of a sample well or divot and does not appreciably form on sidewalls of the sample well.

III. C Sample Well Fabrication

Various fabrication techniques may be employed to fabricate sample wells 3-210 for an integrated device. A few example processes are described below, but the invention is not limited to only these examples.

The sample well 3-210 may be formed by any suitable micro- or nano-fabrication process, which may include, but is not limited to, processing steps associated with photolithography, deep-ultraviolet photolithography, immersion photolithography, near-field optical contact photolithography, EUV lithography, x-ray lithography, nanoimprint lithography, interferometric lithography, step-and-flash lithography, direct-write electron beam lithography, ion beam lithography, ion beam milling, lift-off processing, reactive-ion etching, etc. According to some embodiments, a sample well 3-210 may be formed using photolithography and lift-off processing. Example fabrication steps associated with lift-off processing of a sample well are depicted in FIG. 3-9. Although fabrication of only a single sample well or structure at a pixel is typically depicted in the drawings, it will be understood that a large number of sample wells or structures may be fabricated on a substrate (e.g., at each pixel) in parallel.

According to some embodiments, a layer 3-235 (e.g., an oxide layer) on a substrate may be covered with an anti-reflection (ARC) layer 3-910 and photoresist 3-920, as depicted in FIG. 3-9A. The photoresist may be exposed and patterned using photolithography and development of the resist. The resist may be developed to remove exposed portions or unexposed portions (depending on the resist type), leaving a pillar 3-922 that has a diameter approximately equal to a desired diameter for the sample well, as depicted in FIG. 3-9B. The height of the pillar may be greater than a desired depth of the sample well.

The pattern of the pillar 3-922 may be transferred to the ARC layer 3-910 via anisotropic, reactive ion etching (RIE), for example as shown in FIG. 3-9C. The region may then be coated with at least one material 3-230, e.g., a conductor or metal, that is desired to form the sample well. A portion of the deposited material, or materials, forms a cap 3-232 over the pillar 3-922, as depicted in FIG. 3-9D. The resist and ARC may then be stripped from the substrate, using a selective removal process (e.g., using a chemical bath with or without agitation which dissolves at least the resist and releases or "lifts off" the cap). If the ARC remains, it may be stripped from the substrate using a selective etch, leaving the sample well 3-210 as shown in FIG. 3-9E. According to some embodiments, the sidewalls 3-214 of the sample well may be sloped due to the nature of the deposition of the at least one material 3-230.

As used herein, a "selective etch" means an etching process in which an etchant selectively etches one material that is desired to be removed or etched at a higher rate (e.g., at least twice the rate) than the etchant etches other materials which are not intended to be removed.

Because the resist and ARC are typically polymer based, they are considered soft materials which may not be suitable for forming sample wells having high aspect ratios (e.g., aspect ratios greater than about 2:1 with respect to height-to-width). For sample wells having higher aspect ratios, a hard material may be included in the lift-off process. For example, before depositing the ARC and photoresist, a layer of a hard (e.g., an inorganic material) may be deposited. In some embodiments, a layer of titanium or silicon nitride may be deposited. The layer of hard material should exhibit preferential etching over the material, or materials, 3-230 in which the sample well is formed. After the photoresist is patterned, a pattern of the pillar may be transferred into the ARC and the underlying hard material 3-930 yielding a structure as depicted in FIG. 3-9F. The photoresist and ARC may be then stripped, the material(s) 3-230 deposited, and a lift-off step performed to form the sample well.

According to some embodiments, a lift-off process may be used to form a sample well comprising energy-enhancing structures 3-711, as depicted in FIG. 3-7C and FIG. 3-7D.

An alternative process for forming a sample well is depicted in FIG. 3-10. In this process, the sample well may be directly etched into at least one material 3-230. For example, at least one material 3-230 in which a sample well is to be formed may be deposited on a substrate. The layer may be covered by an ARC layer 3-910 and a photoresist 3-920, as illustrated in FIG. 3-10A. The photoresist may be patterned to form a hole having a diameter approximately equal to a desired diameter of the sample well, as depicted in FIG. 3-10B. The pattern of the hole may be transferred to the ARC and through the layer 3-230 using an anisotropic, reactive ion etch, as shown in FIG. 3-10C for example. The resist and ARC may be stripped, yielding a sample well as depicted in FIG. 3-10D. According to some embodiments, the sidewalls of a sample well formed by etching into the layer of material 3-230 may be more vertical than sidewalls resulting from a lift-off process.

In some embodiments, the photoresist and ARC may be used to pattern a hard mask (e.g., a silicon nitride or oxide layer, not shown) over the material 3-230. The patterned hole may then be transferred to the hard mask, which is then used to transfer the pattern into the layer of material 3-230. A hard mask may allow greater etching depths into the layer of material 3-230, so as to form sample wells of higher aspect ratio.

It will be appreciated that lift-off processes and direct etching fabrication techniques described above may be used to form a sample well when multiple layers of different materials are used to form a stack of material 3-230 in which the sample well is formed. An example stack is shown in FIG. 3-11. According to some embodiments, a stack of material may be used to form a sample well to improve coupling of excitation energy to the excitation region of a sample well, or to reduce transmission or re-radiation of excitation energy into the bulk specimen. For example, an absorbing layer 3-942 may be deposited over a first layer 3-940. The first layer may comprise a metal or metal alloy, and the absorbing layer may comprise a material that inhibits surface plasmons, e.g., amorphous silicon, TaN, TiN, or Cr. In some implementations, a surface layer 3-944 may also be deposited to passivate the surface surrounding the sample well (e.g., inhibit adhesion of molecules).

Formation of a divot 3-216 adjacent a sample well may be done in any suitable manner. In some embodiments, a divot may be formed by etching further into an adjacent layer 3-235, and/or any intervening layer or layers, adjacent the sample well. For example, after forming a sample well in a layer of material 3-230, that layer 3-230 may be used as an etch mask for patterning a divot, as depicted in FIG. 3-12. For example, the substrate may be subjected to a selective, anisotropic reactive ion etch so that a divot 3-216 may be etched into adjacent layer 3-235. For example, in an embodiment where the material 3-230 is metallic and the adjacent layer 3-235 silicon oxide, a reactive-ion plasma etch having a feed gas comprising $CHF_3$ or $CF_4$ may be used to preferentially remove exposed silicon oxide below the sample well and form the divot 3-216. As used herein, "silicon oxide" generally refers to $SiO_x$ and may include silicon dioxide, for example.

In some embodiments, conditions within the plasma (e.g., bias to the substrate and pressure) during an etch may be controlled to determine the etch profile of the divot. For example, at low pressure (e.g., less than about 100 mTorr) and high DC bias (e.g., greater than about 20V), the etching may be highly anisotropic and form substantially straight and vertical sidewalls of the divot, as depicted in the drawing. At higher pressures and lower bias, the etching may be more isotropic yielding tapered and/or curved sidewalls of the divot. In some implementations, a wet etch may be used to form the divot, which may be substantially isotropic and form an approximately spherical divot that may extend laterally under the material 3-230, up to or beyond the sidewalls of the sample well.

FIG. 3-13A through FIG. 3-13C depict process steps that may be used to form a divot 3-216 having a smaller transverse dimension than the sample well 3-210 (for example, a divot like that depicted in FIG. 3-7B). In some implementations, after forming a sample well, a conformal sacrificial layer 3-960 may be deposited over a region including the sample well. According to some embodiments, the sacrificial layer 3-960 may be deposited by a vapor deposition process, e.g., chemical vapor deposition (CVD), plasma-enhanced CVD, or atomic layer deposition (ALD). The sacrificial layer may then be etched back using a first anisotropic etch that is selective to the sacrificial layer 3-960, removes the layer from horizontal surfaces, leaves side wall coatings 3-962 on walls of the sample well, as depicted in FIG. 3-13B. The etch back may be selective and stop on the material 3-230 and adjacent layer 3-235 in some embodiments, or may be a non-selective, timed etch in some embodiments.

A second anisotropic etch that is selective to the adjacent layer 3-235 may be executed to etch a divot 3-216 into the adjacent layer as depicted in FIG. 3-13C. The sacrificial side wall coatings 3-962 may then optionally be removed by a selective wet or dry etch. The removal of the sidewall coatings open up the sample well to have a larger transverse dimension than the divot 3-216.

According to some embodiments, the sacrificial layer 3-960 may comprise the same material as the adjacent layer 3-235. In such embodiments, the second etch may remove at least some of the side wall coating 3-962 as the divot is etched into the adjacent layer 3-235. This etch back of the side wall coating can form tapered sidewalls of the divot in some embodiments.

In some implementations, the sacrificial layer 3-960 may be formed from, or include a layer of, a material that is used to passivate the sidewalls of the sample well (e.g., reduce adhesion of samples at the sidewalls of the sample well). At least some of the layer 3-960 may then be left on the walls of the sample well after formation of the divot.

According to some embodiments, the formation of the sidewall coatings 3-962 occurs after the formation of the divot. In such an embodiment the layer 3-960 coats the sidewalls of the divot. Such a process may be used to passivate the sidewalls of the divot and localize the sample at the center of the divot.

Process steps associated with depositing an adherent 3-211 at a base of a sample well 3-210, and a passivation layer 3-280 are depicted in FIG. 3-14. According to some embodiments, a sample well may include a first passivation layer 3-280 on walls of the sample well. The first passivation layer may be formed, for example, as described above in connection with FIG. 3-13B or FIG. 3-8. In some embodiments, a first passivation layer 3-280 may be formed by any suitable deposition process and etch back. In some embodiments, a first passivation layer may be formed by oxidizing the material 3-230 in which the sample well is formed. For example, the sample well may be formed of aluminum, which may be oxidized to create a coating of alumina on sidewalls of the sample well.

An adherent 3-980 or an adherent precursor (e.g., a material which preferentially binds an adherent) may be deposited on the substrate using an anisotropic physical deposition process, e.g., an evaporative deposition, as depicted in FIG. 3-14A. The adherent or adherent precursor may form an adherent layer 3-211 at the base of the sample well, as depicted in FIG. 3-14B, and may coat an upper surface of the material 3-230 in which the sample well is formed. A subsequent angled, directional deposition depicted in FIG. 3-14C (sometimes referred to as a shadow deposition or shadow evaporation process) may be used to deposit a second passivation layer 3-280 over an upper surface of the material 3-230 without covering the adherent layer 3-211. During the shadow deposition process, the substrate may be rotated around an axis normal to the substrate, so that the second passivation layer 3-280 deposits more uniformly around an upper rim of the sample well. A resulting structure is depicted in FIG. 3-14D, according to some embodiments. As an alternative to depositing the second passivation layer, a planarizing etch (e.g., a CMP step) may be used to remove adherent from an upper surface of the material 3-230.

According to some implementations, an adherent layer 3-211 may be deposited centrally at the base of a tapered sample well, as depicted in FIG. 3-15. For example, an adherent, or adherent precursor, may be directionally deposited, as depicted in FIG. 3-14A, in a tapered sample well, formed as described above. Walls of the sample well may be passivated by an oxidation process before or after deposition of the adherent layer 3-211. Adherent or precursor remaining on a surface of the material 3-230 may be passivated as described in connection with FIG. 3-14D. In some embodiments, an adherent on an upper surface of the material 3-230 may be removed by a chemical-mechanical polishing step. By forming an adherent layer, or an adherent layer precursor, centrally at the base of a sample well, deleterious effects on emission from a sample (e.g., suppression or quenching of sample radiation from sample walls, unfavorable radiation distribution from a sample because it is not located centrally with respect to energy coupling structures formed around a sample well, adverse effects on luminescent lifetime for a sample) may be reduced.

In some embodiments, lift-off patterning, etching, and deposition processes used to form the sample well and divot may be compatible with CMOS processes that are used to form integrated CMOS circuits on an integrated device. Accordingly, an integrated device may be fabricated using conventional CMOS facilities and fabrication techniques, though custom or specialized fabrication facilities may be used in some implementations.

Variations of the process steps described above may be used to form alternative embodiments of sample wells. For example, a tapered sample well such as depicted in FIG. 3-7A or FIG. 3-7B may be formed using an angled deposition process depicted in FIG. 3-14C. For the sample well of FIG. 3-7B, the angle of deposition may be changed during the deposition process. For such embodiments, a sample well having substantially straight and vertical sidewalls may first be formed, and then additional material 3-230 deposited by an angled deposition to taper the sidewalls of the sample well.

In some embodiments, a sample well 3-210 may be formed at a pixel after an excitation source is formed. For example, an excitation source for a pixel may be formed at another region and/or at another level on the integrated device, within or outside a pixel. The type of excitation source may place processing constraints on the steps used to fabricate the sample well 3-210. For example, if the excitation source comprises an organic light-emitting diode (OLED), then processing steps used to fabricate the sample well 3-210 may not exceed temperatures greater than about 100° C. Further, the processing steps may not subject the OLED to harsh chemical environments or oxidizing environments.

Any one or more of the foregoing embodiments of sample wells may be included in an embodiment of an integrated device.

IV. Excitation Sources

Referring again to FIG. 3-1, there are different types of excitations sources 3-240 that may be used on an integrated device to excite a sample 3-101 within a sample well 3-210. According to some embodiments, an excitation source may excite a sample via a radiative process. For example, an excitation source may provide visible radiation (e.g., radiation having a wavelength between about 350 nm and about 750 nm), near-infrared radiation (e.g., radiation having a wavelength between about 0.75 micron and about 1.4 microns), and/or short wavelength infrared radiation (e.g., radiation having a wavelength between about 1.4 microns and about 3 microns) to at least one excitation region 3-215 of at least one sample well. According to some implementations, an excitation source may provide energy that excites a sample via a non-radiative process. For example, energy may be transferred to a sample via Förster resonant energy transfer (FRET) or Dexter energy transfer (DET).

Combinations of energy transfer pathways are also contemplated. For example, a radiative excitation source may provide energy to excite an intermediary (e.g., a molecule, a quantum dot, or a layer of material comprising selected molecules and/or quantum dots) that is immediately adjacent an excitation region of a sample well. The intermediary may transfer its energy to a sample via a non-radiative process (e.g., via FRET or DET).

In some embodiments, an excitation source may provide more than one source of excitation energy. For example, a radiative excitation source may deliver excitation energies having two or more distinct spectral characteristics. As an example, a multi-color LED may emit energies centered at two or more wavelengths, and these energies may be delivered to an excitation region of a sample well.

IV. A. Radiative Excitation Sources

In overview and according to some embodiments, an integrated device may include at least one radiative excitation source arranged on the device to provide excitation energy to at least one excitation region of at least one sample well or to at least one intermediary that converts or couples the excitation energy to at least one sample within one or more excitation regions. As depicted in FIG. 3-2, radiation 3-247 from an excitation source 3-240 may impinge on a region around a sample well 3-210, for example. In some embodiments, there may be excitation-coupling structures (not shown) that aid in concentrating the incident excitation energy within an excitation region 3-215 of the sample well.

A radiative excitation source may be characterized by one or more distinct spectral bands each having a characteristic wavelength. For instructional purposes only, an example of spectral emission from an excitation source is depicted in spectral graph of FIG. 4-1A. The excitation energy may be substantially contained within a spectral excitation band 4-110. A peak wavelength 4-120 of the spectral excitation band may be used to characterize the excitation energy. The excitation energy may also be characterized by a spectral distribution, e.g., a full-width-half-maximum (FWHM) value as shown in the drawing. An excitation source producing energy as depicted in FIG. 4-1A, may be characterized as delivering energy at a wavelength of approximately 540 nm radiation and having a FWHM bandwidth of approximately 55 nm.

Figures 1A, 4:
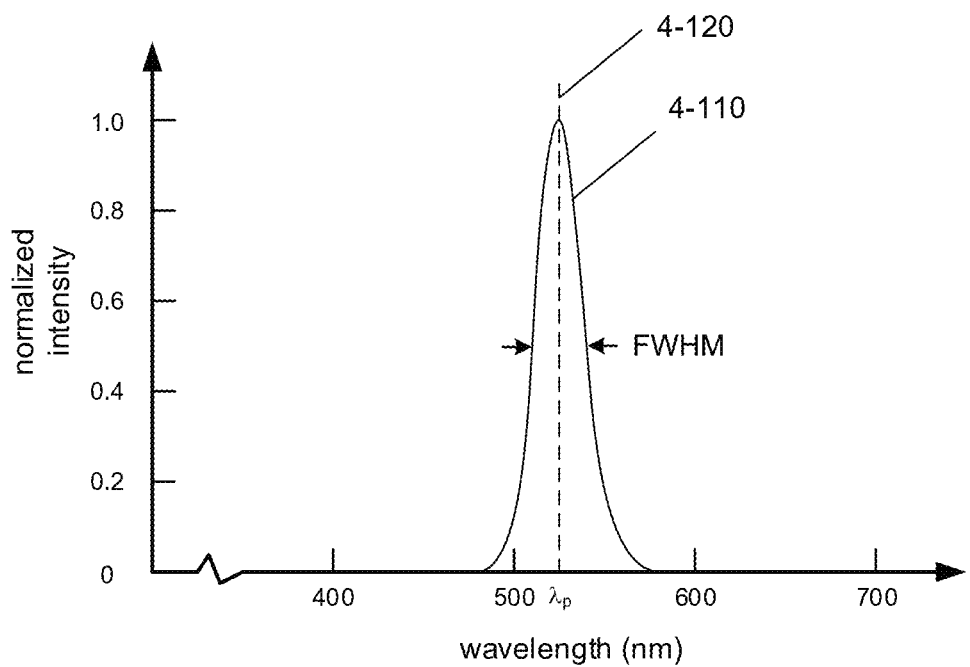
Figures 1B, 4:
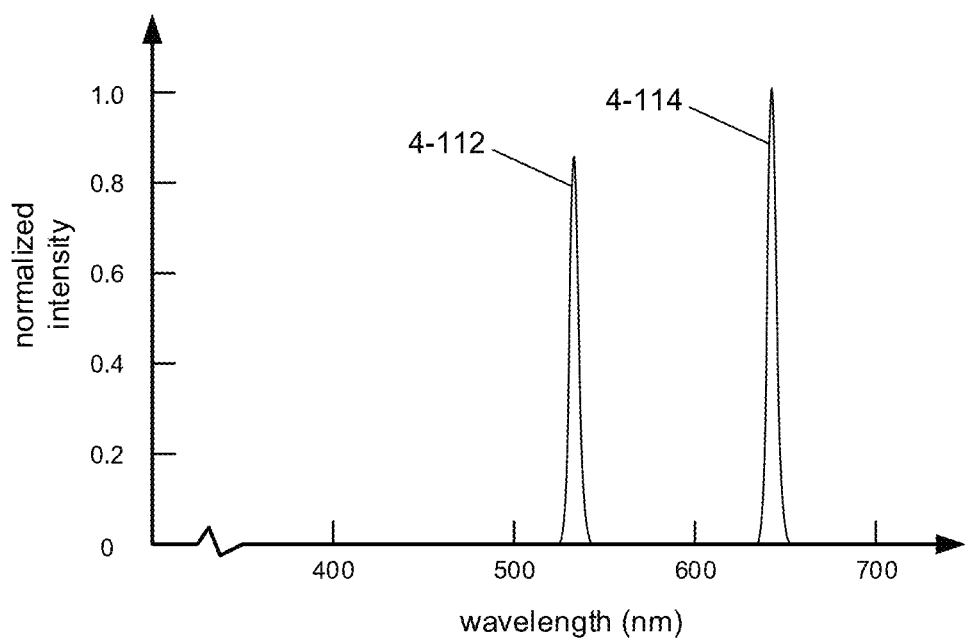
Figures 2A, 4:
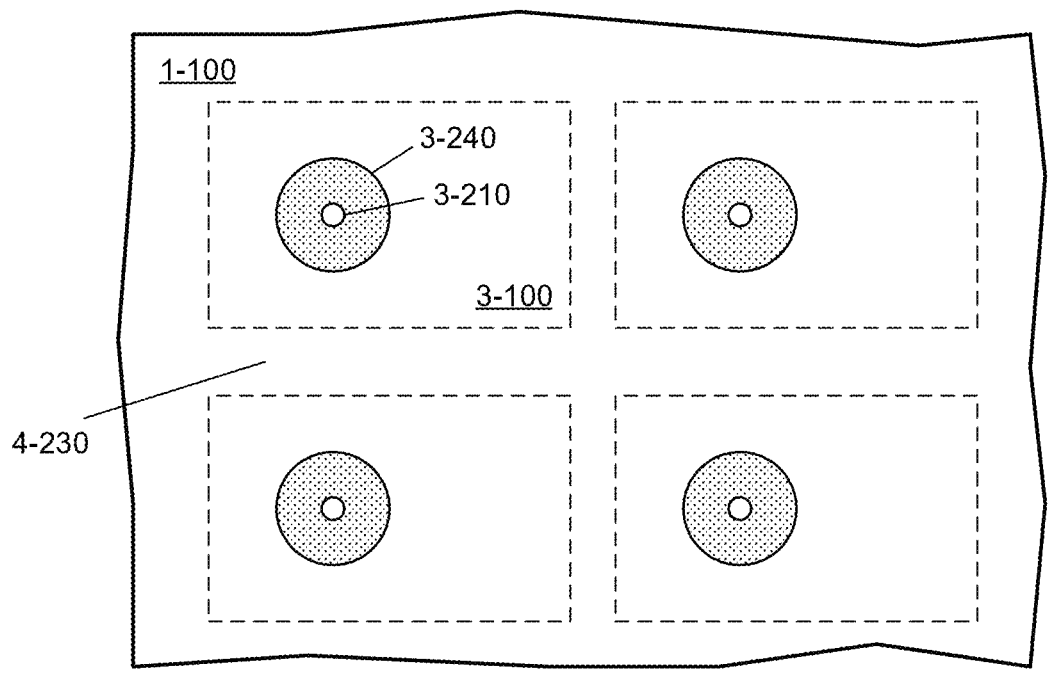
Figures 2B, 4:
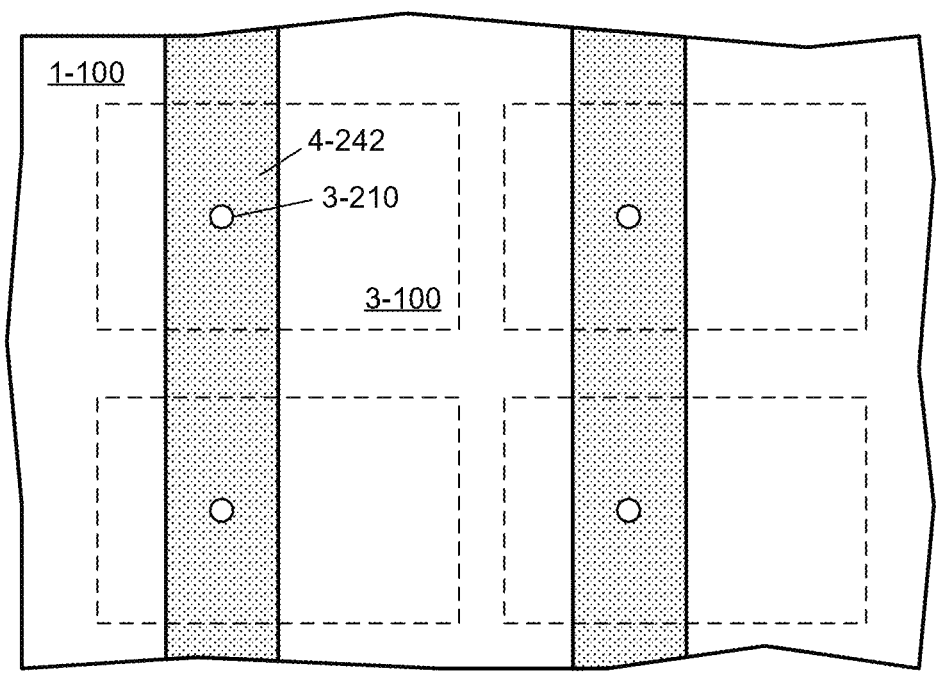

FIG. 4-1B depicts spectral characteristics of an excitation source (or excitation sources) that can provide two excitation energy bands to one or more sample wells. According to some embodiments, a first excitation band 4-112 is at approximately 532 nm, and a second excitation band 4-114 is at approximately 638 nm, as illustrated in the drawing. In some embodiments, a first excitation band may be at approximately 638 nm, and a second excitation band may be at approximately 650 nm. In some embodiments, a first excitation band may be at approximately 680 nm, and a second excitation band may be at approximately 690 nm. According to some embodiments, the peaks of the excitation bands may be within ±5 nm of these values. Other excitation bands may be used in some embodiments.

In some cases, a radiative excitation source may produce a broad excitation band as depicted in FIG. 4-1A. A broad excitation band 4-110 may have a bandwidth greater than approximately 20 nm, according to some embodiments. A broad excitation band may be produced by a light emitting diode (LED), for example. In some implementations, a radiative excitation source may produce a narrow excitation band, as depicted in FIG. 4-1B. A narrow excitation band may be produced by a laser diode, for example, or may be produced by spectrally filtering an output from an LED.

In some embodiments, at least one excitation source 3-240 may be formed at each active pixel 3-100 on a substrate 1-100 of an integrated device, as depicted in FIG. 4-2A. Since a sample well and its excitation region are small (e.g., having a transverse dimension on the order of 100 nm), an excitation source 3-240 may be formed only in the vicinity of a sample well 3-210, as depicted in FIG. 4-2A, according to some embodiments. For example, an excitation source may have a transverse dimension that is less than about 20 times a transverse dimension of a sample well (e.g., less than about 2 microns in diameter for a sample well having a diameter of about 100 nm.) Although FIG. 4-2A depicts only four pixels, there may be many more pixels on a substrate 1-100.

In some aspects, each excitation source may be individually controlled. This may require interconnects and drive circuitry (not shown in FIG. 4-2A) on the substrate 1-100 for row-and-column addressing of each source. The interconnects may run below the pixels and/or in gaps 4-230 between pixels 3-100. According to some embodiments, integrated wiring and circuitry may be arranged to control and drive rows or columns of excitation sources separately. For example, all excitation sources 3-240 in a row may be driven together with a common control signal. In some embodiments, integrated wiring and circuitry may be arranged to control and drive groups of excitation sources on a substrate with a common control signal. In some implementations, integrated wiring and circuitry may be arranged to control and drive all excitation sources with a common control signal. By driving a larger number of excitation sources together, fewer interconnects and drive electronics are required for the excitation sources.

FIG. 4-2B depicts an embodiment where the excitation sources 4-242 are arranged in strips on a substrate 1-100 of an integrated device. When arranged in strips, the excitation sources may exhibit wave guiding properties, and light from the excitation sources may be guided laterally along the strips to the sample wells 3-210. The strip excitation sources 4-242 may be driven individually in some embodiments, or may be driven together. In some embodiments, the strips may be a arranged in a grid pattern intersecting at the sample wells.

In some implementations, there may be fewer excitation sources formed on an integrated device than pixels, and light from an excitation source may be delivered to more than one sample well via an excitation-coupling structure such as a waveguide. In some cases, a single excitation source may extend across all active pixels, be controlled by a single drive signal, and simultaneously illuminate excitation regions in all of the sample wells.

Figures 2C, 4:
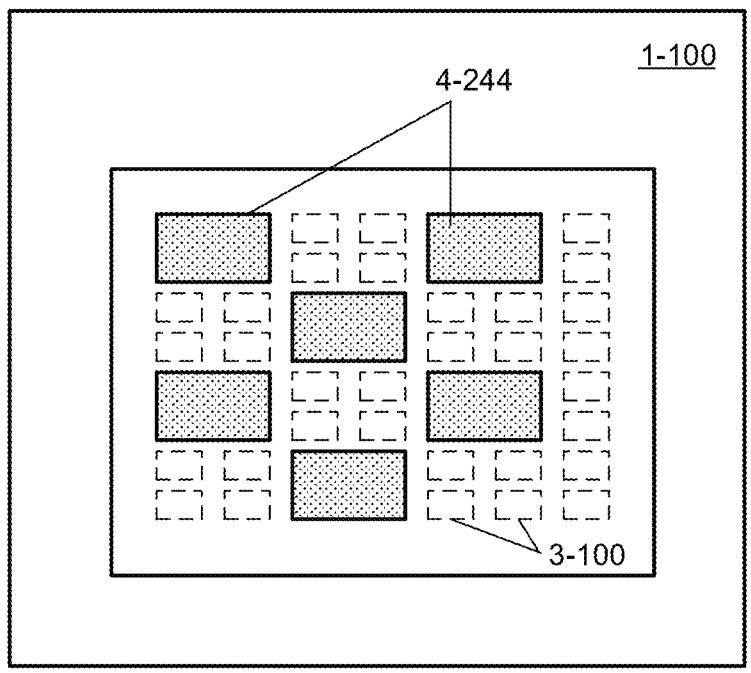

According to some embodiments, excitation sources 4-244 may be arranged in a checkerboard pattern, as depicted in FIG. 4-2C. In such an embodiment, the excitation sources 4-244 may be located in regions where there are no pixels 3-100. Locating excitation sources in regions apart from the pixels may ease fabrication constraints for manufacturing an integrated device. For example, fabrication of the excitation sources may be carried out after fabrication of the sensors and sample wells. Energy from the excitation sources may be provided to the pixels via strip or slab waveguides (not shown), for example. The excitation sources 4-244 may be driven individually according to some embodiments, in groups according to some embodiments, or all together in some embodiments. Driving excitation sources individually may require a greater number of control circuits and interconnects than may be required for driving a group of excitation sources.

Figures 2D, 4:
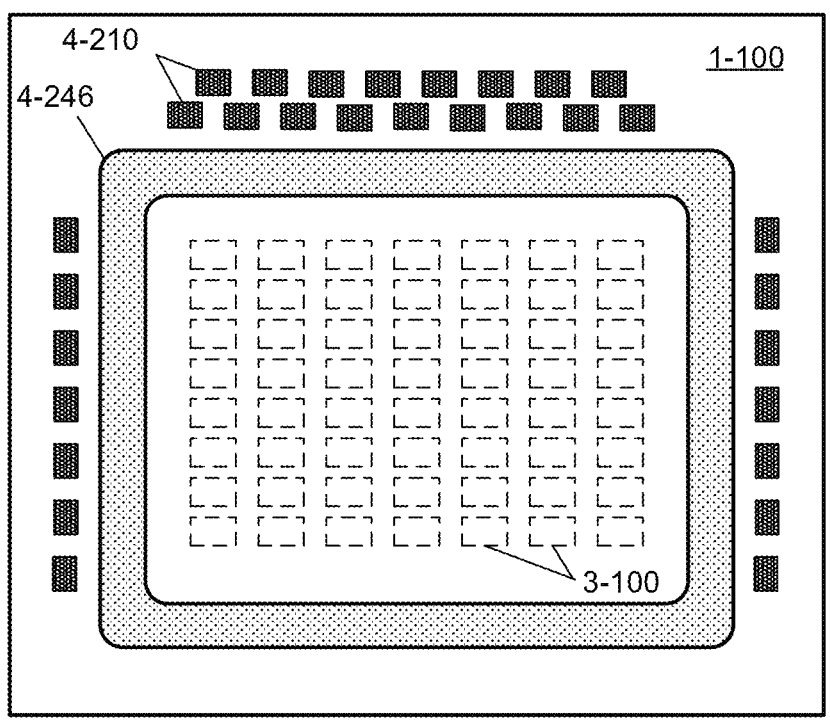

In some implementations, an excitation source 4-246 may be formed around a group of pixels 3-100, as depicted in FIG. 4-2D. Radiation from the excitation source 4-246 may be delivered to the pixels 3-100 via a slab waveguide or strip waveguides, according to some embodiments. In some implementations, there may be a reflective wall at the periphery of the excitation source 4-246 to reflect radiation inward toward the pixels. In some embodiments, there may be integrated circuits 4-210 (e.g., drive electronic devices, amplifiers, transistors, and/or readout circuitry) located around the periphery of the integrated device on substrate 1-100.

By placing the excitation sources in regions where there are no pixels, fabrication of the integrated device may be simplified. For example, a fabrication process for the excitation sources 4-244 may be substantially independent of the fabrication process for the pixels 3-100 For example, the excitation sources depicted in FIG. 4-2C and FIG. 4-2D may be fabricated after fabrication of the pixels and/or integrated circuitry 4-210. This may be desirable when the excitation source comprises an organic or other material that may be sensitive to or degraded by high process temperatures that may be needed to fabricate the pixel structures and/or integrated circuits of the integrated device.

Figures 2E, 4:
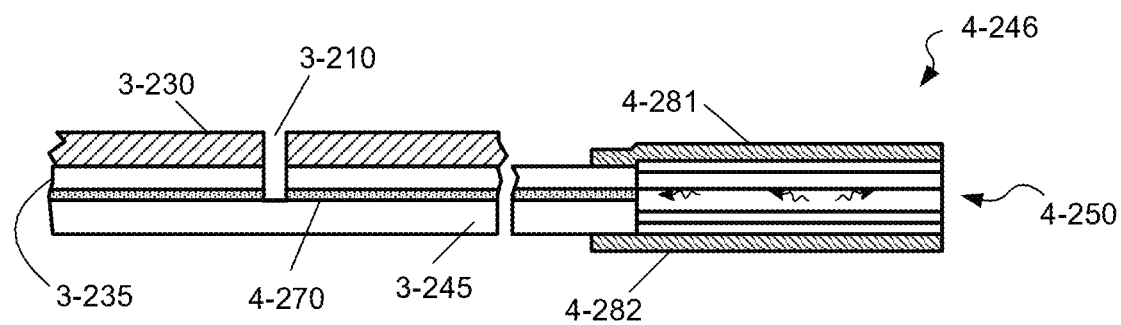

FIG. 4-2E depicts an embodiment where an excitation source 4-246 is patterned in a region of the substrate 1-100 adjacent a group of pixels. The drawing depicts an elevation view of both the excitation source 4-246 and a sample well 3-210 that may be located more than 100 microns from the excitation source. The sample well may be located within any pixel within a group of pixels on the integrated device. The excitation source 4-246 may comprise an edge-emitting light emitting diode (LED) in some implementations, or laser diode in some embodiments, and comprise a diode stack 4-250. Electrical connection to the diode stack may include a cathode pad 4-281 and an anode pad 4-282. The cathode and anode may be metallic and reflective and may include scattering structures to reflect and/or scatter radiation laterally.

According to some embodiments, light from the diode 4-246 may couple into a slab waveguide that guides the radiation to the sample wells within a group of pixels. The slab waveguide may comprise a first dielectric layer 3-235, a core layer 4-270, and a second dielectric layer 3-245. The refractive index of the core layer 4-270 may be greater than the refractive index of the first and second dielectric layers. For example, the core layer may comprise a silicon nitride layer, and the first and second dielectric layers may comprise silicon oxide layers. Light from the excitation source 4-246 may be substantially confined to the core dielectric layer 4-270, and guided to the sample wells 3-210. In some embodiments, a divot of the sample well may extend to, partway through, or fully through the core layer 4-270. In some embodiments, the core layer may serve as an etch stop during etching of the divots at the sample wells.

Although the embodiment depicted in FIG. 4-2E is described in connection with the distributed excitation source 4-246 as depicted in FIG. 4-2D, in other embodiments discrete excitation sources may be located at the periphery of a group of pixels and delivered to at least some pixels (e.g., pixels in one or more rows or columns) via strip waveguides rather than a slab waveguide.

Figures 3A, 4:
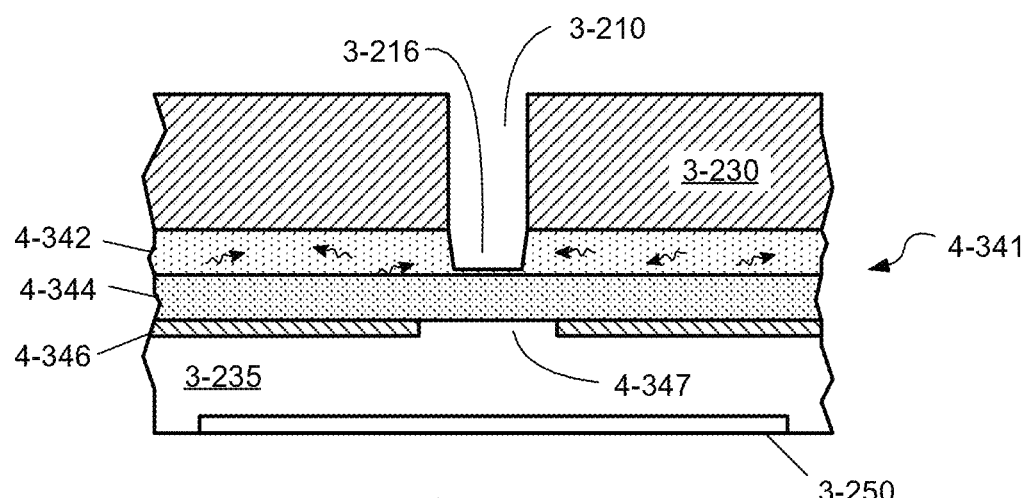
Figures 3B, 4:
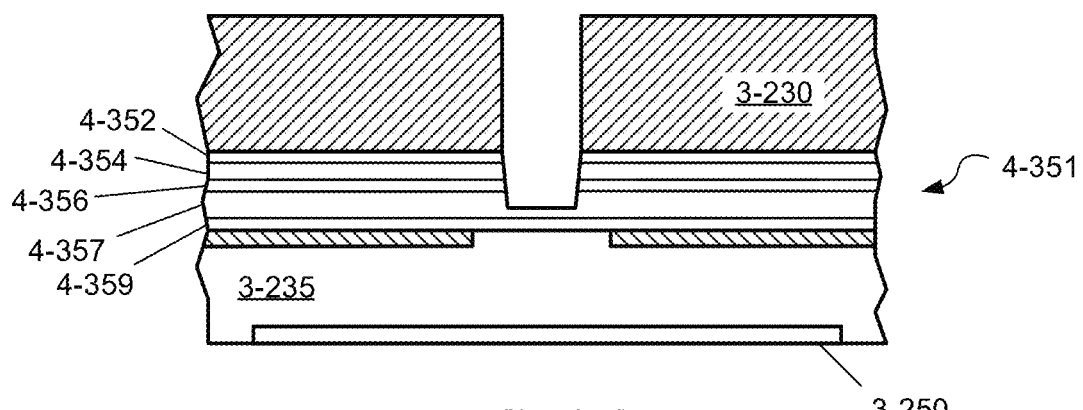
Figures 3C, 4:
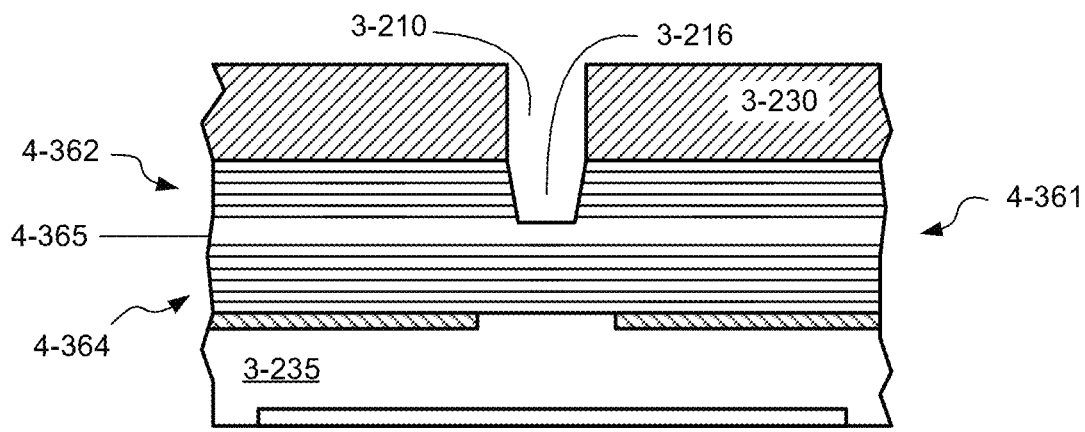
Figures 3D, 4:
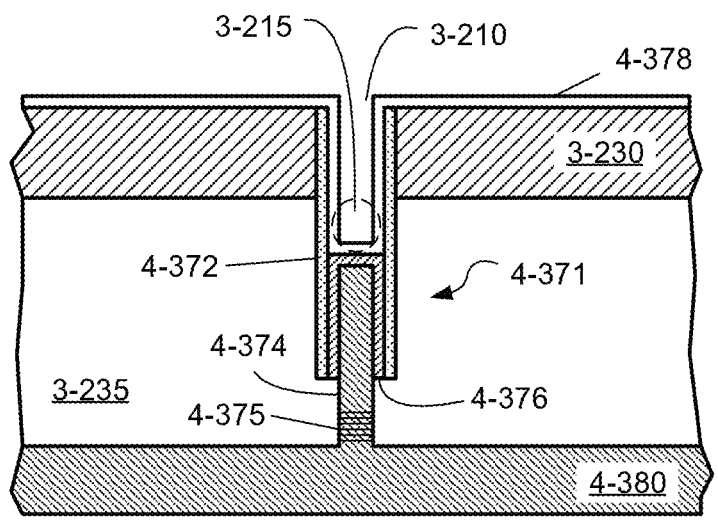
Figures 3E, 4:
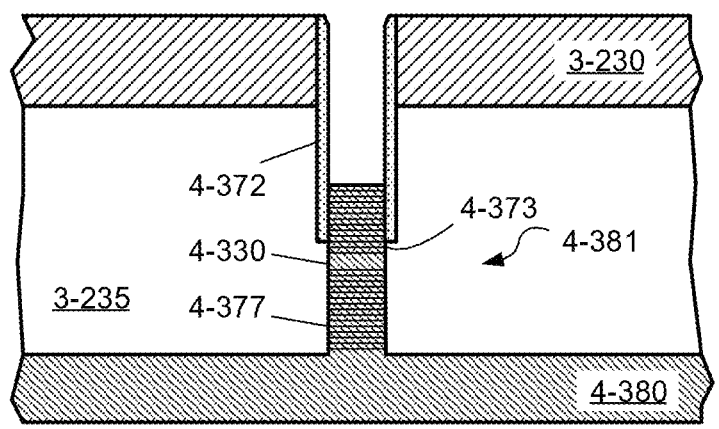

Various types of radiative excitation sources are depicted in FIG. 4-3A through FIG. 4-3E. According to some embodiments, an excitation source may comprise an organic light emitting diode (OLED). An OLED may comprise an organic emissive layer 4-342 and an organic conducting layer 4-344, as depicted in FIG. 4-3A. Each organic layer may comprise organic molecules and/or be formed of an organic polymer. Organic molecules in the emissive layer may be selected to emit at a desired wavelength or a combination of desired wavelengths. Electrical contact to the OLED may be made through a cathode and an anode 4-346. The anode may be formed of any suitable conductive material, and may be formed prior to deposition of the organic layers. The anode 4-346 may include an opening 4-347 adjacent the sample well, so that emission from a sample may pass through the substrate to a sensor located below the sample, according to some embodiments. In some embodiments, the cathode may comprise conductive material 3-230 or a conductive layer in which the sample well 3-210 is formed. In some implementations, a divot 3-216 may be formed into the emissive layer 4-342 of the OLED, so that light from the OLED may be delivered more efficiently into the excitation region of the sample well.

In some implementations, an OLED may be vertically spaced farther from a sample well than is shown in FIG. 4-3A. For example, an OLED may be formed below an insulating or transparent layer 3-235. In such embodiments, a cathode of the OLED may comprise a transparent conductor, such as indium tin oxide (ITO), so that light from the OLED may pass through to the sample well. According to some embodiments, an OLED may be spaced below a sample well between 500 nm and 10 microns.

One advantage of using an OLED for the integrated device is that modern OLEDs are capable of high light intensity output. Another advantage is a low cost of OLEDs. Issues associated with OLED lifetime are not problematic for an integrated device, since an integrated device may be used one or a few times, and may be disposed before there is sufficient use of the OLED to degrade its performance.

Solid-state or semiconductor LEDs may also be used to illuminate sample wells according to some embodiments. FIG. 4-3B depicts an integrated semiconductor light emitting diode that may be fabricated adjacent to a sample well, in some implementations. A semiconductor LED may comprise a plurality of layers, as depicted in the drawing. The layers may include an electron transport layer 4-352, a hole blocking layer 4-354, and emissive layer 4-356, a hole transport layer 4-357, and an electron blocking layer 4-359, in some implementations. The stack of layers may be electrically contacted by an anode and cathode as described in connection with FIG. 4-3A. The LED structure depicted in FIG. 4-3B may be used for other types of LEDs, including but not limited to OLEDs, PhOLEDs, and a quantum dot LEDs (QLEDs).

According to some embodiments, a semiconductor laser diode may be integrated onto the substrate 1-100. FIG. 4-3C depicts a vertical cavity surface emitting laser (VCSEL) that may be used in some implementations. A VCSEL may comprise reflective stacks 4-364, 4-362 formed at opposite ends of a VCSEL cavity. A multiple quantum well 4-365 may be formed within the VCSEL's cavity. In some implementations, a reflective material 3-230 may form a cathode or anode at one end of the VCSEL cavity, and a sample well 3-210 may be formed in the cathode or anode. According to some embodiments, a divot 3-216 may extend into the cavity of the VCSEL, as shown in the drawing.

Since the divot extends into the VCSEL resonator, the sample may be exposed to appreciably higher intensity than it would if it were located outside the cavity. For example, if the reflective stacks of the VCSEL cavity are greater than 90%, then the intensity within the cavity may be between approximately 10 and 100 times higher than the intensity outside the cavity. In some embodiments, at least one reflector of the VCSEL cavity may be dichroic, such that it is highly reflective for the excitation energy (e.g., greater than about 90%) and transmits a high percentage of emission from the sample (e.g., more than about 60%).

In FIG. 4-3B and FIG. 4-3C, the excitation sources extend across an area appreciably larger than the transverse dimension of the sample well. Accordingly, emission from a sample must pass through the excitation source to reach a sensor located below the sample well. Some of the emission from a sample may be absorbed within the excitation source in such embodiments.

FIG. 4-3D and FIG. 4-3E depict nanoscale excitation sources having transverse dimensions approximately equal to the transverse dimension of the sample well. For example, a transverse dimension of a nanoscale excitation source may be between 50 nm and 500 nm, according to some embodiments, though may be larger in other embodiments. These nanoscale excitation sources may be self-aligned to the sample well during fabrication, according to some embodiments. In some embodiments, microscale excitation sources may be formed adjacent the sample well, similar to the nanoscale excitation sources, but having microscale transverse dimensions.

FIG. 4-3D depicts a nano-LED that is formed below a sample well. The nano-LED may comprise a pillar 4-374 having a first type of conductivity and a cap 4-376 having a second type of conductivity to form a p-n junction. The pillar 4-374 may be formed by epitaxial growth from a semiconductor layer 4-380. During growth of the pillar, a reflective stack 4-375 may be formed by alternating materials of the pillar and/or dopant concentration, according to some embodiments. Electrical contact to the pillar 4-374 may be made through the semiconductor layer 4-380. The nano-LED may further comprise a conductive surface coating 4-372 that is used to electrically connect to the cap 4-376 via a conductive material 3-230 in which the sample well is formed. In some embodiments, there may be more layers in the nano-LED than shown in the drawing. For example, the nano-LED may include electron transport, electron blocking, hole transport, and/or hole blocking layers. A passivating layer 4-378 (e.g., an oxide) may be deposited over a region around and within the sample well, according to some embodiments.

In some embodiments, the passivating layer 4-378 in the conductive layer 4-372 may be transparent to radiation emitted by a sample in the sample well. For example, the passivating layer 4-378 may comprise alumina or an oxide. The conductive coating 4-372 may also be transparent to radiation emitted by a sample, and may comprise indium tin oxide (ITO), according to some embodiments. In some implementations, the conductive coating 4-372 may comprise graphene, indium-doped zinc oxide, aluminum-doped zinc oxide, or gallium-doped zinc oxide. Because the passivating layer and conductive coating are transparent, light from a sample may travel to the semiconductor substrate 4-380 without passing through silicon or semiconductor, as may occur in the devices depicted in FIG. 4-3B and FIG. 4-3C. In some embodiments, one or more sensors (not shown) may be formed in the substrate 4-380 to detect emission from the sample.

According to some embodiments, a nano-LED 4-371 or nanoscale excitation source may comprise a vertical waveguide. For example, the refractive index of the nano-LED may be appreciably greater than the refractive index of the surrounding layer 3-235. Accordingly, emission from the nano-LED 4-371 may be vertically guided to and concentrated at an excitation region of a sample well 3-210. As such, the nano-LED may more efficiently illuminate the excitation region than a larger device, such as the diode depicted in FIG. 4-3B, for example.

In some embodiments, the cap 4-376 having a second type of conductivity of the nano-LED may be etched back to expose the pillar. A reflective coating may then be formed on an upper surface, opposite the reflective stack 4-375 to form a nanoscale, vertical edge emitting laser diode (nano-VEELD).

The height of the nano-LED may be carefully controlled by epitaxial growth. Accordingly, a distance between an emitting end of the nano-LED and a lower surface of the material 3-230, in which the sample well is formed, may be carefully controlled. Additionally, a directional physical deposition (such as described in connection with FIG. 3-9D) of a passivating material or dielectric may be used to carefully control a distance between an excitation region of the sample well and the emitting end of the nano-LED. Careful control of these distances in combination with coupling structures formed adjacent the sample well may improve coupling of excitation energy into the excitation region and coupling of emission from the sample to one or more sensors.

FIG. 4-3E depicts a self-aligned, nano-VCSEL formed below a sample well, according to some implementations. The nano-VCSEL may be formed using similar techniques to those used to form the nano-LED (described in further detail below). According to some embodiments, the nano-VCSEL may comprise a first reflective stack 4-377, a multiple quantum well structure 4-330 or quantum dot, and a second reflective stack 4-373 formed during epitaxial growth of the pillar. Electrical connection to one end of the nano-VCSEL may be made by a conductive coating 4-372, as described in connection with the nano-LED.

Because of their small sizes, the nano-LED 4-371 and nano-VCSEL will have low junction capacitances. Accordingly, they may be modulated at high speeds. In some embodiments, a nano-LED, nano-VEELD, or nano-VCSEL may have turn-on and turn-off times less than approximately 1 microsecond. A nano-LED, nano-VEELD, or nano-VCSEL may have turn-on and turn-off times less than approximately 100 nanoseconds in some implementations, less than approximately 10 nanoseconds in some implementations, less than approximately 1 nanosecond in some embodiments, and yet less than approximately 100 picoseconds in some embodiments.

Additionally, since intense excitation energy is only needed at the excitation region of the sample well, a nano-LED, nano-VEELD, or nano-VCSEL may more efficiently excite a sample with less total output power. This may be beneficial in some implementations, since high power dissipation may heat a specimen to unacceptably high temperatures and possibly damage the sample. Further, since the emission from the nano-LED, nano-VEELD, or nano-VCSEL is delivered primarily only to the excitation region, less overall excitation energy is required, as compared to a larger excitation source emitting radiation over an area substantially larger than the excitation region 3-215 of a sample well 3-210. Because less overall excitation energy is required, the signal-to-noise ratio for emission from the sample may increase due to less background radiation from the excitation source, according to some embodiments.

Various techniques may be used to fabricate the excitation sources described in FIG. 4-3A through FIG. 4-3D. According to some embodiments, conventional techniques may be used to form at least one OLED, PhOLED, or QLED on an integrated device. For example, multiple layer depositions may be carried out at regions where the LEDs are formed, while other regions may be masked off to prevent depositions on the substrate at those regions. Because an OLED, PhOLED, or QLED device may be sensitive to elevated temperatures, processing temperatures after formation of such devices may need to be kept below a temperature limit, above which damage may occur to the OLED, PhOLED, or QLED devices. For example, an OLED may be damaged or degraded by exposure to temperatures above approximately 100° C. Accordingly, after formation of an OLED on an integrated device, processing temperatures may be limited to approximately 100° C. during subsequent fabrication steps.

Formation of inorganic semiconductor LEDs, laser diodes, or VCSEL's on an integrated device may be carried out using conventional techniques (e.g., using ion implantations and diffusions and/or multiple epitaxial depositions), according to some embodiments. In other implementations, inorganic semiconductor LEDs, laser diodes, VCSELs, and/or sample wells may be formed on a separate semiconductor-on-insulator (SOI) substrate that is subsequently aligned and bonded to the substrate 1-100 of the integrated device. For example, epitaxial layers for a laser diode or VCSEL may be formed on an SOI substrate, which can then be bonded to a dielectric layer 3-235 depicted in FIG. 4-3B, for example. After bonding, the silicon layer having the formed VCSEL may be released from the SOI substrate, and may further be etched back according to some embodiments. Sample wells 3-210 may then be formed at each pixel.

IV. B. Fabrication of Radiative Excitation Sources

Figures 4, 4A:
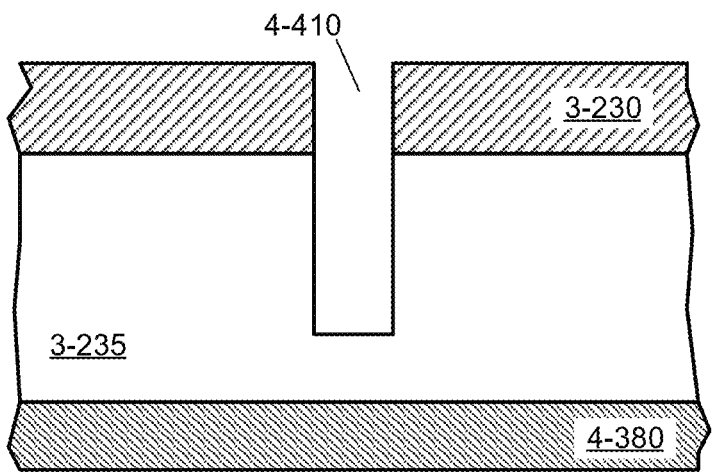
Figures 4, 4B:
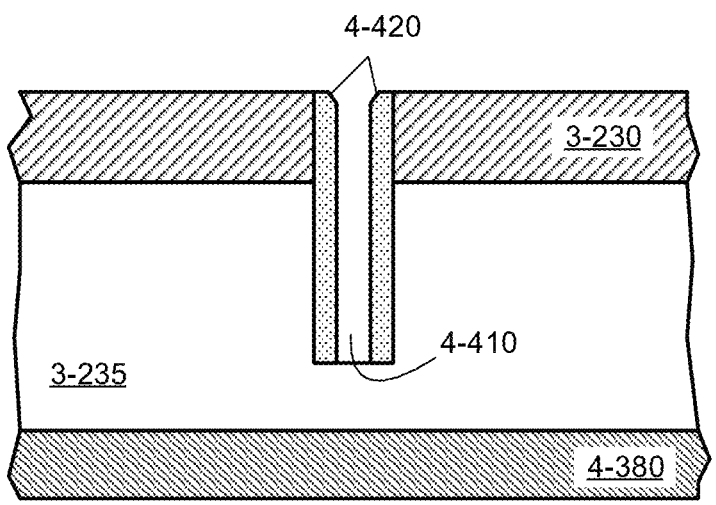
Figures 4, 4C:
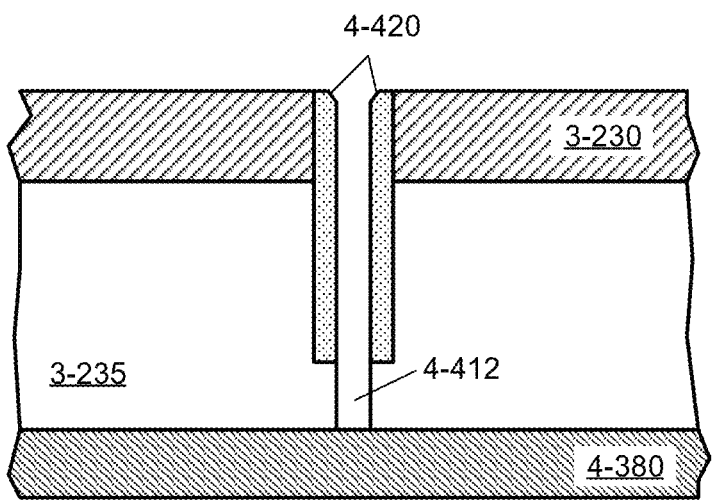
Figures 4, 4D:
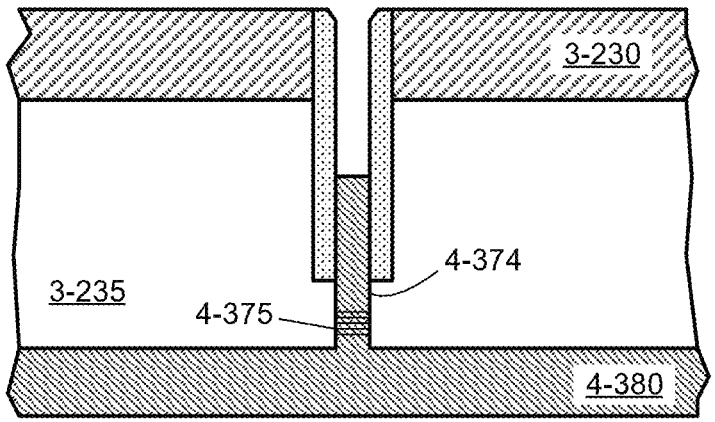
Figures 4, 4E:
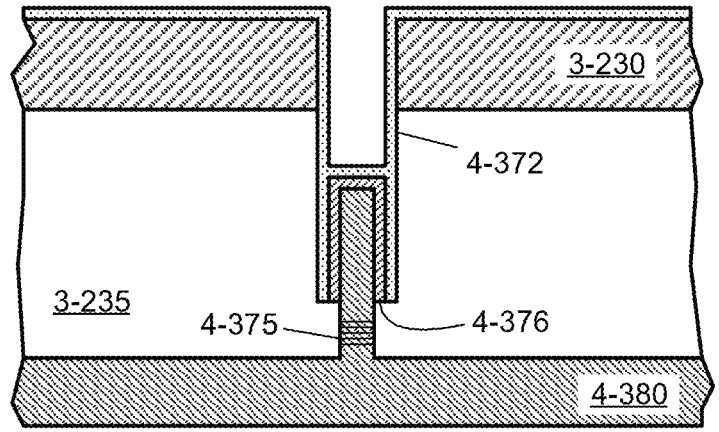
Figures 4, 4F:
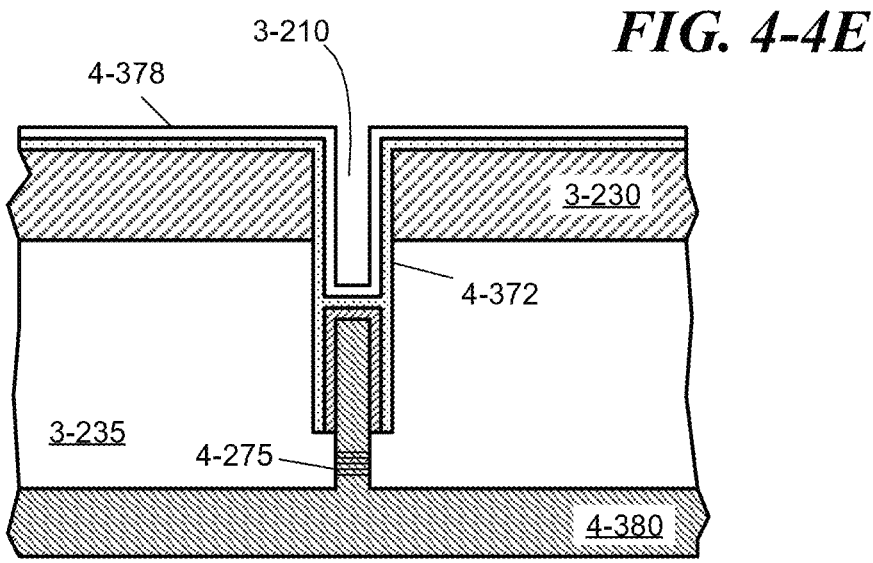
Figures 4, 4G:
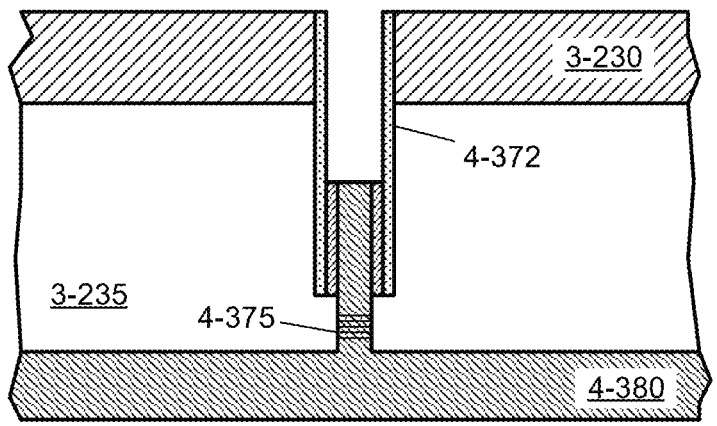
Figures 4, 4H:
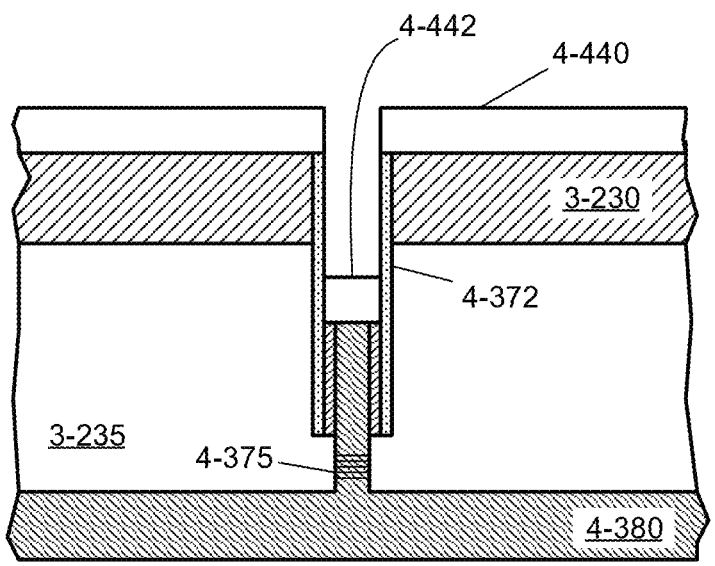
Figures 4, 4I:
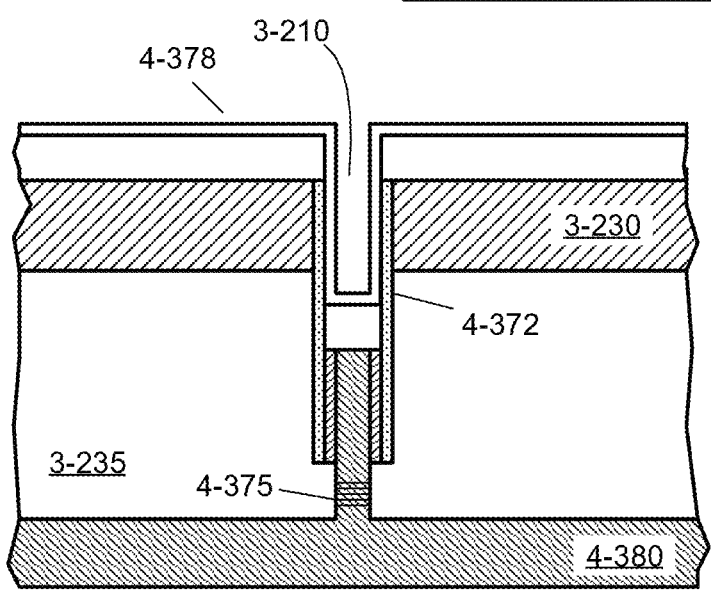

FIG. 4-4A through FIG. 4-4I depict structures associated with process steps that may be used to form a nano-LED, nano-VEELD, or nano-VCSEL that is self-aligned to a sample well, according to some embodiments. The depicted process steps illustrate only some embodiments of methods that may be used to fabricate the devices. The nano-LED, nano-VEELD, or nano-VCSEL devices may be fabricated using other or additional process steps in some embodiments. For example, some processes may require photolithographic alignment of these devices to the sample wells. In some embodiments, microscale excitation sources may be fabricated using one or more steps described for fabrication of nanoscale excitation sources.

According to some implementations, a hole or via 4-410 may be formed in a substrate comprising a semiconductor layer 4-380 an insulating layer 3-235 and a top layer 3-230, as depicted in FIG. 4-4A. The hole may be formed by patterning a hole in resist over the top layer 3-230, as described in connection with FIG. 3-10A through FIG. 3-10D. A first selective anisotropic etch may be used to etch the hole pattern through the top layer, and a second selective anisotropic etch may be used to etch the hole pattern into the insulating layer 3-235.

The top layer may comprise a material or stack of materials in which the sample well is formed, and the hole 4-410 may define the location of a sample well. In some embodiments, the semiconductor layer 4-380 may comprise silicon, though other semiconductor materials may be used. In some cases, the semiconductor layer 4-380 may comprise a thin, or ultrathin (e.g., less than approximately 50 nm thick), semiconductor layer of a SOI substrate, such that emission from the sample well may pass through the layer with less than about 30% loss. The insulating layer 3-235 may comprise an oxide (e.g., SiO$_2$) or any suitable material that transmits radiation from the excitation source and emission from the sample. The top layer 3-230 may comprise a conductive metal, according to some implementations, a stack of materials (e.g., a semiconductor, a metal, and an insulator), or any suitable combination of materials described herein in connection with fabrication of the sample well 3-210.

Figures 3, 4, 5, 6:
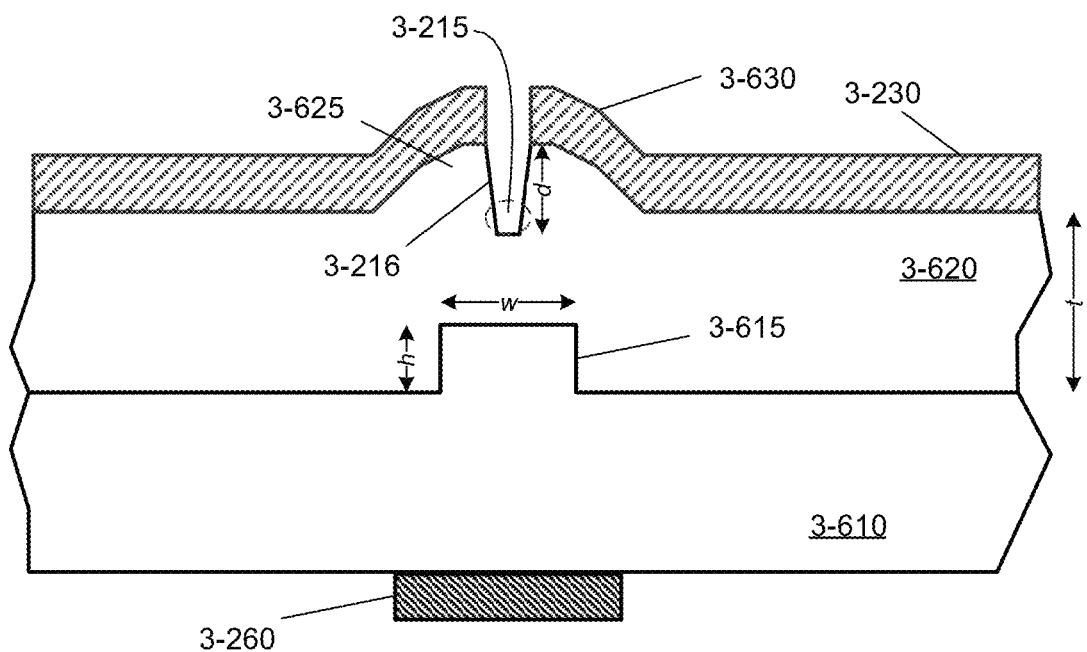
Figures 3, 4, 5, 6, 7, 8:
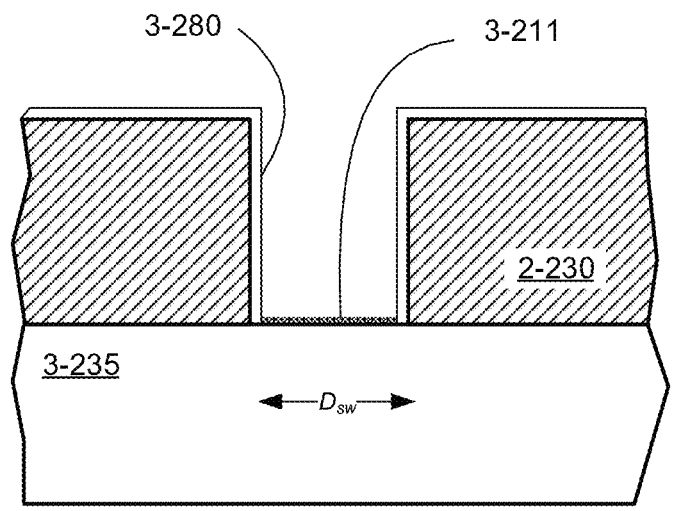
Figures 3, 4, 5, 6, 7, 8, 9, 9A:
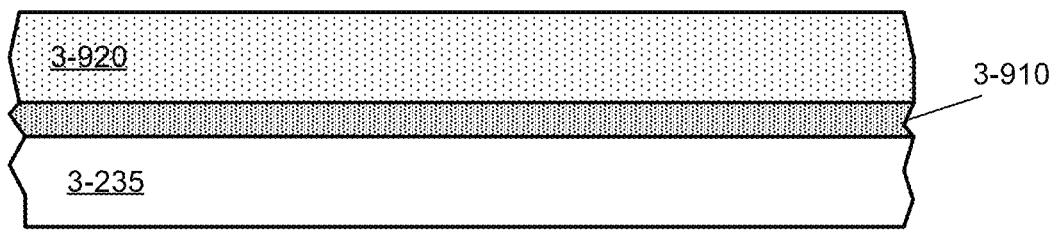
Figures 3, 4, 5, 6, 7, 8, 9, 9B:
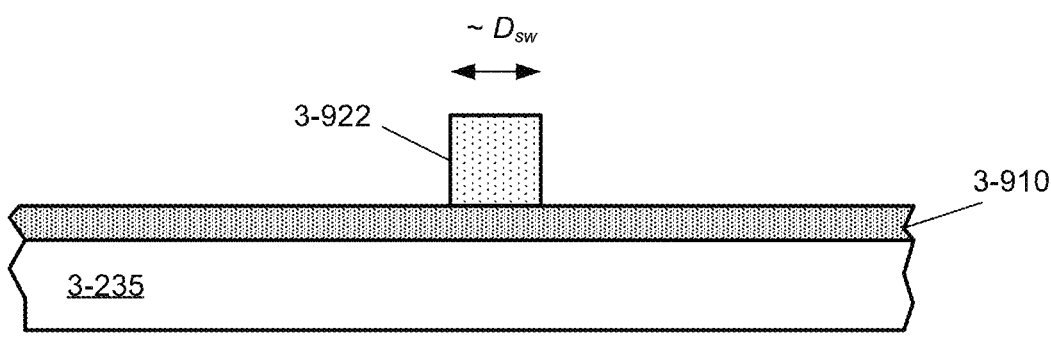
Figures 3, 4, 5, 6, 7, 8, 9, 9C:
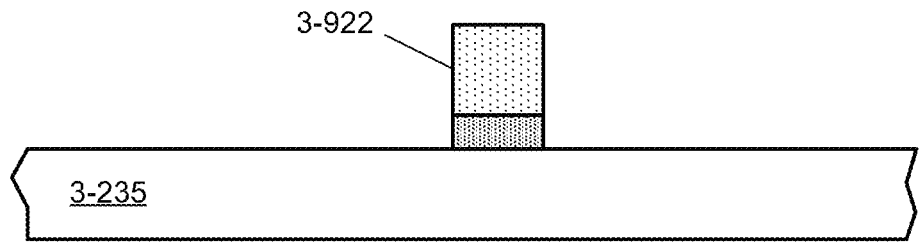
Figures 3, 4, 5, 6, 7, 8, 9, 9D:
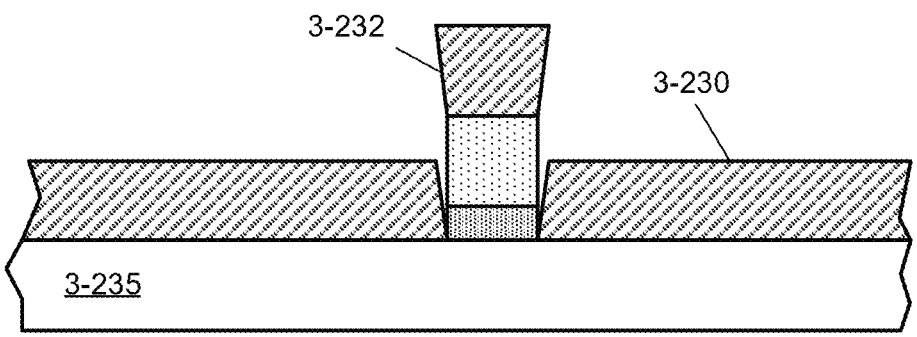
Figures 3, 4, 5, 6, 7, 8, 9, 9E:
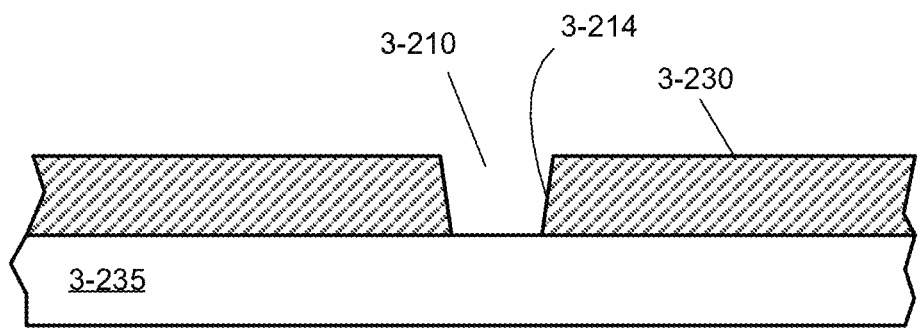
Figures 3, 4, 5, 6, 7, 8, 9, 9F:
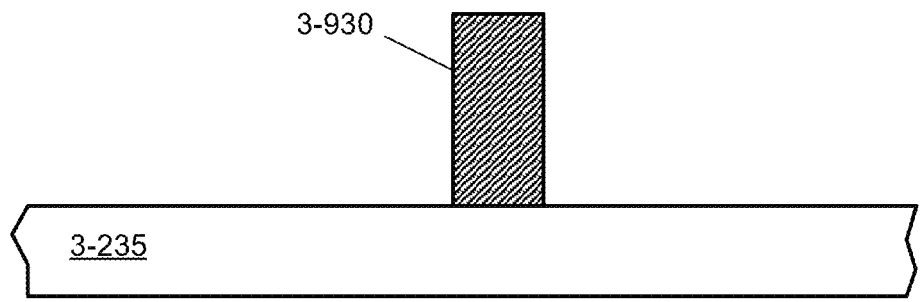
Figures 3, 4, 5, 6, 7, 8, 9, 10, 10A:
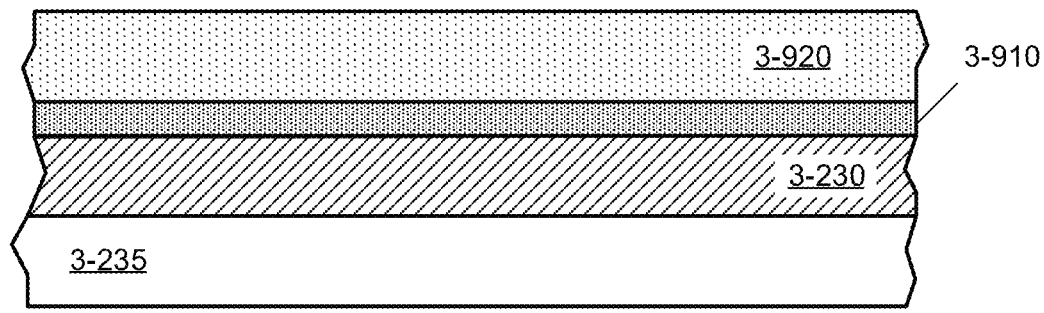
Figures 3, 4, 5, 6, 7, 8, 9, 10, 10B:
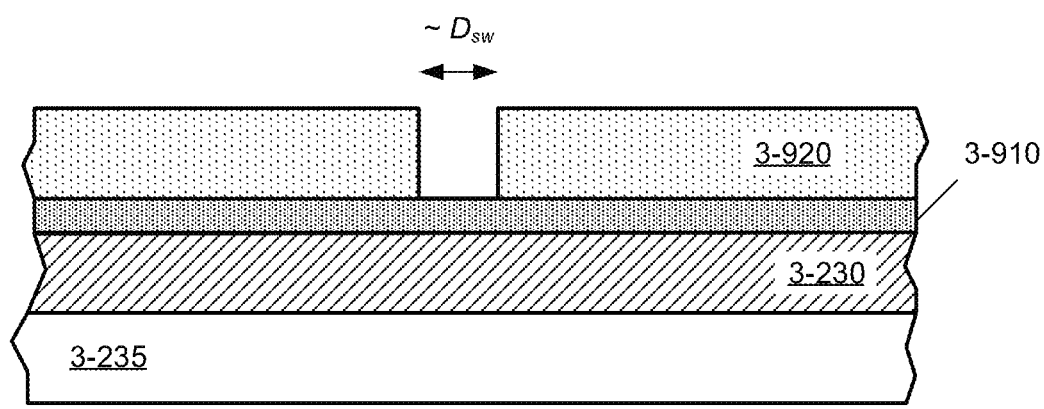
Figures 3, 4, 5, 6, 7, 8, 9, 10, 10C:
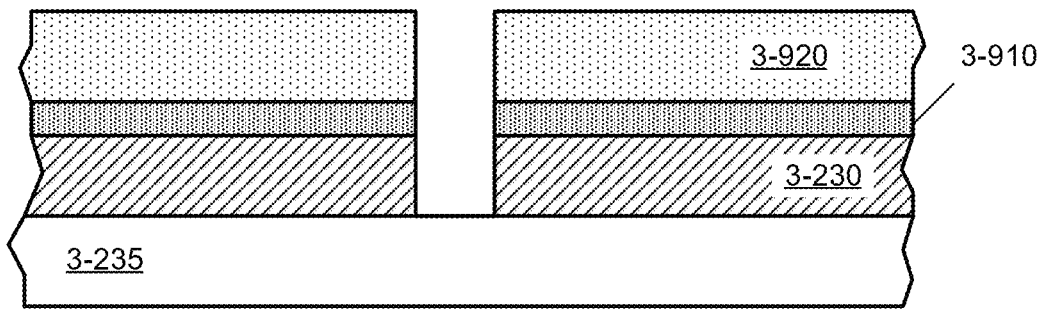
Figures 3, 4, 5, 6, 7, 8, 9, 10, 10D:
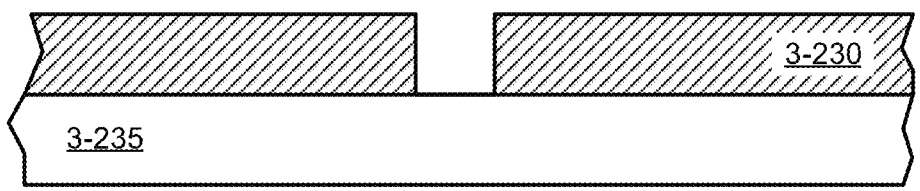
Figures 3, 4, 5, 6, 7, 8, 9, 10, 11:
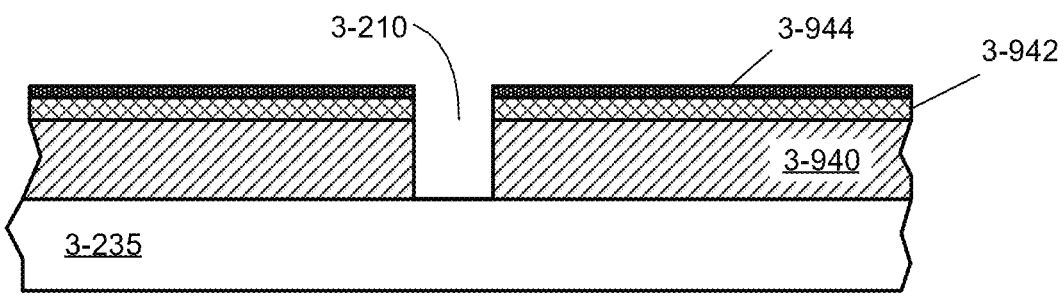
Figures 3, 4, 5, 6, 7, 8, 9, 10, 11, 12:
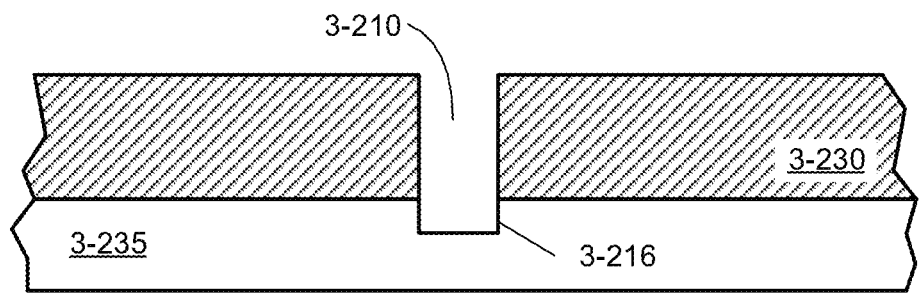
Figures 3, 4, 5, 6, 7, 8, 9, 10, 11, 12, 13, 13A:
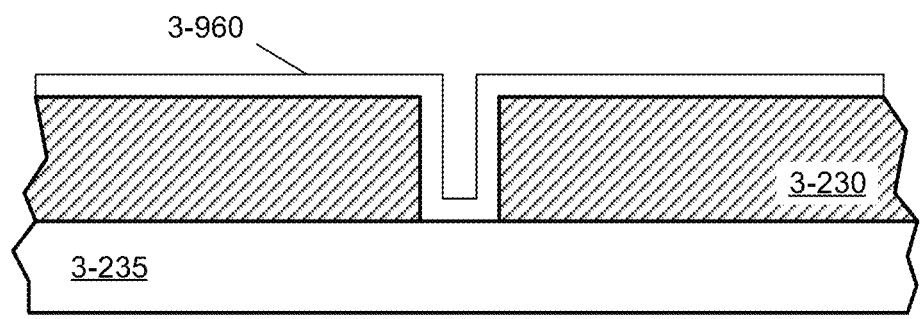
Figures 3, 4, 5, 6, 7, 8, 9, 10, 11, 12, 13, 13B:
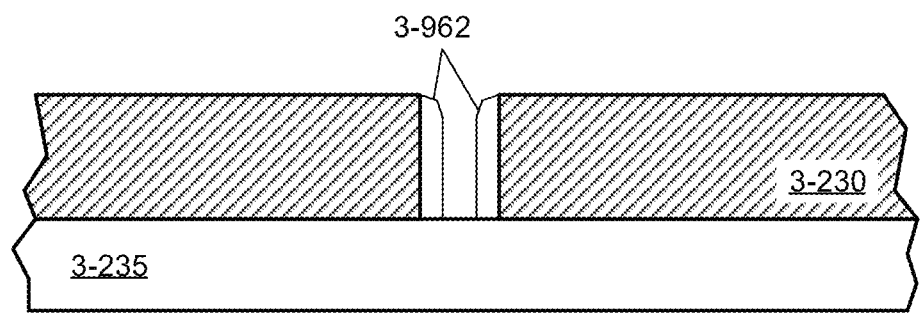
Figures 3, 4, 5, 6, 7, 8, 9, 10, 11, 12, 13, 13C:
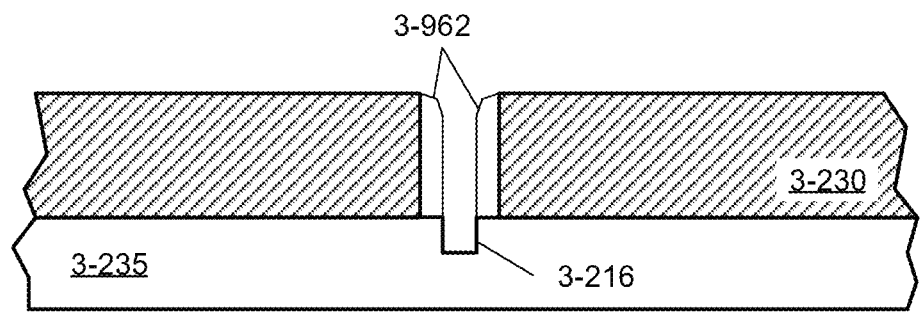
Figures 3, 4, 5, 6, 7, 8, 9, 10, 11, 12, 13, 14, 14A:
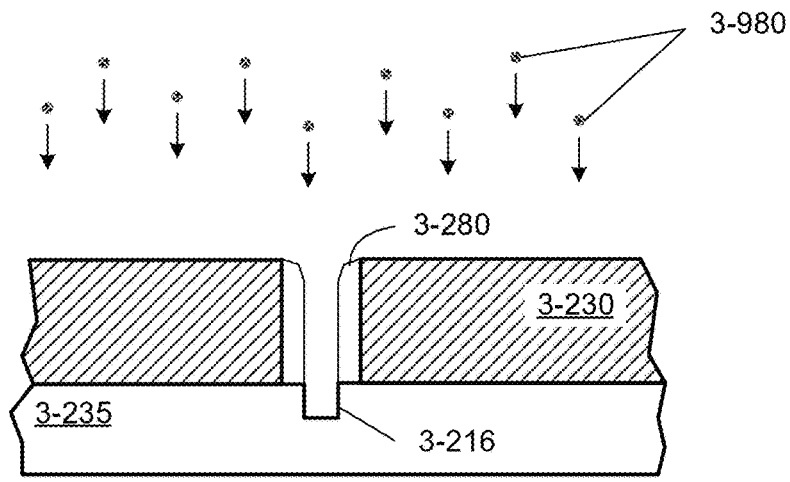
Figures 3, 4, 5, 6, 7, 8, 9, 10, 11, 12, 13, 14, 14B:
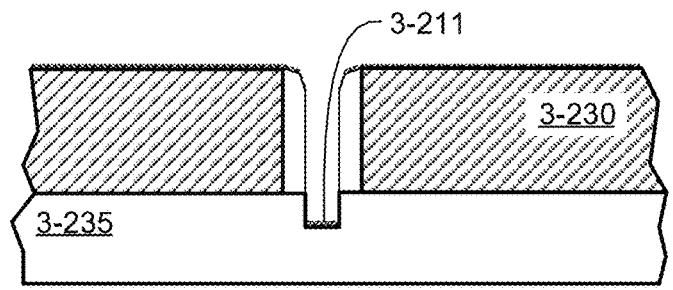
Figures 3, 4, 5, 6, 7, 8, 9, 10, 11, 12, 13, 14, 14C:
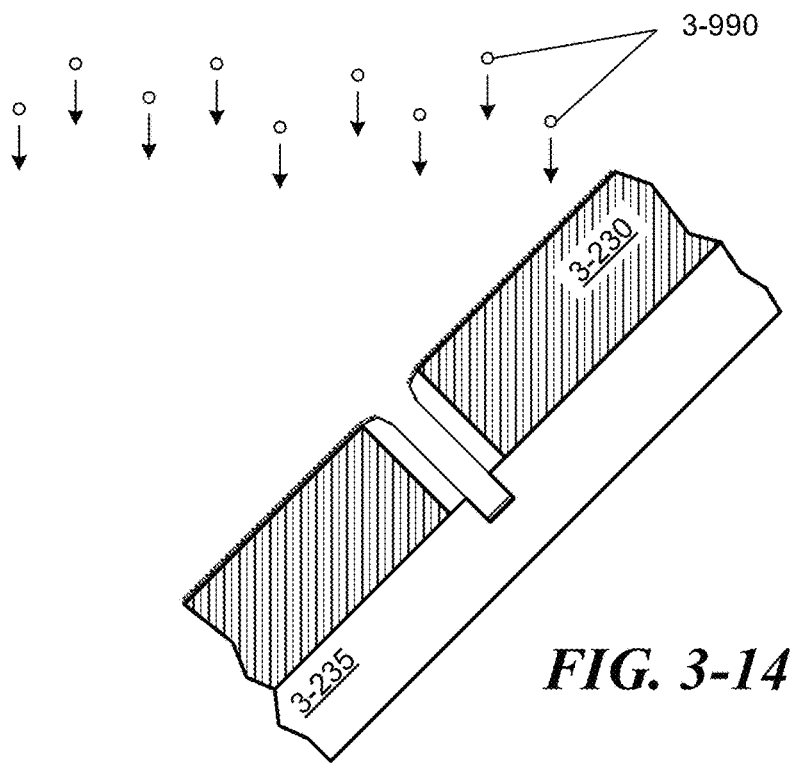
Figures 3, 4, 5, 6, 7, 8, 9, 10, 11, 12, 13, 14, 14D:
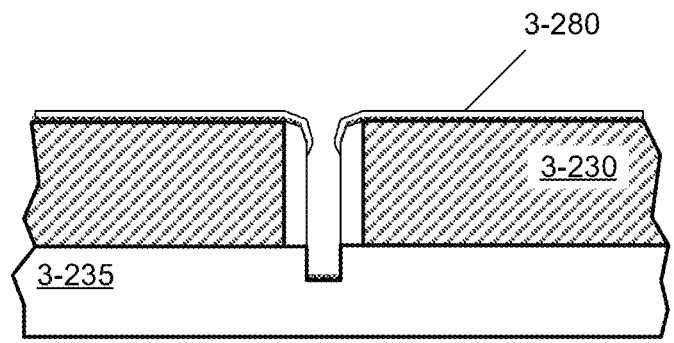
Figures 3, 4, 5, 6, 7, 8, 9, 10, 11, 12, 13, 14, 15:
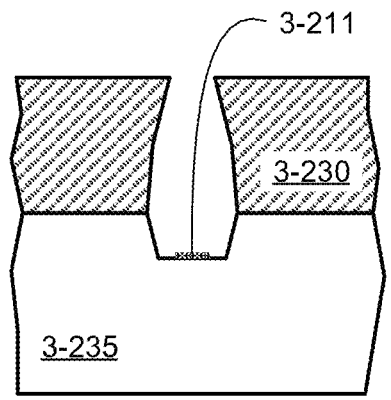

A sacrificial coating 4-420 may then be deposited to line the hole 4-410, as depicted in FIG. 4-4B. The sacrificial coating 4-420 may first be deposited over the region is a uniform layer (not shown). For example, the sacrificial coating may be deposited using a conformal deposition process, such as a chemical vapor deposition (CVD) process or an atomic layer deposition (ALD) process. After deposition, the sacrificial coating may be etched back to remove the sacrificial material on the horizontal planar surfaces (as viewed in the drawing). Such a deposition and etch-back process is described in connection with FIG. 3-13A and FIG. 3-13 B. Any suitable material may be used for the sacrificial coating 4-420. In various embodiments, the material used for the sacrificial coating 4-420 will exhibit etch selectivity over the top layer 3-230, the insulating layer 3-235, and a semiconductor material that will be epitaxially grown from the semiconductor layer 4-380. In some embodiments, the sacrificial coating 4-420 may be formed from silicon nitride, for example. After formation of the sacrificial coating 4-420, a second hole 4-412 may be etched to the semiconductor layer 4-380 to expose a surface of the semiconductor layer. The resulting structure may appear as depicted in FIG. 4-4C, according to some implementations.

A semiconductor pillar 4-374 may then be grown from the semiconductor layer 4-380, as depicted in FIG. 4-4D. According to some embodiments, the pillar may be grown via an epitaxial growth process, such as molecular organic chemical vapor deposition (MOCVD). According to some embodiments, the pillar may form in the hole that was etched to the semiconductor layer and is defined by walls of the insulating layer 3-235 and the sacrificial coating 4-420. The hole may provide a mold for the growth of the pillar. Since a sample well 3-210 will be subsequently formed in an upper portion of the hoe, the pillar 4-374 grows self-aligned to the subsequently formed sample well 3-210.

In some embodiments, during growth of the pillar, a reflective stack 4-375 may, or may not, be formed at the base of the pillar. The reflective stack may exhibit a high reflectivity for emission from the nano-LED, according to some implementations, and may be used to reflect approximately one-half of the emission from the nano-LED toward the sample well. In some embodiments, the reflective stack 4-375 may exhibit a low reflectivity (e.g., less than about 30%) for emission from a sample in the sample well.

The pillar 4-374 may be formed with any selected conductivity type. For example, donor or acceptors species may be added during epitaxial growth of the pillar to define the conductivity type of the pillar. In some embodiments the pillar may be p type, and in other embodiments the pillar may be n type.

After formation of the pillar 4-374, the sacrificial coating 4-420 may be removed by a selective etching process. The etching process may be a wet etch or a dry etch that preferentially removes the sacrificial coating but does not appreciably remove the insulating layer 3-235 top layer 3-230 or semiconductor pillar 4-374. Removal of the sacrificial coating 4-420 leaves an upper portion of the semiconductor pillar exposed within the hole.

A second epitaxial growth may then be executed to form a semiconductor cap 4-376 over the pillar, as depicted in FIG. 4-4E. The conductivity type of the semiconductor cap 4-376 may be made opposite the conductivity type of the pillar 4-374 to form a p-n junction. In some embodiments, the semiconductor cap 4-376 may fill a mid-region of the hole 4-410 as it grows from the exposed pillar. In some implementations, the semiconductor cap may not entirely fill the lower region of the hole, and may leave an open space between it and sidewalls of insulating layer 3-235.

A conductive surface layer 4-372 may then be deposited over the region, as depicted in FIG. 4-4E. The conductive surface layer may comprise a layer of ITO in some embodiments, and provide electrical connection from the top layer 3-230 to the semiconductor cap 4-376 (e.g., an electrical connection to a p or n region of the nano-LED). The conductive surface layer 4-372 may be deposited by any suitable conformal deposition process, e.g., atomic layer deposition or chemical vapor deposition, according to some embodiments.

In some implementations, a passivating layer 4-378 may then be deposited conformably over the region, as depicted in FIG. 4-4F. The passivation layer may be an insulating layer according to some embodiments, such as alumina or silicon oxide. An adherent (not shown) may be deposited at a base of the sample well, as described in connection with FIG. 3-14 or FIG. 3-15, for example. As can be seen in FIG. 4-4F, the resulting sample well 3-210 and nano-LED are self-aligned.

Structures associated with process steps for alternative embodiments of fabricating a nano-LED are shown in FIG. 4-4G through FIG. 4-4I. After obtaining a structure depicted in FIG. 4-4B, for example, selective anisotropic etching steps may be executed to selectively remove horizontal planar surfaces of the coating layer 4-372 and a portion of the semiconductor cap 4-376 and semiconductor pillar 4-374. The resulting structure may appear as depicted in FIG. 4-4G.

In some embodiments, a spacing layer 4-440 may then be deposited over the region. The spacing layer may comprise a transparent material, for example, silicon oxide. The spacing layer may be deposited by a physical deposition process, e.g., electron beam evaporation. The spacing layer may form a plug 4-442 at the bottom of the sample well. The plug may be used to carefully space the location of a sample from an end of the nano-LED. Since the thickness of a deposited layer can be controlled very accurately, to within a few nanometers, the spacing between an end of the nano-LED and the location of the sample can be controlled quite precisely. A passivation layer 4-378 may then be deposited over the region, as depicted in FIG. 4-4I, and an adherent subsequently deposited.

Some process steps used to form a self-aligned, nano-LED may also be used to fabricate a self-aligned nano-VEELD or self-aligned nano-VCSEL. Fabrication of a nano-VCSEL may not require steps depicted in FIG. 4-4B and FIG. 4-4C. Instead, the hole 4-410 may be etched to the semiconductor layer 4-380, and a first portion of the VCSEL pillar (e.g., a p-type portion), including a reflective stack 4-375, may be formed in the hole by epitaxial growth. Subsequently, an n-type portion of the pillar may be formed, and electrical contact made to the n-type portion using a step as depicted in FIG. 4-4E, for example.

According to some implementations, a thickness of the insulating layer 3-235 for forming a nano-LED, nano-VEELD, or nano-VCSEL may be between approximately 100 nm and approximately 2 microns. In some implementations, one or more sensors 3-260 (not shown in the drawings) may be patterned in the semiconductor layer 4-380 to detect emission from the sample well 3-210. The one or more sensors may be patterned near the nanoscale excitation source, so that the excitation source, sample well, and sensor are contained within a volume measuring less than about 20 microns in a maximum transverse dimension and less than about 2 microns in height. In some embodiments, the volume may be less than about 5 microns in a maximum transverse dimension.

If greater photon flux is needed, a nano-LED, nano-VEELD, or nano-VCSEL may be fabricated to have a transverse dimension larger than a transverse dimension of the sample well, using process steps similar to those depicted in FIG. 3-13A and FIG. 3-13B after formation of the nanoscale excitation source.

IV. C. Non-Radiative Excitation Sources

Samples 3-101 in an excitation region of a sample well may be excited via non-radiative processes, according to some embodiments. A non-radiative process may include Förster resonant energy transfer (FRET), which may occur over distances up to about 10 nm, or Dexter energy transfer (DET), which may occur over distances up to about 1 nm. Accordingly, non-radiative excitation sources that may be included in an integrated device have also been contemplated by the inventors. As with the radiative excitation sources, there may be one or more separately-controllable, non-radiative excitation sources on an integrated device. For example, in some embodiments a single non-radiative source may be shared by a group of pixels or an entire pixel array of an integrated device. In some implementations, a non-radiative excitation source may be fabricated at each pixel.

Figures 4, 5, 5A:
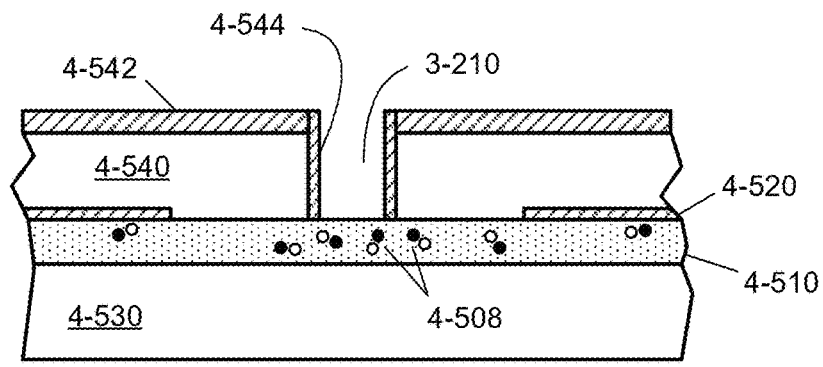

FIG. 4-5A depicts just one embodiment of a non-radiative excitation source that may be formed at a pixel of an integrated device. According to some embodiments, a semiconductor layer 4-510 may be formed on an insulating substrate 4-530. The semiconductor layer may comprise an organic semiconductor or an inorganic semiconductor. In some implementations, the semiconductor layer may be a thin, or ultrathin, semiconductor layer of an SOI substrate. The semiconductor layer may have a thickness between approximately 10 nm and approximately 100 nm, according to some embodiments. First electrodes 4-520 may be disposed on the semiconductor layer. The electrodes 4-520 may run along a surface of the semiconductor layer 4-510, e.g., extending along spaces between sample wells 3-210, and provide a first electrical connection to the semiconductor layer. A second insulating layer 4-540 may be formed adjacent the semiconductor layer and the first electrodes 4-520. A conductive layer 4-542 may be formed adjacent the second insulating layer 4-540. A sample well 3-210 may be formed in the second insulating layer and in the conductive layer 4-542, according to some embodiments, and a conductive coating 4-544 may be formed on walls of the sample well, as depicted in the drawing. The conductive coating 4-544 may provide a second electrical contact to the semiconductor layer.

In operation, and electrical bias may be applied between the first electrodes 4-520 and the conductive layer 4-542. A current may flow through the semiconducting layer 4-510 near the sample well, and generate excitons 4-508 within the semiconductor layer 5-510. The excitons may be generated by collisional excitation, according to some embodiments, and may diffuse to the surface of the semiconductor layer 4-510 at the sample well 3-210. When near the surface at the sample well, the excitons may deliver energy to a sample within the sample well via FRET or DET.

Figures 4, 5, 5B:
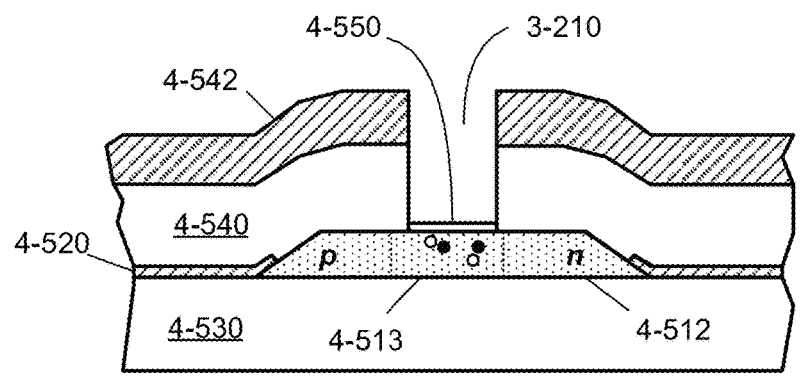

An alternative embodiment of a non-radiative excitation source is depicted in FIG. 4-5B. According to some embodiments, a non-radiative excitation source may comprise a lateral diode 4-512 formed adjacent a base of sample well 3-210. In some embodiments, the diode may comprise p-n junction or may comprise an intrinsic or undoped region 4-513 to form a p-i-n junction. A non-radiative excitation source as depicted in FIG. 4-5B may include cathode and anode electrodes 4-520 for making electrical contact to the p and n regions of the diode. In some embodiments, there may be a thin passivating layer (e.g., less than 10 nm) and/or adherent layer 4-550 formed at the junction region of the diode.

Figures 4, 5, 5C:
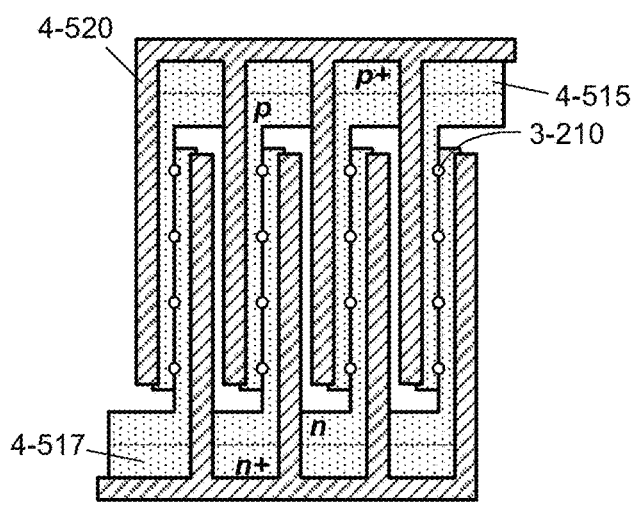

A plan view of one embodiment of a non-radiative excitation source depicted in FIG. 4-5B is shown in FIG. 4-5C, according to some embodiments. The plan view is taken at the an interface between the first insulating layer 4-530 and the second insulating layer 4-540. The plan view depicts just one embodiment of how the p and n regions of the diode and electrodes may be arranged on the integrated device. In some embodiments, heavily doped regions of semiconductor 4-515, 4-517 may be formed near the electrodes, and may extend to a region near each sample well. Any suitable pattern may be used to arrange the p and n regions of the diodes in an integrated device. For example, instead of using an interdigitated pattern as depicted in FIG. 4-5C, a serpentine pattern of the diodes may be used instead.

Figures 4, 5, 5D:
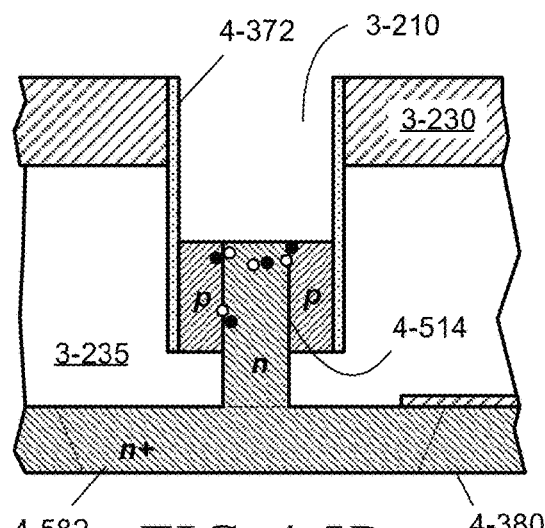

FIG. 4-5D depicts in an alternative embodiment of a non-radiative excitation source that may be formed by vertical growth at a sample well 3-210. In some implementations, the source comprises a diode 4-514 that is self-aligned to the sample well 3-210. The diode may comprise a nanoscale p-n or p-i-n diode having a cylindrical pillar formed of a semiconductor having a first type of conductivity that is surrounded by a semiconductor cylindrical shell having a second type of conductivity, as depicted in the drawing. The shape of the nano-diode may be any suitable shape and need not be cylindrical. For example, if the sample well is formed to have a square, rectangular, or polygonal cross-section, then the nano-diode may assume a similar shape.

A connection to a first region (e.g., an n region) of the diode may be made through a semiconductor layer 4-380. In some embodiments, a heavily-doped well 4-582 may be formed on the semiconductor layer at a base of the nano-diode to improve electrical connection to the diode. A connection to the second region of the diode may be made through a conductive layer 3-230, in which the sample well is formed, and a conductive coating 4-372. In some embodiments, the conductive coating 4-372 may comprise ITO.

In operation, electrical current within the nano-diode may generate excitons that diffuse to the surface of the diode where a majority recombines. In some cases, excitons may transfer energy non-radiatively to a sample within the sample well 3-210 upon recombination. Accordingly, sample excitation within a sample well may occur without radiative emission from an excitation source. A benefit of non-radiative excitation is that the excitation source may contribute no appreciable radiation noise at the sensor during signal detection. A second benefit is that sample excitation is localized to within about 10 nm from the excitation source. This may be beneficial for coupling energy from the sample to the sensor, and may also reduce or eliminate noise radiation from other samples in the specimen that are more than about 10 nm from the excitation source.

Various fabrication techniques may be used to fabricate non-radiative sources depicted in FIG. 4-5A through FIG. 4-5D. Fabrication of a device depicted in FIG. 4-5A may employ conventional patterning and etching process steps, and may include process steps associated with forming a sample well as described herein. In some embodiments, a nano-diode as depicted in FIG. 4-5A may be formed employing fabrication steps that are used to form the nano-LED, as described in connection with FIG. 4-4G.

IV. D. Fabrication of Non-Radiative Excitation Sources

FIG. 4-6A through FIG. 4-6U depict structures associated with process steps that may be used to form a lateral-junction, non-radiative excitation source that is self-aligned to a sample well, as depicted in FIG. 4-5B, for example. The intrinsic region, or p-n junction may be self-aligned to a base of the sample well.

According to some embodiments, the process may begin with obtaining a silicon on insulator substrate as depicted in FIG. 4-6A, comprising a semiconductor substrate 4-535, an insulating layer 4-530, and an intrinsic or undoped semiconductor layer 4-513. In some embodiments, integrated circuitry may be formed in the semiconductor substrate 4-535, such as one or more sensors used to detect emission from a sample and associated integrated circuits that may be used in the integrated device. The insulating layer 4-530 may have a thickness between about 50 nm and about 500 nm, according to some embodiments, though other thicknesses may be used in other embodiments. The semiconducting layer 4-513 may be disposed on the insulating layer and have a thickness between approximately 10 nm and approximately 100 nm.

A mask 4-610 comprising bars may be patterned on the semiconducting layer 4-513, as depicted in FIG. 4-6B. The bars may run along the surface of the semiconducting layer, and may have the appearance of a grating. The mask may be a hard mask in some embodiments, for example a mask formed from silicon oxide, though other materials may be used. In other embodiments a soft mask, e.g., formed from a polymer, may be used. The mask may exhibit etch selectivity over the semiconductor layer 4-513. A thickness of the mask may be between approximately 50 nm and approximately 250 nm. A spacing between the bars of the mask may be on the order of the separation distance between pixels of the integrated device. A width of the bars may also be on the order of the separation distance between pixels of the integrated device. The bars may extend across the active pixel region of the integrated device. In some implementations, the mask 4-610 may be aligned to the substrate such that edges of the bars are approximately centered over sensors formed on the semiconductor substrate 4-535.

In some embodiments, a layer 4-620 may be conformably deposited over the mask 4-610, as depicted in FIG. 4-6C. The layer may comprise a hard material, such as silicon nitride, according to some embodiments. The layer 4-620 may exhibit etch selectivity over the semiconductor layer 4-513 and over the mask 4-610, according to some embodiments. A thickness of the layer 4-620 may be approximately equal to a desired size of the sample well 3-210, in some implementations. For example, a thickness of the layer 4-620 may be between approximately 80 nm and approximately 250 nm, though other thicknesses may be used in some embodiments.

The layer 4-620 may then be etched back using a selective anisotropic etch process, yielding the structure as shown in FIG. 4-6D. The etch of the layer 4-620 removes horizontal portions of the layer and leaves the vertical sidewalls 4-622 adjacent the mask bars 4-610. The region of the substrate may then be subjected to ion implantation, as depicted in the drawing. For example donor or acceptor ions may be implanted into the semiconducting layer 4-513 where the layer is exposed. The ions may be blocked from entering the semiconductor layer by the vertical sidewalls 4-622 and the mask 4-610. In some embodiments, the ion implantation may comprise donors and produce n-type semiconductor regions 4-632, as depicted in FIG. 4-6E. The regions under the vertical sidewalls and the mask may remain intrinsic regions of semiconductor 4-630.

A thin layer 4-624 may then be conformably deposited over the region, as depicted in FIG. 4-6F. According to some embodiments, the thin layer may be formed of a same material as the layer 4-620. According to some embodiments the thin layer may be silicon nitride, though other materials may be used in other embodiments. A thickness of the layer 4-624 may be between approximately 5 nm and approximately 20 nm, according to some embodiments.

A planarizing material 4-640 may then be deposited over the region, as depicted in FIG. 4-6G. According to some embodiments, the planarizing material 4-640 exhibits etch selectivity over the mask 4-610, the vertical sidewalls 4-622, and the thin layer 4-624. In some embodiments, the planarizing material may further exhibit etch selectivity over the intrinsic region of the semiconductor layer 4-630. According to some implementations, the planarizing material 4-640 may comprise amorphous silicon, though other materials may be used in other embodiments.

The material 4-640 and surface of the substrate may then be planarized, as depicted in FIG. 4-6H. For example, a chemical mechanical polishing (CMP) step may be used to planarize the region. The CMP step may selectively etch the material 4-640 but not etch the layer 4-624, and essentially stop on the layer 4-624, in some implementations. A non-selective planarizing etch may then be used to etch back the substrate to expose the mask bars 4-610, as depicted in FIG. 4-6I.

The mask bars 4-610 may then be removed by a selective etching process. The selective etching process may be a dry etch or a wet etch. The resulting structure may appear as depicted in FIG. 4-6J. The substrate may then be subjected to a second ion implantation as indicated in the drawing. For example, acceptor ions may be implanted into the exposed regions of the intrinsic semiconductor layer 4-512, converting these regions to p-type semiconductor regions 4-634. The planarizing material 4-640 may then be removed by a selective dry or wet etch.

In some embodiments, an additional planarizing polymer or oxide layer (not shown) may be formed on the substrate to protect the p-type regions 4-634 and planarized to expose the planarizing material 4-640, before removing the planarizing material 4-640. After removal of the planarizing material 4-640, the additional planarizing material may be selectively etched leaving portions of the vertical sidewalls 4-622 and the remaining portion of the thin layer 4-624.

When the vertical sidewalls 4-622 and the thin layer 4-624 are exposed, they may be etched back with an anisotropic selective etch to remove the horizontal portion of the thin layer 4-624 covering the n-type regions 4-632. The resulting structure may appear as depicted in FIG. 4-6K, and shows remaining vertical bars 4-626 that comprise remaining portions of the vertical sidewalls 4-622 and remaining portion of the thin layer 4-624. Undoped, intrinsic regions 4-630 of the semiconductor layer remain under the vertical bars 4-626. In some embodiments, a thermal diffusion process, e.g., a spike anneal, may be used to drive dopants under the vertical bars to reduce the spatial extent of a p-i-n junction, or if a p-n junction is preferred instead of a p-i-n junction.

A resist 4-650 (e.g., a photoresist) may be deposited over the region, according to some embodiments, as indicated in FIG. 4-6L. The resist may be patterned using a mask that is aligned to the vertical bars 4-626, such that portions of the resist over the n- and p-type regions of the lateral diode structure are exposed and developed away. Electrodes 4-520 may then be formed using a lift-off process, according to some embodiments. For example, electrode material may be deposited on the exposed n- and p-type regions of the diode. The remaining resist may be stripped from the substrate lifting off portions of the electrode material on top of the resist 4-650, leaving the vertical bars and electrodes over the lateral p-i-n regions.

A planarizing material 4-660 may then be deposited over the region and the material and region planarized, as depicted in FIG. 4-6M. The planarizing material 4-660 may be an oxide in some embodiments or polymer in some embodiments. In some implementations, a CMP step may be used to planarize the region and expose the vertical bars 4-626. FIG. 4-6N depicts a plan view of the region after planization, according to some embodiments. The dashed line indicates the location of a cross-section corresponding to the elevation view shown in FIG. 4-6M.

Additional masking bars 4-670 may then be patterned on top of the active pixel region, as depicted in the plan view of FIG. 4-6O. The bars may be patterned using any suitable lithography process, and may have a width that is approximately equal to a width of the vertical bars 4-626. The masking bars 4-670 may be oriented transverse to the vertical bars 4-626, and the masking bars may be spaced apart a distance that is approximately equal to a distance between pixels of the integrated device. In various embodiments, the masking bars are aligned to centers of sensors that may be located in the semiconductor substrate 4-535 below the vertical bars 4-626. According to some embodiments the masking bars 4-670 exhibit etch selectivity over the vertical bars 4-626. For example, the mask bars may be formed of a polymer or an oxide, and a vertical bars may comprise silicon nitride.

As indicated in FIG. 4-6P, a selective anisotropic etch may be used to etch away portions of the vertical bars 4-626 to expose the underlying intrinsic regions 4-630 of the semiconductor layer. Because of the masking bars 4-670, portions of the vertical bars 4-626 remain underneath the mask bars.

The masking bars 4-670 may then be removed from the region, and a planarizing layer 4-680 (e.g., an oxide layer) deposited over the region. A CMP step may be used to planarize the pixel region yielding a structure as depicted in FIG. 4-6Q, in plan view, and FIG. 4-6R, in elevation view. The remaining portions of the vertical bars form vertical pillars 4-628, according to some embodiments. In some implementations, a transverse dimension of the vertical pillars 4-628 is between approximately 80 nm and approximately 250 nm. The vertical pillars may have an approximately square or rectangular cross-sectional shape. The pillars 4-628 may then be selectively etched and remove from the substrate to produce sample wells that are substantially self-aligned to the underlying diode junction, as depicted in FIG. 4-6S.

As depicted in FIG. 4-6Q, a spacing between the pillars 4-628 may be approximately equivalent in a first direction (a vertical direction as viewed on the page). The spacing between the pillars may not be equivalent in the second direction (a horizontal direction as viewed on the page). In some embodiments, a width and spacing of the mask bars 4-610, a thickness of the layer 4-622, and a thickness of the layer 4-624 may be selected to produce approximately equivalent spacing between the sample wells in the second direction.

In some implementations, instead of a single material being deposited for the planarizing layer 4-680 (as depicted in FIG. 4-6R), a stack of materials may be deposited, for example, a combination of an insulator, a semiconductor, and a metal. The stack may then be planarized to produce a layered structure for the sample well.

Figures 4, 5, 6, 6A:
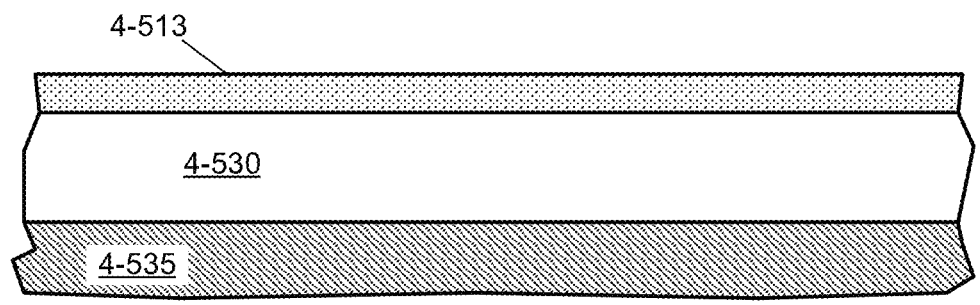
Figures 4, 5, 6, 6B:
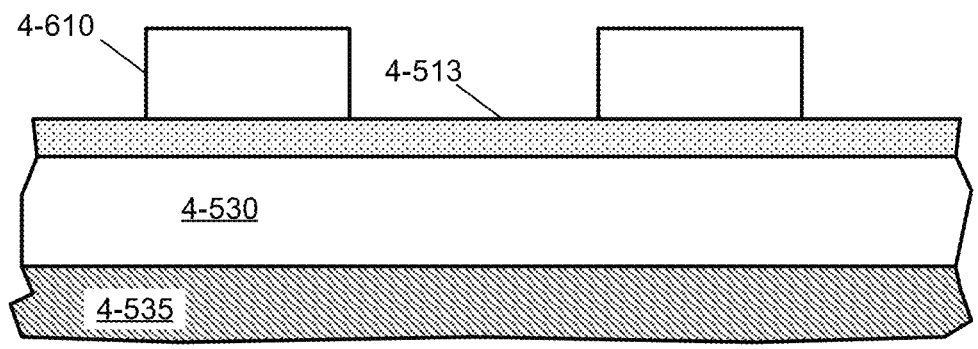

In FIG. 4-6S, the p- and n-type regions of the diodes are planar. In some embodiments, and referring back to FIG. 4-6L, the exposed p- and n-type regions may be etched after patterning the resist 4-650 and before depositing the electrodes, as depicted in FIG. 4-6T. As an example, a wet anisotropic etch may be used to selectively etch along crystallographic planes of the semiconductor. The etch may be a timed etch that undercuts the remaining resist 4-650 as indicated in the drawing, according to some embodiments. The electrode material may then be deposited as depicted in FIG. 4-6U.

In some embodiments, the electrode material 4-520 may be a transparent conductor, for example ITO, so that emission from a sample may pass through the electrode material. In some implementations, a thin semiconductor layer 4-512 is used, so that absorption of emission from a sample that passes through the semiconductor layer is less than about 30%. For example, a thickness of the semiconductor layer from which the diodes are formed may be less than approximately 50 nm.

Any one or more of the foregoing embodiments of excitation sources may be included in an embodiment of an integrated device.

V. Excitation Coupling

Coupling of energy from an excitation source to a sample well may be improved or affected by forming excitation-coupling structures within and/or adjacent a sample well. Excitation-coupling structures may comprise micro- or nanoscale structures fabricated around a sample well in some embodiments, or may comprise structures or particles formed at a sample well in some embodiments. Excitation-coupling structures may affect radiative excitation of a sample in some implementations, and may affect non-radiative excitation of a sample in some implementations. In various embodiments, radiative excitation-coupling structures may increase an intensity of excitation energy within an excitation region of a sample well. Non-radiative excitation-coupling structures may improve and/or alter non-radiative energy-transfer pathways from an excitation source (which may be radiative or non-radiative) to a sample.

V. A. Radiative Plasmonic Excitation-Coupling Structures

There are a number of different types of radiative, excitation-coupling structures that may be used to affect coupling of excitation energy from an excitation source to an excitation region within a sample well. Some radiative coupling structures may be formed of a conductor (e.g., include a metal layer), and support surface plasmon oscillations that locally affect the excitation energy (e.g., locally alter an electromagnetic field). In some cases, surface-plasmon structures may enhance the excitation energy within an excitation region of the sample well by a factor of two or more. Some radiative coupling structures may alter the phase and/or amplitude of an excitation field to enhance excitation energy within a sample well. Various embodiments of radiative excitation-coupling structures are described in this section.

FIG. 5-1A depicts just one example of a surface-plasmon structure 5-120 that may be used to enhance coupling of excitation energy into a sample well. The drawing depicts a plan view of a region around a surface-plasmon structure 5-120, and represents results of a numerical simulation of electric field intensity around the structure. The drawing depicts a surface-plasmon structure comprising three triangular features having sharp apexes that are located in close proximity to a sample well (not shown). According to some embodiments, a surface-plasmon structure may comprise a metal or conductor (e.g., a patterned thin film of any one or combination of the following metals or metal alloys: Al, Au, Ag, Ti, TiN). A thickness of the film may be between approximately 10 nm and approximately 100 nm in some embodiments, though other thicknesses may be used in other embodiments. A surface-plasmon structure, in some embodiments, may include sharp features 5-110 located in close proximity to a sample well (e.g., within about 100 nm).

FIG. 5-1B depicts a cross-section, elevation view of the surface-plasmon structure of FIG. 5-1A, taken at the dashed line. The simulation shows a localized, high-intensity region 3-505 of the excitation energy adjacent an apex of a triangle of the surface-plasmon structure. For this simulation, the surface-plasmon structure 5-120 was located on a dielectric layer 5-135 (e.g., silicon dioxide) above a waveguide 5-130. The surface-plasmon structure taps energy from an evanescent field of the waveguide, and enhances the intensity at the sample well.

In some embodiments, enhancement of excitation energy by a surface-plasmon structure may be localized to an extent that a sample well 3-215 is not needed. For example, if a high-intensity region 3-505 is formed having a diameter of approximately 100 nm with a peak intensity value greater than about 80% of the intensity outside the region, then a deep sample well may not be needed. Only samples within the high-intensity region 3-505 may contribute appreciable emission for purposes of detection.

When an incident electromagnetic field interacts with a surface-plasmon structure, surface-wave currents are generated in the structure. The shape of the structure can affect the intensity and distribution of these surface-plasmons. These localized currents can interact with and significantly alter and intensify the incident electromagnetic field in the immediate vicinity of the surface-plasmon structure, e.g., as depicted by the high-intensity region 3-505 in FIG. 5-1B. In some embodiments, an emitter (e.g., a fluorescing tag) that emits radiation near a surface-plasmon structure can have its emission altered by the structure, so as to alter a far-field radiation pattern from the emitter.

Figures 1A, 5:
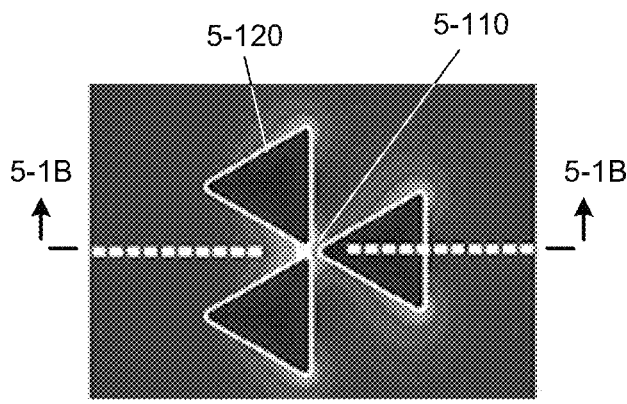
Figures 1B, 5:
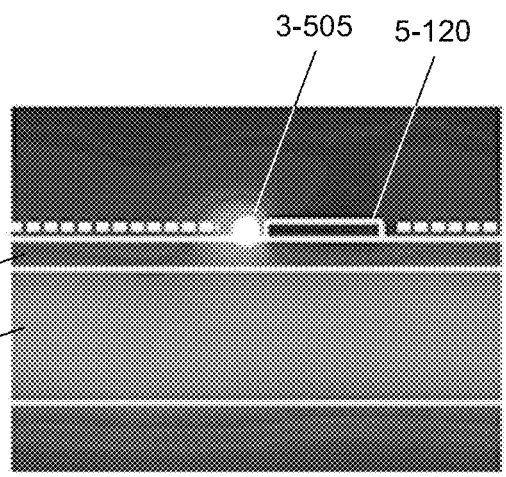
Figures 1C, 5:
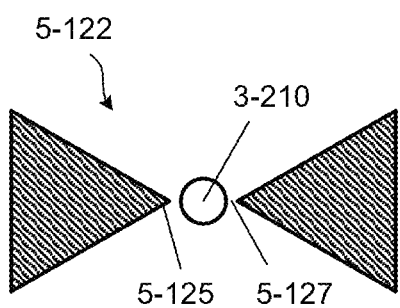

Another embodiment of a surface-plasmon structure 5-122 is depicted in the plan view of FIG. 5-1C. The illustrated bow-tie structure comprises two triangular metallic structures located adjacent a sample well 3-210. The structures may be patterned below a sample well, for example, and/or adjacent an excitation region of the sample well. There may be a gap 5-127 between the sample well and sharp features 5-125 of the surface-plasmon structure, in some implementations. The gap 5-127 may be between approximately 10 nm and approximately 200 nm, according to some embodiments. In some implementations, the gap 5-127 may be between approximately 10 nm and approximately 100 nm. The sharp features 5-125 may comprise a point or sharp bend in an edge of the surface-plasmon structure, as depicted in the drawing. The sharp features may have any suitable shape. In some embodiments a bend radius of a sharp feature 5-125 may be less than approximately five wavelengths associated with the incident excitation energy. In some embodiments a bend radius of a sharp feature 5-125 may be less than approximately two wavelengths associated with the incident excitation energy. In some embodiments a bend radius of a sharp feature 5-125 may be less than approximately five wavelengths associated with a surface-plasmon wave that is excited by the incident excitation energy. In some embodiments a bend radius of a sharp feature 5-125 may be less than approximately two wavelengths associated with a surface-plasmon wave that is excited by the incident excitation energy.

Figures 1D, 5:
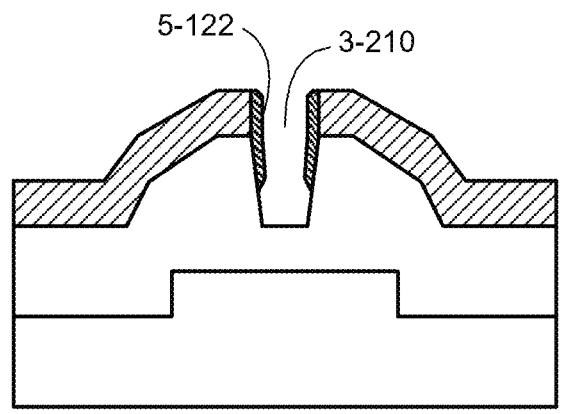
Figures 1E, 5:
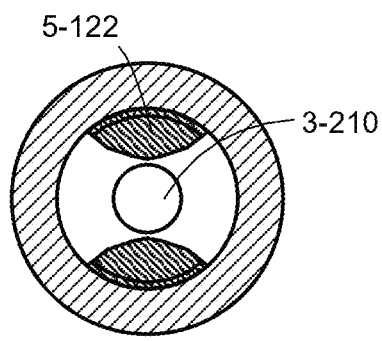
Figures 2A, 5:
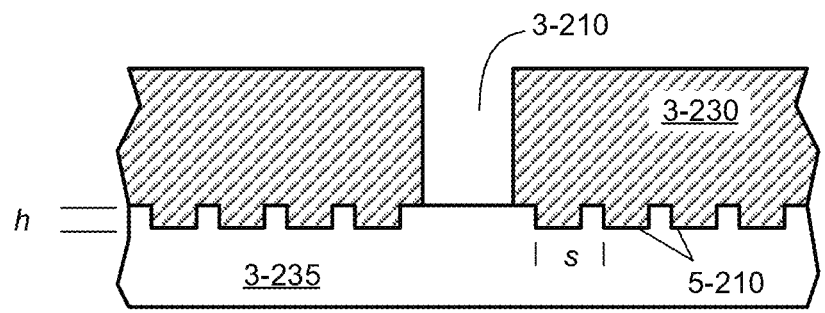
Figures 2B, 5:
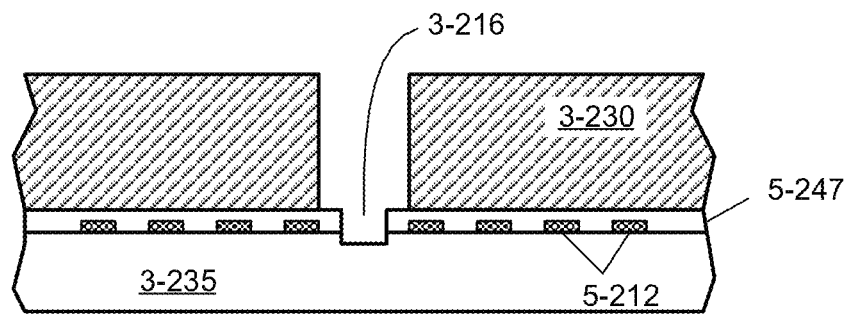
Figures 2C, 5:
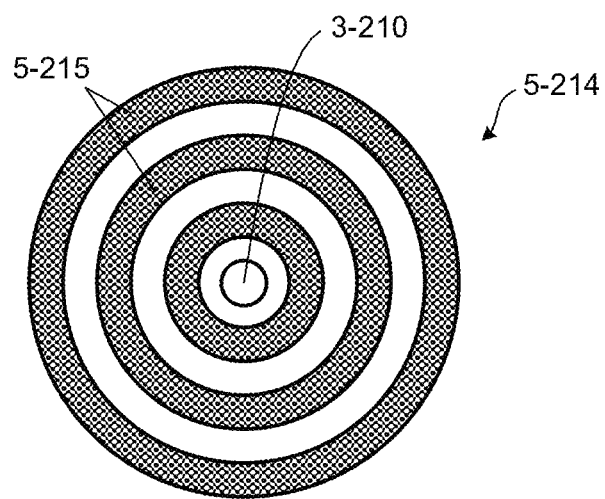

According to some embodiments, surface-plasmon structures 5-122 may be patterned within a sample well 3-210 as illustrated in the elevation view of FIG. 5-1D. In some embodiments, a surface-plasmon structure within a sample well may comprise one or more fingers (e.g., metallic fingers) patterned onto sidewalls of the sample well, as depicted in the drawing. FIG. 5-1E depicts a plan view of the sample well 3-210 showing the surface-plasmon structures 5-122 formed on sidewalls within the sample well. In some embodiments, the lower ends of these surface-plasmon structures 5-122 form sharp features or bends where the electromagnetic field will be enhanced. The surface-plasmon structures 5-122 may, or may not, extend to a base of the sample well.

In some embodiments, the surface-plasmon structures 5-122 may be arranged to affect the polarization of the excitation energy and/or emitted radiation from the sample well. For example, a pattern as depicted in FIG. 5-1E may be used to affect a preferred orientation of linear or elliptical excitation polarization and/or a preferred orientation of linear or elliptical polarization from an emitter within the sample well.

Surface-plasmon structures may be patterned in shapes other than those depicted in FIG. 5-1A through FIG. 5-1E. For example, surface-plasmon structures may be patterned as regular or periodic structures, as depicted in FIG. 5-2A, according to some embodiments. For example, a surface-plasmon structure may be patterned is an array of protruding features 5-210 on a lower surface of a material 3-230 in which the sample well 3-210 is formed. Periodic surface-plasmon structures may be formed in a regular array, for example, a grating, a grid, a lattice, a circular grating, a spiral grating, an elliptical grating, or any other suitable structure. In some implementations, there may be a substantially uniform spacing s between the protrusions 5-210 of a surface-plasmon structure. In some implementations, the spacing s may have any value between approximately 40 nm and approximately 250 nm. According to some embodiments, the protrusions may have a height h between approximately 20 nm and approximately 100 nm. In some implementations, the spacing s may be non-uniform or may be chirped (having a decreasing value at larger radial distances). In some embodiments, the protrusions 5-210 of a surface-plasmon structure may be patterned as a Fresnel zone plate. According to some embodiments, a surface-plasmon structure of 5-210 may be formed adjacent a transparent layer and/or dielectric layer 3-235.

In some implementations, a surface-plasmon structure 5-212 may be spaced from a material 3-230 in which the sample well is formed as depicted in FIG. 5-2B. For example, there may be an intervening dielectric layer 5-247 between the surface-plasmon structure 5-212 and the material 3-230. According to some embodiments, a surface plasmons structure 5-212 may be located adjacent a divot 3-216 of a sample well, as depicted in the drawing. For example, a surface-plasmon structure 5-212 may be located adjacent sidewalls of a divot 3-216, as depicted in FIG. 5-2B.

FIG. 5-2C illustrates a surface-plasmon structure 5-214 that is formed as a concentric, circular grating. The structure 5-214 may comprise concentric conducting rings 5-215, according to some embodiments. The rings may be separated by a regular spacing s and have a height h, as described in connection with FIG. 5-2A. According to some embodiments, a sample well 3-210 with an optional divot may be located at a center of the rings. The circular grating may be patterned adjacent a base of the sample well.

A periodicity of a surface-plasmon structure may be selected to form a resonant structure according to some embodiments. For example a spacing s of a surface-plasmon structure may be selected to be approximately one-half wavelength of a surface-plasmon wave that is generated in the structure by the excitation energy. When formed as a resonant structure, a surface-plasmon structure may accumulate and resonate excitation energy along the direction of the periodic surface-plasmon structure. Such a resonant behaviour can intensify electromagnetic energy within a sample well, or adjacent a sample well, as depicted in FIG. 5-2D.

FIG. 5-2D represents numerically simulated electromagnetic field results at the base of the sample well and around a periodic surface-plasmon structure. The surface-plasmon structure 5-216 is located adjacent the material 3-230 in which the sample well is formed, and is adjacent a base of a sample well 3-210. The surface-plasmon structure may be in the form of a grating or circular grating that repeats at regular spacing intervals in regions away from the sample well and outside the simulated region. For example, there may be between three and 50 repeated grating protrusions of the surface-plasmon structure 5-216. A region of high intensity 5-240 can be seen at the base of the sample well 3-210. The intensity within this region has been enhanced by more than a factor of 2 over the surrounding region just below the surface-plasmon structure.

FIG. 5-2E depicts, in elevation view, an alternative embodiment of a resonant surface-plasmon structure 5-218. According to some embodiments, a surface-plasmon structure may be formed as periodic grating or grid patterns, and may be patterned in multiple layers 5-247. A sample well 3-210 may be patterned through the multiple layers 5-247 and within the resonant surface-plasmon structure 5-218, according to some embodiments. In some implementations, a resonant surface-plasmon structure may comprise discrete conductive elements 5-222 is depicted in the plan view of FIG. 5-2F. In some implementations, a resonant surface-plasmon structure may comprise a continuous lattice pattern 5-250, as depicted in FIG. 5-2G. A dielectric filler 5-252 may be located in voids of the conductive material 5-250, and a sample well 3-210 may be located with a void.

Figures 2H, 5:
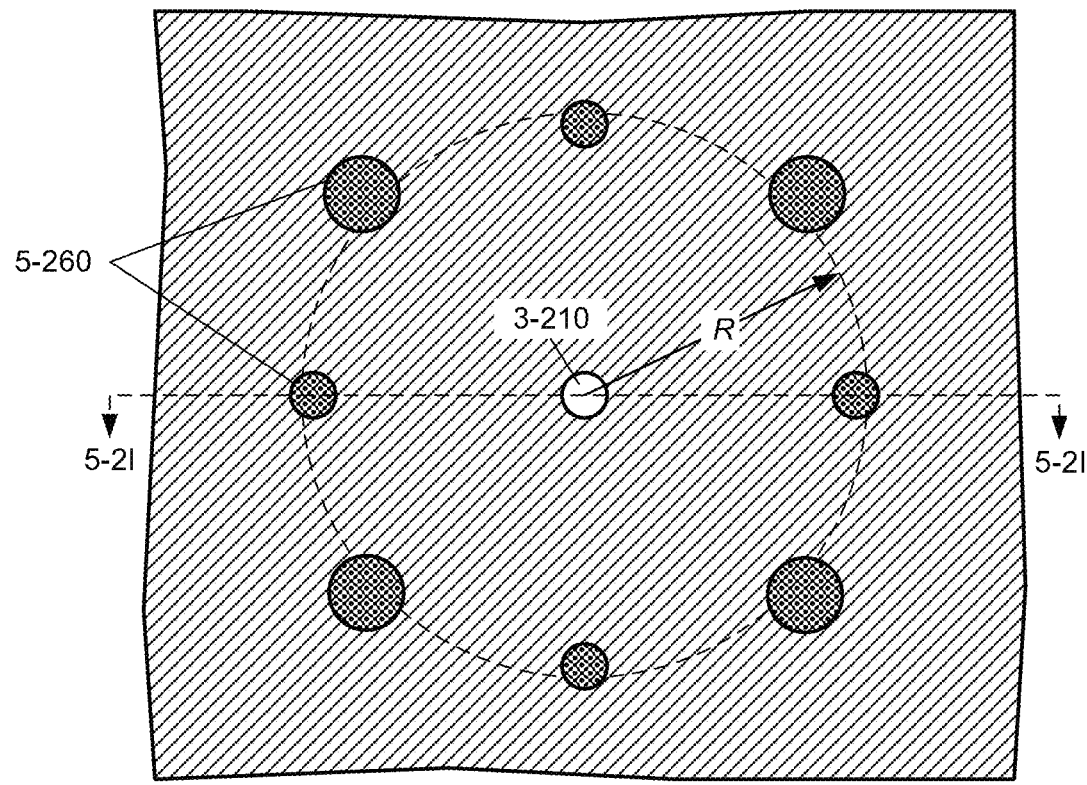
Figures 2I, 5:
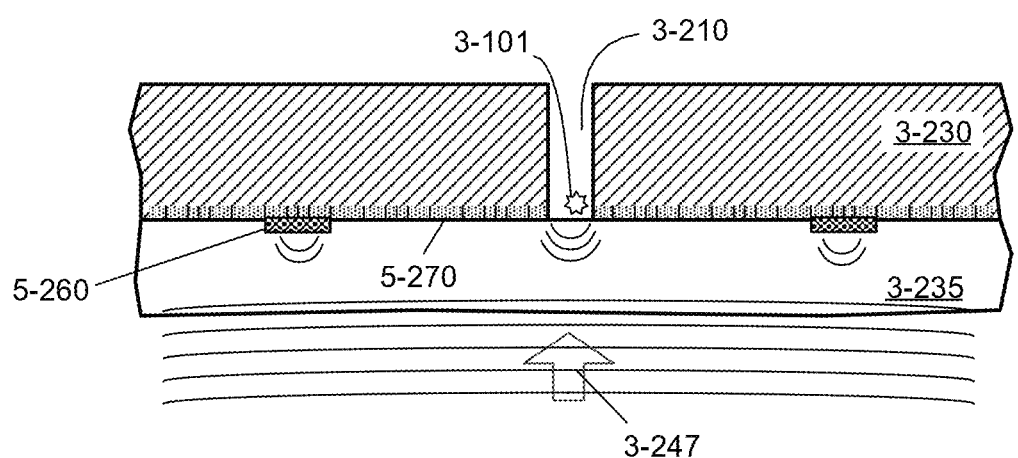
Figures 3A, 5:
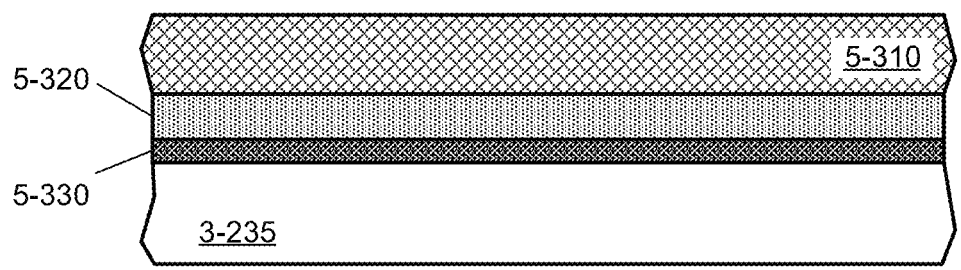
Figures 3B, 5:
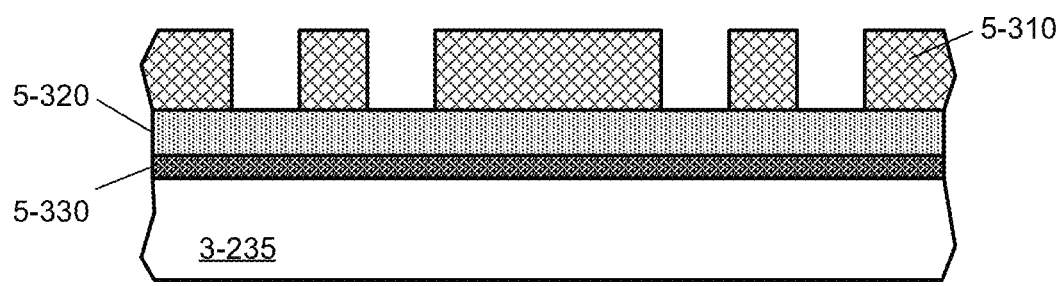
Figures 3C, 5:
Figures 3D, 5:
Figures 3E, 5:
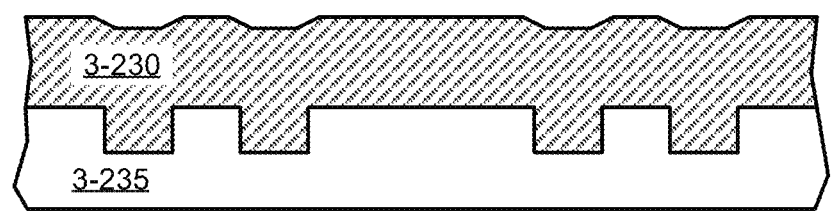
Figures 4A, 5:
Figures 4B, 5:
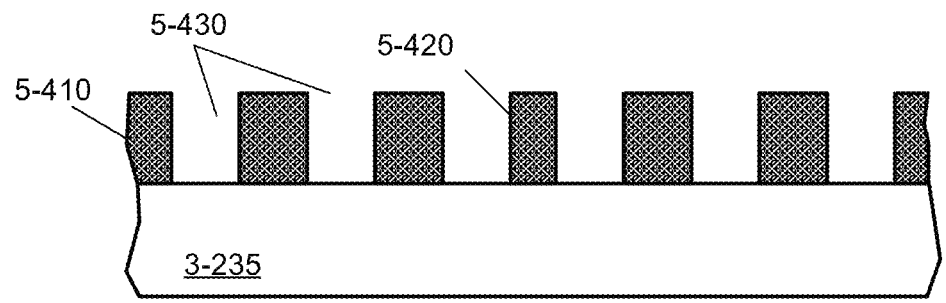
Figures 4C, 5:
Figures 4D, 5:
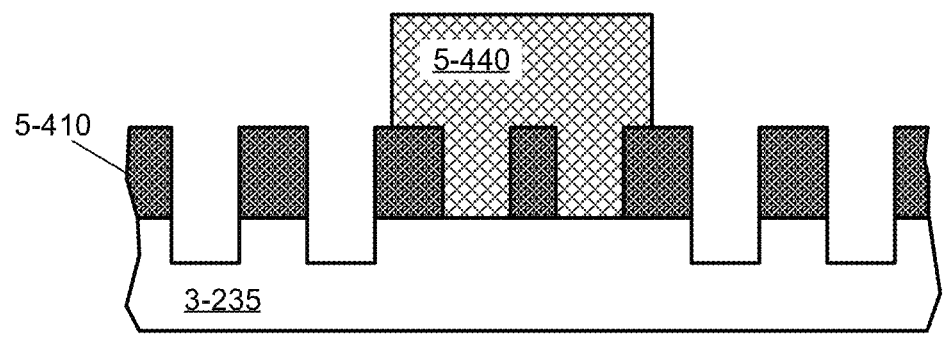
Figures 4E, 5:
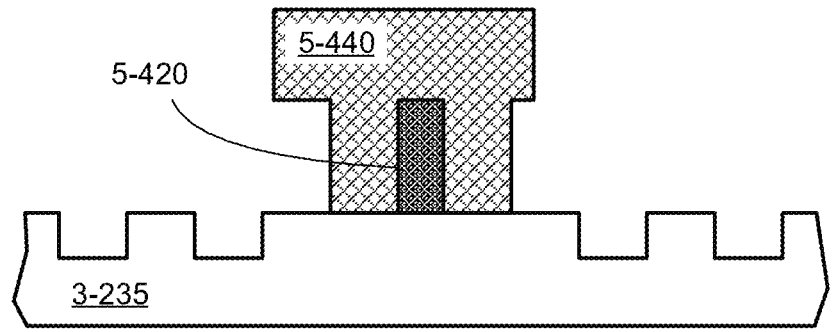
Figures 4F, 5:
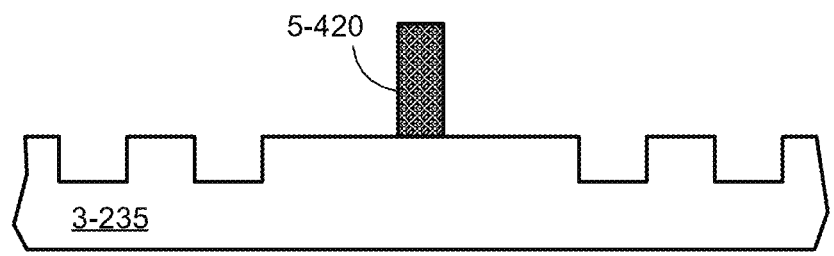
Figures 4G, 5:
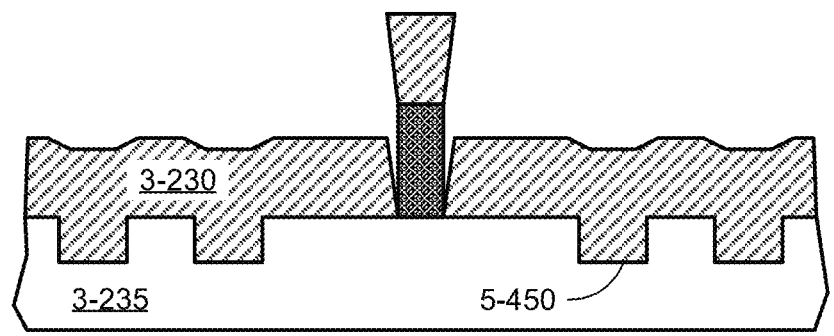
Figures 5, 5A:
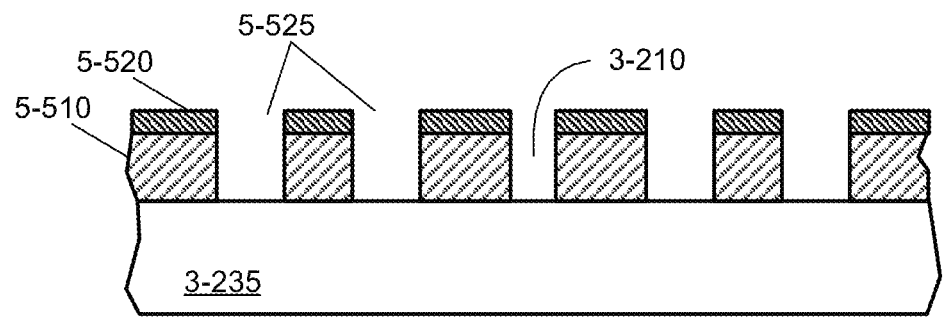
Figures 5, 5B:
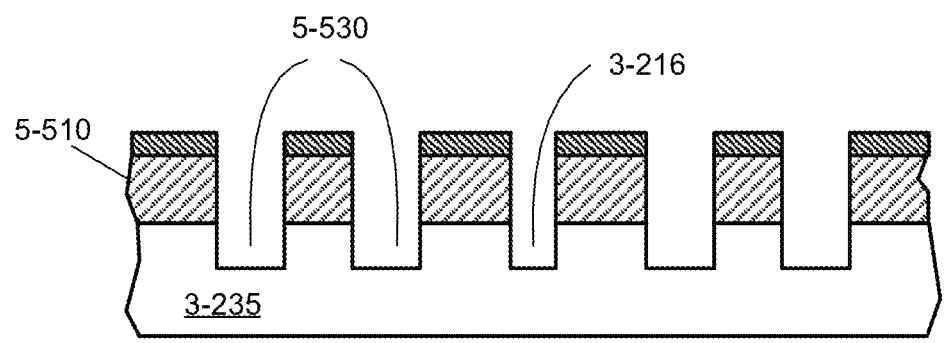
Figures 5, 5C:
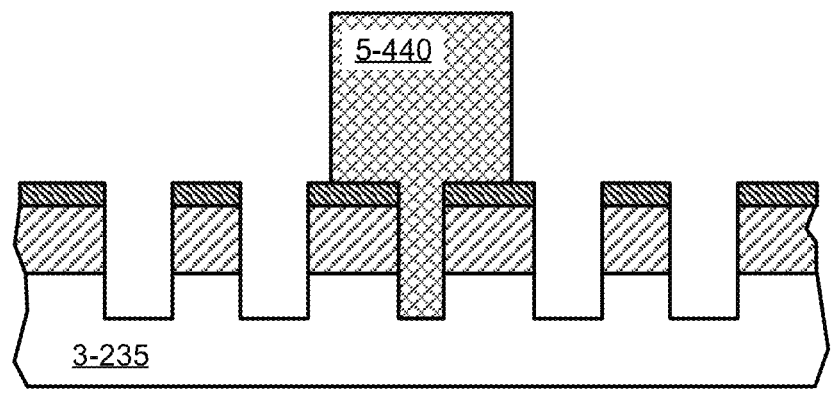
Figures 5, 5D:
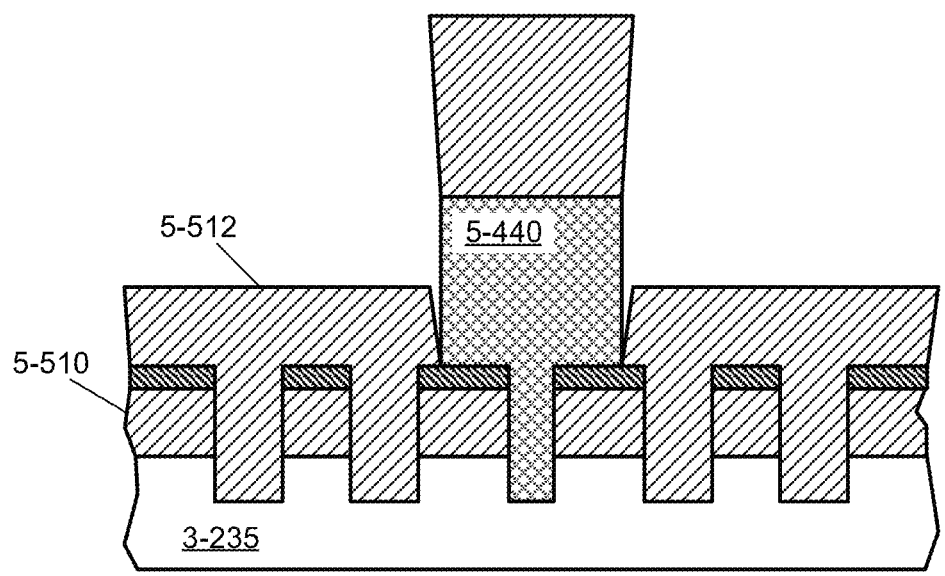

There are a variety of different surface-plasmon structures that may be used to enhance coupling into a sample well or to affect emission from a sample within the sample well. FIG. 5-2H depicts, in plan view, yet an alternative embodiment of the surface-plasmon structure. An elevation view of the structure is depicted in FIG. 5-2I. According to some implementations, a surface-plasmon structure may comprise an array of discs distributed around a sample well 3-210. In some implementations, instead of using conductive discs 5-260, a surface-plasmon structure may comprise a conductive layer through which a distributed pattern of holes is formed. Such a structure may be referred to as a "nanoantenna."

V. B. Fabrication of Plasmonic Excitation-Coupling Structures

Figures 5, 5E:
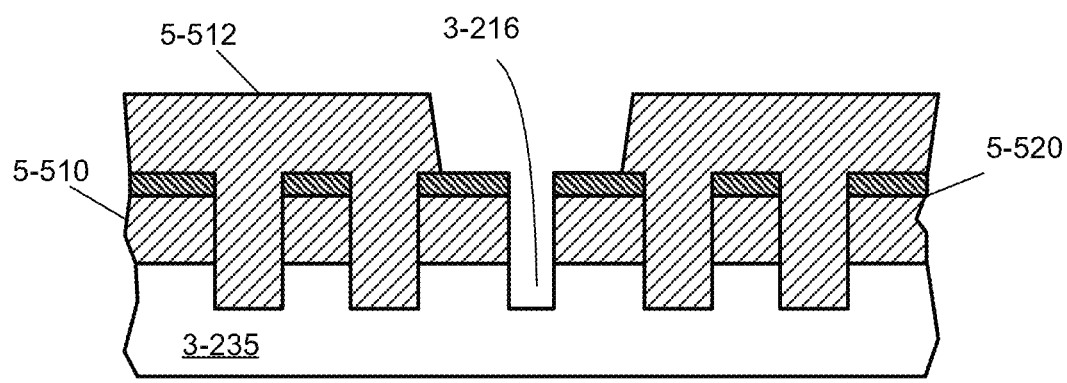
Figures 5, 6, 6A:
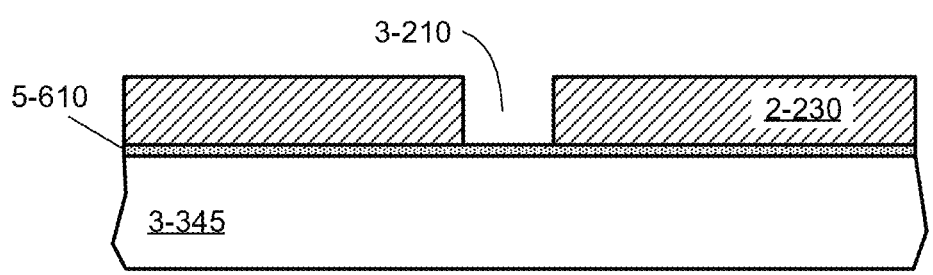
Figures 5, 6, 6B:
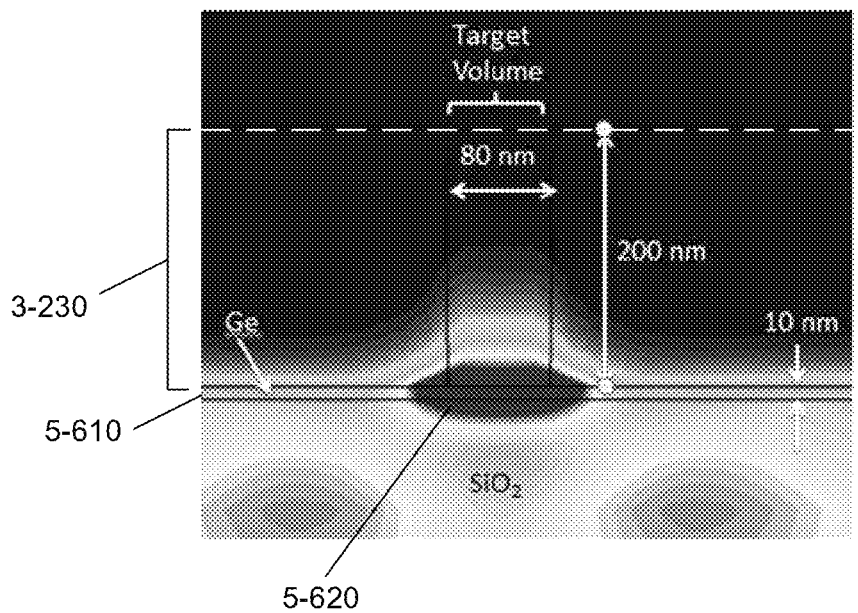
Figures 5, 6, 6C:
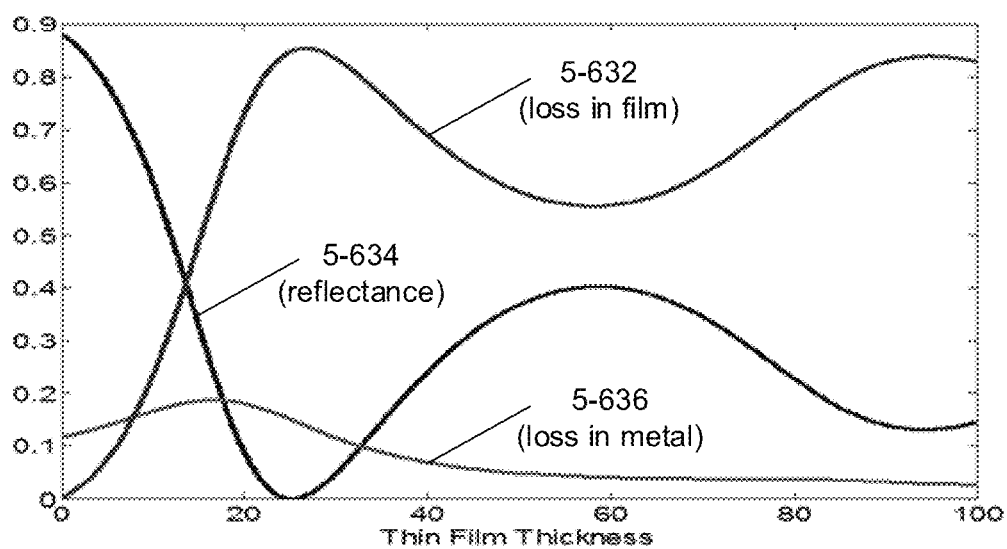
Figures 5, 6, 6D:
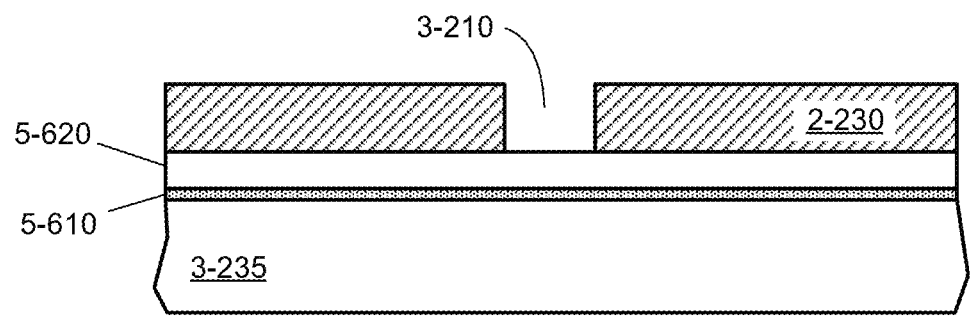
Figures 5, 6, 6E:
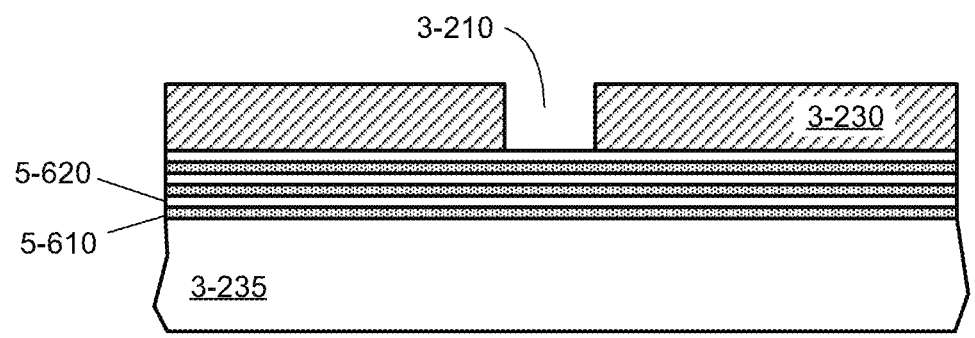

A variety of different processes may be used to pattern surface-plasmon structures adjacent a sample well. FIG. 5-3A through FIG. 5-5E depict structures associated with process steps that may be used to form surface-plasmon structures adjacent to a sample well, according to some embodiments. Referring now to FIG. 5-3A, a process for forming a surface-plasmon structure may comprise forming a resist layer 5-310 on an anti-reflective coating (ARC) 5-320 on a masking layer 5-330. The layers may be disposed on a transparent dielectric layer 3-235, according to some implementations. The resist layer 5-310 may comprise a photoresist or an electron- or ion-beam resist that may be lithographically patterned. The masking layer 5-330 may comprise a hard mask formed of an inorganic material (e.g., silicon or silica nitride, or any other suitable material), according to some embodiments.

In some implementations, a photolithographic process may be used to pattern the resist 5-310 as depicted in FIG. 5-3B. The selected pattern may comprise a layout of protrusions or holes that will be used to form a desired surface-plasmon structure. After development of the resist 5-310, regions of the ARC will be exposed, and the pattern may be etched into the ARC layer 5-320 and then into the masking layer 5-330. The resist and ARC may be stripped from the substrate, and a resulting structure may appear as shown in FIG. 5-3C. The masking layer 5-330 may then be used as an etch mask, so that the pattern may be transferred into the underlying dielectric layer 3-235 via a selective anisotropic etch, as depicted in FIG. 5-3D.

A conductive material 3-230, or a layer of materials comprising a conductor, may then be deposited over the region, as illustrated in FIG. 5-3E. Any suitable conductive material may be used for forming a surface plasmon structure, whether or not it is deposited as a separate layer from the material 3-230. For example, in some cases, a first conductive material may be deposited as a base layer of material 3-230 in which a surface-plasmon structure is formed. Examples of materials that may be used for forming a surface-plasmon structure include, but are not limited to, Au, Al, Ti, TiN, Ag, Cu, and alloys or combination layers thereof.

The material 3-230, or layer of materials, may be deposited by any suitable deposition process, including but not limited to a physical deposition process or a chemical vapor deposition process. In some embodiments, the material 3-230 may have a thickness between approximately 80 nm and approximately 300 nm. In some implementations, the material 3-230 may be planarized (e.g., using a CMP process), though planarization is not necessary. A sample well may be formed in the material 3-230 using any suitable process described herein in connection with fabricating a sample well.

The inventors have recognized that forming a surface-plasmon structure according to the steps shown in FIG. 5-3A through FIG. 5-3E may require accurate alignment of the sample well to the surface-plasmon structure. For example, a surface-plasmon structure comprising a concentric grating, as depicted in FIG. 5-2C, may require accurate alignment of the sample well 3-210 to the center of the surface-plasmon structure 5-214. To avoid fabrication difficulties associated with such accurate alignment, the inventors have developed self-alignment processes that are depicted in FIG. 5-4A through FIG. 5-5E.

Referring now to FIG. 5-4A, a process for forming a surface-plasmon structure and sample well that is self-aligned to the surface-plasmon structure may comprise forming a masking layer 5-410 on a transparent dielectric layer 3-235. The masking layer may comprise a hard mask formed of an inorganic material, such as silicon or silica nitride, according to some embodiments. A thickness of the masking layer 5-410 may be approximately equal to a desired height of a sample well 3-210. For example, the thickness of the masking layer may be between approximately 50 nm and approximately 200 nm, according to some embodiments, though other thicknesses may be used in other embodiments.

The masking layer 5-410 may be patterned to create voids 5-430 having the desired pattern of a surface-plasmon structure that will be patterned in the dielectric layer 3-235. The patterning of the masking layer 5-410 may be done with any suitable lithography process (e.g., photolithography, electron-beam lithography, ion-beam lithography, EUV lithography, x-ray lithography). The resulting structure may appear as shown in FIG. 5-4B. The structure may include a central pillar 5-420, which will be used subsequently to form the self-aligned sample well.

A resist 5-440 (e.g., a photoresist) may then be patterned over the patterned masking layer 5-410, as depicted in FIG. 5-4C. Alignment for patterning the resist 5-440 (e.g., mask to substrate alignment) need not be highly accurate, and only requires the resist 5-440 to cover a central pillar 5-420 and not cover voids 5-430 that will be used to form the surface-plasmon structure.

A selective anisotropic etch may then be used to etch the dielectric layer 3-235 and transfer the pattern of the surface-plasmon structure into the dielectric, as depicted in FIG. 5-4D according to some embodiments. A selective isotropic etch may then be used to remove the exposed portions of the masking layer 5-410. The isotropic etch may be a wet etch, for example, though an isotropic dry etch may be used in some embodiments. Because the resist 5-440 covers the central pillar 5-420, the central pillar will not be etched and remain on the substrate, as depicted in FIG. 5-4E. The resist 5-440 may then be stripped from the substrate exposing the pillar 5-420, as depicted in FIG. 5-4F.

According to some embodiments, a metal conductive material 3-230, or a stack of materials including a conductive material, may then be deposited over the region as illustrated in FIG. 5-4G. The central pillar 5-420 and a cap of deposited material over the pillar may then be removed by a selective wet etch of the pillar, lifting off the cap. The removal of the central pillar leaves a sample well that is self-aligned to the underlying surface-plasmon structure 5-450.

An alternative process may be used to form a sample well that is self-aligned to a surface-plasmon structure, and is depicted in FIG. 5-5A through FIG. 5-5E. According to some embodiments, one or more conductive layers 5-510, 5-520 may be patterned on a transparent dielectric layer 3-235 using any suitable lithography process, as depicted in FIG. 5-5A. In some implementations, a first layer 5-510 may comprise aluminum, and a second layer 5-520 may comprise titanium nitride, though other material combinations may be used in various embodiments. A total thickness of the one or more layers may be approximately equivalent to a desired height of the sample well, according to some embodiments. The patterning may form a sample well 3-210, and voids 5-525 adjacent the sample well in the one or more metal layers. The voids may be arranged in the pattern of a desired surface-plasmon structure.

In some implementations, the dielectric layer 3-235 may be etched to transfer the pattern of the surface-plasmon structure and sample well 3-210 into the dielectric layer, as depicted in FIG. 5-5B. The etch depth into the dielectric may be between approximately 20 nm and approximately 150 nm, according to some embodiments. A resist 5-440 may be patterned to cover the sample well, as depicted in FIG. 5-5C. Alignment for patterning the resist need not be highly accurate, and only need cover the sample well without covering adjacent etched regions of the dielectric layer 3-235 that will be used to form the surface-plasmon structure.

As illustrated in FIG. 5-5D, a conductive material 5-512, or layers of materials including a conductor, may be deposited over the region using any suitable deposition process. The material 5-512 may fill the etched regions of the dielectric layer, and may extend above the one or more layers 5-510, 5-520. The resist 5-440 and the material covering the resist may then be removed according to a lift-off process. The resulting structure, shown in FIG. 5-5E, leaves a sample well that is self-aligned to the surrounding surface-plasmon structure. The sample well includes a divot 3-216.

In some embodiments the process depicted in FIG. 5-5A through FIG. 5-5E may be used to form a sample well that does not have a divot 3-216. For example, the resist 5-440 may be patterned over the sample well 3-210 before the dielectric layer 3-235 is etched. The dielectric layer 3-235 may then be etched, which will transfer the pattern of the surface-plasmon structure to the dielectric layer but not form a divot. The process may then proceed as illustrated in FIG. 5-5D and FIG. 5-5 E to create a self-aligned sample well having no divot.

V. C. Amplitude/Phase Excitation-Coupling Structures

Other structures, in addition to or as an alternative to surface-plasmon structures, may be patterned in the vicinity of the sample well 3-210 to increase the excitation energy within the sample well. For example some structures may alter the phase and/or the amplitude of the incident excitation field so as to increase the intensity of the excitation energy within the sample well. FIG. 5-6A depicts a thin lossy film 5-610 that may be used to alter the phase and amplitude of incident excitation radiation and increase the intensity of electromagnetic radiation within the sample well.

According to some embodiments, a thin lossy film may create constructive interference of the excitation radiation, resulting in field enhancement within an excitation region of the sample well. FIG. 5-6B depicts a numerical simulation of excitation radiation incident upon a sample well where a thin lossy film 5-610 has been formed immediately adjacent the sample well. For the simulation, the sample well has a diameter of approximately 80 nm and is formed in a metallic layer of gold approximately 200 nm thick. The sample well comprises an SCN, and suppresses propagation of excitation radiation through the sample well. The thin lossy film 5-610 is approximately 10 nm thick, is formed from germanium, and covers an underlying transparent dielectric comprising silicon dioxide. The thin lossy film extends across an entrance aperture of the sample well. The simulation shows that the intensity of the excitation radiation is a highest value at the entrance aperture of the sample well. The intensity of the excitation radiation in this bright region 5-620 is more than twice the value of the intensity to the left and right of the sample well.

A thin lossy film may be made from any suitable material. For example, a thin lossy film may be made from a material where the index of refraction n is approximately the same order of magnitude as the extinction coefficient k for the material. In some embodiments, a thin lossy film may be made from a material where the index of refraction n is within about two orders of magnitude difference from the value of the extinction coefficient k of the material. Non-limiting examples of such materials at visible wavelengths are germanium and silicon.

A thin lossy film may be any suitable thickness, which may depend upon a characteristic wavelength, or wavelengths, associated with the excitation source, or sources. In some embodiments, a thin lossy film may be between approximately 1 nm and approximately 45 nm thick. In other embodiments, a thin lossy film may be between approximately 15 nm and approximately 45 nm thick. In still other embodiments, a thin lossy film may be between approximately 1 nm and approximately 20 nm thick.

Figures 4, 5, 6, 6C:
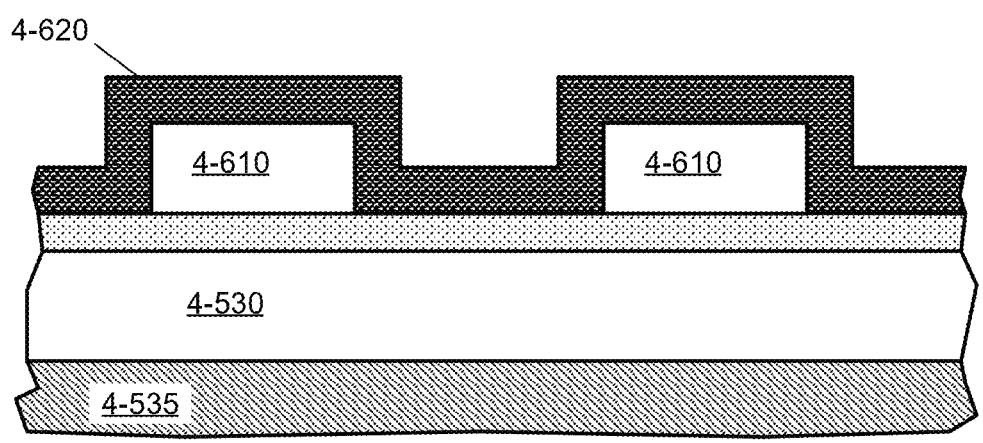

Effects of a thin lossy film on reflectance from the material 3-230 in which a sample well is formed, excitation energy loss within the thin lossy film, and excitation energy loss within the material 3-230 are shown in the graph of FIG. 5-6C. One curve plotted in the graph represents a reflectance curve 5-634, and shows how reflectance from the material 3-230 and the thin lossy film 5-610 vary as the thickness of the thin lossy film changes from 0 nm to 100 nm. The reflectance reaches a minimum value at about 25 nm, according to the simulated embodiment. The reflectance minimum will occur at different thicknesses depending on a characteristic wavelength of the excitation energy and materials used for the thin lossy film and material 3-230. In some implementations a thickness of thin lossy film is selected such that the reflectance is approximately at its minimal value.

Figures 4, 5, 6, 6D:
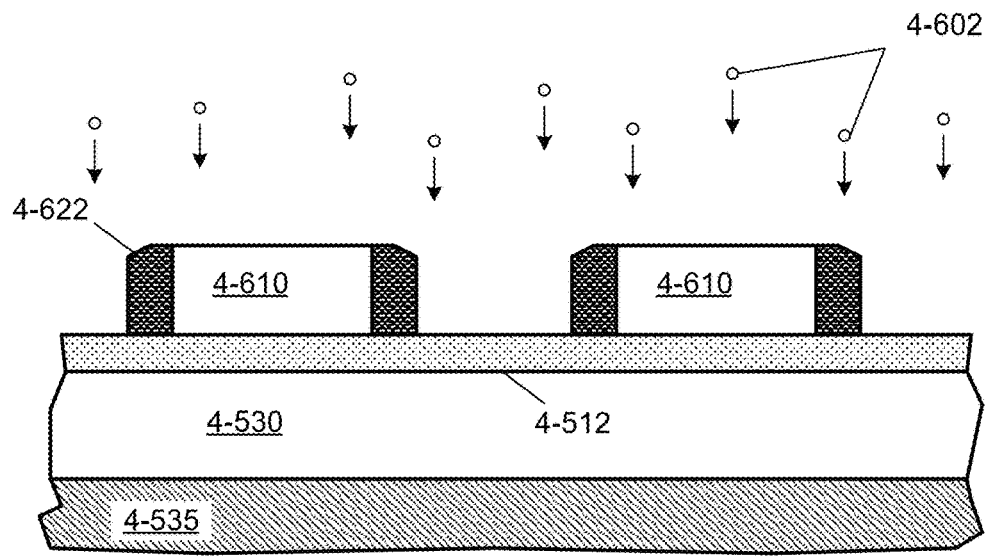

In some embodiments, a thin lossy film 5-610 may be spaced from a sample well 3-210 and material 3-230, as depicted in FIG. 5-6D. For example, a thin dielectric layer 5-620 (e.g., a silicon oxide $SiO_x$) may be formed over a thin lossy film, and a sample well 3-210 may be formed adjacent the dielectric layer 5-620. A thickness of the dielectric layer 5-620 may be between approximately 10 nm and approximately 150 nm according to some embodiments, though other thicknesses may be used in some embodiments.

Figures 4, 5, 6, 6E:
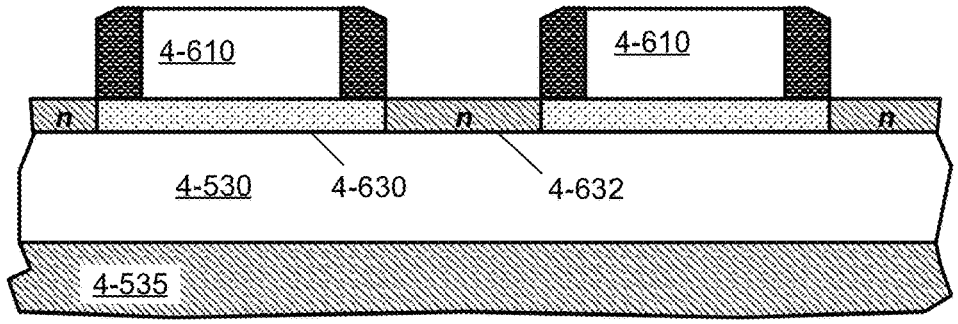
Figures 4, 5, 6, 6F:
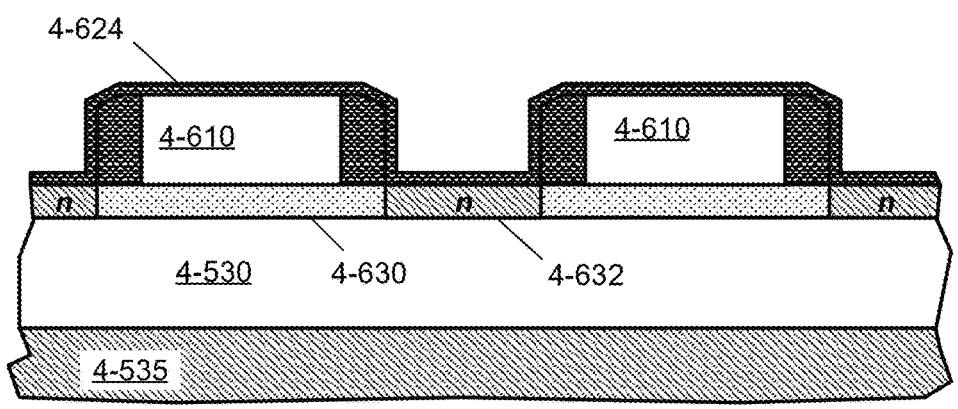
Figures 4, 5, 6, 6G:
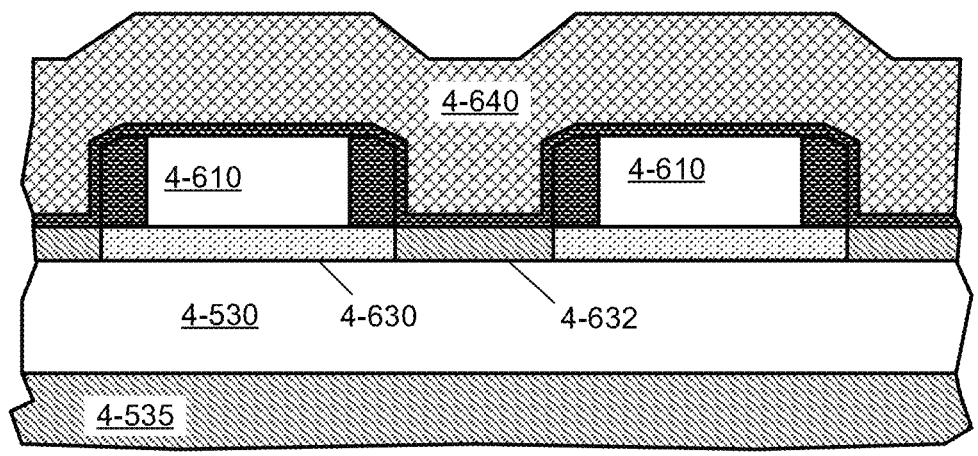
Figures 4, 5, 6, 6H:
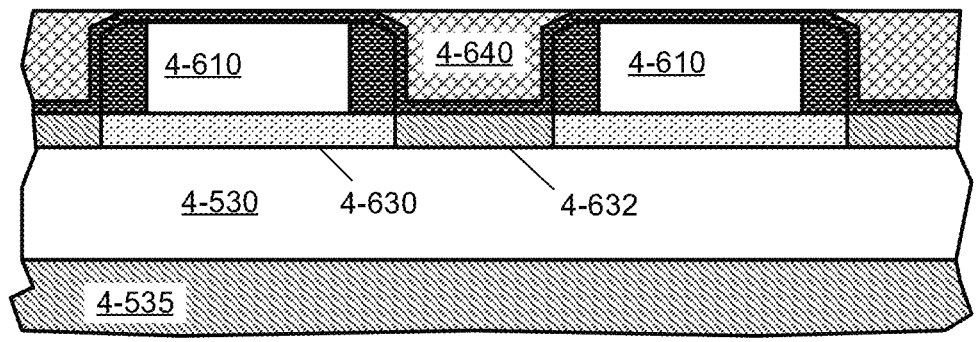
Figures 4, 5, 6, 6I:
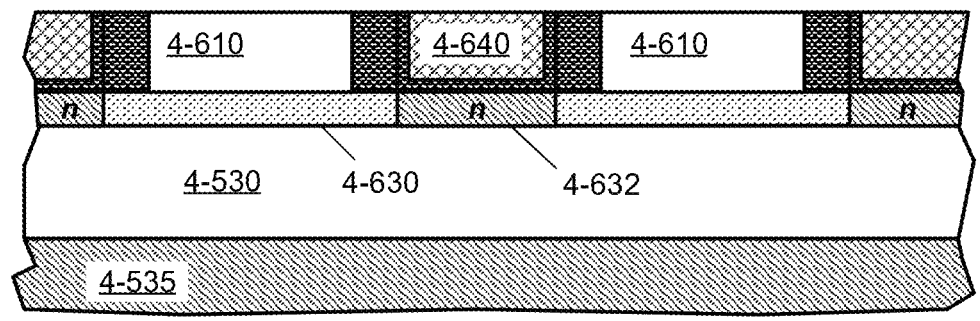
Figures 4, 5, 6, 6J:
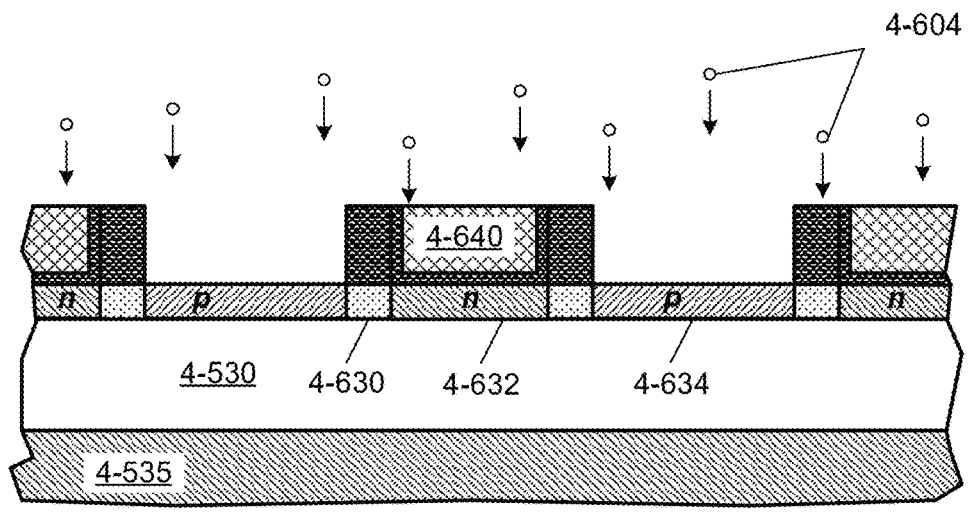
Figures 4, 5, 6, 6K:
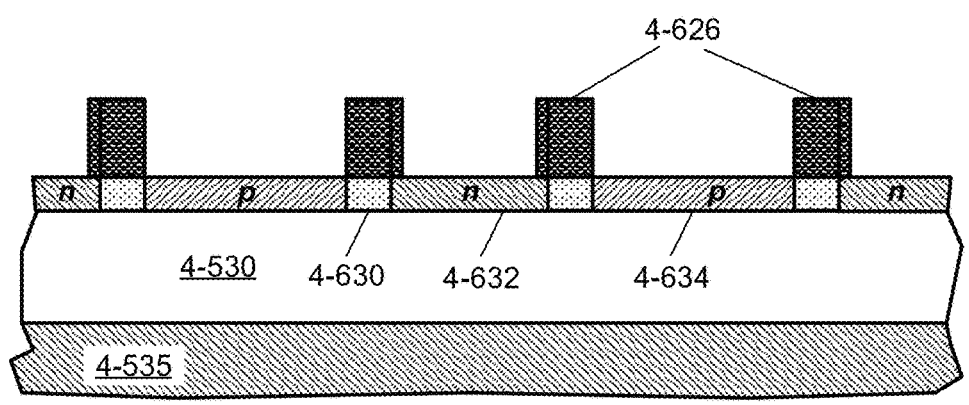
Figures 4, 5, 6, 6L:
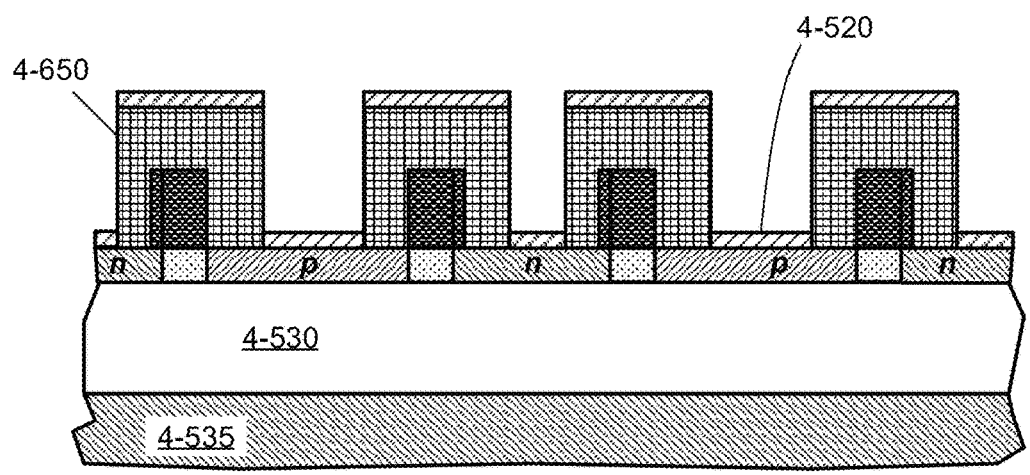
Figures 4, 5, 6, 6M:
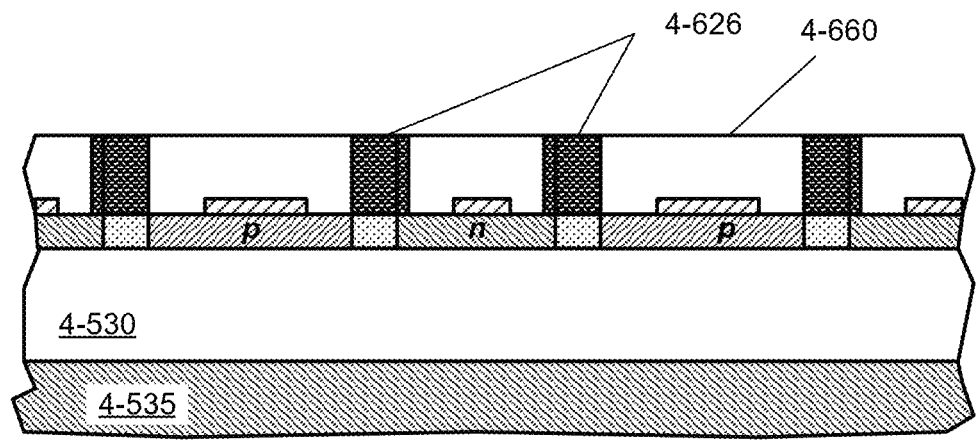
Figures 4, 5, 6, 6N:
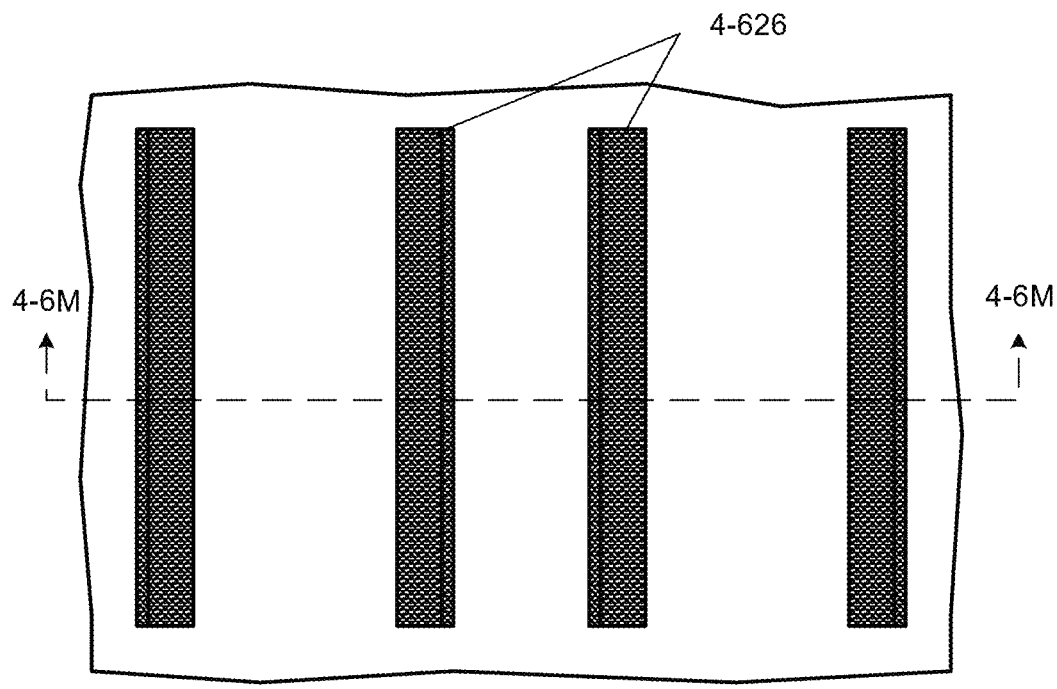
Figures 4, 5, 6, 6O:
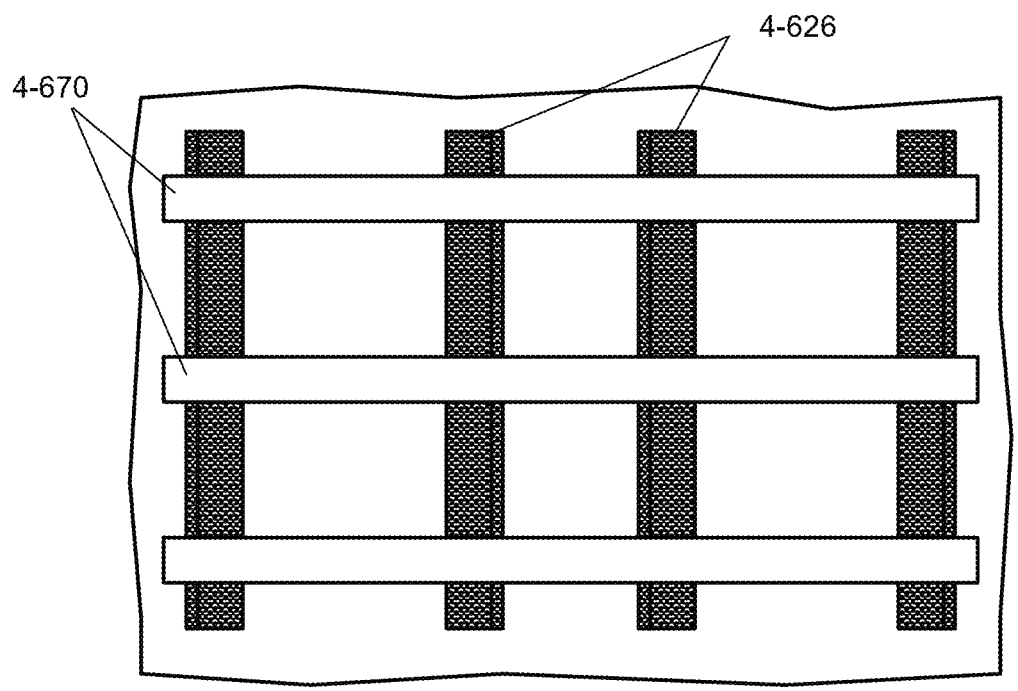
Figures 4, 5, 6, 6P:
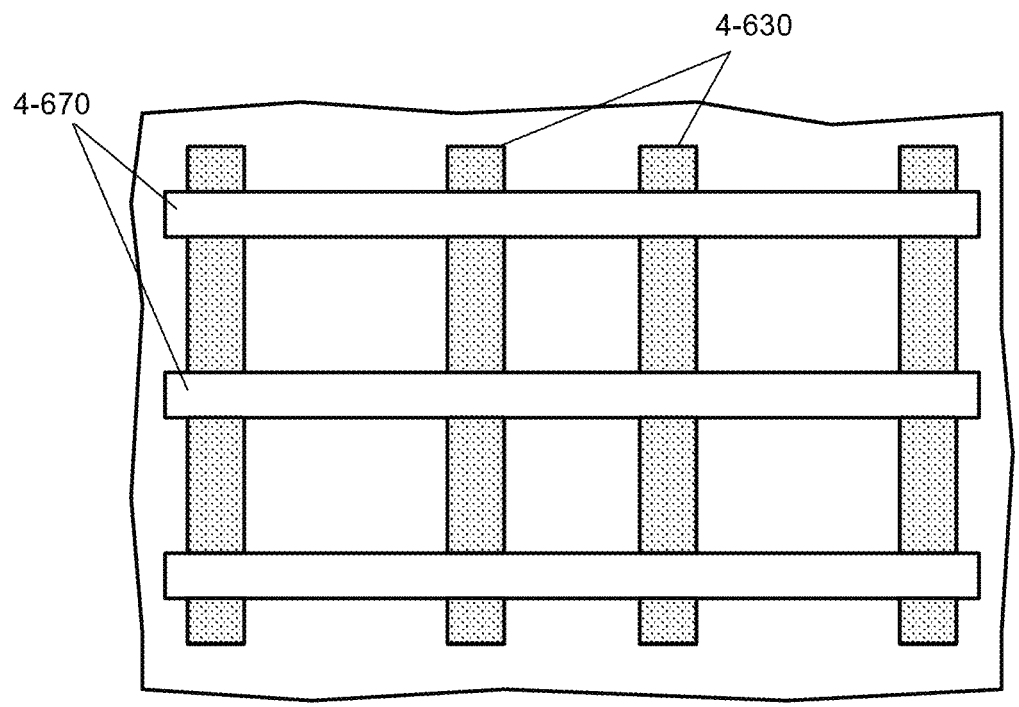
Figures 4, 5, 6, 6Q:
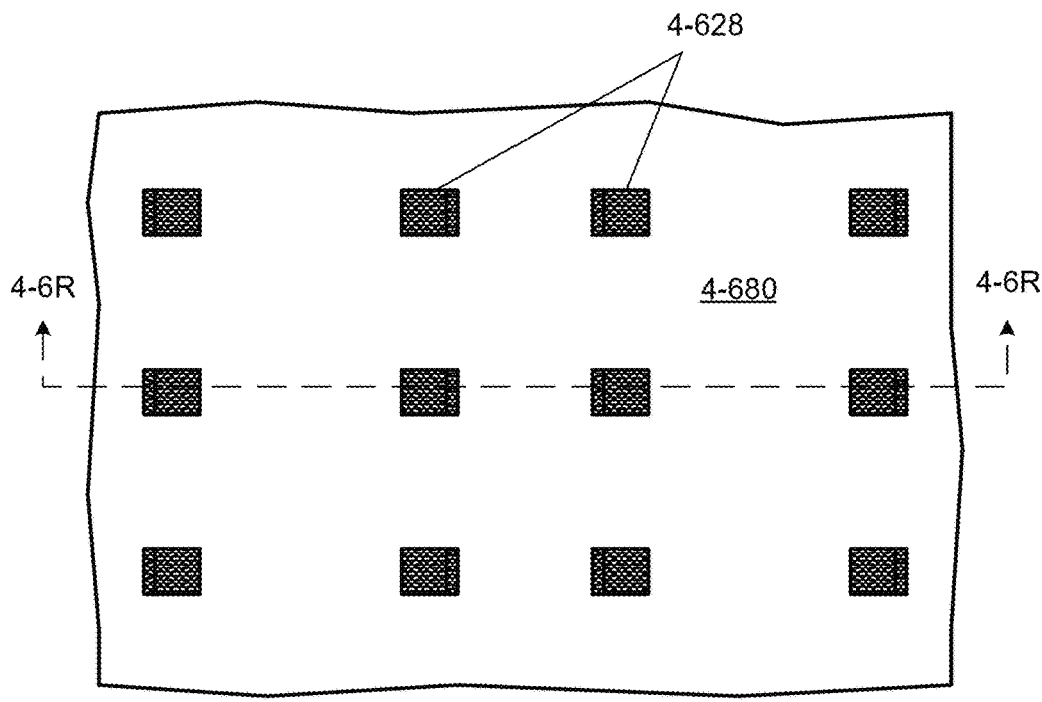
Figures 4, 5, 6, 6R:
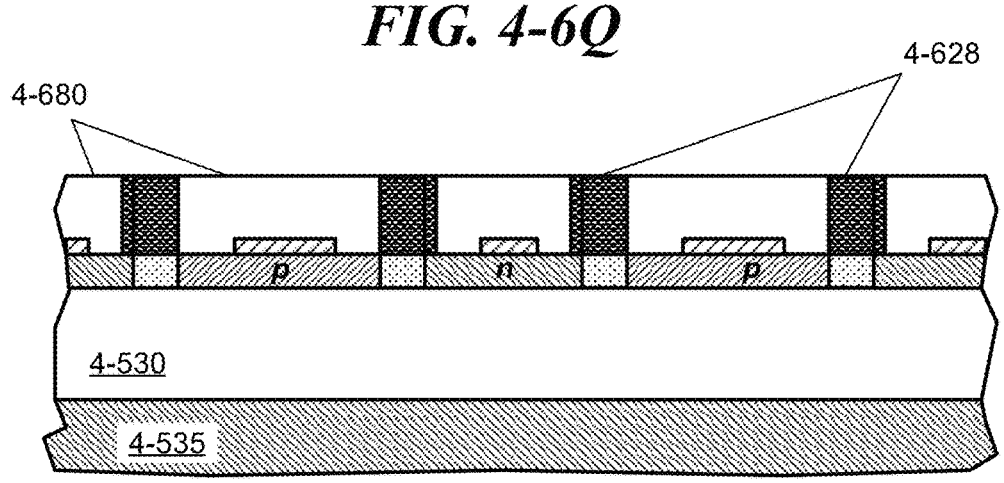
Figures 4, 5, 6, 6S:
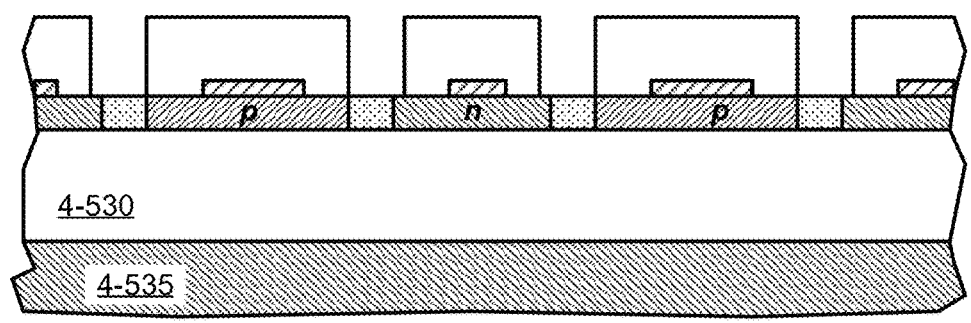
Figures 4, 5, 6, 6T:
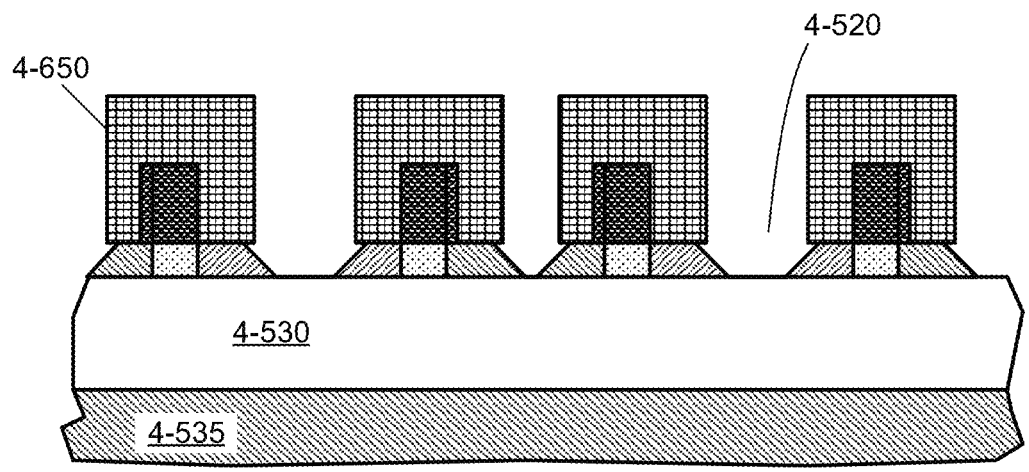
Figures 4, 5, 6, 6U:
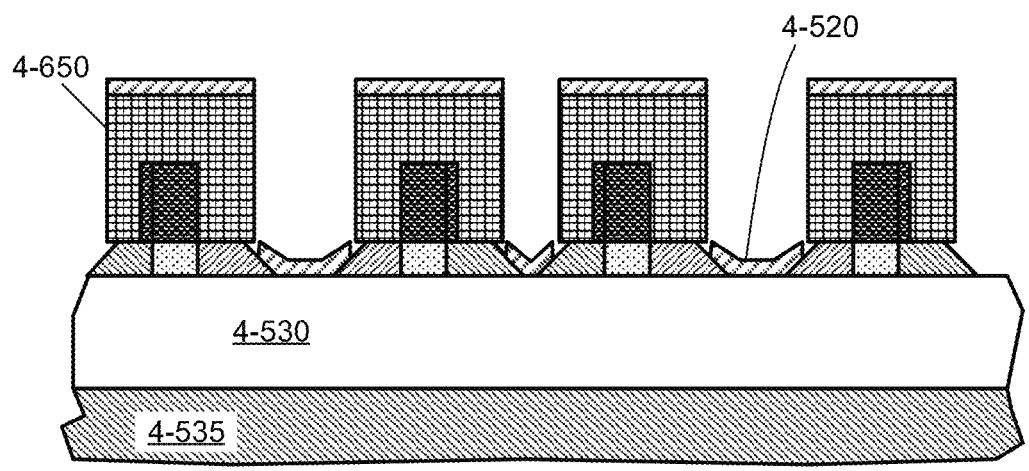

Although depicted as a single layer, a thin lossy film may comprise multiple layers of two or more materials. In some implementations, a multilayer stack comprising alternating layers of a thin lossy film 5-610 and a dielectric layer 5-620 may be formed adjacent a sample well 3-210, as depicted in FIG. 5-6E. A thickness of a thin lossy film 5-610 in a stack of layers may be between approximately 5 nm and approximately 100 nm, and a thickness of a dielectric layer 5-620 within the stack may be between approximately 5 nm and approximately 100 nm, according to some embodiments. In some implementations, the multilayer stack may comprise a layer of silicon dioxide having a thickness between approximately 2 nm and approximately 8 nm, a layer of silicon having a thickness between approximately 5 nm and approximately 20 nm, and a layer of germanium having a thickness between approximately 2 nm and approximately 12 nm, though other thicknesses may be used in other embodiments. In some implementations, the multilayer stack may comprise a layer of silicon dioxide (approximately 4.2 nm thick), a layer of silicon (approximately 14.4 nm thick), and a layer of germanium (approximately 6.5 nm thick), though other thicknesses may be used in other embodiments.

A thin lossy film may be fabricated from any suitable material that exhibits at least some loss to the incident radiation. In some embodiments, a thin lossy film may comprise a semiconductor material, for example silicon and germanium, though other materials may be used (e.g., SiGe, Ga, N, C, GaN, InP, AlGaN, InGaP, etc.). In some implementations, a thin lossy film may comprise inorganic material or a metal. In some embodiments, a thin lossy film may comprise an alloy or compound semiconductor. For example, a thin lossy film may comprise an alloy including Si (57.4% by weight), Ge (25.8% by weight), and $SiO_2$ (16.8% by weight), though other ratios and compositions may be used in other embodiments.

According to some embodiments, a thin lossy film may be formed on the substrate using any suitable blanket deposition process, for example, a physical deposition process, a chemical vapor deposition process, a spin on process, or a combination thereof. In some embodiments, a thin lossy film may be treated after deposition, e.g., baked, annealed and/or subjected to ion implantation.

Other phase/amplitude altering structures may be used additionally or alternatively to enhance excitation energy within the sample well. According to some implementations and as shown in FIG. 5-7A, a reflective stack 5-705 may be spaced from a sample well 3-210. In some embodiments, a reflective stack may comprise a dielectric stack of materials having alternating indices of refraction. For example a first dielectric layer 5-710 may have a first index of refraction, and a second dielectric layer 5-720 may have a second index of refraction different than the first index of refraction. The reflective stack 5-705 may exhibit a high reflectivity for excitation radiation in some embodiments, and exhibit a low reflectivity for radiative emission from an emitter within the sample well. For example, a reflective stack 5-705 may exhibit a reflectivity greater than approximately 80% for excitation radiation and a reflectivity lower than approximately 40% for emission from a sample, though other reflectivity values may be used in some embodiments. A dielectric layer 5-730 that transmits the excitation energy may be located between the reflective stack and the sample well.

According to some implementations, a reflective stack 5-705 depicted in FIG. 5-7A may form a resonator or resonant cavity with the material 3-230 in which the sample well 3-210 is formed. For example, the reflective stack may be spaced from the material 3-230 by a distance that is approximately equal to one-half the wavelength of the excitation radiation within the dielectric material 5-730, or an integral multiple thereof. By forming a resonator, excitation energy may pass through the reflective stack, resonate, and build up in the space between the material 3-230 and the reflective stack 5-705. This can increase excitation intensity within the sample well 3-210. For example, the intensity may increase within the resonant structure by more than a factor of 2 in some embodiments, and more than a factor of 5 in some embodiments, and yet more than a factor of 10 in some embodiments.

A resonant cavity formed at the sample well may comprise a Gires-Tournois resonator, according to some embodiments. In some implementations, a resonant structure may comprise a linear resonant cavity or ring resonator. In some implementations, a resonant structure may comprise a distributed Bragg reflector formed adjacent the sample well. The distributed Bragg reflector may comprise alternating layers of material having different indices of refraction. In some implementations, a resonant cavity may comprise a microcavity. The microcavity may have microscale dimensions. In some aspects, a microcavity may have a size that is approximately equal to one-half the characteristic wavelength of an excitation source or an integral multiple thereof (as modified by the refractive index n of the resonant cavity). For example, the dimension of a microcavity may be $M\lambda/2n$, where M is an integer.

Additional structures may be added in the vicinity of the sample well, as depicted in FIG. 5-7B and FIG. 5-7C. According to some embodiments, a dielectric plug 5-740 having a first index of refraction that is higher than a second index of refraction of the dielectric layer 5-730 may be formed adjacent the sample well 3-210, as depicted in FIG. 5-7B. The plug may be in the shape of a cylinder having a diameter approximately equal to that of the sample well, though other shapes and sizes may be used. Because of its higher refractive index, the dielectric plug 5-740 may condense and guide excitation radiation toward the sample well.

A dielectric structure, such as the plug 5-740, may be used with or without a reflective stack 5-705, according to some embodiments. Such a dielectric structure may be referred to as a dielectric resonant antenna. The dielectric resonant antenna may have any suitable shape, for example, cylindrical, rectangular, square, polygon old, trapezoidal, or pyramid.

FIG. 5-7C and FIG. 5-7D depict a photonic bandgap (PBG) structure that may be formed in the vicinity of a sample well 3-210, according to some embodiments. A photonic bandgap structure may comprise a regular array or lattice of optical contrast structures 5-750. The optical contrast structures may comprise dielectric material having a refractive index that is different from a refractive index of the surrounding dielectric material, according to some embodiments. In some implementations, the optical contrast structures 5-750 may have a loss value that is different from the surrounding medium. In some implementations, a sample well 3-210 may be located at a defect in the lattice as depicted in FIG. 5-7D. According to various embodiments, the defect in the photonic lattice may confine photons within the region of the defect can enhance the intensity of the excitation energy at the sample well. The confinement due to the photonic bandgap structure may be substantially in two dimensions transverse to a surface of the substrate. When combined with the reflective stack 5-705, confinement may be in three dimensions at the sample well. In some embodiments, a photonic bandgap structure may be used without a reflective stack.

Various methods have been contemplated for fabricating the excitation-coupling structures depicted in FIG. 5-6A through FIG. 5-7D. Structures that require thin planar films (e.g., dielectric films of alternating refractive index) may be formed by planar deposition processes, according to some embodiments. Planar deposition processes may comprise physical deposition (for example, electron beam evaporation or sputtering) or chemical vapor deposition processes. Structures that require discrete embedded dielectrics formed in three-dimensional shapes, such as a dielectric resonant antenna 5-740 shown in FIG. 5-7B or the optical contrast structures 5-750 shown in FIG. 5-7C, may be formed using lithographic patterning and etching processes to etch the pattern into the substrate, and using subsequent deposition of a dielectric layer, and a planarization of the substrate, for example. Also contemplated are self-alignment processing techniques for forming dielectric resonant antennas as well as photonic bandgap structures in the vicinity of the sample well 3-210.

V. D. Fabrication of Amplitude/Phase Excitation-Coupling Structures

FIG. 5-8A through FIG. 5-8G depict structures associated with process steps for just one self-alignment process that may be used to form a photonic bandgap structure and a self-aligned sample well as illustrated in FIG. 5-7C. According to some embodiments, a reflective stack 5-705 may be first formed on a substrate above a dielectric layer 3-235, as illustrated in FIG. 5-8A. A second dielectric layer 5-730 may then be deposited over the reflective stack. The thickness of the dielectric layer 5-730 may be approximately equal to about one-half a wavelength of the excitation radiation in the material, or an integral multiple thereof. Process steps described in connection with FIG. 5-4A through FIG. 5-4E may then be carried out to form a pillar 5-420 above the dielectric layer 5-730 and a pattern of etched features 5-810 for the photonic bandgap structure. The etched features may extend into the dielectric layer 5-730 and optionally into the reflective stack 5-705. The resulting structure may appear as shown in FIG. 5-8A.

A resist 5-440 covering the pillar 5-420 may be stripped from the substrate and a conformal deposition performed to fill the etched features with a filling material 5-820, as depicted in FIG. 5-8B. The filling material 5-820 may be the same material that is used to form the pillar 5-420, according to some embodiments. For example the filling material 5-820 and the pillar 5-420 may be formed of silicon nitride and the dielectric layer 5-730 may comprise an oxide, e.g., $SiO_2$.

An anisotropic etch may then be carried out to etch back the filling material 5-820. The filling material may be etched back to expose a surface of the dielectric layer 5-730, according to some embodiments, resulting in a structure as depicted in FIG. 5-8C. The etch may leave a pillar 5-830 comprising the original pillar 5-420 and sidewalls 5-822 that remain from the filling material 5-820.

A resist 5-440 may then be patterned over the substrate as depicted in FIG. 5-8D. For example, the resist may be coated onto the substrate, a hole patterned in the resist, and the resist developed to open up a region in the resist around the pillar 5-830. Alignment of the hole to the pillar need not be highly accurate, and only need expose the pillar 5-830 without exposing the underlying photonic bandgap structures embedded in the dielectric layer 5-730.

After the pillar 5-830 is exposed, and isotropic etch may be used to reduce the transverse dimension of the pillar. According to some embodiments, the resulting pillar shape may appear as depicted in FIG. 5-8E. The resist 5-440 may then be stripped from the substrate and a material 3-230, or layers of materials, may be deposited over the region. In some embodiments, the material 3-230 may be etched back using a CMP process to planarize the region as depicted in FIG. 5-8F. Subsequently, a selective dry wet etch may be used to remove the remaining pillar structure leaving a sample well 3-210, as illustrated in FIG. 5-8G. As indicated by the drawings, the sample well 3-210 is self-aligned to the photonic bandgap structure patterned in the dielectric layer 5-730.

As an alternative process, the filling material 5-820 may comprise a different material than the material used to form the pillar 5-420. In this process, the steps associated with FIG. 5-8D and FIG. 5-8E may be omitted. After deposition of material 3-230 and planarization, as depicted in FIG. 5-8F, a selective etch may be performed to remove the pillar 5-420. This may leave sidewalls of the filling material 5-820 lining the sample well 3-210.

V. E. Non-Radiative Excitation-coupling Structures and Fabrication

Structures for non-radiative coupling of excitation energy to a sample within the sample well have also been contemplated by the inventors. Just one embodiment of a non-radiative coupling structure is depicted in FIG. 5-9A. According to some embodiments, a non-radiative coupling structure may comprise a semiconductor layer 5-910 formed immediately adjacent a sample well 3-210. The semiconductor layer 5-910 may be an organic semiconductor in some embodiments, or an inorganic semiconductor in some embodiments. In some implementations, a divot 3-216 may, or may not, be formed in the semiconductor layer. The semiconductor layer 5-910 may have a thickness between approximately 5 nm and approximately 100 nm according to some embodiments, though other thicknesses may be used in some embodiments. According to some implementations, excitation radiation or photons 5-930 from an excitation source may impinge upon the semiconductor layer 5-910 and produce excitons 5-920. The excitons may diffuse to a surface of the sample well where they may non-radiatively recombine and transfer energy to a sample adjacent the walls of the sample well.

FIG. 5-9B depicts another embodiment in which a semiconductor layer 5-912 may be used to non-radiatively transfer energy from excitation energy to a sample. In some embodiments, a semiconductor layer 5-912 may be formed at the bottom of a sample well or in a divot of the sample well 3-210, as depicted in the drawing. The semiconductor layer 5-912 may be formed in a sample well by using a directional deposition process as described herein in connection with process steps for depositing an adherent at the base of the sample well, according to some embodiments. The semiconductor layer 5-912 may have a thickness between approximately 5 nm and approximately 100 nm according to some embodiments, though other thicknesses may be used in other embodiments. Incident radiation may generate excitons within the semiconductor layer, which may then diffuse to the a bottom surface of the sample well 3-210. The excitons may then non-radiatively transfer energy to a sample within the sample well.

Multiple non-radiative pathways for transferring excitation energy to a sample have also been contemplated by the inventors. According to some embodiments, and as depicted in FIG. 5-9C, an energy-transfer particle 5-940 may be deposited within a sample well. The energy-transfer particle may comprise a quantum dot in some embodiments, or may comprise a molecule in some embodiments. In some implementations, the energy-transfer particle 5-940 may be functionalized to a surface of the sample well through a linking molecule. A thin semiconductor layer 5-910 may be formed adjacent the sample well, or within the sample well, and excitons may be generated within the semiconductor layer from the excitation radiation incident upon the semiconductor layer, as depicted in the drawing. The excitons may diffuse to the surface of the sample well, and non-radiatively transfer energy to the energy-transfer particle 5-940. The energy-transfer particle 5-940 may then non-radiatively transfer energy to a sample 3-101 within the sample well.

According to some implementations, there may be more than one energy-transfer particle 5-940 within a sample well. For example, a layer of energy-transfer particles 5-942 may be deposited within a sample well, such as the sample well depicted in FIG. 5-9C.

FIG. 5-9D illustrates a layer of energy-transfer particles 5-942 deposited at a base of a sample well adjacent to an electrically-excited semiconductor layer 4-510. Excitons generated within the semiconductor layer 4-510 may transfer energy non-radiatively to the energy-transfer particles 5-942 which may in turn transfer energy non-radiatively to a sample 3-101 within the well. A structure depicted in FIG. 5-9D is described herein in connection with FIG. 4-5A.

In some implementations, energy-transfer particles 5-942, or a single energy-transfer particle 5-940, may be deposited at a base of a sample well, as depicted in FIG. 5-9E. The energy-transfer particle, or particles, may radiatively or non-radiatively transfer excitation energy to a sample 3-101 within the well. For example, an energy-transfer particle may absorb incident radiation to form an excited state of the energy-transfer particle, and then radiatively or non-radiatively transfer energy to the sample 3-101.

In some implementations, an energy-transfer particle may absorb incident excitation energy, and then re-emit radiative energy at a wavelength that is different than the wavelength of the absorbed excitation energy. The re-emitted energy may then be used to excite a sample within the sample well. FIG. 5-9F represents spectral graphs associated with a down-converting energy-transfer particle. According to some embodiments, a down-converting energy-transfer particle comprises a quantum dot that may absorb short wavelength radiation (higher energy), and emit one or more longer wavelength radiations (lower energy). An example absorption curve 5-952 is depicted in the graph as a dashed line for a quantum dot having a radius between 6 to 7 nm. The quantum dot may emit a first band of radiation illustrated by the curve 5-954, a second band of radiation illustrated by the curve 5-956, and a third band of radiation illustrated by the curve 5-958.

In some implementations an energy-transfer particle may up convert energy from an excitation source. FIG. 5-9G depicts spectra associated with up conversion from an energy-transfer particle. According to some embodiments, a quantum dot may be excited with radiation at approximately 980 nm, and then re-emit into one of three spectral bands as illustrated in the graph. A first band may be centered at approximately 483 nm, a second band may be centered at approximately 538 nm, and a third band may be centered at approximately 642 nm. The re-emitted photons from the quantum dot are more energetic than the photons of the radiation used to excite the quantum dot. Accordingly, energy from the excitation source is up-converted. One or more of the emitted spectral bands may be used to excite one or more one or more samples within the sample well.

Any one or more of the foregoing embodiments of excitation-coupling structures may be included in an embodiment of an integrated device.

VI. Emission Coupling

One or more emission-coupling components may be formed between a sample well and a corresponding sensor in a pixel to improve collection of emission energy from the sample well by the sensor. Emission-coupling components may improve the signal-to-noise ratio of the emission energy signal to a background signal in order to improve detection of a tag, for example, for purposes of analyzing a sample. According to some embodiments, emission-coupling components may be configurationed to spatially direct and/or spatially separate emission energies of different characteristic wavelengths.

In some implementations, emission-coupling components may direct excitation energy from a sample well to one or more sensor segments within a pixel. In some embodiments, the location of the emission-coupling structure with respect to the sample well is selected so as to direct the emission energy from the sample well in a particular way toward one or more sensor segments. For example, an emission-coupling structure may be configured to direct emission energy into a radiation distribution pattern which has a shape that depends on the characteristic wavelength emitted by a tag. A sensor may be configured to discern different spatial distribution patterns and produce signals that can be analyzed to differentiate between the different patterns. Accordingly, multiple different tags, each emitting within different spectral bands, may be distinguishable by their respective radiation patterns that form when the emission couples to, and is affected by, an emission-coupling structure formed adjacent the sample well. Other components, such as filters, may be included within a pixel and may reduce background radiation (e.g., excitation energy and other energy not associated with emission from the sample).

VI. A. Surface Optics

Emission-coupling components or structures may be formed within a pixel and located near the sample well (e.g., within about 5 microns from the sample well in some implementations). These emission-coupling components may be referred to as "surface optics," and may support surface plasmons. In various embodiments, emission-coupling components may be configured to couple with and affect or alter the emission from a sample with the sample well. In some embodiments, surface-optical structures may be formed at an interface between two layers within a pixel of the integrated device. For example, some emission-coupling components may be formed at the interface between a layer in which the sample well is formed and an adjacent layer at an entrance aperture end of the sample well. In some instances, the layer adjacent the sample well is a dielectric layer, though other materials (e.g., lossy films, semiconductor, transparent conductor) may be used for the adjacent layer.

Surface-energy coupling elements may be surface optical structures that are excited by and interact with radiative emission from the sample well. The surface optical structures may be configured to form different spatial radiation patterns for emission energies of different characteristic wavelengths.

A characteristic dimension of a surface-optical structure, such as a grating period, feature size, or distance from the sample well may be selected to maximally couple a parallel component of an emission energy momentum vector into a surface wave momentum vector for a surface plasmon. For example, the parallel component of the emission energy momentum vector may be matched to the surface wave momentum vector for a surface plasmon supported by the structure, according to some embodiments. In some embodiments, a distance d from the sample well to an edge or characteristic feature of a surface optical structure may be selected so as to direct emission energy from the sample well in a selected direction, such as normal to the surface or inclined at an angle $\theta$ from normal to the surface. For example, the distance, d, may be an integral number of surface-plasmon wavelengths for directing emission normal to the surface. In some embodiments, distance, d, may be selected to be a fractional surface-plasmon wavelength, or wavelength modulo thereof, for directing emission at an angle $\theta$ from normal to the surface.

In operation, an emission-coupling component and sample well may be configured to increase the amount of emission energy that is radiated from the sample well toward one or more sensor segments in the pixel containing the sample well. Without an emission-coupling component, an excited sample may emit radiation in a half-shell or Lambertian distribution due mainly to the presence of the layer in which the sample well is formed. If the sample well allows propagation of emission energy, some emission may go into the bulk specimen. If the sample well comprises a ZMW, for example, the emission may be approximately Lambertian in the direction of a sensor. The addition of emission-coupling components at the sample well may create a highly anisotropic emission distributions that may significantly differ from a Lambertian distribution, and the distribution pattern may be dependent upon emission wavelength.

According to some embodiments, an emission-coupling structure may couple radiative emission energy from a sample well at a first characteristic wavelength in a first direction and/or in a first characteristic spatial pattern. The coupled energy may be directed in the first direction in a narrowed, anisotropic radiation pattern, for example. In some embodiments, the emission-coupling structure may further couple radiative emission energy from the same sample well at a second characteristic wavelength in a second direction and/or second characteristic spatial pattern that is different from the first direction and/or in a first characteristic spatial pattern. The second emission may also be direction in a narrowed, anisotropic radiation pattern. In some embodiments, radiation with a first characteristic wavelength is directed in a narrowed lobe normal to the surface at which the surface optical structure is formed, and radiation of a second characteristic wavelength is directed in annular lobes at an angle from normal to the surface. Other spatial distribution patterns may be produced at other characteristic wavelengths for the same emission-coupling structure.

A non-limiting example of an emission-coupling structure is a concentric grating, as depicted in FIG. 6-1A. According to some embodiments, a concentric grating structure may be formed in a pixel of the integrated device and configured to direct emission energy towards one or more sensor segments within the pixel. A concentric grating may comprise annular rings or protrusions, arranged in a bulls-eye pattern, formed around a sample well. The concentric grating structure may couple with emission from the sample well to improve propagation of emission energy out of the sample well and concentration of the emission energy at one or more sensor segments within the pixel.

An example of a concentric, circular grating 6-102 emission-coupling structure is depicted in FIG. 6-1A. The circular grating may comprise any suitable number of rings and the number of rings shown in FIG. 6-1A is a non-limiting example. The circular grating may comprise protruding rings from a surface of a conductive film. For example, the circular grating may be formed at the interface of the sample well layer and a dielectric layer formed underneath the sample well layer. The sample well layer may be a conductive material and the concentric grating may be formed by patterning the grating structure at the interface between the conductive material and the dielectric. The rings of the circular grating may be on a regular periodic spacing, or may have irregular or aperiodic spacings between the rings. The sample well may be located at or near the center of the circular grating. In some embodiments, the sample well may be located off-center to the circular grating and may be positioned a certain distance from the center of the grating.

In some embodiments, a grating-type emission-coupling component may comprise a spiral grating. An example of a spiral grating 6-202 is depicted in FIG. 6-1B. A spiral grating 6-202 may comprise a spiral aperture in a conductive film in some embodiments, or may comprise a spiral protrusion formed on a conductive layer according to some embodiments. Any suitable dimensions of the spiral grating may be used to form the spiral grating.

A grating structure such as those depicted in FIG. 6-1A or FIG. 6-1B formed adjacent a sample well may produce different spatial distribution patterns for emission originating from the sample well. Examples of possible spatial distribution patterns that may form due to the influence of the grating is depicted in FIG. 6-2A through FIG. 6-2D. For example, a layer 6-306 of an integrated device may contain a sample well with a concentric grating structure 6-302 positioned underneath the sample well. When emission energy having a first characteristic wavelength is emitted by a sample in the sample well, the emission energy couples with the concentric grating and forms a first spatial distribution pattern 6-304 illustrated in FIG. 6-2A. Additionally, when emission energy having a second characteristic wavelength is emitted by a sample in the sample well, a second distribution pattern may form, such as the distribution pattern 6-404 shown in FIG. 6-2B. Similarly, FIG. 6-2C illustrates a third spatial distribution pattern 6-504 for emission energy having a third characteristic wavelength and FIG. 6-2D illustrates a fourth spatial distribution pattern 6-604 having a fourth characteristic wavelength. The different spatial distribution patterns may be detected by spatially separated sensor segments within the pixel to differentiate among the first, second, third, and fourth characteristic wavelengths.

Another example of a surface optic or surface plasmon structure is a nano-antenna structure, an example of which is depicted in FIG. 6-3A. A nano-antenna structure may be configurationed to spatially direct and/or spatially separate emission energies of different characteristic wavelengths. In some embodiments, the location of the nano-antenna structure with respect to the sample well is selected so as to direct the emission energy from the sample well in a particular way toward one or more sensor segments. Nano-antennas may comprise nanoscale dipole antenna structures that are configurationed to produce a directional radiation pattern when excited by emission energy. The nano-antennas may be distributed around a sample well. The directional radiation pattern may result from a summation of the antennas' electromagnetic fields. In some embodiments, the directional radiation pattern may result from a summation of the antennas' electromagnetic fields with the field emitted directly from the sample. In some implementations, the field emitted directly from the sample may be mediated by surface plasmon waves associated with the nano-antenna structure.

The dimensions of the individual nano-antennas that form the nano-antenna structure may be selected for the combined ability of the overall nano-antenna structure to produce specific distribution patterns of one or more emission energies. For example, the diameters of the individual nano-antennas may vary within a nano-antenna structure. However, in some instances, the diameters may be the same within a set of nano-antennas. In other implementations, a few selected diameters may be used throughout the overall nano-antenna structure. Some nano-antennas may be distributed on a circle of radius R and some may be shifted in a radial direction from the circle. Some nano-antennas may be equally spaced around a circle of radius R (e.g., centered on equivalent polar-angle increments), and some may be shifted from equal spacing around the circle. In some embodiments, the nano-antennas may be arranged in a spiral configuration around a sample well. Additionally or alternatively, other configurations of nano-antennas are possible, such as a matrix array around the sample well, a cross distribution, and star distributions. Individual nano-antennas may be shapes other than a circle, such as square, rectangular, cross, triangle, bow-tie, annular ring, pentagon, hexagon, polygons, etc. In some embodiments, the circumference of an aperture or disc may be approximately an integer multiple of a fractional wavelength, e.g., $(N/2)\lambda$.

A nano-antenna array may direct emission energy from a sample into concentrated radiation lobes that have a spatial pattern dependent upon a characteristic wavelength of the emission energy. When a sample emits energy, it may excite surface plasmons that propagate from the sample well to the nano-antennas distributed around the sample well. The surface plasmons may then excite radiation modes or dipole emitters at the nano-antennas that emit radiation perpendicular to the surface of the sample well layer. The phase of an excited mode or dipole at a nano-antenna will depend upon the distance of the nano-antenna from the sample well. Selecting the distance between the sample well and an individual nano-antenna controls the phase of radiation emitted from the nano-antenna. The spatial radiation mode excited at a nano-antenna will depend upon the geometry and/or size of the nano-antenna. Selecting the size and/or geometry of an individual nano-antenna controls the spatial radiation mode emitted from the nano-antenna. Contributions from all nano-antennas in the array and, in some instances the sample well, may determine an overall radiation lobe or lobes that form the radiation pattern. As may be appreciated, phase and spatial radiation mode emitted from an individual nano-antenna may depend upon wavelength, so that the overall radiation lobe or lobes that form the radiation pattern will also be dependent upon wavelength. Numerical simulations of the electromagnetic fields may be employed to determine overall radiation lobe patterns for emission energies of different characteristic wavelengths.

The nano-antenna may comprise an array of holes or apertures in a conductive film. For example, the nano-antenna structure may be formed at the interface between a conductive sample well layer and an underlying dielectric layer. The holes may comprise sets of holes distributed in concentric circles surrounding a central point. In some embodiments, a sample well is located at the central point of the array, while in other embodiments the sample well may be off-center. Each circularly-distributed set of holes may comprise a collection of different diameters arranged smallest to largest around the circular distribution. The hole diameters may be different between the sets (e.g., a smallest hole in one set may be larger than a smallest hole in another set), and the location of the smallest hole may be oriented at a different polar angle for each set of circles. In some embodiments, there may be one to seven sets of the circularly-distributed holes in a nano-antenna. In other embodiments, there may be more than seven sets. In some embodiments, the holes may not be circular, but may be any suitable shape. For example, the holes may be ellipses, triangles, rectangles, etc. In other embodiments, the distribution of holes may not be circular, but may create a spiral shape.

FIGS. 6-3A and 6-3B illustrate an exemplary nano-antenna structure comprised of holes or apertures in a conductive layer. FIG. 6-3A shows a top planar view of the surface of an integrated device with a sample well 6-108 surrounded by holes 6-122. The nano-antenna holes are distributed approximately around a circle of radius R. In this non-limiting example, the hole diameters vary by incrementally increasing around the circumference of the circle of holes. FIG. 6-3B shows a schematic elevation view of the nano-antenna shown in FIG. 6-3A along line B-B. A sample well layer 6-116 may comprise a conductor and include the sample well 6-108 and apertures 6-122 that are part of the nano-antenna structure. An adjacent layer 6-118 may be a dielectric material and/or an optically transparent material.

In some embodiments, a nano-antenna structure may comprise a plurality of disks. The disks of the nano-antenna structure may be formed as conductive disks protruding from a surface of a conductive material. The conductive material may be adjacent an optically-transparent material, according to some embodiments. In some embodiments, the nano-antennas may be distributed around a sample well. In some instances, the nano-antennas may be distributed around a sample well with their centers approximately at a circle of radius R. A nano-antenna array may comprise multiple sets of nano-antennas distributed approximately on additional circles of different radii around a sample well.

FIGS. 6-3C and 6-3D illustrate an exemplary embodiment of a nano-antenna structure comprising disks protruding from a conductive layer. FIG. 6-3C shows a top planar view schematic of the surface of an integrated device with a sample well 6-208 surrounded by disks 6-224. The nano-antenna disks are distributed approximately around a circle of radius R. In this non-limiting example, two diameters are used for the disks and the disks alternate between these two diameters around the circumference of the circle of nano-antenna. FIG. 6-3D shows a schematic elevation view of the nano-antenna shown in FIG. 6-3C along line D-D. A sample well layer 6-216 may comprise a conductor and include the sample well 6-208 and disks 6-224 that are part of the nano-antenna structure. The disks 6-224 protrude from the sample well layer 6-216 by a certain distance. In some embodiments, the distance the disks extend from the sample well layer may vary within a nano-antenna structure. An adjacent layer 6-218 may comprise a dielectric material and/or an optically-transparent material. The sample well layer 6-216 and the protruding disks may be a conductive material.

The holes and/or disks that form a nano-antenna structure may be any suitable pattern or distribution such that emission energy from sample well couples with one or more of the nano-antennas of the nano-antenna structure. Another example of a nano-antenna structure is illustrated in FIG. 6-4A, which represents a spiral pattern in which a nano-antenna may be formed. A sample well may be located within a sample well layer at position 6-308 with respect to nano-antenna structure 6-312. Surface plasmons may form in the area of the nano-antenna structure when emission energy is emitted from the sample well. FIG. 6-4B illustrates results from a numerical simulation of surface plasmons in the vicinity of a nano-antenna structure, according to some embodiments. The results also show electromagnetic field intensity with the apertures of the nano-antenna. Other exemplary patterns and distributions of nano-antennas that form a nano-antenna structure within a pixel are shown in FIG. 6-4C through FIG. 6-4E.

A nano-antenna structure may be used to distinguish emissions at different characteristic wavelengths. The nano-antenna aperture structure may produce radiation lobes that extend from the sample well in different directions for emission energy of different characteristic wavelengths. The radiation lobes form a spatial distribution pattern that differs depending on the characteristic wavelength of the emission energy. Examples of possible spatial distribution patterns that form as a result of having a nano-antenna structure positioned underneath a sample well is depicted in FIG. 6-5A through FIG. 6-5D. For example, a layer 6-906 within a pixel may contain a sample well with a nano-aperture structure 6-902 positioned adjacent the sample well. When emission energy having a first characteristic wavelength is emitted by a sample in the sample well, the emission energy couples with the nano-antennas in the nano-antenna structure which directs the emission energy into a first spatial distribution pattern 6-904 illustrated in FIG. 6-5A. Additionally, when emission energy having a second characteristic wavelength is emitted by a sample in the sample well, a second distribution pattern may form, such as the distribution pattern 6-1004 shown in FIG. 6-5B. Similarly, FIG. 6-5C illustrates a third spatial distribution pattern 6-1104 for emission energy having a third characteristic wavelength, and FIG. 6-5D illustrates a fourth spatial distribution pattern 6-1204 having a fourth characteristic wavelength. The different spatial distribution patterns may be detected by spatially separated sensors within the pixel to differentiate among the first, second, third, and fourth characteristic wavelengths.

VI. B. Far Field Optics

Emission energy emitted from a sample in the sample well may be transmitted to the sensor of a pixel in a variety of ways, some examples of which are described in detail below. Some embodiments may use optical and/or plasmonic components to increase the likelihood that light of a particular wavelength is directed to one or more segments of the sensor. The sensor may include multiple segments for simultaneously detecting emission energy of different wavelengths.

FIG. 6-6A is a schematic diagram of a single pixel of an integrated device according to some embodiments where at least one sorting element is used to direct emission energy of a particular wavelength to a respective sensor segment, according to some embodiments. A sample well 6-601 formed in a conductive material 6-603 receives a sample and may emit emission energy 6-604. For clarity, details of any optical and plasmonic components at the sample well are not shown. The emission energy 6-604 travels through a dielectric material 6-605 until it reaches a sorting element 6-607. The sorting element 6-607 couples the wavelength of the emission energy 6-604 to a spatial degree of freedom, thereby separating the emission energy into its constituent wavelength components, referred to as sorted emission energy. FIG. 6-6B illustrates schematically the emission energy 6-604 being split into four sorted emission energy paths through a dielectric material 6-609, each of the four paths associated with a sub-sensor 6-611 through 6-614 of the pixel. In this way, each sensor segment may be associated with a different portion of the spectrum, forming a spectrometer for each pixel of the integrated device.

Any suitable sorting element 6-607 may be used to separate the different wavelengths of the emission energy. Embodiments may use optical or plasmonic elements. Examples of optical sorting elements include, but are not limited to, holographic gratings, phase mask gratings, amplitude mask gratings, frequency selective surfaces, diffractive optical elements, and offset Fresnel lenses. Examples of plasmonic sorting elements include, but are not limited to phased nano-antenna arrays, and plasmonic quasi-crystals.

FIG. 6-6B is a schematic diagram of a single pixel of an integrated device according to some embodiments where at least one filtering element is used to direct emission energy of a particular wavelength to a respective sub-sensor and prevent emission energy of other wavelengths from reaching the sub-sensor. Where the components of FIG. 6-6B are similar to those of FIG. 6-6A, the same reference numerals are used. A sample well 6-601 formed in a conductive material 6-603 receives a sample and may emit emission energy 6-604. For clarity, details of optical and plasmonic components at the sample well are not shown. The emission energy 6-604 travels through a dielectric material 6-605 until it reaches one of the filtering elements 6-621 through 6-624. The filtering elements 6-621 through 6-624, may each be associated with a particular segment of a sensor 6-611 through 6-614, and are each configured to transmit emission energy of a respective wavelength and reject emission energy of other wavelengths by absorbing the emission energy (not illustrated in FIG. 6-6B) and/or reflecting the emission energy. After passing through a respective filtering element, the filtered emission energy travels through a dielectric material 6-609 and impinges on a corresponding sub-sensor 6-611 through 6-614 of the pixel. In this way, each sub-sensor is associated with a different portion of the spectrum, forming a spectrometer for each pixel of the integrated device.

Any suitable filtering elements may be used to separate the different wavelengths of the emission energy. Embodiments may use optical or plasmonic filtering elements. Examples of optical sorting elements include, but are not limited to, reflective multilayer dielectric filters or absorptive filters. Examples of plasmonic sorting elements include, but are not limited to frequency selective surfaces configurationed to transmit energy at a particular wavelength and photonic band-gap crystals.

Alternatively, or in addition to the above mentioned sorting elements and filtering elements, additional filtering elements may be placed adjacent to each sub-sensor 6-61 through 6-614. The additional filtering elements may include a thin lossy film configured to create constructive interference for emission energy of a particular wavelength at the sensor or sensor segment for a particular wavelength. The thin lossy film may be a single or multi-layer film. The thin lossy film may be made from any suitable material. For example, the thin lossy film may be made from a material where the index of refraction n is approximately the same order of magnitude as the extinction coefficient k. In other embodiments, the thin lossy film may be made from a material where the index of refraction n is within about two orders of magnitude difference from the value of the extinction coefficient k of the material. Non-limiting examples of such materials at visible wavelengths are germanium and silicon.

Figures 5, 6, 7, 7A:
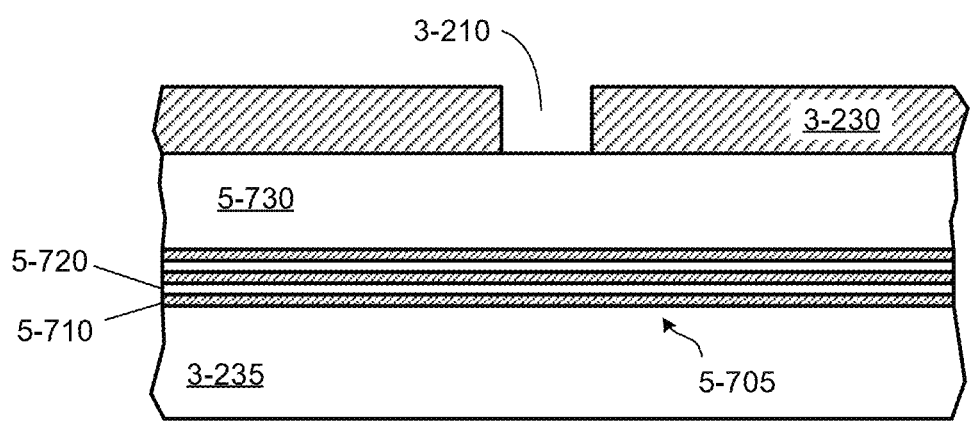

The thin lossy film may be any suitable thickness. In some embodiments, the thin lossy film may be 1-45 nm thick. In other embodiments, the thin lossy film may be 15-45 nm thick. In still other embodiments, the thin lossy film may be 1-20 nm thick. FIG. 6-7A illustrates an embodiment where the thin lossy films 6-711 through 6-714 each have a different thickness determined at least in part by the wavelength that is associated with each sub-sensor 6-61 through 6-614. The thickness of the film determines, at least in part, a distinct wavelength that will selectively pass through the thin lossy film to the sub-sensor. As illustrated in FIG. 6-7A, thin lossy film 6-711 has a thickness d1, thin lossy film 6-712 has a thickness d2, thin lossy film 6-713 has a thickness d3, and thin lossy film 6-714 has a thickness d4. The thickness of each subsequent thin lossy film is less than the previous thin lossy film such that $d1>d2>d3>d4$.

Figures 5, 6, 7, 7B:
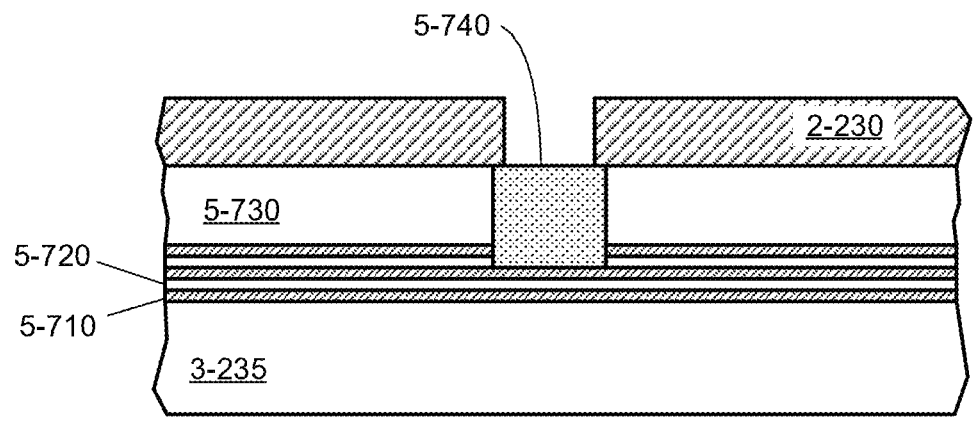
Figures 5, 6, 7, 7C:
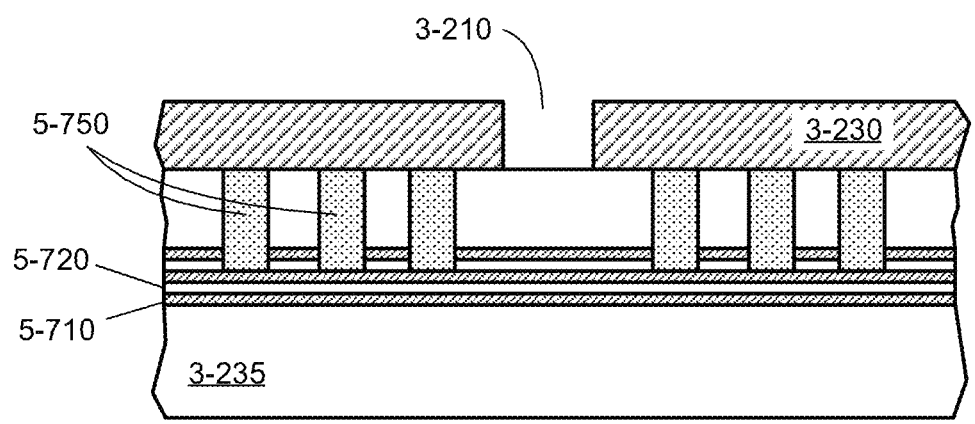
Figures 5, 6, 7, 7D:
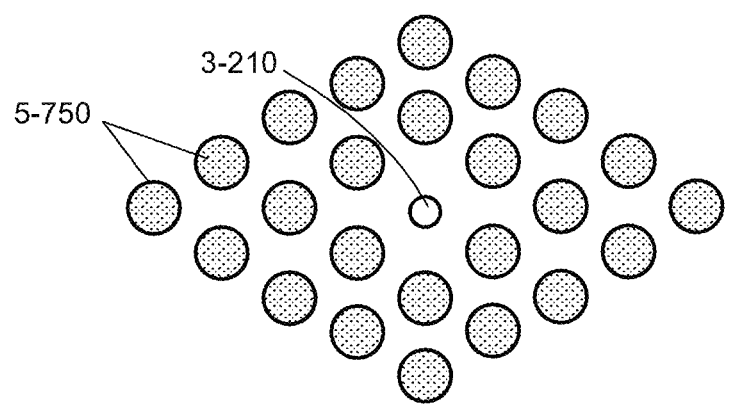
Figures 5, 6, 7, 8, 8A:
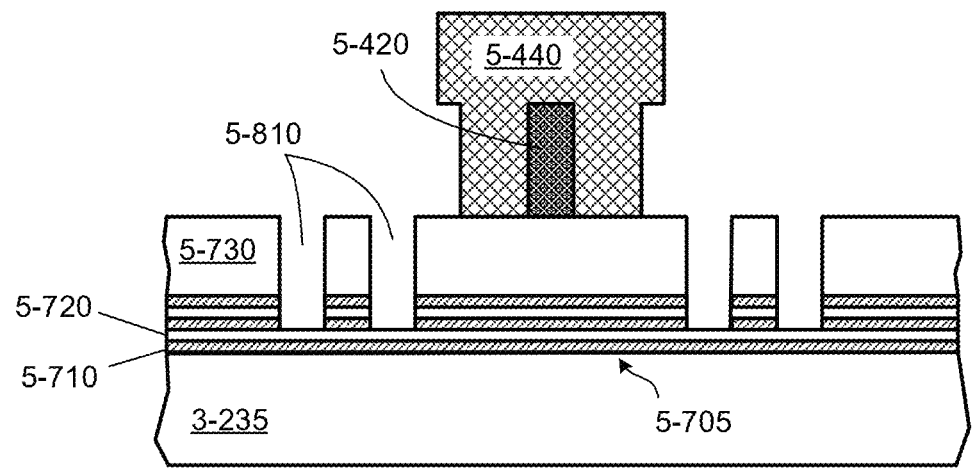
Figures 5, 6, 7, 8, 8B:
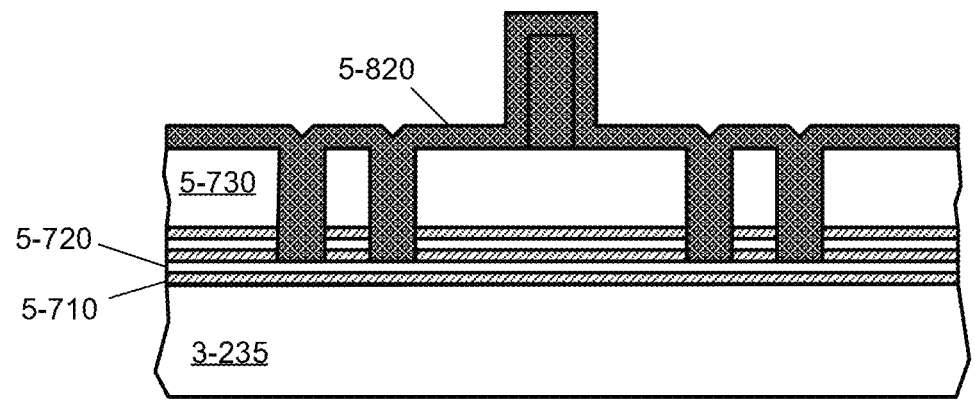
Figures 5, 6, 7, 8, 8C:
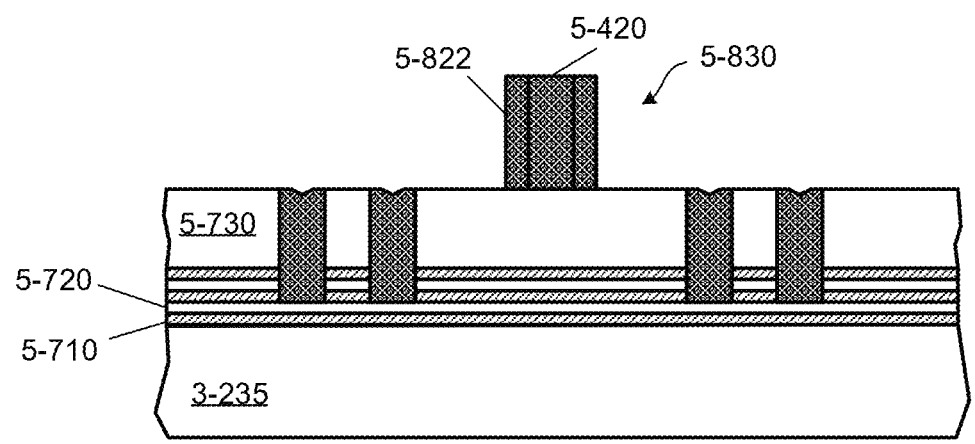
Figures 5, 6, 7, 8, 8D:
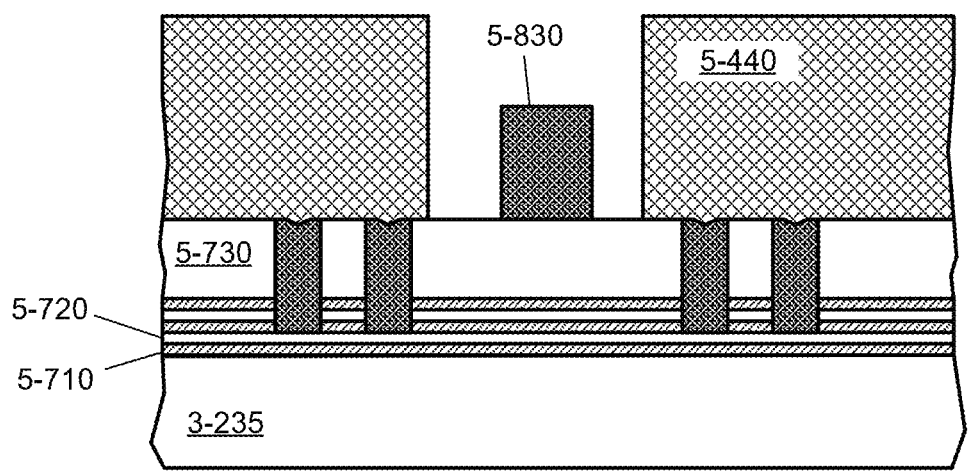
Figures 5, 6, 7, 8, 8E:
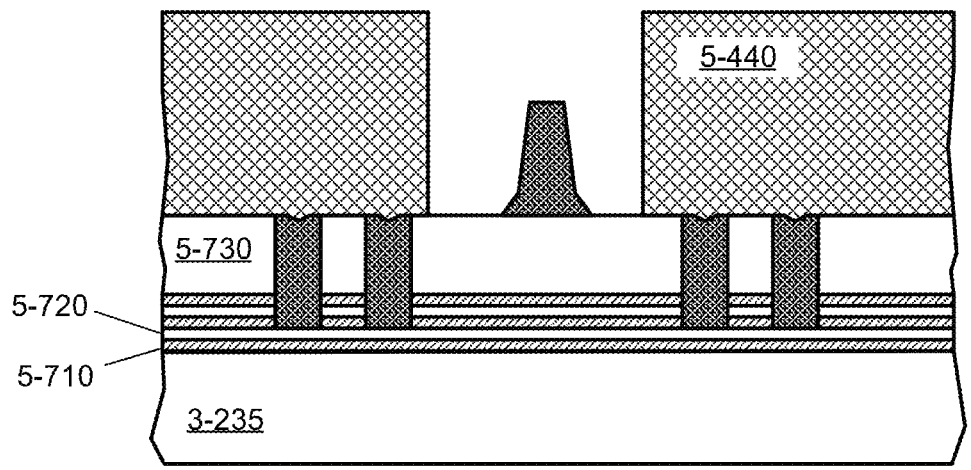
Figures 5, 6, 7, 8, 8F:
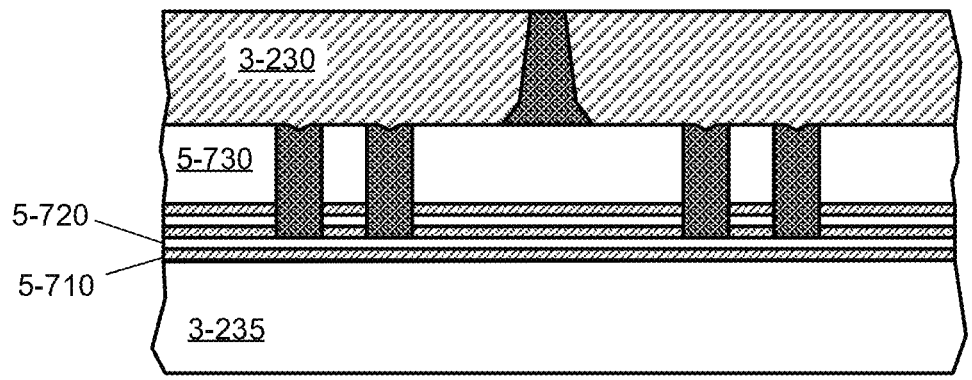
Figures 5, 6, 7, 8, 8G:
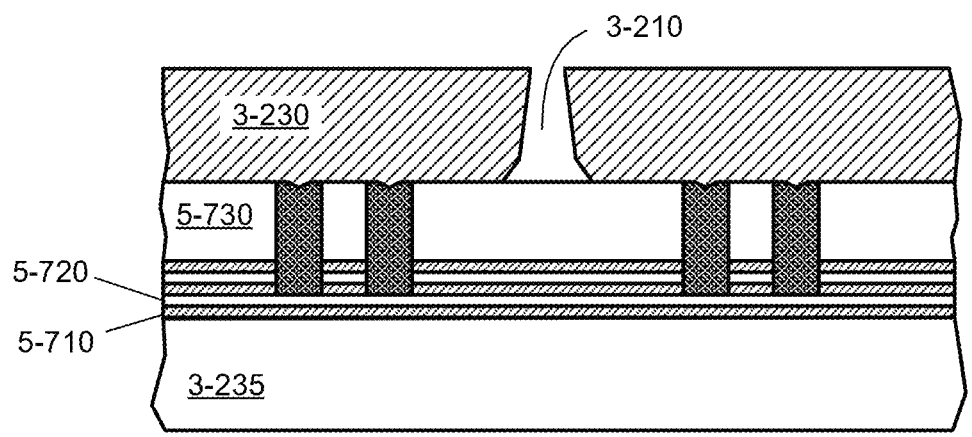
Figures 5, 6, 7, 8, 9, 9A:
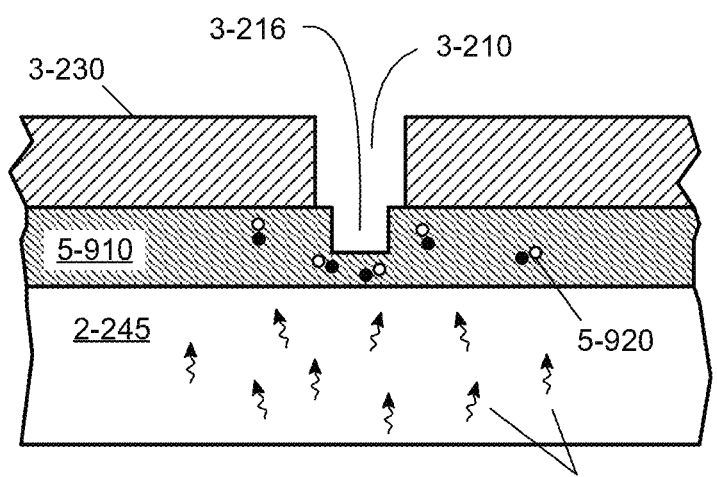
Figures 5, 6, 7, 8, 9, 9B:
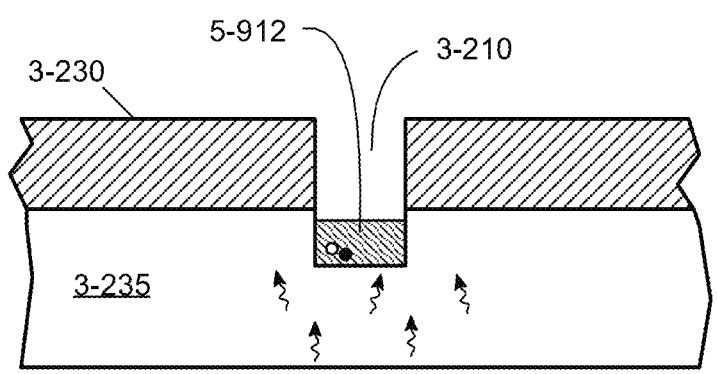
Figures 5, 6, 7, 8, 9, 9C:
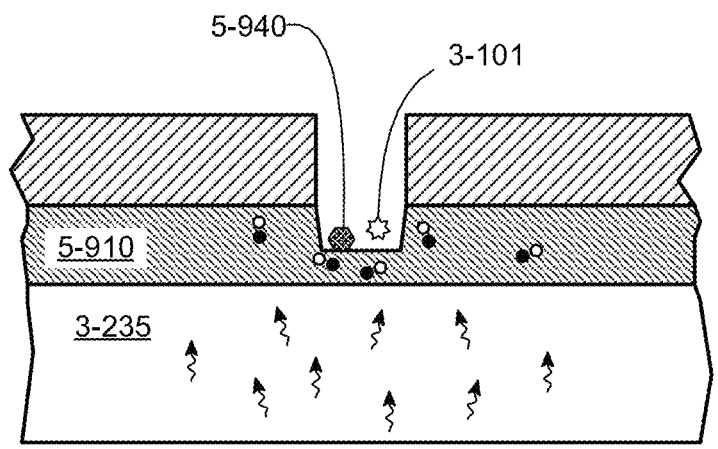
Figures 5, 6, 7, 8, 9, 9D:
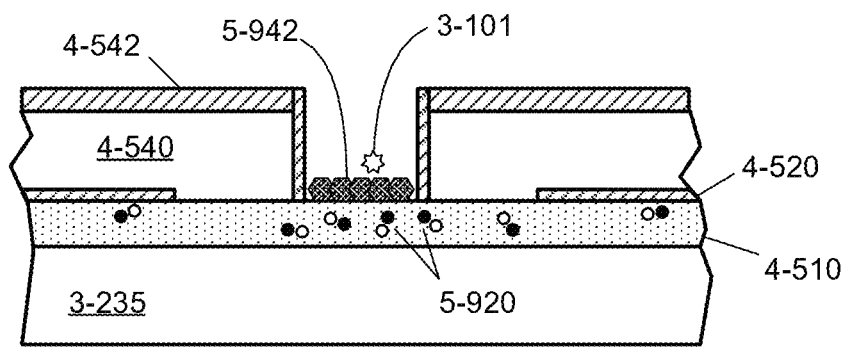
Figures 5, 6, 7, 8, 9, 9E:
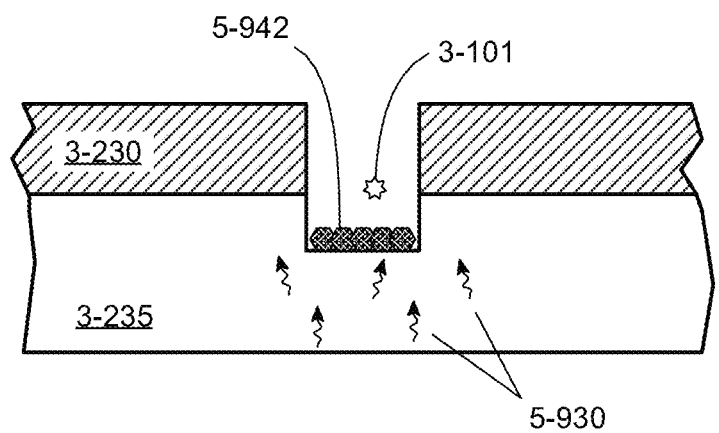
Figures 5, 6, 7, 8, 9, 9F:
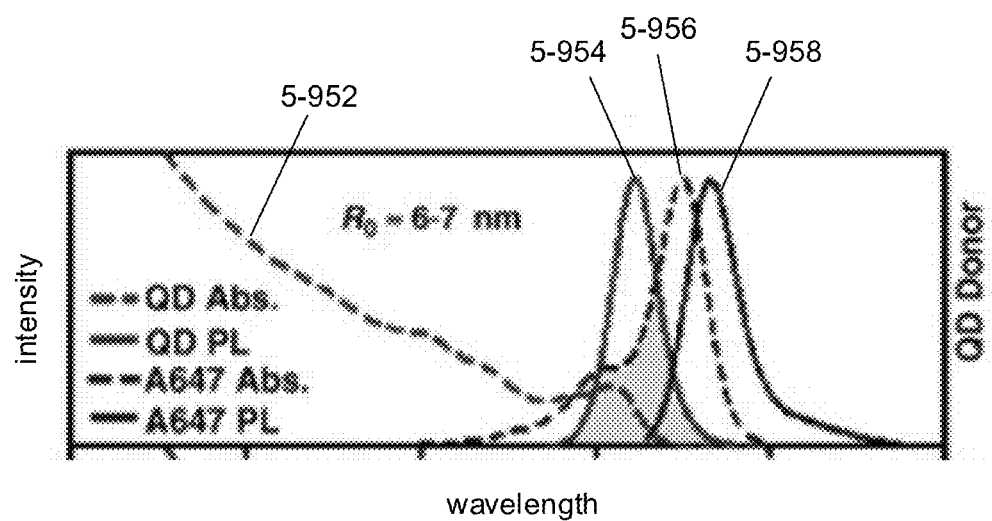
Figures 5, 6, 7, 8, 9, 9G:
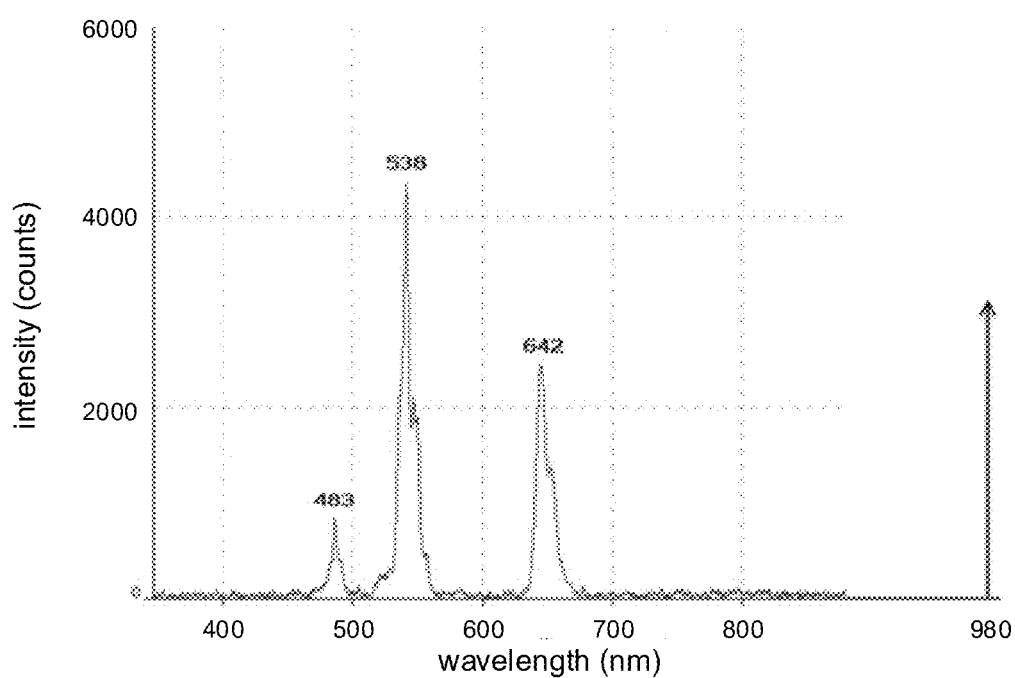
Figures 1A, 6:
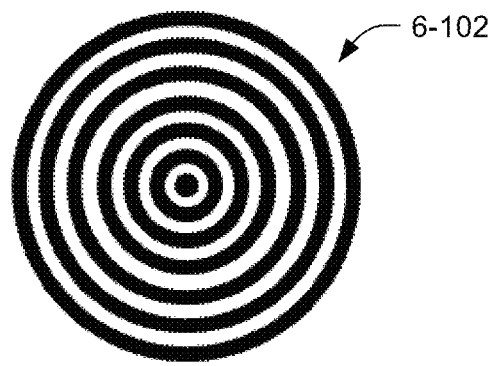
Figures 1B, 6:
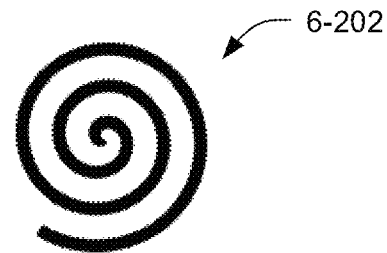
Figures 2A, 6:
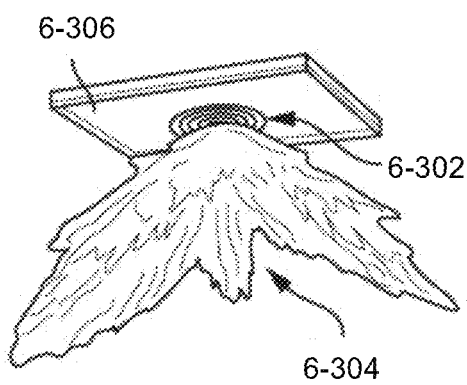
Figures 2B, 6:
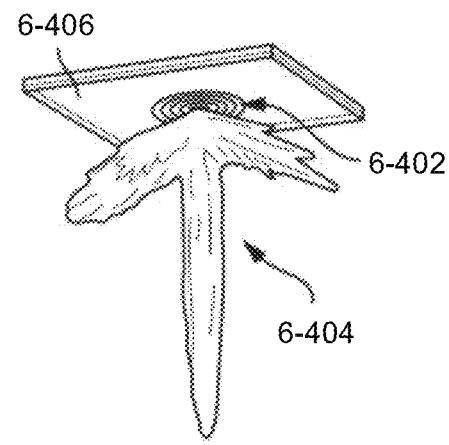
Figures 2C, 6:
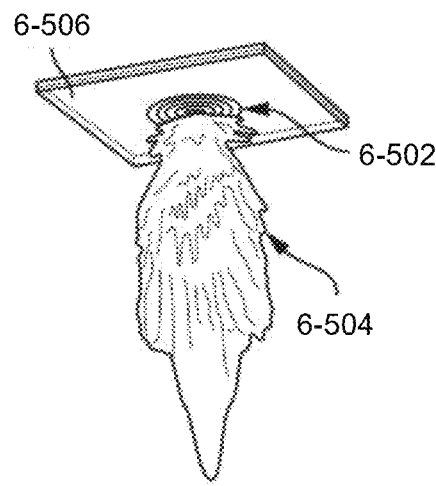
Figures 2D, 6:
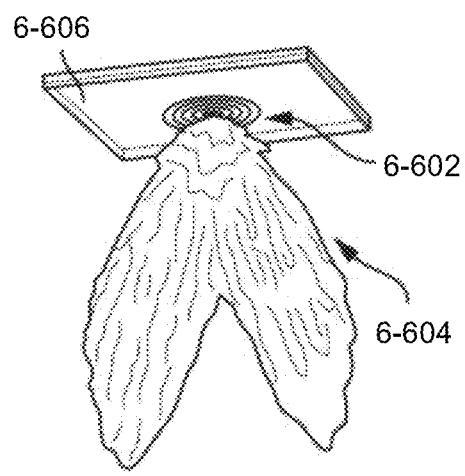
Figures 3A, 6:
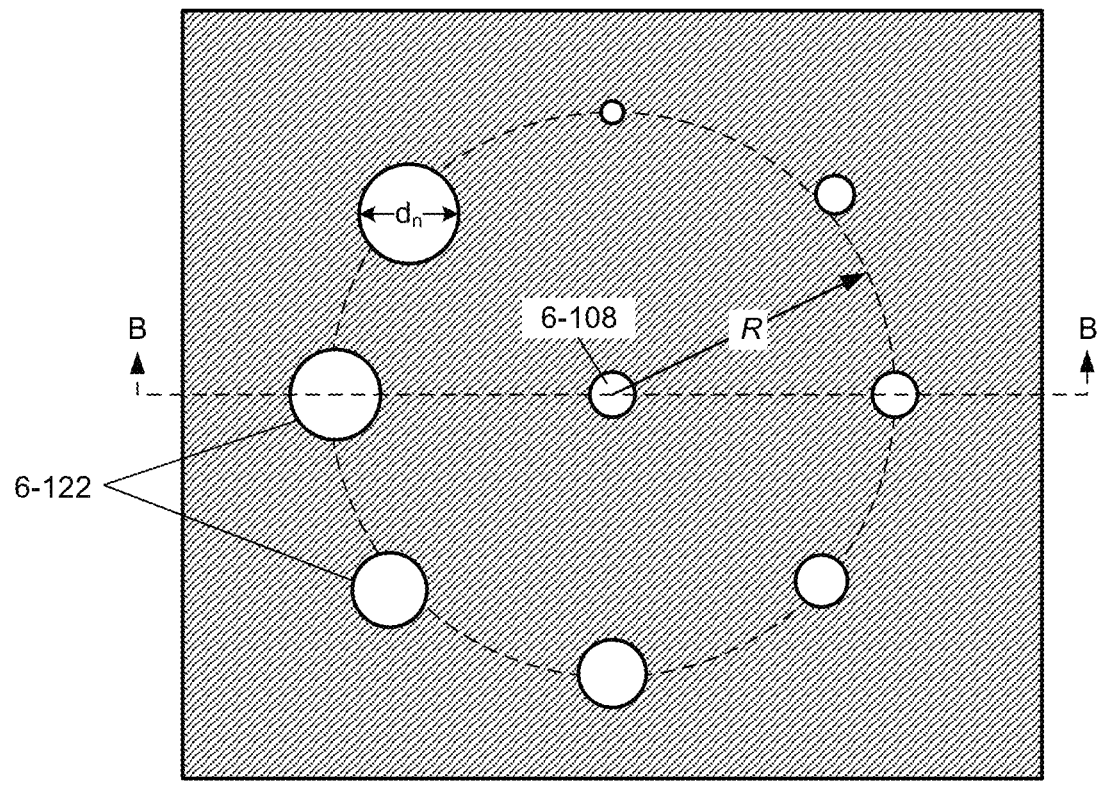
Figures 3B, 6:
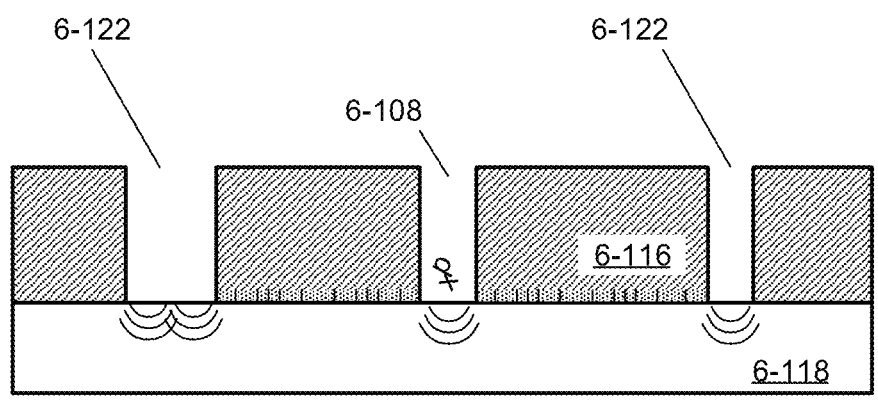
Figures 3C, 6:
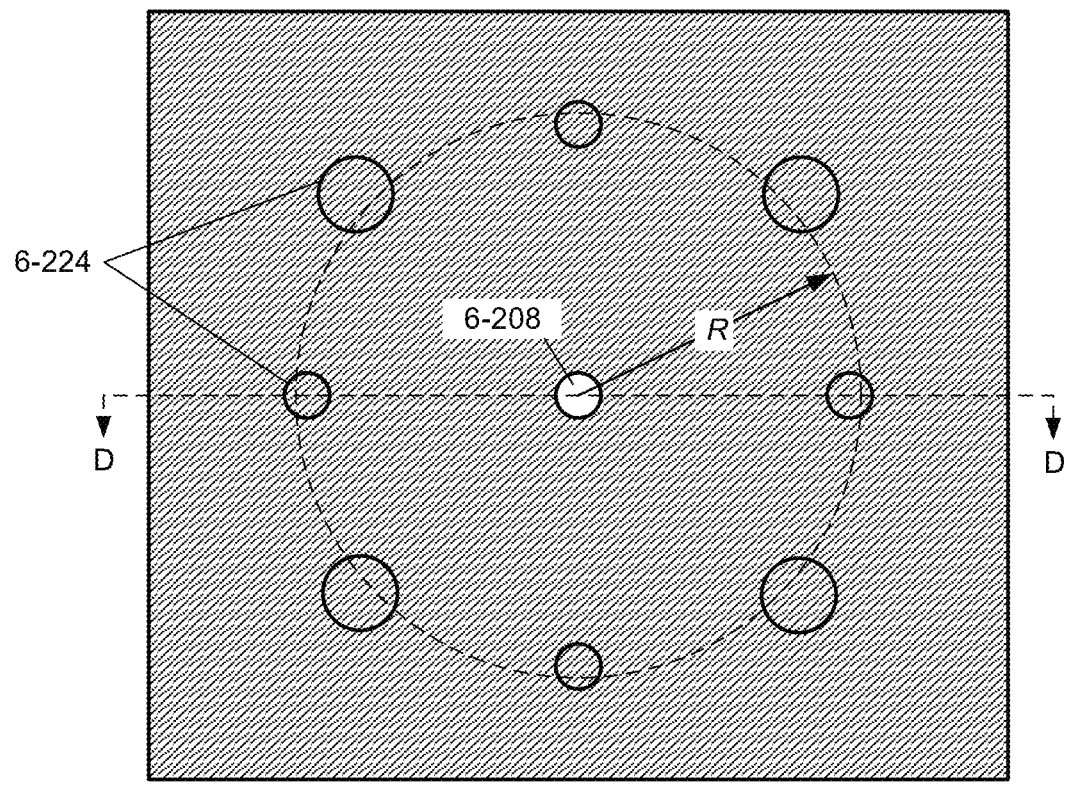
Figures 3D, 6:
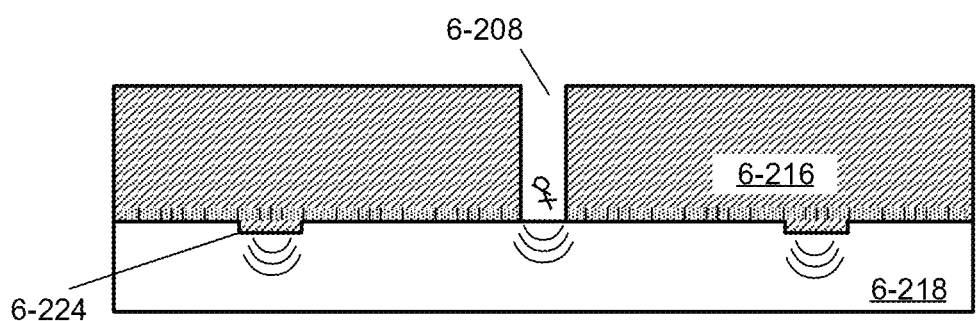
Figures 4A, 6:
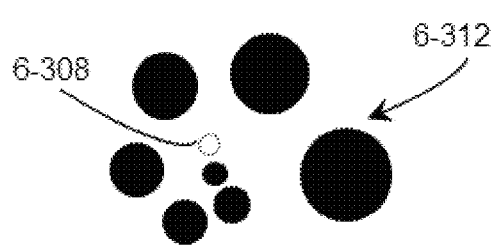
Figures 4B, 6:
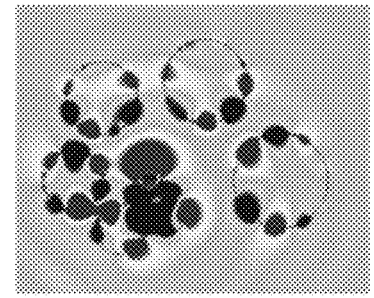
Figures 4C, 6:
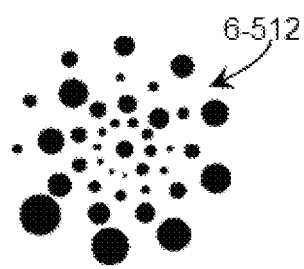
Figures 4D, 6:
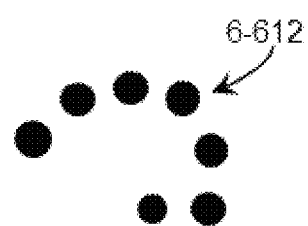
Figures 4E, 6:
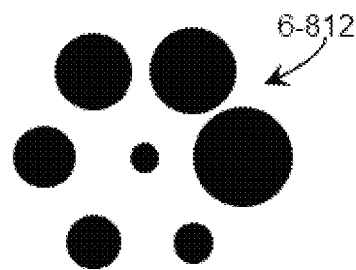
Figures 5A, 6:
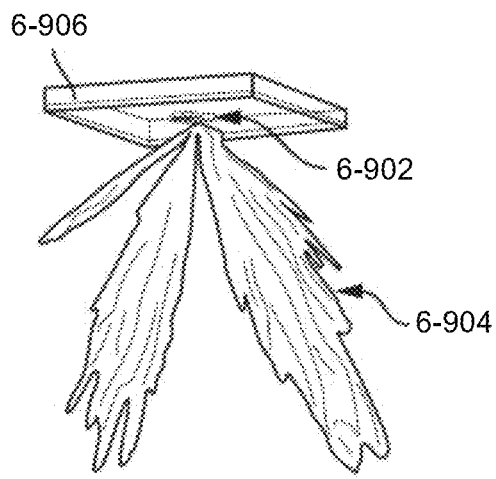
Figures 5B, 6:
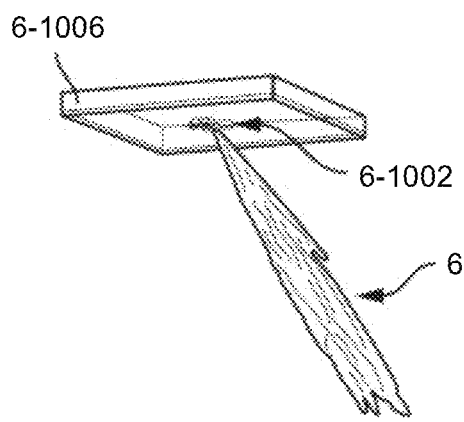
Figures 5C, 6:
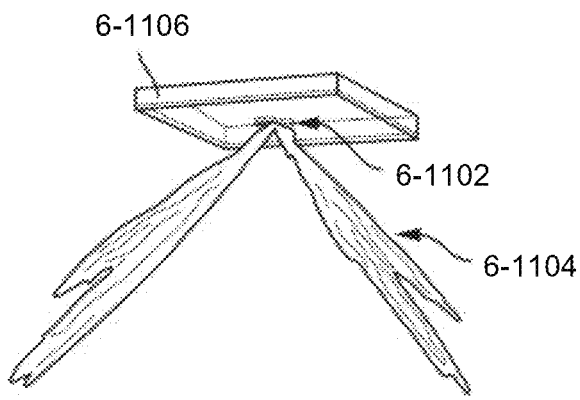
Figures 5D, 6:
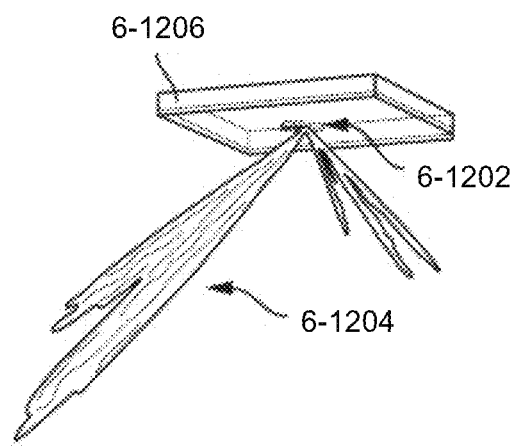
Figures 6, 6A:
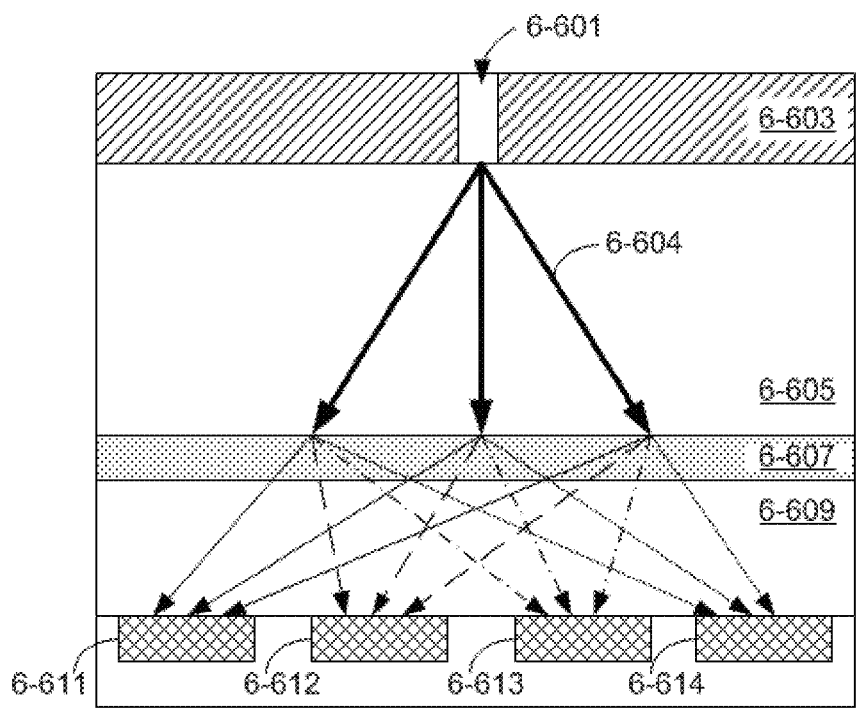
Figures 6, 6B:
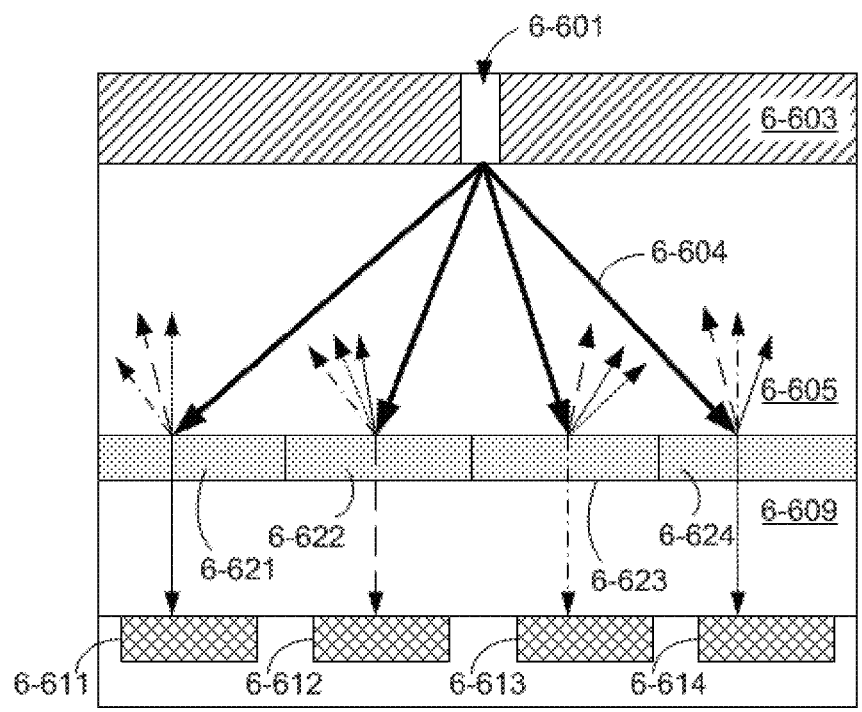
Figures 6, 7, 7A:
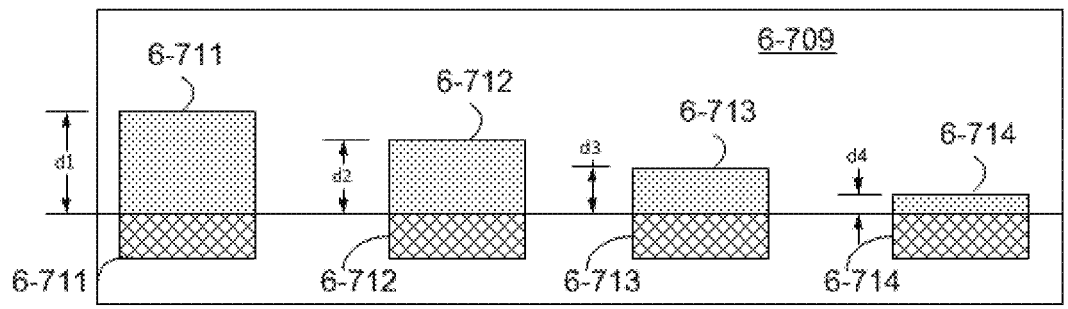
Figures 6, 7, 7B:
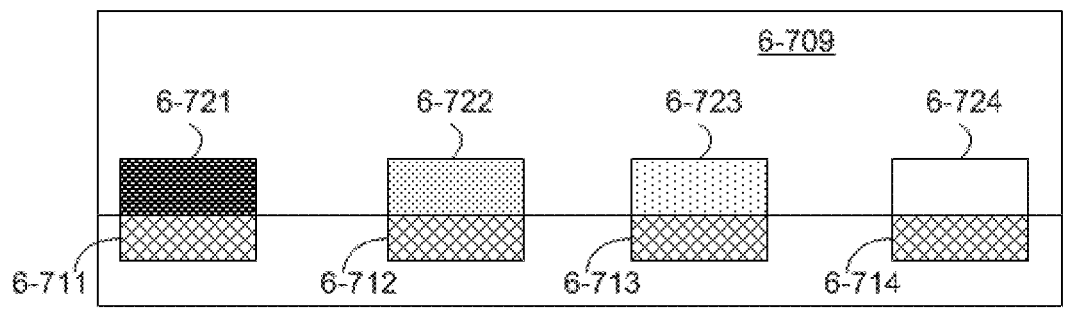

Additionally, or alternatively, the thin lossy films may be formed of a different material with a different properties such that emission energy of different wavelengths constructively interfere at each respective sub-sensor. For example, the index of refraction n and/or the extinction coefficient k may be selected to optimize transmission of emission energy of a particular wavelength. FIG. 6-7B illustrates thin lossy films 6-721 through 6-724 with the same thickness but each thin lossy film is formed from a different material. In some embodiments, both the material of the thin lossy films and the thickness of the thin lossy films may be selected such that emission energy of a desired wavelength constructively interferes and is transmitted through the film.

Any one or more of the foregoing embodiments of emission-coupling elements may be included in an embodiment of an integrated device.

VII. Sensors

Various embodiments of sensors, sensor operation, and signal processing methods have been contemplated by the inventors. According to some embodiments, a sensor 3-260 at a pixel may comprise any suitable sensor capable of receiving emission energy from one or more tags in the sample well, and producing one or more (e.g., at least 2, 3, or 4) electrical signals representative of the received emissions. In some embodiments, a sensor may comprise at least one, two, three, or four photodetectors. Each photodetector may comprise a p-n junction formed in a semiconductor substrate. FIG. 7-1A depicts just one embodiment of a sensor that may be fabricated within a pixel 3-100 of an integrated device.

According to some embodiments, a sensor 3-260 may be formed at each active pixel 3-100 of an integrated device. The sensor may be centered about a sample well 3-210, and spaced from the sample well by a distance between approximately 1 micron and approximately 20 microns. There may be one or more transparent layers 7-110 between the sample well and the sensor, so that emission from the sample well may travel to the sensor without significant attenuation. The sensor 3-260 may be formed in a semiconductor substrate 7-120 at a base of the pixel, according to some embodiments, and be located on a same side of the sample well as the excitation source (not shown).

The sensor may comprise one or more semiconductor junction photodetector segments. Each semiconductor junction may comprise a well of a first conductivity type. For example, each semiconductor junction may comprise an n-type well formed in a p-type substrate, as depicted in the drawing. According to some embodiments, a sensor 3-260 may be arranged as a bulls-eye detector 7-162, as depicted in the plan view of FIG. 7-1B. A first photodetector 7-124 may be located at a center of the sensor, and a second annular photodetector 7-122 may surround the center photodetector. Electrical contacts to the wells may be made through conductive traces 7-134 formed at a first or subsequent metallization level and through conductive vias 7-132. There may be a region of highly doped semiconductor material 7-126 at contact regions of the vias. In some embodiments, a field oxide 7-115 may be formed at surfaces between the photodetectors and or may cover a portion of each photodetector. In some implementations, there may be additional semiconductor devices 7-125 (e.g., transistors, amplifiers, etc.) formed within the pixel adjacent to the sensor 3-260. There may be additional metallization levels 7-138, 7-136 within the pixel.

In some implementations, a metallization levels 7-136 may extend across a majority of the pixel and have an opening below the sample well 3-210, so that emission from the sample well can reach the sensor. In some cases, a metallization level 7-136 may serve as a reference potential or a ground plane, and additionally serve as an optical block to prevent at least some background radiation (e.g., radiation from an excitation source or from the ambient environment) from reaching the sensor 3-260.

As depicted in FIG. 7-1A and FIG. 7-1B, a sensor 3-260 may be subdivided into a plurality of photodetector segments 7-122, 7-124 that are spatially and electrically separated from each other. In some embodiments, segments of a sensor 3-260 may comprise regions of oppositely-doped semiconductor material. For example, a first charge accumulation well 7-124 for a first sensor segment may be formed by doping a first region of a substrate to have a first conductivity type (e.g., n-type) within the first well. The substrate may be p-type. A second charge accumulation well 7-122 for a second sensor segment may be formed by doping a second region of the substrate to have the first conductivity type within the second well. The first and second wells may be separated by a p-type region of the substrate.

The plurality of segments of the sensor 3-260 may be arranged in any suitable way other than a bulls-eye layout, and there may be more than two segments in a sensor. For example, in some embodiments, a plurality of photodetector segments 7-142 may be laterally separated from one another to form a stripe sensor 7-164, as depicted in FIG. 7-1C. In some embodiments, a quadrant sensor 7-166 may be formed by arranging the segments 7-144 in a quad pattern, as depicted in FIG. 7-1D. In some implementations, arc segments 7-146 may be formed in combination with a bulls-eye pattern, as depicted in FIG. 7-1E, to form an arc-segmented sensor 7-168. Another sensor configuration may comprise pie-piece sections, which may include individual sensors arranged in separate sections of a circle. In some cases, sensor segments may be arranged symmetrically around a sample well 3-210 or asymmetrically around a sample well. The arrangement of sensor segments is not limited to only the foregoing arrangements, and any suitable distribution of sensor segments may be used.

The inventors have found that a quadrant sensor 7-166, pie-sector sensor, or similar sector sensor can scale to smaller pixel sizes more favorably than other sensor configurations. Quadrant and sector detectors may consume less pixel area for a number of wavelengths detected and active sensor area. Quadrant and sector detectors may be used in combination with nano-antenna arrays or surface-plasmon structures to produce distinct spatial distribution patterns that are discernable by the detectors. Sensors may be arranged in various geometric configurations. In some examples, sensors are arranged in a square configuration or hexagonal configuration.

Sensors of the present disclosure may be independently (or individually) addressable. An individually addressable sensor is capable of detecting emission from a corresponding sample well and providing output signals independent of other sensors. An individually addressable sensor may be individually readable.

Figures 1A, 7:
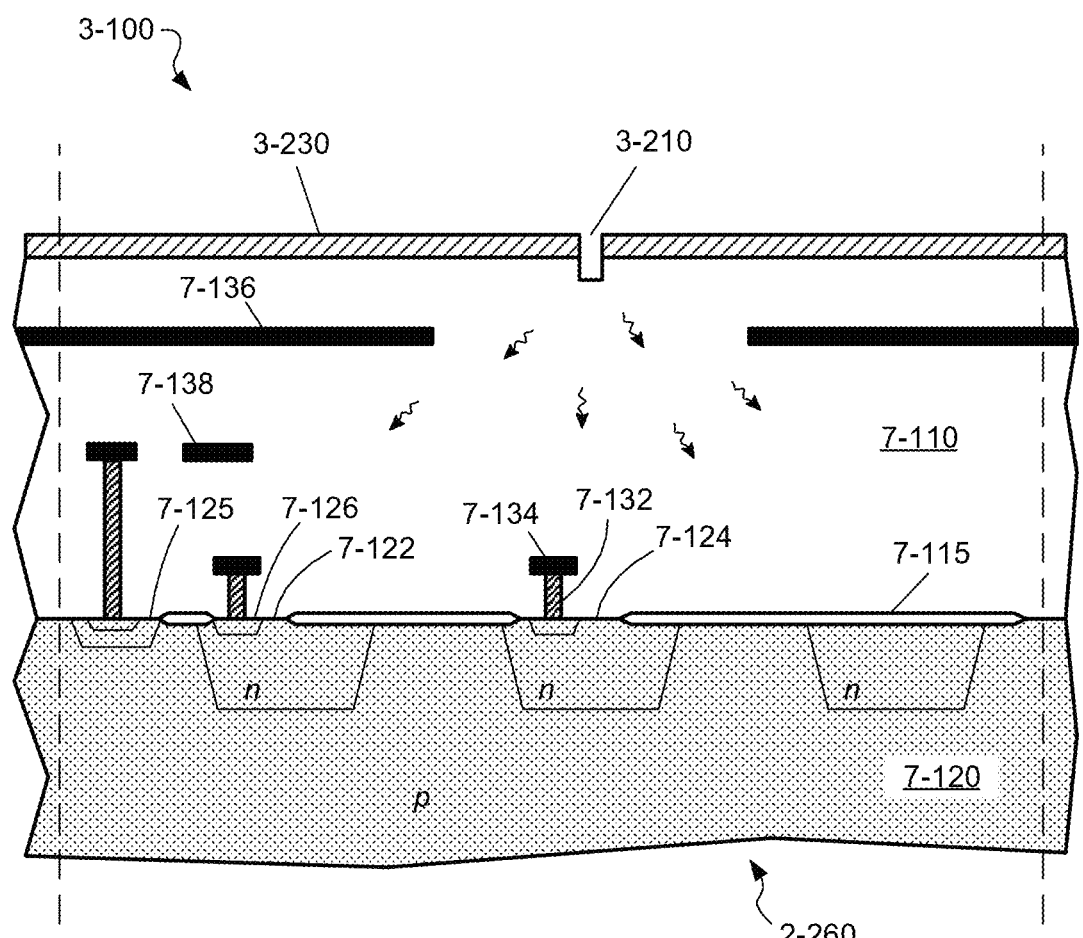
Figures 1B, 7:
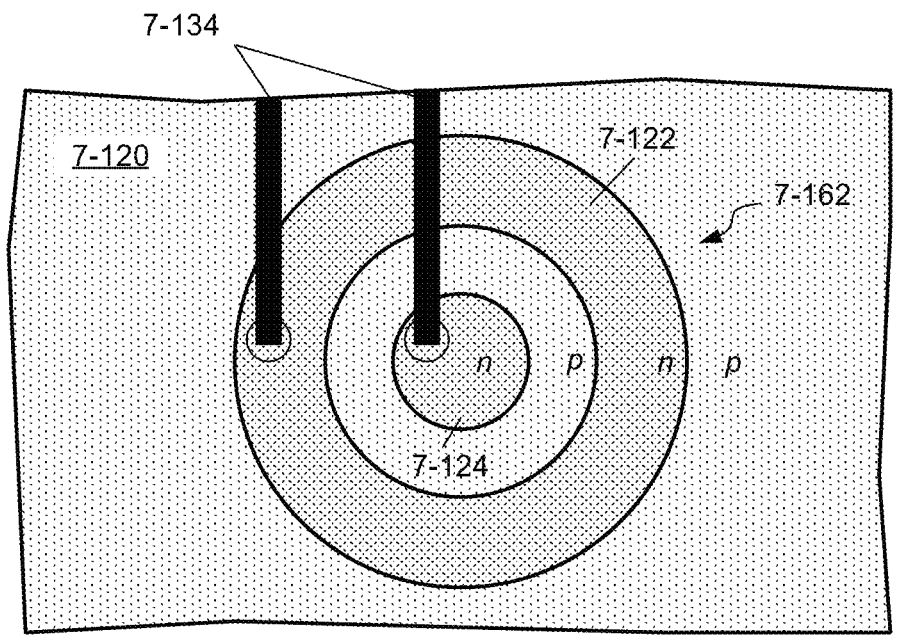
Figures 1C, 7:
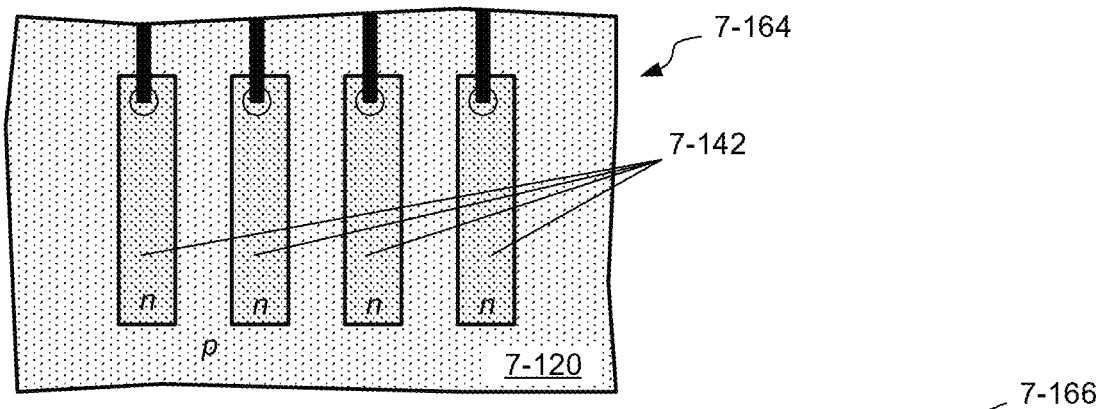
Figures 1D, 7:
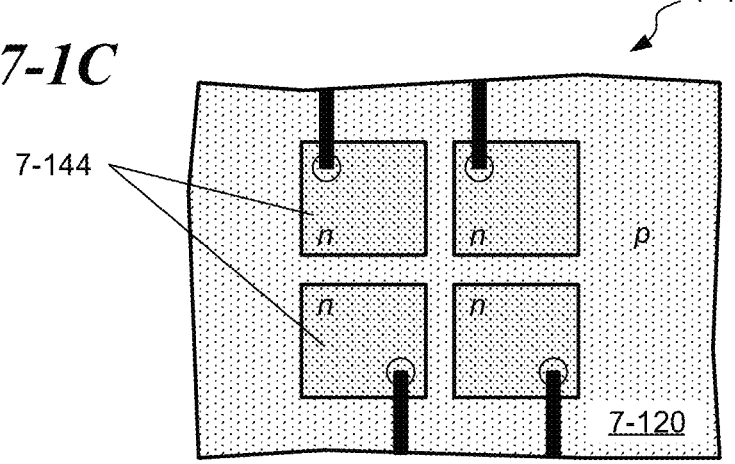
Figures 1E, 7:
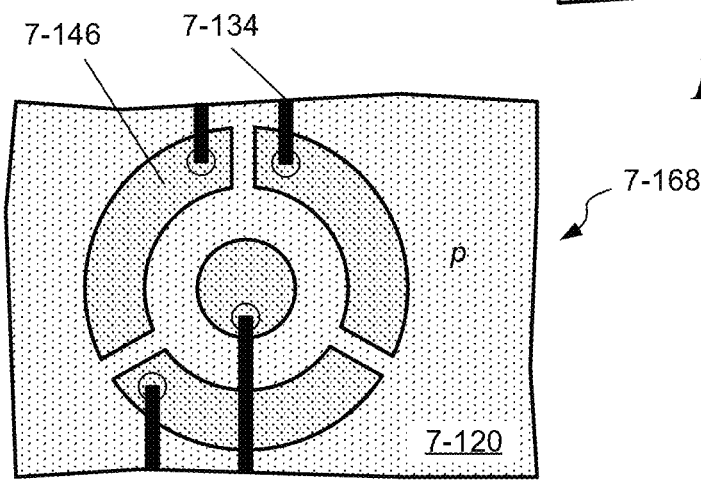
Figures 1F, 7:
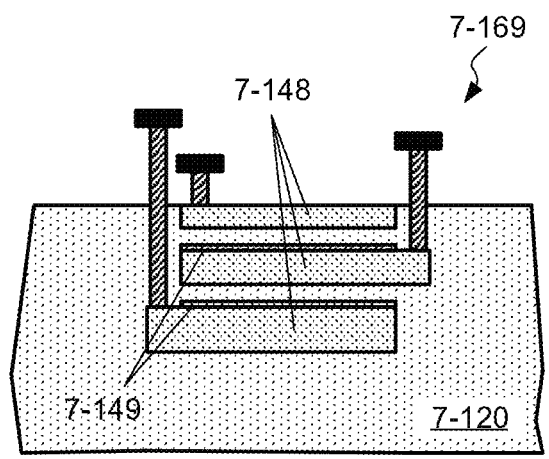
Figures 2A, 7:
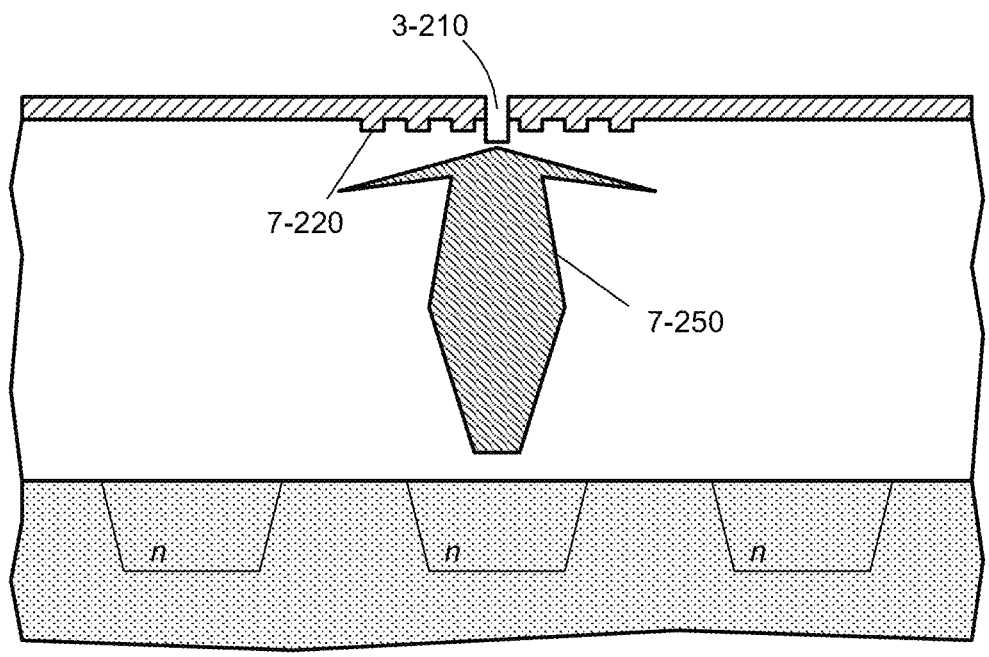
Figures 2B, 7:
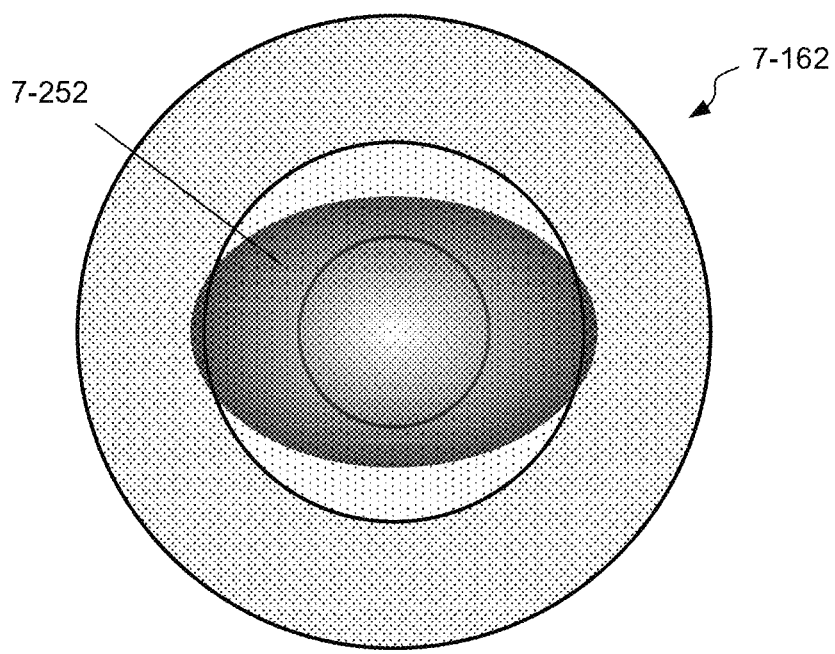
Figures 2C, 7:
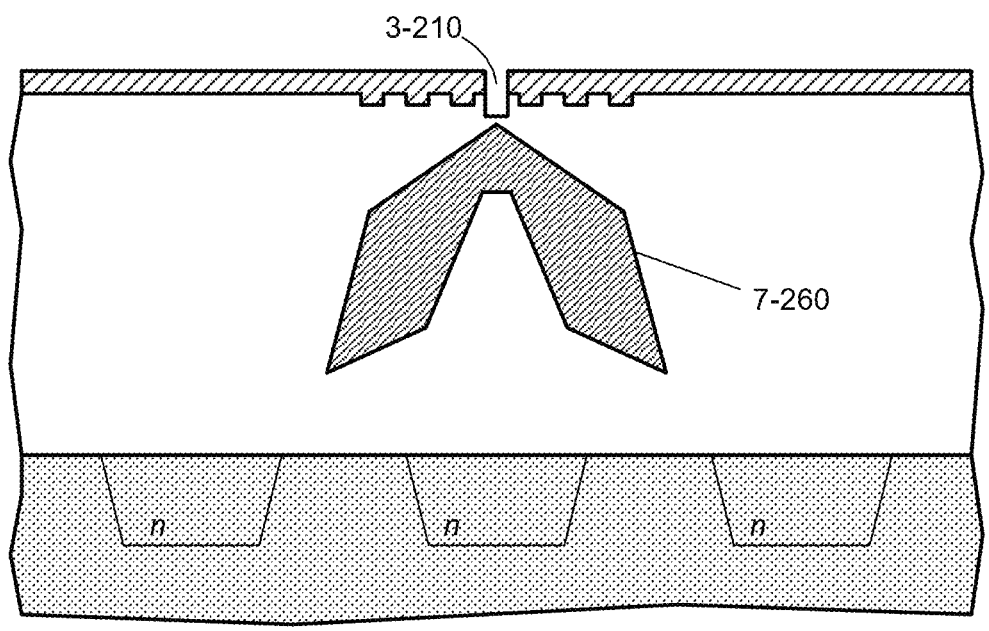
Figures 2D, 7:
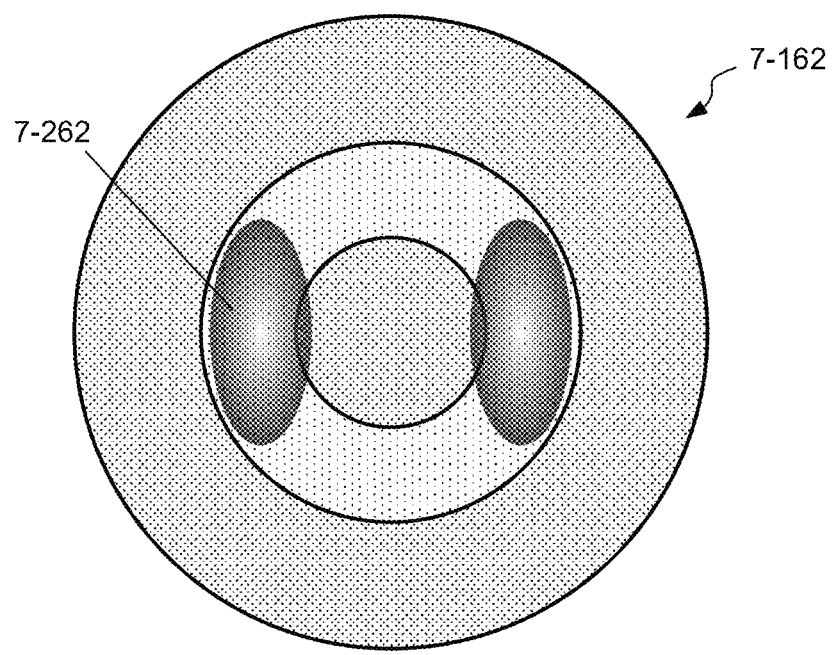
Figures 3A, 7:
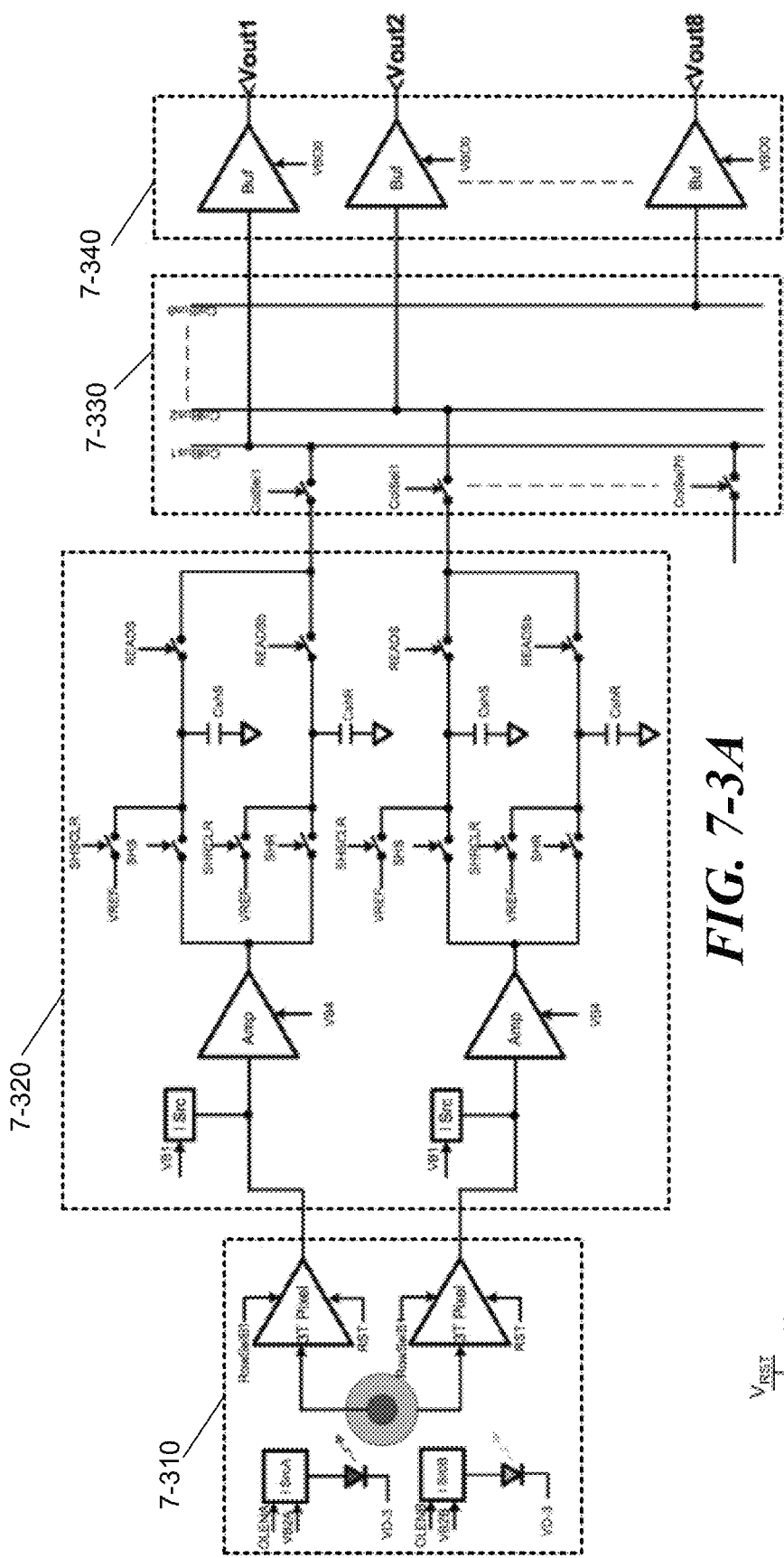
Figures 3B, 7:
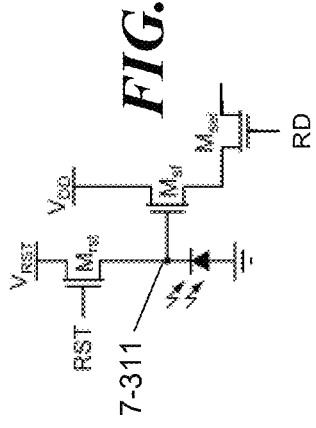
Figures 3C, 7:
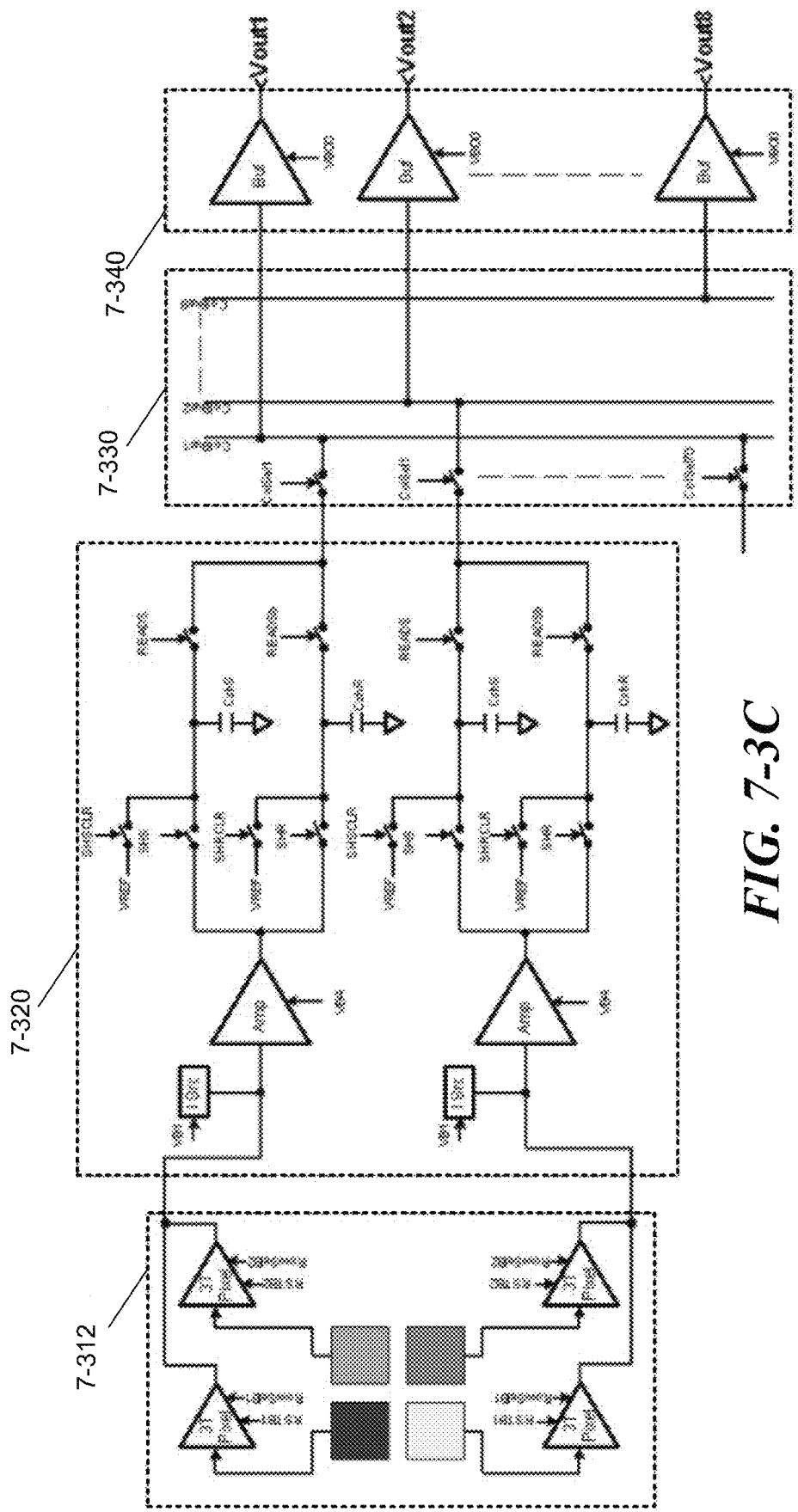
Figures 4A, 7:
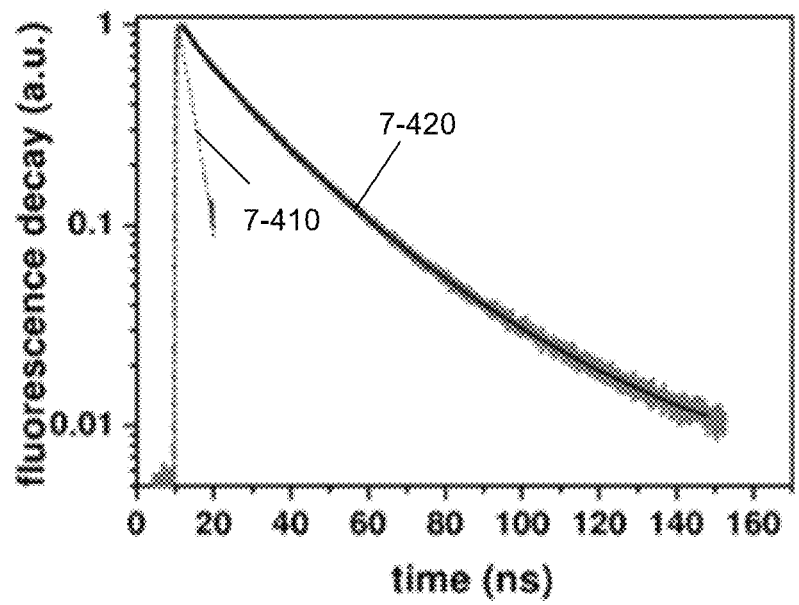
Figures 4B, 7:
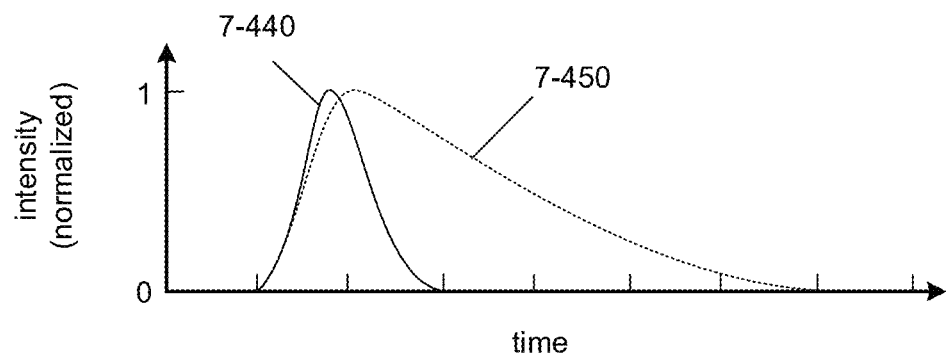
Figures 4C, 7:
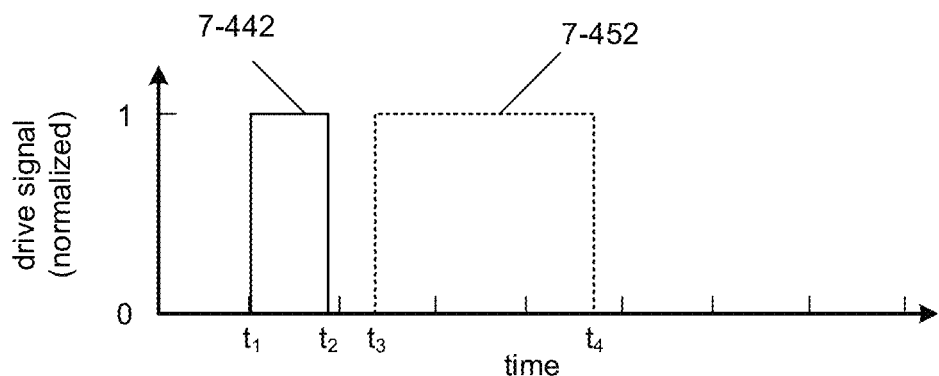
Figures 4D, 7:
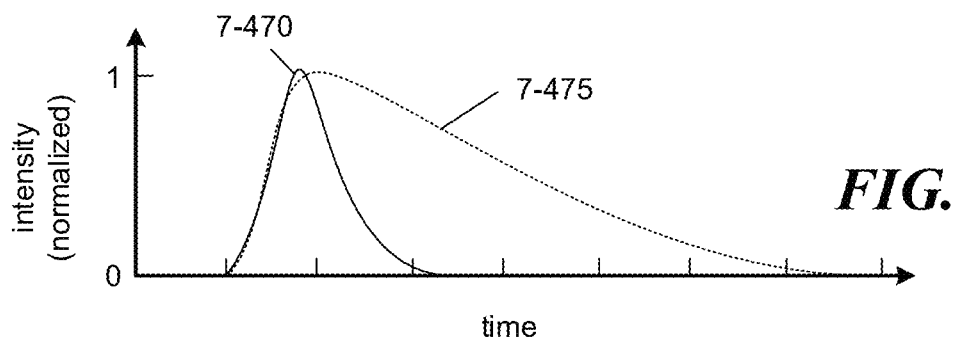
Figures 4E, 7:
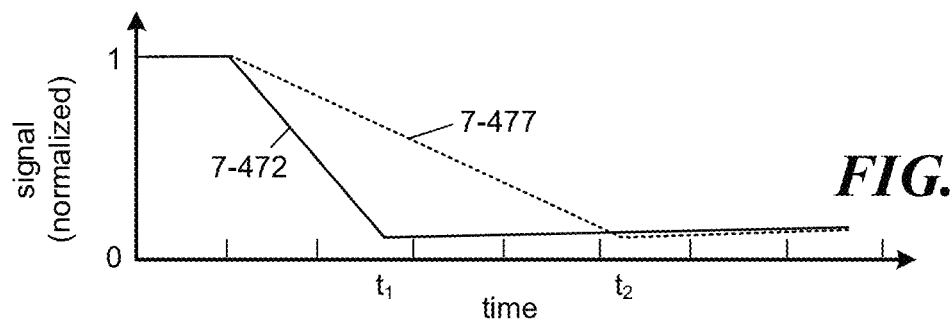
Figures 4F, 7:
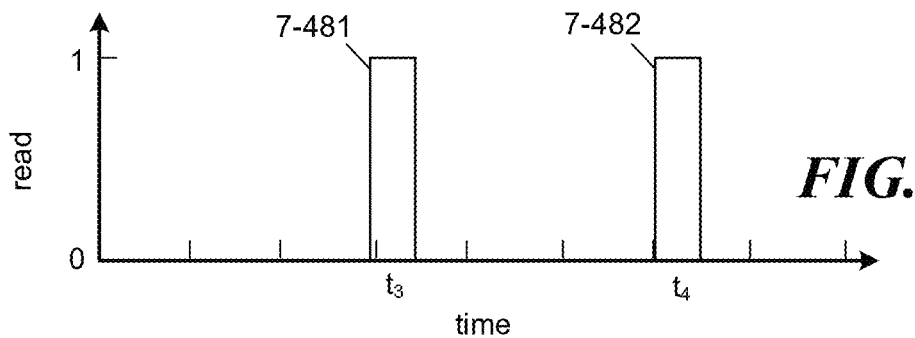
Figures 4G, 7:
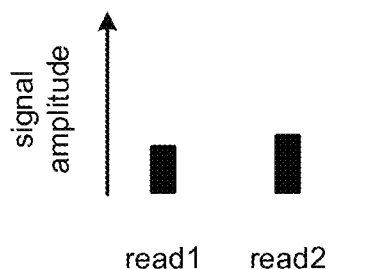
Figures 4H, 7:
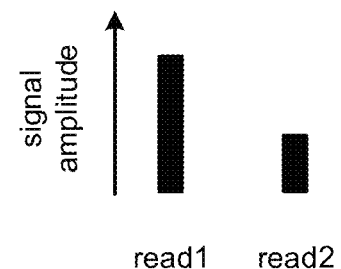
Figures 1, 8:
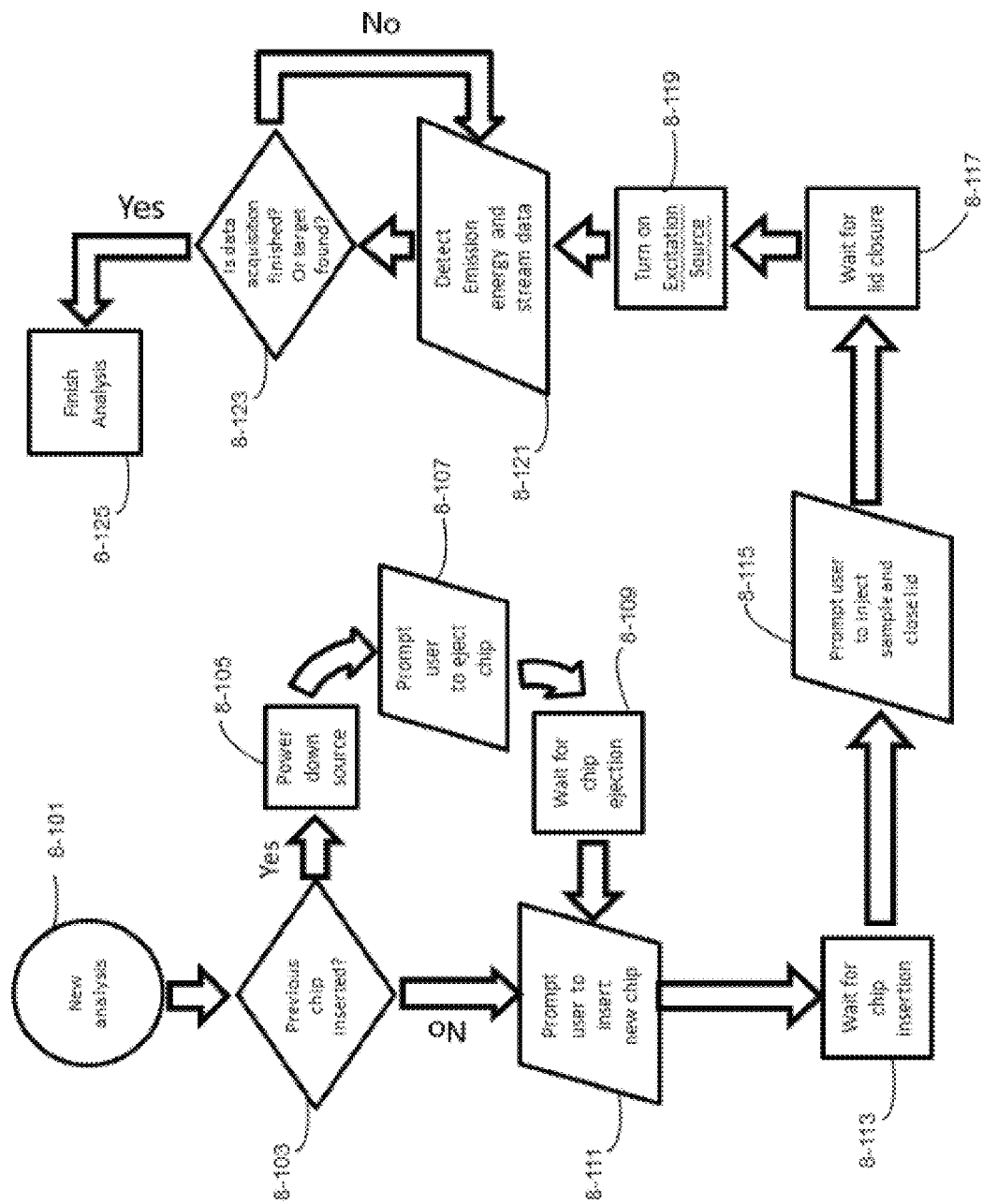
Figures 2, 8:
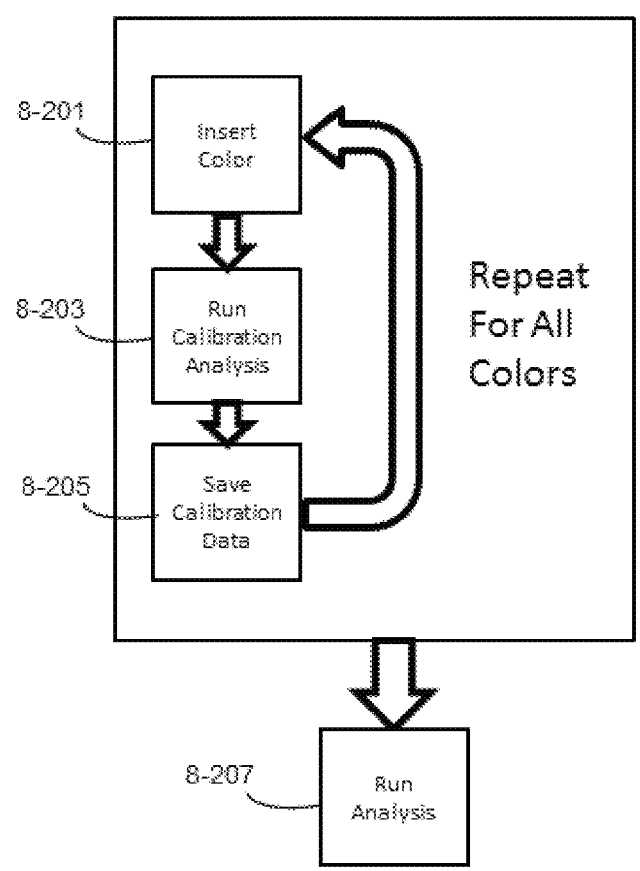
Figures 3, 8:
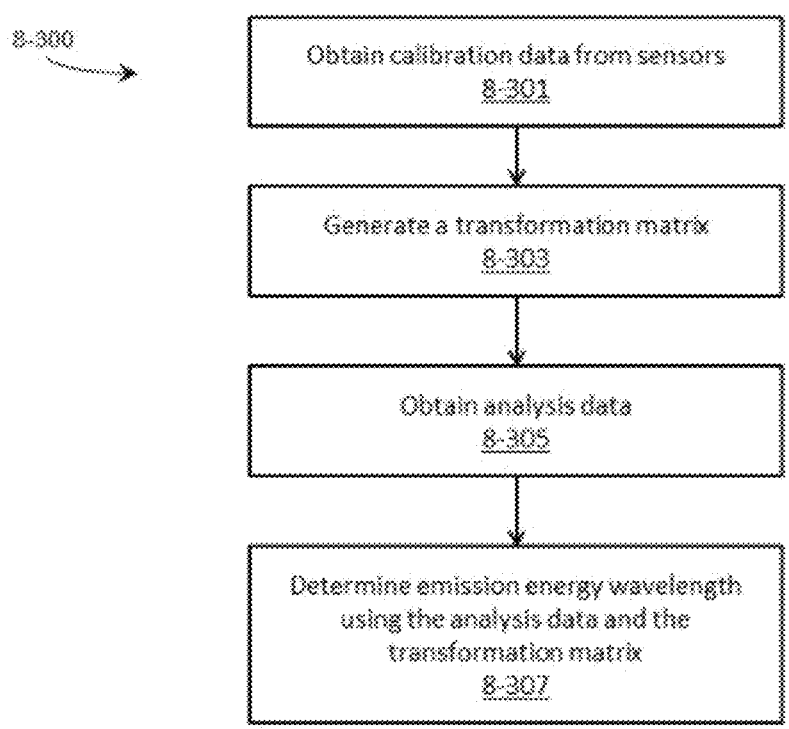

In some embodiments, a stacked sensor 7-169 may be formed by fabricating a plurality of separated sensor segments 7-148 in a vertical stack, as depicted in FIG. 7-1F. For example, the segments may be located one above the other, and there may, or may not, be insulating layers between the stacked segments. Each vertical layer may be configured to absorb emission energy of a particular energy, and pass emission at different energies. For example, a first detector may absorb and detect shorter-wavelength radiation (e.g., blue-wavelength radiation below about 500 nm from a sample). The first detector may pass green- and red-wavelength emissions from a sample. A second detector may absorb and detect green-wavelength radiation (e.g., between about 500 nm and about 600 nm) and pass red emissions. A third detector may absorb and detect the red emissions. Reflective films 7-149 may be incorporated in the stack, in some embodiments, to reflect light of a selected wavelength band back through a segment. For example, a film may reflect green-wavelength radiation that has not been absorbed by the second segment back through the second segment to increase its detection efficiency.

In some embodiments with vertically-stacked sensor segments, emission-coupling components may not be included at the sample well to produce distinct spatial distribution patterns of sample emission that are dependent on emission wavelength. Discernment of spectrally different emissions may be achieved with a vertically-stacked sensor 7-169 by analyzing the ratio of signals from its stacked segment, according to some embodiments.

In some embodiments, segments of a sensor 3-260 are formed from silicon, though any suitable semiconductor (e.g., Ge, GaAs, SiGe, InP, etc.) may be used. In some embodiments, a sensor segment may comprise an organic photoconductive film. In other embodiments, quantum dot photodetectors may be used for sensor segments. Quantum dot photodetectors may respond to different emission energies based on the size of the quantum dot. In some embodiments, a plurality of quantum dots of varying sizes may be used to discriminate between different emission energies or wavelengths received from the sample well. For example, a first segment may be formed from quantum dots having a first size, and a second segment may be formed from quantum dots having a second size. In various embodiments, sensors 2-260 may be formed using conventional CMOS processes.

As described above, emission-coupling components may be fabricated adjacent the sample well in some embodiments. The emission-coupling components can alter emission from a sample within the sample well 3-210 to produce distinct spatial distribution patterns of sample emission that are dependent on emission wavelength. FIG. 7-2A depicts an example of a first spatial distribution pattern 7-250 that may be produced from a first sample at a first wavelength. The first spatial distribution pattern 7-250 may have a prominent central lobe directed toward a central segment of a bulls-eye sensor 7-162, for example. As just one example, such a pattern 7-250 may be produced from a sample well surrounded by a circular grating 7-220 emission-coupling structure, where the sample emits at a wavelength of about 663 nm. A projected pattern 7-252 incident on the sensor may appear as illustrated in FIG. 7-2B.

FIG. 7-2C depicts a spatial distribution pattern 7-260 that may be produced from a second sample emitting at a second wavelength from the same sample well, according to some embodiments. The second spatial distribution pattern 7-260 may comprise two lobes of radiation and differ from the first spatial distribution pattern 7-250. A projected pattern 7-262 of the second spatial distribution pattern 7-260 may appear as depicted in FIG. 7-2D, according to some embodiments. As just one example, a second spatial distribution pattern 7-260 may be produced from the same sample well surrounded by the circular grating 7-220 emission-coupling structure, where the sample emits at a wavelength of about 687 nm.

The segments of a sensor 3-260 may be arranged to detect particular emission energies, according to some embodiments. For example, emission-coupling structures adjacent the sample well and segments of a sensor may be configurationed in combination to increase signal differentiation between particular emission energies. The emission energies may correspond to selected tags that will be used with the integrated device. As an example, a bulls-eye sensor 7-162 could have its segments sized and/or located to better match the projected patterns 7-260, 7-262 from a sample, so that regions of higher intensity fall more centrally within active segments of the sensor. Alternatively or additionally, emission-coupling structures may be configurationed to alter the projected patterns 7-260, 7-262 so that intense regions fall more centrally within segments of the sensor.

Although a sensor 3-260 may comprise two segments, it is possible in some embodiments to discern more than two spectrally-distinct emission bands from a sample. For example, each emission band may produce a distinct projected pattern on the sensor segments and yield a distinct combination of signals from the sensor segments. The combination of signals may be analyzed to discern and identify the emission band. FIG. 7-2E through FIG. 7-2H represent results from numerical simulations of signal sets from a two-segment sensor 3-260 exposed to four distinct emission patterns from four different emitters. The emission patterns were simulated as being produced at four wavelengths (565 nm, 595 nm, 663 nm, 687 nm) from a sample well having a circular grating formed adjacent the sample well. As can be seen, each combination of signals (or signal set) from the two sensor segments is distinct, and can be used to discriminate between emitters at the four wavelengths. For the simulation, because the outer detector segment of the bulls-eye sensor 7-162 had a larger area, more signal was integrated for that detector. Additionally, light that impinged on an area between the detectors generated carriers that may drift towards either detector segment and contribute to signals from both segments.

In some embodiments, there may be N photodetector segments per pixel, where N may be any integer value. In some embodiments, N may be greater than or equal to 1 and less than or equal to 10. In other embodiments, N may be greater than or equal to 2 and less than or equal to 5. The number M of discernible sample emissions (e.g., distinct emission wavelengths from different luminescent tags) that may be detected by the N detectors may be equal to or greater than N. The discernment of M sample emissions may be achieved by evaluating the ratio of signals from each sensor segment, according to some embodiments. In some implementations, the ratio, sum and/or amplitudes of the received signals may be measured and analyzed to determine a characteristic wavelength of emission from the sample well.

In some embodiments, more than one emitter may emit at different characteristic wavelengths in a given time window within a sample well 3-210. A sensor 3-260 may simultaneously detect signals from multiple emissions at different wavelengths and provide the summed signal for data processing. In some implementations, multi-wavelength emission may be distinguishable as another set of signal values from the sensor segments (e.g., signal values different from those shown in FIG. 7-2E through FIG. 7-2H). The signal values may be analyzed to discern that multi-wavelength emission has occurred and to identify a particular combination of emitters associated with the emissions.

The inventors have also contemplated and analyzed a bulls-eye sensor having at least two, three, or four concentric segments. Signal sets from the segments are plotted in FIG. 7-2I and FIG. 7-2J for the same emission conditions associated with FIG. 7-2G and FIG. 7-2H, respectively. The four-segment bulls-eye sensor also shows discernable signals that may be analyzed to identify a particular emitter within the sample well.

When wavelength filtering is used at each sensor segment, or the spectral separation is high, each segment of a sensor may detect substantially only a selected emission band. For example, a first wavelength may be detected by a first segment, a second wavelength may be detected by a second segment, and a third wavelength may be detected by a third segment.

Referring again to FIG. 7-1A, there may be additional electronic circuitry 7-125 within a pixel 2-205 that may be used to collect and readout signals from each segment of a sensor 3-260. FIG. 7-3A and FIG. 7-3D depict circuitry that may be used in combination with a multi-segment sensor, according to some embodiments. As an example, signal collection circuitry 7-310 may comprise three transistors for each sensor segment. An arrangement of the three transistors is depicted in FIG. 7-3B, according to some implementations. A signal level at a charge accumulation node 7-311 associated with each segment may be reset by a reset transistor RST prior to a charge-accumulation period, and a signal level for the segment (determined by the amount of charge at the charge accumulation node) may be read out with a read transistor RD during and/or at the conclusion of a charge-accumulation period. Signals may be provided to a processor (not shown) for analysis to discern the detection of M different emission wavelengths from the sample detected by N spatially-separated detectors, as described above.

The pixel circuitry may further include amplification and correlated double-sampling circuitry 7-320, according to some embodiments. The amplification and double-sampling circuitry may comprise transistors configured to amplify signals from the sensor segments as well as transistors configured to reset the voltage level at the charge-accumulation node and to read a background, or "reset", signal at the node when no emission radiation is present on the sensor (e.g., prior to application of excitation energy at the sample well) and to read a subsequent emission signal, for example.

According to some embodiments, correlated double sampling is employed to reduce background noise by subtracting a background or reset signal level from the detected emission signal level. The collected emission signal and background signal associated with each segment of the sensor may be read out onto column lines 7-330. In some embodiments, an emission signal level and background signal are time-multiplexed onto a common column line. There may be a separate column line for each sensor segment. Signals from the column lines may be buffered and/or amplified with amplification circuitry 7-340 (which may be located outside of an active pixel array), and provided for further processing and analysis. In some embodiments the subtraction of the double-sampled signals is calculated off-chip, e.g., by a system processor. In other embodiments, the subtraction may be performed on chip or in circuitry of the base instrument.

Some embodiments of correlated double sampling may operate by selecting a row to sample, wherein the sensors associated with the row have integrated signal charges over a sampling period and contain signal levels. The signal levels may be simultaneously read out onto the columns lines. After sampling the integrated signal levels, all the pixels in the selected row may be reset and immediately sampled. This reset level may be correlated to the next integrated signal that starts accumulating after the reset is released, and finishes integrating a frame time later when the same row is selected again. In some embodiments, the reset values of the frame may be stored off-chip so that when the signals have finished integrating and have been sampled, the stored correlated reset values can be subtracted.

In some embodiments, a sensor 3-260 with more than two segments may require additional circuitry. FIG. 7-3C depicts signal-collection 7-312, amplification 7-320, and double-sampling circuitry associated with a quad sensor. According to some embodiments, signals from two or more segments may be time-multiplexed onto a common signal channel at the pixel, as depicted in the drawing. The time-multiplexed signals may include sampled background signals for each segment for noise cancellation. Additionally, the signals from two or more segments may be time-multiplexed onto a common column line.

According to some embodiments, temporal signal-acquisition techniques may be used to reduce background signal levels from an excitation source or sources, and/or discern different emissions from different emitters associated with a sample. FIG. 7-4A depicts fluorescent emission and decay from two different emitters that may be used to tag a sample, according to some embodiments. The two emissions have appreciably different time-decay characteristics. A first time-decay curve 7-410 from a first emitter may correspond to a common fluorescent molecule such as rhodamine. A second time-decay curve 7-420 may be characteristic of a second emitter, such as a quantum dot or a phosphorescent emitter. Both emitters exhibit an emission-decay tail that extends for some time after initial excitation of the emitter. In some embodiments, signal-collection techniques applied during the emission-decay tail may be timed to reduce a background signal from an excitation source, in some embodiments, and to distinguish between the emitters, in some embodiments.

According to some implementations, time-delayed sampling may be employed during the emission-decay tail to reduce a background signal due to radiation from an excitation source. FIG. 7-4B and FIG. 7-4C illustrate time-delay sampling, according to some embodiments. FIG. 7-4B depicts the temporal evolution of an excitation pulse 7-440 of excitation radiation from an excitation source, and a subsequent emission pulse 7-450 that may follow from a sample that is excited within the sample well. The excitation pulse 7-440 may result from driving the excitation source with a drive signal 7-442 for a brief period of time, as depicted in FIG. 7-4C. For example, the drive signal may begin at a first time $t_1$ and end at a second time $t_2$. The duration of the drive signal $(t_2-t_1)$ may be between about 1 picosecond and about 50 nanoseconds, according to some embodiments, though shorter durations may be used in some implementations.

At a time $t_3$ following termination of the drive signal for the excitation source, a sensor 3-260 (or sensor segment) at the pixel may be gated to accumulate charge at a charge accumulation node 7-311 (with reference to FIG. 7-3B) during a second time interval extending from a time $t_3$ to a time $t_4$. The second time interval may be between about 1 nanosecond and about 50 microseconds, according to some embodiments, though other durations may be used in some implementations. As can be seen in reference to FIG. 7-4B, a charge accumulation node will collect more signal charges due to the emitting sample then due to the excitation source. Accordingly, an improved signal-to-noise ratio may be obtained.

Referring again to FIG. 7-4A, because of the different temporal emission characteristics of the emitters, corresponding signals at a sensor may peak at different times. In some implementations, signal-acquisition techniques applied during the emission-decay tail may be used to discern different emitters. In some embodiments, temporal detection techniques may be used in combination with spatial and spectral techniques (as described above in connection with FIG. 7-2, for example) to discern different emitters.

FIG. 7-4D through FIG. 7-4H illustrate how double-sampling at a sensor, or sensor segment, can be used to distinguish between two emitters having different temporal emission characteristics. FIG. 7-4D depicts emission curves 7-470, 7-475 associated with a first emitter and second emitter, respectively. As an example, the first emitter may be a common fluorophore such as rhodamine, and the second emitter may be a quantum dot or phosphorescent emitter.

FIG. 7-4E represents dynamic voltage levels at a charge accumulation node 7-311 that may occur in response to the two different emission characteristics of FIG. 7-4D. In the example, a first voltage curve 7-472 corresponding to the fluorescent emitter may change more rapidly, because of the shorter emission span, and reach its maximum (or minimum, depending on the polarity of the node) at a first time $t_1$. The second voltage curve 7-477 may change more slowly due to the longer emission characteristics of the second emitter, and reach its maximum (or minimum) at a second time $t_2$.

In some embodiments, sampling of the charge-accumulation node may be done at two times $t_3$, $t_4$ after the sample excitation, as depicted in FIG. 7-4F. For example, a first read signal 7-481 may be applied to read out a first voltage value from the charge-accumulation node at a first time $t_3$. Subsequently, a second read signal 7-482 may be applied to read out a second voltage value from the charge-accumulation node at a second time $t_4$ without resetting the charge-accumulation node between the first read and second read. The first read and second read at times $t_3$ and $t_4$ may occur during a same charge-accumulation period for the sensor during the emission from the sample well. An analysis of the two sampled signal values may then be used to identify which of the two emitters provided the detected signal levels.

FIG. 7-4G depicts an example of a first signal set from the first read and second read that may be obtained for the first emitter having an emission curve 7-470 as depicted in FIG. 7-4D. FIG. 7-4H depicts an example of a second signal set from the first read and second read that may be obtained for the second emitter having an emission curve 7-475 as depicted in FIG. 7-4D. For example the sampling sequence shown in FIG. 7-4F for the first emitter will sample the curve 7-472 and obtain approximately the same values at the two read times. In the case of the second emitter, the sampling sequence depicted in FIG. 7-4F samples two different values of the curve 7-477 at the two read times. The resulting pairs of signals from the two read times distinguish between the two emitters, and can be analyzed to identify each emitter. According to some embodiments, double sampling for background subtraction may also be executed to subtract a background signal from the first and second read signals.

In operation, sensors 2-260 of an integrated device may be subjected to a wavelength calibration procedure prior to data collection from a specimen to be analyzed. The wavelength calibration procedure may include subjecting the sensors to different known energies having characteristic wavelengths that may, or may not, correspond to fluorophore wavelengths that may be used with an integrated device. The different energies may be applied in a sequence so calibration signals can be recorded from the sensors for each energy. The calibration signals may then be stored as reference signals, that may be used to process real data acquisition and to determine what emission wavelength or wavelengths are detected by the sensors.

According to some embodiments, a sensor may comprise a semiconductor junction formed adjacent the sample well 3-210. The semiconductor junction may be as depicted in FIG. 4-5B or FIG. 4-5D, for example. In some implementations, the semiconductor junction may be formed as a multilayer structure, and the sample well may be formed in the multilayer structure, as depicted in FIG. 3-7F, for example. In some embodiments, an excited sample may non-radiatively transfer emission energy to a semiconductor junction formed adjacent the sample well via FRET or DET, creating excitons at the semiconductor junction. The semiconductor junction may comprise a p-n or p-i-n junction that converts the received energy to an electrical signal that is detected by CMOS circuitry associated with the sample well. In some implementations, a quantum dot or molecule may be attached to the semiconductor junction via a linker and may participate in non-radiative energy transfer from an excited sample to the semiconductor junction.

Any one or more of the foregoing embodiments of sensors may be included in an embodiment of an integrated device.

VIII. Instrument Operation

The instrument 2-120 may be controlled using software and/or hardware. For example, the instrument may be controlled using a processing device 1-123, such as an ASIC, an FPGA and/or a general purpose processor executing software.

FIG. 8-1 illustrates a flowchart of operation of the instrument 2-120 according to some embodiments. After a user has acquired a specimen to analyze, the user begins a new analysis at act 8-101. This may be done by providing an indication to the instrument 2-120 via the user interface 2-125 by, e.g., pressing a button. At act 8-103, the instrument 2-120 checks whether the integrated device 2-110 from a previously performed analysis is still inserted in the instrument 2-120. If it is determined that an old integrated device is present, then the power to excitation source may be turned off at act 8-105, the user is prompted at act 8-107 to eject the previous integrated device using an indicator of the user interface 2-125 and the instrument 2-120 waits for the old integrated device to be ejected at act 8-109.

When the previous integrated device is ejected by the user, or if the instrument 2-120 determined at act 8-103 that the previous integrated device was already removed, the user is prompted to insert a new integrated device 2-110 for the new analysis at act 8-111. The instrument 2-120 then waits for the new integrated device 2-110 to be inserted at act 8-113. When the user inserts the new integrated device, the user is prompted at act 8-115 by an indicator of the user interface 2-125 to place the specimen to be analyzed onto the exposed top surface of the integrated device 2-110 and also prompted to close the lid on the instrument 2-120. The instrument 2-120 then waits for the lid to be closed at act 8-117. When the lid is closed by the user, at act 8-119 the excitation source may be driven to produce excitation energy for exciting the sample portions of the specimen present in the sample wells of the integrated device 2-110.

At act 8-121, the emission energy from the samples is detected by the sensor 2-122 and data from the sensor 2-122 is streamed to the processing device 2-123 for analysis. In some embodiments, the data may be streamed to external computing device 2-130. At act 2-123, the instrument 2-120 checks whether the data acquisition is complete. The data acquisition may be complete after a particular length of time, a particular number of excitation pulses from the excitation source or one a particular target has been identified. When the data acquisition is completed, the data analysis is finished at 8-125.

FIG. 8-2 illustrates an example self-calibration routine according to some embodiments. The calibration routine may be executed at any suitable time prior to the analysis of a specimen. For example, it may be done once by the manufacturer for each instrument prior to shipment to the end user. Alternatively, the end user may perform a calibration at any suitable time. As discussed above, the instrument 2-120 is capable of distinguishing between emission energy having different wavelengths emitted from different samples. The instrument 2-120 and/or computing device 2-130 may be calibrated with calibration associated with each particular color of light associated with, for example, a luminescent tag used to tag molecules of a specimen being analyzed. In this way, the precise output signal associated with a particular color may be determined.

To calibrate the device, a calibration specimen associated with a single luminescent tag is provided to the instrument 2-120 one at a time. The self-calibration begins at act 8-201 when a user places a specimen comprising luminescent tags that emit emission energy of a single wavelength on an integrated device 2-110 and inserts the integrated device 2-110 into the instrument 2-120. Using the user interface 2-125, the user instructs the instrument 2-120 to begin the self-calibration. In response, at act 8-203, the instrument 2-120 runs the calibration analysis by illuminating the assay chop 2-110 with excitation energy and measuring the single wavelength emission energy from the calibration specimen. The instrument 2-120 may then, at act 8-205, save the detection pattern measured on the array of sub-sensors of the sensor 2-122 for each pixel of the sensor array. The detection pattern for each luminescent tag may be considered a detection signature associated with the luminescent tag. In this way, the signatures may be used as a training data set used to analyze the data received from unknown samples analyzed in subsequent analysis runs.

The above calibration routine may then be executed for every calibration specimen associated with a single luminescent tag. In this way, each sensor 2-122 of the array of pixels is associated with calibration data that may be used to determine the luminescent tag present in a sample well during a subsequent analysis implemented at act 8-207 after the competition of the calibration routine.

FIG. 8-3 further illustrates how the calibration data may be acquired and used to analyze the data according to some embodiments. At act 8-301 calibration data is obtained from the sensors. This may be done using the aforementioned self-calibration routine. At act 8-303, a transformation matrix is generated based on the calibration data. The transformation matrix maps sensor data to the emission wavelength of a sample and is a m×n matrix, where m is the number of luminescent tags with different emission wavelengths and n is the number of sub-sensors used to detect the emission energy per pixel. Thus, each column of the transformation matrix represents the calibration values for the sensor. For example, if there are four sub-sensors per pixel and five different luminescent tags, then the transformation matrix is a 4×5 matrix (i.e., four rows and five columns) and each column is associated with a different luminescent tag, the values in the column corresponding to the measured values obtained from the sub-sensors during the self-calibration routine. In some embodiments, each pixel may have its own transformation matrix. In other embodiments, the calibration data from at least some of the pixels may be averaged and all the pixels may then use the same transformation matrix based on the averaged data.

At act 8-305, the analysis data associated with a bioassay is obtained from the sensors. This may be done in any of the ways described above. At act 8-307, the wavelength of the emission energy and/or the identity of the luminescent tag may be determined using the transformation matrix and the analysis data. This may be done in any suitable way. In some embodiments, the analysis data is multiplied by the pseudo-inverse of the transformation matrix, resulting in a m×1 vector. The luminescent tag associated with the vector component with the maximum value may then be identified as the luminescent tag present in the sample well. Embodiments are not limited to this technique. In some embodiments, to prevent possible pathologies that may arise when the inverse of a matrix with small values is taken, a constrained optimization routine, such as a least square method or a maximum likelihood technique, may be performed to determine the luminescent tag present in the sample well.

The foregoing method of using the calibration data to analyze data from the sensors may be implement by any suitable processor. For example, processing device 2-123 of the instrument 2-120 may perform the analysis, or computing device 2-130 may perform the analysis.

FIG. 8-2 illustrates the base instrument control of the aforementioned correlated double sampling of the pixels of the integrated bioanalysis device 212 according to some embodiments. At the start of a new frame of data acquisition, a row shift register is reset. The pixel reset value from the previous frame is read by incrementing the column register. Simultaneously the current frames pixel sample levels are stored within the reading element on the integrated device. Once the desired number of columns to be measured is reached, the column register is reset. Then the pixel sample levels from the current frame are read by incrementing the column register and outputting the sample values eight pixels at a time to a buffer, in some embodiments the first frame of sample levels can be discarded. The buffer can be located off integrated device in memory or in some embodiments it can be stored locally on the integrated device. Once the number of columns to be measured is met the row register is incremented. This processes is repeated until a frame is completed. Upon finishing a frame of data the processes is started again with the change that the frames sample levels are subtracted from the previous frames reset levels.

IX. Conclusion

Having thus described several aspects of several embodiments of an integrated bioanalysis device, it is to be appreciated that various alterations, modifications, and improvements will readily occur to those skilled in the art. Such alterations, modifications, and improvements are intended to be part of this disclosure, and are intended to be within the spirit and scope of the invention. While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

For example, embodiments may be modified to include any configuration of excitation source, energy-coupling components, target volume, and energy-collection components described above. Moreover, the integrated device may be used to quantitatively analyze non-biological samples. Additionally, various optical elements described herein, such as waveguides, reflectors, and cavities, may be replaced with their photonic crystal equivalent; any metal material may be replaced with a highly degenerately doped semiconductor; graphene may be used in place of metals and/or semiconductors; phosphorescence may be used instead of luminescence; and any single functional layer may be replaced with a plurality of functional layers.

While various inventive embodiments have been described and illustrated, those of ordinary skill in the art will readily envision a variety of other means and/or structures for performing the function and/or obtaining the results and/or one or more of the advantages described, and each of such variations and/or modifications is deemed to be within the scope of the inventive embodiments described. More generally, those skilled in the art will readily appreciate that all parameters, dimensions, materials, and configurations described are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure may be directed to each individual feature, system, system upgrade, and/or method described. In addition, any combination of two or more such features, systems, and/or methods, if such features, systems, system upgrade, and/or methods are not mutually inconsistent, is included within the inventive scope of the present disclosure.

Further, though some advantages of the present invention may be indicated, it should be appreciated that not every embodiment of the invention will include every described advantage. Some embodiments may not implement any features described as advantageous. Accordingly, the foregoing description and drawings are by way of example only.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used are for organizational purposes only and are not to be construed as limiting the subject matter described in any way.

The terms "program" or "software" may be used in the present disclosure to refer to computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

The term "associated with," when used in connection with data structures, may be used to describe a combination of data structures in some embodiments. For example, first data associated with second data may mean adding the first data to a data record containing the second data, or vice versa. "Associated with" may mean establishing a relational data structure between first and second data in some embodiments. For example, first data may be entered in a table or augmented with an identifier that cross-references or links the first data to second data, even though the first and second data may be stored in different data stores.

The term "transmit," when used in connection with data structures, may be used to describe one or more acts of retrieving data, preparing the data in a format suitable for transmission, identifying at least one destination for the data, and providing the data to a data-transmission device.

Where user-interactive displays are described, active text or buttons may alter their appearance when selected or clicked on by a user. For example, active text or buttons may change color or be highlighted in any suitable manner when selected, so as to indicate that the text or button has been selected.

Also, the technology described may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used, should be understood to control over dictionary definitions, definitions in documents incorporated by reference, and/or ordinary meanings of the defined terms.

The indefinite articles "a" and "an," as used in the specification and in the claims, unless clearly indicated to the contrary, should be understood to mean "at least one."

The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

The invention claimed is:

1. An integrated device for analyzing a plurality of samples in parallel, the device comprising:
  a plurality of pixels arranged on a substrate, wherein an individual pixel of the plurality of pixels comprises:
    a sample well having an excitation region configured to retain a biological sample;
    a first structure located adjacent to or within the sample well and configured to affect coupling of at least excitation energy into the excitation region; and
    a sensing system including a sensor that is configured to discriminate between at least two different emissions from the sample well, wherein the at least two different emissions comprise spectral and/or temporal differences;
  at least one excitation source on the substrate that is arranged to provide the excitation energy to the sample well; and
  circuitry arranged on the substrate to receive at least one signal from the sensor.

2. The integrated device of claim 1, wherein the first structure comprises a three-dimensional, micro- or nanoscale plasmonic structure that improves coupling of the excitation energy into the excitation region via plasmons excited at the first structure.

3. The integrated device of claim 1, wherein the first structure comprises a micro-optical or nano-optical structure that increases an intensity of the excitation energy within the excitation region.

4. The integrated device of claim 1, wherein the pixel further comprises a second structure located adjacent to the sample well that is configured to direct emitted radiations from the sample well into a plurality of different spatial distributions that are dependent upon wavelengths of the emitted radiations and to condense the emitted radiations in each of a plurality of different directions.

5. The integrated device of claim 1, wherein the plurality of pixels are arranged in an N×M array on the substrate, where N is a number of pixels the array extends in a first direction and M is a number of pixels the array extends in a second direction, wherein each of N and M has a value between 50 pixels and 100000 pixels.

6. The integrated device of claim 1, further comprising a walled chamber formed around the plurality of pixels that is configured to hold a specimen.

7. The integrated device of claim 1, further comprising a divot extending from the sample well into an optically-transparent material, wherein the excitation region includes the divot.

8. The integrated device of claim 1, wherein the integrated device and sample well are arranged to receive samples in a fluid suspension.

9. The integrated device of claim 1, wherein the sample well comprises an entrance aperture at which excitation energy is received.

10. The integrated device of claim 9, wherein a diameter of the entrance aperture is between approximately 30 nanometers and approximately 250 nanometers.

11. The integrated device of claim 1, further comprising a reflector spaced from the sample well, wherein the reflector and material in which the sample well is formed comprises a resonant cavity that increases an intensity of excitation energy at the excitation region.

12. The integrated device of claim 1, further comprising an adherent arranged within the excitation region, wherein the adherent is configured to retain a sample in the excitation region.

13. The integrated device of claim 12, wherein the adherent comprises a biological or chemical substance formed on at least one surface within the sample well.

14. The integrated device of claim 1, wherein the first structure comprises a resonant structure for a characteristic frequency of the excitation energy and the sample well is positioned at a position corresponding to a coupling region of the resonant structure.

15. The integrated device of claim 14, wherein the resonant structure is a linear resonator or ring resonator.

16. The integrated device of claim 2, wherein the micro- or nanoscale plasmonic structure comprises a nano-antenna.

17. The integrated device of claim 2, wherein the micro- or nanoscale plasmonic structure comprises a resonant structure.

18. The integrated device of claim 2, wherein the plasmonic structure is configured to resonate at more than one frequency, wherein the more than one frequency includes a characteristic frequency of the excitation energy and/or characteristic frequencies of the emissions from the sample well.

19. The integrated device of claim 3, wherein the first structure comprises a diffractive optical element configured to concentrate the excitation energy at the excitation region.

20. The integrated device of claim 3, wherein the first structure comprises a thin lossy film adjacent the sample well.

21. The integrated device of claim 20, further comprising a dielectric layer disposed between the thin lossy film and the sample well.

22. The integrated device of claim 20, wherein an index of refraction of the thin lossy film is within a same order of magnitude as an extinction coefficient for the thin lossy film at a wavelength of the excitation energy.

23. The integrated device of claim 20, wherein the thin lossy film is formed of silicon or germanium, or a combination thereof.

24. The integrated device of claim 20, wherein a thickness of the thin lossy film is between approximately 3 nm and approximately 80 nm.

25. The integrated device of claim 20, wherein the thin lossy film includes multiple layers of at least two different materials.

26. The integrated device of claim 3, wherein the first structure comprises a microcavity located adjacent to the sample well and configured to concentrate the excitation energy at the excitation region.

27. The integrated device of claim 1, wherein the sensing system comprises a filter configured to suppress an amount of excitation energy at the sensor.

28. The integrated device of claim 27, wherein the filter comprises a multi-layer stack.

29. The integrated device of claim 27, wherein the filter comprises a frequency-selective surface.

30. The integrated device of claim 1, wherein the sensing system comprises an optical block that blocks at least some excitation energy from the excitation source.

31. The integrated device of claim 1, wherein the sensing system comprises at least one phase mask.

32. The integrated device of claim 4, wherein the second structure comprises a plasmonic structure, wherein the plasmonic structure is formed in an optical near field of the sample well.

33. The integrated device of claim 32, wherein the plasmonic structure is formed at least in part in a same layer in which the sample well is formed.

34. The integrated device of claim 32, wherein the plasmonic structure comprises a plurality of annular projections formed in a layer and centered on the sample well.

35. The integrated device of claim 32, wherein the plasmonic structure comprises a spiral grating.

36. The integrated device of claim 32, wherein the plasmonic structure comprises a nano-antenna array having an array of circular holes distributed around the sample well and wherein the circular holes are formed in a conductive layer.

37. The integrated device of claim 36, wherein the conductive layer in which the circular holes are formed is a same layer in which the sample well is formed.

38. The integrated device of claim 36, wherein the nano-antenna array comprises an array of circular discs distributed around the sample well, wherein the circular discs are formed in a conductive material.

39. The integrated device of claim 4, wherein the second structure comprises a circular grating, a spiral grating, or an aperture array formed in an optical far field of the sample well.

40. The integrated device of claim 1, wherein the sensor comprises a bullseye photodetector having a central light detector and at least one ring-shaped light detector spaced from and surrounding the central light detector.

41. The integrated device of claim 1, wherein the sensor comprises at least two spatially-separated detectors.

42. The integrated device of claim 40, further comprising read-out circuitry configured to discern four different emission energies from the sample detected by two or more spatially-separated detectors, wherein the sensor and read-out circuitry comprise CMOS circuit elements.

43. The integrated device of claim 1, wherein the at least one excitation source comprises at least one source of optical radiation having a characteristic wavelength between approximately 350 nm and approximately 1000 nm and is configured to excite at least one sample well.

44. The integrated device of claim 1, wherein the at least one excitation source is located between the sample well and the sensor.

45. The integrated device of claim 1, wherein the at least one excitation source comprises an organic light-emitting diode (OLED), wherein an electrode of the OLED is formed from a conductive layer in which the sample well is formed and further comprising surface features patterned in the electrode adjacent to the sample well and arranged to enhance a surface wave that is excited by the OLED and delivers excitation energy to the excitation region.

46. The integrated device of claim 1, wherein the circuitry comprises CMOS circuitry that includes multi-channel analog-to-digital converters.

47. The integrated device of claim 46, wherein the CMOS circuitry includes at least one field-programmable gate array (FPGA) and/or at least one application-specific integrated circuit (ASIC).

48. A portable instrument comprising:
at least one processor;
a dock configured to receive an integrated device having:
    a plurality of pixels arranged on a substrate, wherein an individual pixel of the plurality of pixels comprises:
        a sample well having an excitation region configured to retain a biological sample;
        a first structure located adjacent to or within the sample well and configured to affect coupling of at least excitation energy into the excitation region; and
        a sensing system including a sensor that is configured to discriminate between at least two different emissions from the sample well, wherein the at least two different emissions comprise spectral and/or temporal differences; and
    circuitry arranged on the substrate to receive at least one signal from the sensor;
a cover configured to exclude a majority of external light from entering the dock; and
a first plurality of electrical contacts configured to connect to a second plurality of electrical contacts on the integrated device, wherein power may be provide to the integrated device through at least some of the first plurality of electrical contacts and the at least one signal from each sensor may be received through at least some of the first plurality of electrical contacts.

49. The portable instrument of claim 48, wherein the first plurality of electrical contacts is formed on a user-removable interposer.

* * * * *